(12) United States Patent
Jaynes et al.

(10) Patent No.: US 9,492,499 B2
(45) Date of Patent: Nov. 15, 2016

(54) PEPTIDES HAVING ANTI-INFLAMMATORY PROPERTIES

(71) Applicant: Riptide Bioscience, Inc., Vallejo, CA (US)

(72) Inventors: Jesse M. Jaynes, Auburn, AL (US); Henry W. Lopez, Napa, CA (US); George R. Martin, Rockville, MD (US); Clayton Yates, Auburn, AL (US); Charles E. Garvin, Redwood City, CA (US)

(73) Assignee: Riptide Bioscience, Inc., Vallejo, CA (US)

( * ) Notice: Subject to any disclaimer, the term of this patent is extended or adjusted under 35 U.S.C. 154(b) by 0 days.

(21) Appl. No.: 14/882,293

(22) Filed: Oct. 13, 2015

(65) Prior Publication Data

US 2016/0101150 A1    Apr. 14, 2016

Related U.S. Application Data

(60) Provisional application No. 62/063,909, filed on Oct. 14, 2014.

(51) Int. Cl.

| | |
|---|---|
| *A61K 45/06* | (2006.01) |
| *A61K 38/08* | (2006.01) |
| *A61K 38/10* | (2006.01) |
| *C07K 14/00* | (2006.01) |
| *C07K 7/08* | (2006.01) |
| *A61K 38/16* | (2006.01) |

(Continued)

(52) U.S. Cl.
CPC ........... *A61K 38/16* (2013.01); *A61K 31/7068* (2013.01); *A61K 38/04* (2013.01); *A61K 38/08* (2013.01); *A61K 38/10* (2013.01); *A61K 45/06* (2013.01); *C07K 5/08* (2013.01); *C07K 5/10* (2013.01); *C07K 7/06* (2013.01); *C07K 7/08* (2013.01); *C07K 14/00* (2013.01)

(58) Field of Classification Search
CPC ........... C07K 7/06; C07K 7/08; A61K 38/00
See application file for complete search history.

(56) References Cited

U.S. PATENT DOCUMENTS

| | | | |
|---|---|---|---|
| 5,717,064 A * | 2/1998 | Julian | .................... A61K 38/10 530/324 |
| 5,861,478 A | 1/1999 | Jaynes | |

(Continued)

FOREIGN PATENT DOCUMENTS

| | | |
|---|---|---|
| WO | WO9012866 | 11/1990 |
| WO | WO9842634 | 10/1998 |
| WO | WO2005046714 | 5/2005 |

OTHER PUBLICATIONS

Oxytocin, NCBI, PRF:229114, GI:229114 (Jul. 10, 1992), 1 page, also available at http://www.ncbi.nlm.nih.gov/protein/229114 (last visited Jan. 28, 2016).*

(Continued)

*Primary Examiner* — James H Alstrum Acevedo
*Assistant Examiner* — Randall L Beane
(74) *Attorney, Agent, or Firm* — Bret E. Field; Bozicevic, Field & Francis LLP

(57) ABSTRACT

Aspects of the present invention relate to peptides having anti-inflammatory activity, compositions containing one or more of the peptides, and use of the peptides to treat conditions associated with excessive inflammation in animals, particularly humans and other mammals.

26 Claims, 14 Drawing Sheets

(51) Int. Cl.
*C07K 7/06* (2006.01)
*C07K 5/10* (2006.01)
*C07K 5/08* (2006.01)
*A61K 31/7068* (2006.01)
*A61K 38/04* (2006.01)

(56) References Cited

U.S. PATENT DOCUMENTS

| | | | |
|---|---|---|---|
| 5,955,573 A * | 9/1999 | Garbarino | A61K 38/10 530/324 |
| 5,962,410 A | 10/1999 | Jaynes | |
| 6,255,282 B1 | 7/2001 | Jaynes | |
| 6,514,692 B2 * | 2/2003 | Jaynes | A61K 38/04 424/184.1 |
| 6,559,281 B1 | 5/2003 | Jaynes | |
| 6,635,740 B1 | 10/2003 | Enright | |
| 7,288,622 B1 * | 10/2007 | Jaynes | A61K 9/0014 424/78.05 |
| 7,566,777 B2 | 7/2009 | Enright | |
| 7,803,755 B2 | 9/2010 | Jaynes | |
| 8,258,100 B2 | 9/2012 | Enright | |
| 8,734,775 B2 | 5/2014 | Yates-Binder | |
| 2004/0018967 A1 | 1/2004 | Enright | |
| 2005/0187151 A1 * | 8/2005 | Strom | C07K 14/4723 514/2.4 |
| 2010/0016227 A1 | 1/2010 | Enright | |
| 2012/0270770 A1 * | 10/2012 | Jaynes | C07K 14/43572 514/1.9 |
| 2014/0329753 A1 | 11/2014 | Jaynes | |

OTHER PUBLICATIONS

Jankowski et al., Basic Res Cardiol, vol. 105:205-218 (Dec. 12, 2009).*
Jaynes, et al., "Structure/Function Link Between Cytokine Domains and Natural and Designed Lytic Peptides: Medical Promise", 2012 American Chemical Society, pp. 21-45, 2012.
Ko, et al. "FOLFIRINOX: A Small Step or a Great Leap Forward?", Journal of Clinical Oncology. vol. 29. No. 28, Oct. 1, 2011, pp. 3727-3729.
Park, et al. "Melittin Inhibits Inflammatory Target Gene Expression and Mediator Generation Via Interaction With kappaB Kinase", Biochemical Pharmacology. Sep. 29, 2006, vol. 73, No. 2; pp. 237-247.
Wang, et al. "A Cell-Penetrating Peptide Suppresses Inflammation by Inhbiting NF-kappa-Beta Signaling", Molecular Therapy, May 10, 2011, vol. 19, No. 10; pp. 1849-1857.

* cited by examiner

Anti-PD-1 antibody
ABCAM ab 52587 though the claim to priority is to U.S. Provisional Patent Application Ser. No. 62/063,909, filed Oct. 14, 2014, the disclosure of which application is hereby incorporated by reference herein in its entirety.

SEQUENCE LISTING

```
<160> NUMBER OF SEQ ID NOS: 413

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 1

Phe Phe Phe Xaa Phe Phe Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)
```

```
<400> SEQUENCE: 2

Trp Trp Trp Xaa Trp Trp Trp
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 3

Tyr Tyr Tyr Xaa Tyr Tyr Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 4

Leu Leu Leu Xaa Leu Leu Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 5

Cys Cys Cys Xaa Cys Cys Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 6

Met Met Met Xaa Met Met Met
1               5

<210> SEQ ID NO 7
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 7

Val Val Val Xaa Val Val Val
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is selected from Arg (R), His (H), Lys (K),
      Glu (E), Gln (Q), Asn (N), and Asp (D)

<400> SEQUENCE: 8

Ile Ile Ile Xaa Ile Ile Ile
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 9

Phe Xaa Xaa Phe Phe Xaa Xaa Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 10

Phe Xaa Xaa Phe Phe Xaa Xaa Trp
1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 11

Trp Xaa Xaa Phe Phe Xaa Xaa Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 12

Phe Xaa Xaa Phe Trp Xaa Xaa Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 13

Phe Xaa Xaa Trp Phe Xaa Xaa Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 14

Phe Xaa Xaa Trp Trp Xaa Xaa Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 15

Trp Xaa Xaa Trp Trp Xaa Xaa Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 16

Phe Xaa Xaa Trp Trp Xaa Xaa Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 17
```

```
Trp Xaa Xaa Trp Trp Xaa Xaa Trp
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 18

Phe Xaa Xaa Phe Phe Xaa Xaa Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 19

Tyr Xaa Xaa Phe Phe Xaa Xaa Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 20

Phe Xaa Xaa Phe Tyr Xaa Xaa Phe
1               5

<210> SEQ ID NO 21
<211> LENGTH: 8
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 21

Phe Xaa Xaa Tyr Phe Xaa Xaa Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 22

Phe Xaa Xaa Tyr Tyr Xaa Xaa Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 23

Tyr Xaa Xaa Tyr Tyr Xaa Xaa Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K), -continued Glu (E), Gln (Q), Asn (N), and Asp (D)

<400> SEQUENCE: 24

Phe Xaa Xaa Tyr Tyr Xaa Xaa Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 25

Tyr Xaa Xaa Tyr Tyr Xaa Xaa Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 26

Tyr Xaa Xaa Tyr Tyr Xaa Xaa Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 27

Trp Xaa Xaa Tyr Tyr Xaa Xaa Tyr
1               5

<210> SEQ ID NO 28
<211> LENGTH: 8

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 28

Tyr Xaa Xaa Tyr Trp Xaa Xaa Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 29

Tyr Xaa Xaa Trp Tyr Xaa Xaa Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 30

Tyr Xaa Xaa Trp Trp Xaa Xaa Tyr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
```

```
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 31

Trp Xaa Xaa Trp Trp Xaa Xaa Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is selected from Arg (R), His (H), Lys (K),
      Glu (E), Gln (Q), Asn (N), and Asp (D)
<220> FEATURE:
<221> NAME/KEY: MISC_FEATURE
<222> LOCATION: (6)..(7)
<223> OTHER INFORMATION: Xaa is selected from Arg (R), His (H), Lys (K),
      Glu (E), Gln (Q), Asn (N), and Asp (D)

<400> SEQUENCE: 32

Tyr Xaa Xaa Trp Trp Xaa Xaa Trp
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Asn Phe Asn Phe Phe Phe Arg Phe Phe Phe
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Trp Trp Trp Arg Trp Trp Trp Glu Trp Gln
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Glu Phe Asn Phe Phe Phe Arg Phe Phe Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 36

Asp Phe Glu Phe Phe Phe Arg Phe Phe Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide

<400> SEQUENCE: 37

Gln Phe Glu Phe Phe Phe Arg Phe Phe Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide

<400> SEQUENCE: 38

Glu Phe Glu Phe Phe Phe Arg Phe Phe Phe
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Phe Phe Phe Arg Phe Phe Phe Glu Phe Gln
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic peptide

<400> SEQUENCE: 40

Phe Phe Phe Arg Phe Phe Phe Glu Phe Glu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Phe Phe Phe Arg Phe Phe Phe Glu Phe Asp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 42

Phe Phe Phe Arg Phe Phe Phe Asn Phe Glu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Phe Phe Phe Arg Phe Phe Phe Asp Phe Glu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide

<400> SEQUENCE: 44

Phe Phe Phe Arg Phe Phe Phe Asn Phe Asn
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Phe Phe Phe His Phe Phe Phe Glu Phe Gln
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic peptide

<400> SEQUENCE: 46

Phe Phe Phe His Phe Phe Phe Asn Phe Glu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Phe Phe Phe His Phe Phe Phe Glu Phe Asn
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48
```

Glu Phe Asn Phe Phe Phe His Phe Phe Phe
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic peptide

<400> SEQUENCE: 49

Phe Phe Phe Arg Phe Phe Phe Glu Phe Asn
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Phe Phe Phe His Phe Phe Phe Glu Phe Glu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Gln Phe Glu Phe Phe Phe His Phe Phe Phe
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Phe Phe Phe His Phe Phe Phe Glu Phe Asp
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Phe Phe Phe His Phe Phe Phe Asp Phe Glu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic peptide

<400> SEQUENCE: 54

```
Tyr Tyr Tyr Arg Tyr Tyr Glu Tyr Gln
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

Asn Phe Glu Phe Phe Phe His Phe Phe Phe
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

Phe Phe Phe Lys Phe Phe Phe Lys Phe Glu
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide

<400> SEQUENCE: 57

Glu Phe Asp Phe Phe Phe Arg Phe Phe Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic peptide

<400> SEQUENCE: 58

Phe Phe Phe His Phe Phe Phe Asp Phe Asp
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic peptide

<400> SEQUENCE: 59

Phe Phe Phe His Phe Phe Phe Asn Phe Asn
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic peptide

<400> SEQUENCE: 60

Phe Phe Phe Arg Phe Phe Phe Asp Phe Asp
```

```
1               5                   10
```

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

```
Phe Phe Phe Lys Phe Phe Phe Lys Phe Asn
1               5                   10
```

<210> SEQ ID NO 62
<211> LENGTH: 10
<212> TYPE: PRT
<213> ORGANISM: Artificial Sequence
<220> FEATURE:
<223> OTHER INFORMATION: Synthetic peptide

<400> SEQUENCE: 62

```
Phe Phe Phe Lys Phe Phe Phe Glu Phe Glu
1               5                   10
```

<210> SEQ ID NO 63
<211> LENGTH: 10
<212> TYPE: PRT
<213> ORGANISM: Artificial Sequence
<220> FEATURE:
<223> OTHER INFORMATION: Synthetic peptide

<400> SEQUENCE: 63

```
Phe Phe Phe Glu Phe Phe Phe Lys Phe Glu
1               5                   10
```

<210> SEQ ID NO 64
<211> LENGTH: 10
<212> TYPE: PRT
<213> ORGANISM: Artificial Sequence
<220> FEATURE:
<223> OTHER INFORMATION: Synthetic peptide

<400> SEQUENCE: 64

```
Phe Phe Phe Gln Phe Phe Phe Gln Phe Gln
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Synthetic peptide

<400> SEQUENCE: 65

```
Phe Phe Phe Lys Phe Phe Phe Gln Phe Gln
1               5                   10
```

<210> SEQ ID NO 66
<211> LENGTH: 10
<212> TYPE: PRT
<213> ORGANISM: Artificial Sequence
<220> FEATURE:
<223> OTHER INFORMATION: Synthetic peptide

<400> SEQUENCE: 66

```
Phe Phe Phe Lys Phe Phe Phe Asn Phe Asn
1               5                   10
```

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide

<400> SEQUENCE: 67

Phe Phe Phe Asn Phe Phe Phe Asn Phe Asn
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Phe Phe Phe Lys Phe Phe Phe Glu Phe Gln
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic peptide

<400> SEQUENCE: 69

Phe Phe Phe Lys Phe Phe Phe Lys Phe Gln
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70

Phe Phe Phe Lys Phe Phe Phe Gln Phe Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide

<400> SEQUENCE: 71

Phe Phe Phe Lys Phe Phe Phe Lys Phe Asp
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide

<400> SEQUENCE: 72

Phe Phe Phe Lys Phe Phe Phe Asp Phe Asp
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Phe Phe Phe Asn Phe Phe Phe Lys Phe Asn
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide

<400> SEQUENCE: 74

Phe Phe Phe Asp Phe Phe Phe Asp Phe Asp
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide

<400> SEQUENCE: 75

Phe Phe Phe Lys Phe Phe Phe Glu Phe Lys
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide

<400> SEQUENCE: 76

Phe Phe Phe Lys Phe Phe Phe Asp Phe Lys
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic peptide

<400> SEQUENCE: 77

Phe Phe Phe Glu Phe Phe Phe Glu Phe Glu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic peptide

<400> SEQUENCE: 78

Phe Phe Phe Asp Phe Phe Phe Lys Phe Asp
1               5                   10

```
<210> SEQ ID NO 79
<211> LENGTH: 10
<212> TYPE: PRT
<213> ORGANISM: Artificial Sequence
<220> FEATURE:
<223> OTHER INFORMATION: Synthetic peptide

<400> SEQUENCE: 79

Phe Phe Phe Lys Phe Phe Phe Lys Phe Lys
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic peptide

<400> SEQUENCE: 80

Phe Phe Phe Glu Phe Phe Phe Lys Phe Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic peptide

<400> SEQUENCE: 81

Phe Phe Phe Gln Phe Phe Phe Lys Phe Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic peptide

<400> SEQUENCE: 82

Phe Phe Phe Lys Phe Phe Phe Asn Phe Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic peptide

<400> SEQUENCE: 83

Phe Phe Phe Asn Phe Phe Phe Lys Phe Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide

<400> SEQUENCE: 84

Phe Phe Phe Gln Phe Phe Phe Lys Phe Gln
1               5                   10

<210> SEQ ID NO 85
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 85

Phe Phe Phe Asp Phe Phe Phe Lys Phe Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

Leu Leu Leu Arg Leu Leu Leu Glu Leu Gln
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic peptide

<400> SEQUENCE: 87

Phe Val Phe Lys Phe Val Phe Lys Phe Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Cys Cys Cys Arg Cys Cys Cys Glu Cys Gln
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic peptide

<400> SEQUENCE: 89

Met Met Met Arg Met Met Met Glu Met Gln
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

Val Val Val Arg Val Val Val Glu Val Gln
1               5                   10

<210> SEQ ID NO 91
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 91

Ile Ile Ile Arg Ile Ile Ile Glu Ile Gln
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic peptide

<400> SEQUENCE: 92

Gly Gly Gly Arg Gly Gly Gly Glu Gly Gln
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic peptide

<400> SEQUENCE: 93

Pro Pro Pro Arg Pro Pro Pro Glu Pro Gln
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide

<400> SEQUENCE: 94

Thr Thr Thr Arg Thr Thr Thr Glu Thr Gln
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Ala Ala Ala Arg Ala Ala Ala Glu Ala Gln
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide

<400> SEQUENCE: 96

Ala Ala Ala Lys Ala Ala Ala Lys Ala Ala
1               5                   10

<210> SEQ ID NO 97
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 97

Ala Ala Ala Glu Ala Ala Ala Glu Ala Glu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide

<400> SEQUENCE: 98

Ser Ser Ser Arg Ser Ser Ser Glu Ser Gln
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide

<400> SEQUENCE: 99

His His His Arg His His His Glu His Gln
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

Arg Arg Arg Arg Arg Arg Arg Glu Arg Gln
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic peptide

<400> SEQUENCE: 101

Gln Gln Gln Arg Gln Gln Gln Glu Gln Gln
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic peptide

<400> SEQUENCE: 102

Glu Glu Glu Arg Glu Glu Glu Glu Glu Gln
1               5                   10

<210> SEQ ID NO 103
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 103

Asn Asn Asn Arg Asn Asn Asn Glu Asn Gln
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic peptide

<400> SEQUENCE: 104

Asp Asp Asp Arg Asp Asp Asp Glu Asp Gln
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic peptide

<400> SEQUENCE: 105

Lys Lys Lys Arg Lys Lys Lys Glu Lys Gln
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic peptide

<400> SEQUENCE: 106

Phe Phe Gln Lys Phe Phe Lys Arg Trp Arg
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic peptide

<400> SEQUENCE: 107

Phe Phe Arg Lys Phe Phe Lys Arg Phe Arg
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic peptide

<400> SEQUENCE: 108

Arg Phe Arg Lys Phe Phe Lys Arg Phe Phe
1               5                   10

<210> SEQ ID NO 109
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 109

Arg Phe Arg Lys Phe Phe Lys Gln Phe Phe
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic peptide

<400> SEQUENCE: 110

Phe Phe Gln Lys Phe Phe Lys Arg Phe Arg
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic peptide

<400> SEQUENCE: 111

Arg Trp Arg Lys Phe Phe Lys Gln Phe Phe
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic peptide

<400> SEQUENCE: 112

Phe Phe Glu His Phe Trp Lys Glu Phe Asn
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic peptide

<400> SEQUENCE: 113

Phe Phe Gln His Phe Trp Lys Gln Phe Asn
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic peptide

<400> SEQUENCE: 114

Gln Phe Asn His Phe Phe Lys Glu Phe Phe
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic peptide

<400> SEQUENCE: 115

Phe Phe Asp Lys Phe Phe His Asp Phe Gln
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic peptide

<400> SEQUENCE: 116

Gln Phe Asp His Phe Phe Lys Asp Phe Phe
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic peptide

<400> SEQUENCE: 117

Phe Phe Glu Lys Phe Phe His Asn Phe Gln
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic peptide

<400> SEQUENCE: 118

Asn Phe Glu Lys Trp Phe His Glu Phe Phe
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic peptide

<400> SEQUENCE: 119

Leu Phe Arg Arg Ala Phe Lys Gln Leu Asp
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic peptide

<400> SEQUENCE: 120

Asn Phe Gln Lys Trp Phe His Gln Phe Phe
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 121

Lys Phe Arg Lys Ala Phe Lys Arg Phe Phe
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic peptide

<400> SEQUENCE: 122

Phe Phe Arg Lys Phe Ala Lys Arg Phe Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic peptide

<400> SEQUENCE: 123

Phe Phe Lys Lys Phe Phe Lys Lys Phe Lys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic peptide

<400> SEQUENCE: 124

Lys Phe Lys Lys Phe Phe Lys Lys Phe Phe
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic peptide

<400> SEQUENCE: 125

Lys Ala Arg Lys Ala Phe Lys Arg Phe Phe
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic peptide

<400> SEQUENCE: 126

Trp Val Lys Asp Ala Met Gln His Leu Asp
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic peptide

<400> SEQUENCE: 127
```

Phe Phe Lys Lys Phe Ala Lys Lys Phe Lys
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic peptide

<400> SEQUENCE: 128

Phe Ala Glu Lys Phe Phe Lys Asn Phe Lys
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic peptide

<400> SEQUENCE: 129

Lys Phe Asn Lys Phe Phe Lys Glu Ala Phe
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic peptide

<400> SEQUENCE: 130

Phe Ala Lys Gln Phe Phe Asn Lys Phe Lys
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic peptide

<400> SEQUENCE: 131

Lys Phe Asn Lys Ala Phe Lys Gln Ala Phe
1               5                   10

<210> SEQ ID NO 132
<211> LENGTH: 4
<212> TYPE: PRT
<213> ORGANISM: Artificial Sequence
<220> FEATURE:
<223> OTHER INFORMATION: Synthetic peptide

<400> SEQUENCE: 132

His Tyr Trp His
1

<210> SEQ ID NO 133
<211> LENGTH: 10
<212> TYPE: PRT
<213> ORGANISM: Artificial Sequence
<220> FEATURE:
<223> OTHER INFORMATION: Synthetic peptide

<400> SEQUENCE: 133

Phe Ala Gln Lys Phe Phe Lys Asp Phe Lys
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic peptide

<400> SEQUENCE: 134

Phe Ala Glu Glu Phe Ala Glu Glu Phe Glu
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic peptide

<400> SEQUENCE: 135

Lys Phe Lys Lys Phe Phe Lys Lys Ala Phe
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic peptide

<400> SEQUENCE: 136

Lys Phe Lys Asn Phe Phe Gln Lys Ala Phe
1               5                   10

<210> SEQ ID NO 137
<211> LENGTH: 433
<212> TYPE: PRT
<213> ORGANISM: Homo sapiens

<400> SEQUENCE: 137

Met Val Trp Lys Val Ala Val Phe Leu Ser Val Ala Leu Gly Ile Gly
1               5                   10                  15

Ala Ile Pro Ile Asp Asp Pro Glu Asp Gly Gly Lys His Trp Val Val
            20                  25                  30

Ile Val Ala Gly Ser Asn Gly Trp Tyr Asn Tyr Arg His Gln Ala Asp
        35                  40                  45

Ala Cys His Ala Tyr Gln Ile Ile His Arg Asn Gly Ile Pro Asp Glu
    50                  55                  60

Gln Ile Val Val Met Met Tyr Asp Asp Ile Ala Tyr Ser Glu Asp Asn
65                  70                  75                  80

Pro Thr Pro Gly Ile Val Ile Asn Arg Pro Asn Gly Thr Asp Val Tyr
                85                  90                  95

Gln Gly Val Pro Lys Asp Tyr Thr Gly Glu Asp Val Thr Pro Gln Asn
            100                 105                 110

Phe Leu Ala Val Leu Arg Gly Asp Ala Glu Ala Val Lys Gly Ile Gly
        115                 120                 125

Ser Gly Lys Val Leu Lys Ser Gly Pro Gln Asp His Val Phe Ile Tyr
    130                 135                 140

Phe Thr Asp His Gly Ser Thr Gly Ile Leu Val Phe Pro Asn Glu Asp
145                 150                 155                 160

```
Leu His Val Lys Asp Leu Asn Glu Thr Ile His Tyr Met Tyr Lys His
            165                 170                 175
Lys Met Tyr Arg Lys Met Val Phe Tyr Ile Glu Ala Cys Glu Ser Gly
        180                 185                 190
Ser Met Met Asn His Leu Pro Asp Asn Ile Asn Val Tyr Ala Thr Thr
    195                 200                 205
Ala Ala Asn Pro Arg Glu Ser Ser Tyr Ala Cys Tyr Tyr Asp Glu Lys
210                 215                 220
Arg Ser Thr Tyr Leu Gly Asp Trp Tyr Ser Val Asn Trp Met Glu Asp
225                 230                 235                 240
Ser Asp Val Glu Asp Leu Thr Lys Glu Thr Leu His Lys Gln Tyr His
            245                 250                 255
Leu Val Lys Ser His Thr Asn Thr Ser His Val Met Gln Tyr Gly Asn
        260                 265                 270
Lys Thr Ile Ser Thr Met Lys Val Met Gln Phe Gln Gly Met Lys Arg
    275                 280                 285
Lys Ala Ser Ser Pro Val Pro Leu Pro Pro Val Thr His Leu Asp Leu
290                 295                 300
Thr Pro Ser Pro Asp Val Pro Leu Thr Ile Met Lys Arg Lys Leu Met
305                 310                 315                 320
Asn Thr Asn Asp Leu Glu Glu Ser Arg Gln Leu Thr Glu Glu Ile Gln
            325                 330                 335
Arg His Leu Asp Ala Arg His Leu Ile Glu Lys Ser Val Arg Lys Ile
        340                 345                 350
Val Ser Leu Leu Ala Ala Ser Glu Ala Glu Val Glu Gln Leu Leu Ser
    355                 360                 365
Glu Arg Ala Pro Leu Thr Gly His Ser Cys Tyr Pro Glu Ala Leu Leu
370                 375                 380
His Phe Arg Thr His Cys Phe Asn Trp His Ser Pro Thr Tyr Glu Tyr
385                 390                 395                 400
Ala Leu Arg His Leu Tyr Val Leu Val Asn Leu Cys Glu Lys Pro Tyr
            405                 410                 415
Pro Leu His Arg Ile Lys Leu Ser Met Asp His Val Cys Leu Gly His
        420                 425                 430
Tyr

<210> SEQ ID NO 138
<211> LENGTH: 10
<212> TYPE: PRT
<213> ORGANISM: Artificial Sequence
<220> FEATURE:
<223> OTHER INFORMATION: Synthetic peptide

<400> SEQUENCE: 138

Phe Ala Lys Gln Phe Ala Asn Lys Phe Lys
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic peptide

<400> SEQUENCE: 139

Lys Phe Lys Asn Ala Phe Gln Lys Ala Phe
1               5                   10
```

```
<210> SEQ ID NO 140
<211> LENGTH: 360
<212> TYPE: PRT
<213> ORGANISM: Homo sapiens

<400> SEQUENCE: 140

Met Ser Asp Ser Lys Glu Pro Arg Leu Gln Gln Gly Leu Leu Val
1               5                   10                  15

Ser Lys Val Pro Ser Ser Ile Ser Gln Gln Ser Arg Gln Asp Ala
                20                  25                  30

Ile Tyr Gln Asn Leu Thr Gln Leu Lys Ala Ala Val Gly Glu Leu Ser
                35                  40                      45

Glu Lys Ser Lys Leu Gln Glu Ile Tyr Gln Glu Leu Thr Gln Leu Lys
                50                      55                  60

Ala Ala Val Gly Glu Leu Pro Glu Lys Ser Lys Leu Gln Glu Ile Tyr
65                      70                  75                  80

Gln Glu Leu Thr Arg Leu Lys Ala Ala Val Gly Glu Leu Pro Glu Lys
                    85                  90                  95

Ser Lys Leu Gln Glu Ile Tyr Gln Glu Leu Thr Trp Leu Lys Ala Ala
                100                     105                 110

Val Gly Glu Leu Pro Glu Lys Ser Lys Met Gln Glu Ile Tyr Gln Glu
                115                     120                 125

Leu Thr Arg Leu Lys Ala Ala Val Gly Glu Leu Pro Glu Lys Ser Lys
                130                     135                 140

Gln Gln Glu Ile Tyr Gln Glu Leu Thr Arg Leu Lys Ala Ala Val Gly
145                     150                     155             160

Glu Leu Pro Glu Lys Ser Lys Gln Gln Glu Ile Tyr Gln Glu Leu Thr
                165                     170                 175

Arg Leu Lys Ala Ala Val Gly Glu Leu Pro Glu Lys Ser Lys Gln Gln
                180                     185                 190

Glu Ile Tyr Gln Glu Leu Thr Gln Leu Lys Ala Ala Val Glu Arg Leu
                195                     200                 205

Cys His Pro Cys Pro Trp Glu Trp Thr Phe Phe Gln Gly Asn Cys Tyr
                210                     215                 220

Phe Met Ser Asn Ser Gln Arg Asn Trp His Asp Ser Ile Thr Ala Cys
225                 230                     235                 240

Lys Glu Val Gly Ala Gln Leu Val Val Ile Lys Ser Ala Glu Glu Gln
                245                     250                 255

Asn Phe Leu Gln Leu Gln Ser Ser Arg Ser Asn Arg Phe Thr Trp Met
                260                     265                 270

Gly Leu Ser Asp Leu Asn Gln Glu Gly Thr Trp Gln Trp Val Asp Gly
                275                     280                 285

Ser Pro Leu Leu Pro Ser Phe Lys Gln Tyr Trp Asn Arg Gly Glu Pro
                290                     295                 300

Asn Asn Val Gly Glu Glu Asp Cys Ala Glu Phe Ser Gly Asn Gly Trp
305                 310                     315                 320

Asn Asp Asp Lys Cys Asn Leu Ala Lys Phe Trp Ile Cys Lys Lys Ser
                325                     330                 335

Ala Ala Ser Cys Ser Arg Asp Glu Glu Gln Phe Leu Ser Pro Ala Pro
                340                     345                 350

Ala Thr Pro Asn Pro Pro Ala
                355                 360
```

```
<210> SEQ ID NO 141
<211> LENGTH: 10
<212> TYPE: PRT
<213> ORGANISM: Artificial Sequence
<220> FEATURE:
<223> OTHER INFORMATION: Synthetic peptide

<400> SEQUENCE: 141

Phe Ala Lys Lys Phe Phe Lys Lys Phe Lys
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic peptide

<400> SEQUENCE: 142

Lys Phe Lys Lys Ala Phe Lys Lys Phe Phe
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic peptide

<400> SEQUENCE: 143

Phe Ala Glu Lys Phe Ala Glu Lys Phe Glu
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic peptide

<400> SEQUENCE: 144

Asp Leu His Gln Met Ala Asp Lys Val Trp
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic peptide

<400> SEQUENCE: 145

Lys Ala Arg Lys Ala Ala Lys Arg Phe Phe
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic peptide

<400> SEQUENCE: 146

Phe Ala Lys Asn Phe Ala Lys Lys Phe Lys
1               5                   10

<210> SEQ ID NO 147
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 147

Phe Ala Glu Lys Phe Ala Lys Asn Phe Lys
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic peptide

<400> SEQUENCE: 148

Lys Phe Lys Lys Ala Phe Lys Lys Ala Phe
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic peptide

<400> SEQUENCE: 149

Phe Ala Lys Asn Phe Ala Lys Asn Phe Lys
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic peptide

<400> SEQUENCE: 150

Phe Ala Lys Glu Phe Ala Lys Glu Phe Glu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic peptide

<400> SEQUENCE: 151

Lys Phe Asp Lys Ala Phe Lys Gln Ala Phe
1               5                   10

<210> SEQ ID NO 152
<211> LENGTH: 335
<212> TYPE: PRT
<213> ORGANISM: Homo sapiens

<400> SEQUENCE: 152

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45
```

-continued

```
Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 153
<211> LENGTH: 10
<212> TYPE: PRT
<213> ORGANISM: Artificial Sequence
<220> FEATURE:
<223> OTHER INFORMATION: Synthetic peptide

<400> SEQUENCE: 153

Phe Ala Glu Lys Phe Ala Lys Lys Phe Lys
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic peptide

<400> SEQUENCE: 154

Phe Ala Glu Lys Phe Ala Glu Lys Phe Lys
```

-continued

<210> SEQ ID NO 155
<211> LENGTH: 10
<212> TYPE: PRT
<213> ORGANISM: Artificial Sequence
<220> FEATURE:
<223> OTHER INFORMATION: Synthetic peptide

<400> SEQUENCE: 155

Phe Ala Lys Lys Phe Ala Lys Lys Phe Lys
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic peptide

<400> SEQUENCE: 156

Phe Ala Lys Asn Phe Ala Lys Asn Phe Asn
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic peptide

<400> SEQUENCE: 157

Phe Ala Gln Lys Phe Ala Lys Asn Phe Lys
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic peptide

<400> SEQUENCE: 158

Phe Ala Asn Asn Phe Ala Asn Asn Phe Asn
1               5                   10

<210> SEQ ID NO 159
<211> LENGTH: 198
<212> TYPE: PRT
<213> ORGANISM: Homo sapiens

<400> SEQUENCE: 159

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

```
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly
        195

<210> SEQ ID NO 160
<211> LENGTH: 10
<212> TYPE: PRT
<213> ORGANISM: Artificial Sequence
<220> FEATURE:
<223> OTHER INFORMATION: Synthetic peptide

<400> SEQUENCE: 160

Phe Ala Asn Lys Phe Ala Asn Lys Phe Asn
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic peptide

<400> SEQUENCE: 161

Phe Ala Asn Lys Phe Ala Lys Lys Phe Lys
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic peptide

<400> SEQUENCE: 162

Phe Ala Gln Lys Phe Ala Lys Asp Phe Lys
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Synthetic peptide

<400> SEQUENCE: 163

Phe Ala Lys Glu Phe Ala Lys Glu Phe Lys
1               5                   10

<210> SEQ ID NO 164
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 164

Phe Ala Asn Lys Phe Ala Asn Lys Phe Lys
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Synthetic peptide

<400> SEQUENCE: 165

Lys Phe Asp Lys Phe Phe Lys Gln Ala Phe
1               5                   10

<210> SEQ ID NO 166
<211> LENGTH: 435
<212> TYPE: PRT
<213> ORGANISM: Homo sapiens

<400> SEQUENCE: 166

Met Ala Ala Ser Ser Leu Glu Gln Lys Leu Ser Arg Leu Glu Ala Lys
1               5                   10                  15

Leu Lys Gln Glu Asn Arg Glu Ala Arg Arg Arg Ile Asp Leu Asn Leu
            20                  25                  30

Asp Ile Ser Pro Gln Arg Pro Arg Pro Ile Ile Val Ile Thr Leu Ser
        35                  40                  45

Pro Ala Pro Ala Pro Ser Gln Arg Ala Ala Leu Gln Leu Pro Leu Ala
    50                  55                  60

Asn Asp Gly Gly Ser Arg Ser Pro Ser Ser Glu Ser Ser Pro Gln His
65                  70                  75                  80

Pro Thr Pro Pro Ala Arg Pro Arg His Met Leu Gly Leu Pro Ser Thr
                85                  90                  95

Leu Phe Thr Pro Arg Ser Met Glu Ser Ile Glu Ile Asp Gln Lys Leu
            100                 105                 110

Gln Glu Ile Met Lys Gln Thr Gly Tyr Leu Thr Ile Gly Gly Gln Arg
        115                 120                 125

Tyr Gln Ala Glu Ile Asn Asp Leu Glu Asn Leu Gly Glu Met Gly Ser
    130                 135                 140

Gly Thr Cys Gly Gln Val Trp Lys Met Arg Phe Arg Lys Thr Gly His
145                 150                 155                 160

Val Ile Ala Val Lys Gln Met Arg Arg Ser Gly Asn Lys Glu Glu Asn
                165                 170                 175

Lys Arg Ile Leu Met Asp Leu Asp Val Val Leu Lys Ser His Asp Cys
            180                 185                 190

Pro Tyr Ile Val Gln Cys Phe Gly Thr Phe Ile Thr Asn Thr Asp Val
        195                 200                 205

Phe Ile Ala Met Glu Leu Met Gly Thr Cys Ala Glu Lys Leu Lys Lys
    210                 215                 220

Arg Met Gln Gly Pro Ile Pro Glu Arg Ile Leu Gly Lys Met Thr Val
225                 230                 235                 240

Ala Ile Val Lys Ala Leu Tyr Tyr Leu Lys Glu Lys His Gly Val Ile
                245                 250                 255

His Arg Asp Val Lys Pro Ser Asn Ile Leu Leu Asp Glu Arg Gly Gln
            260                 265                 270
```

-continued

```
Ile Lys Leu Cys Asp Phe Gly Ile Ser Gly Arg Leu Val Asp Ser Lys
            275                 280                 285

Ala Lys Thr Arg Ser Ala Gly Cys Ala Ala Tyr Met Ala Pro Glu Arg
        290                 295                 300

Ile Asp Pro Pro Asp Pro Thr Lys Pro Asp Tyr Asp Ile Arg Ala Asp
305                 310                 315                 320

Val Trp Ser Leu Gly Ile Ser Leu Val Glu Leu Ala Thr Gly Gln Phe
                325                 330                 335

Pro Tyr Lys Asn Cys Lys Thr Asp Phe Glu Val Leu Thr Lys Val Leu
            340                 345                 350

Gln Glu Glu Pro Pro Leu Leu Pro Gly His Met Gly Phe Ser Gly Asp
        355                 360                 365

Phe Gln Ser Phe Val Lys Asp Cys Leu Thr Lys Asp His Arg Lys Arg
    370                 375                 380

Pro Lys Tyr Asn Lys Leu Leu Glu His Ser Phe Ile Lys Arg Tyr Glu
385                 390                 395                 400

Thr Leu Glu Val Asp Val Ala Ser Trp Phe Lys Asp Val Met Ala Lys
                405                 410                 415

Thr Glu Ser Pro Arg Thr Ser Gly Val Leu Ser Gln Pro His Leu Pro
            420                 425                 430

Phe Phe Arg
        435

<210> SEQ ID NO 167
<211> LENGTH: 10
<212> TYPE: PRT
<213> ORGANISM: Artificial Sequence
<220> FEATURE:
<223> OTHER INFORMATION: Synthetic peptide

<400> SEQUENCE: 167

Lys Phe Asn Lys Ala Phe Lys Glu Ala Phe
1               5                   10

<210> SEQ ID NO 168
<211> LENGTH: 888
<212> TYPE: PRT
<213> ORGANISM: Saccharomyces cerevisiae

<400> SEQUENCE: 168

Met Tyr Val Tyr Lys Arg Asp Gly Arg Lys Glu Pro Val Gln Phe Asp
1               5                   10                  15

Lys Ile Thr Ala Arg Ile Ser Arg Leu Cys Tyr Gly Leu Asp Pro Lys
            20                  25                  30

His Ile Asp Ala Val Lys Val Thr Gln Arg Ile Ile Ser Gly Val Tyr
        35                  40                  45

Glu Gly Val Thr Thr Ile Glu Leu Asp Asn Leu Ala Ala Glu Thr Cys
    50                  55                  60

Ala Tyr Met Thr Thr Val His Pro Asp Tyr Ala Thr Leu Ala Ala Arg
65                  70                  75                  80

Ile Ala Ile Ser Asn Leu His Lys Gln Thr Thr Lys Gln Phe Ser Lys
                85                  90                  95

Val Val Glu Asp Leu Tyr Arg Tyr Val Asn Ala Ala Thr Gly Lys Pro
            100                 105                 110

Ala Pro Met Ile Ser Asp Asp Val Tyr Asn Ile Val Met Glu Asn Lys
        115                 120                 125
```

```
Asp Lys Leu Asn Ser Ala Ile Val Tyr Asp Arg Asp Phe Gln Tyr Ser
    130                 135                 140

Tyr Phe Gly Phe Lys Thr Leu Glu Arg Ser Tyr Leu Leu Arg Ile Asn
145                 150                 155                 160

Gly Gln Val Ala Glu Arg Pro Gln His Leu Ile Met Arg Val Ala Leu
                165                 170                 175

Gly Ile His Gly Arg Asp Ile Glu Ala Ala Leu Glu Thr Tyr Asn Leu
            180                 185                 190

Met Ser Leu Lys Tyr Tyr Thr His Ala Ser Pro Thr Leu Phe Asn Ala
        195                 200                 205

Gly Thr Pro Lys Pro Gln Met Ser Ser Cys Phe Leu Val Ala Met Lys
    210                 215                 220

Glu Asp Ser Ile Glu Gly Ile Tyr Asp Thr Leu Lys Glu Cys Ala Leu
225                 230                 235                 240

Ile Ser Lys Thr Ala Gly Gly Ile Gly Leu His Ile His Asn Ile Arg
                245                 250                 255

Ser Thr Gly Ser Tyr Ile Ala Gly Thr Asn Gly Thr Ser Asn Gly Leu
            260                 265                 270

Ile Pro Met Ile Arg Val Phe Asn Asn Thr Ala Arg Tyr Val Asp Gln
        275                 280                 285

Gly Gly Asn Lys Arg Pro Gly Ala Phe Ala Leu Tyr Leu Glu Pro Trp
    290                 295                 300

His Ala Asp Ile Phe Asp Phe Ile Asp Ile Arg Lys Asn His Gly Lys
305                 310                 315                 320

Glu Glu Ile Arg Ala Arg Asp Leu Phe Pro Ala Leu Trp Ile Pro Asp
                325                 330                 335

Leu Phe Met Lys Arg Val Glu Glu Asn Gly Thr Trp Thr Leu Phe Ser
            340                 345                 350

Pro Thr Ser Ala Pro Gly Leu Ser Asp Cys Tyr Gly Asp Glu Phe Glu
        355                 360                 365

Ala Leu Tyr Thr Arg Tyr Glu Lys Glu Gly Arg Gly Lys Thr Ile Lys
    370                 375                 380

Ala Gln Lys Leu Trp Tyr Ser Ile Leu Glu Ala Gln Thr Glu Thr Gly
385                 390                 395                 400

Thr Pro Phe Val Val Tyr Lys Asp Ala Cys Asn Arg Lys Ser Asn Gln
                405                 410                 415

Lys Asn Leu Gly Val Ile Lys Ser Ser Asn Leu Cys Cys Glu Ile Val
            420                 425                 430

Glu Tyr Ser Ala Pro Asp Glu Thr Ala Val Cys Asn Leu Ala Ser Val
        435                 440                 445

Ala Leu Pro Ala Phe Ile Glu Thr Ser Glu Asp Gly Lys Thr Ser Thr
    450                 455                 460

Tyr Asn Phe Lys Lys Leu His Glu Ile Ala Lys Val Val Thr Arg Asn
465                 470                 475                 480

Leu Asn Arg Val Ile Asp Arg Asn Tyr Tyr Pro Val Glu Glu Ala Arg
                485                 490                 495

Lys Ser Asn Met Arg His Arg Pro Ile Ala Leu Gly Val Gln Gly Leu
            500                 505                 510

Ala Asp Thr Phe Met Leu Leu Arg Leu Pro Phe Asp Ser Glu Glu Ala
        515                 520                 525

Arg Leu Leu Asn Ile Gln Ile Phe Glu Thr Ile Tyr His Ala Ser Met
    530                 535                 540

Glu Ala Ser Cys Glu Leu Ala Gln Lys Asp Gly Pro Tyr Glu Thr Phe
```

```
                545                 550                 555                 560
        Gln Gly Ser Pro Ala Ser Gln Gly Ile Leu Gln Phe Asp Met Trp Asp
                        565                 570                 575

Gln Lys Pro Tyr Gly Met Trp Asp Trp Asp Thr Leu Arg Lys Asp Ile
                        580                 585                 590

Met Lys His Gly Ile Arg Asn Ser Leu Thr Met Ala Pro Met Pro Thr
                        595                 600                 605

Ala Ser Thr Ser Gln Ile Leu Gly Tyr Asn Glu Cys Phe Glu Pro Val
                        610                 615                 620

Thr Ser Asn Met Tyr Ser Arg Arg Val Leu Ser Gly Glu Phe Gln Val
        625                 630                 635                 640

Val Asn Pro Tyr Leu Leu Arg Asp Leu Val Asp Leu Gly Ile Trp Asp
                        645                 650                 655

Glu Gly Met Lys Gln Tyr Leu Ile Thr Gln Asn Gly Ser Ile Gln Gly
                        660                 665                 670

Leu Pro Asn Val Pro Gln Glu Leu Lys Asp Leu Tyr Lys Thr Val Trp
                        675                 680                 685

Glu Ile Ser Gln Lys Thr Ile Ile Asn Met Ala Ala Asp Arg Ser Val
                        690                 695                 700

Tyr Ile Asp Gln Ser His Ser Leu Asn Leu Phe Leu Arg Ala Pro Thr
        705                 710                 715                 720

Met Gly Lys Leu Thr Ser Met His Phe Tyr Gly Trp Lys Lys Gly Leu
                        725                 730                 735

Lys Thr Gly Met Tyr Tyr Leu Arg Thr Gln Ala Ala Ser Ala Ala Ile
                        740                 745                 750

Gln Phe Thr Ile Asp Gln Lys Ile Ala Asp Gln Ala Thr Glu Asn Val
                        755                 760                 765

Ala Asp Ile Ser Asn Leu Lys Arg Pro Ser Tyr Met Pro Ser Ser Ala
                        770                 775                 780

Ser Tyr Ala Ala Ser Asp Phe Val Pro Ala Val Thr Ala Asn Ala
        785                 790                 795                 800

Thr Ile Pro Ser Leu Asp Ser Ser Glu Ala Ser Arg Glu Ala Ser
                        805                 810                 815

Pro Ala Pro Thr Gly Ser His Ser Leu Thr Lys Gly Met Ala Glu Leu
                        820                 825                 830

Asn Val Gln Glu Ser Lys Val Glu Val Pro Glu Val Pro Ala Pro Thr
                        835                 840                 845

Lys Asn Glu Glu Lys Ala Ala Pro Ile Val Asp Asp Glu Glu Thr Glu
        850                 855                 860

Phe Asp Ile Tyr Asn Ser Lys Val Ile Ala Cys Ala Ile Asp Asn Pro
        865                 870                 875                 880

Glu Ala Cys Glu Met Cys Ser Gly
                        885

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide

<400> SEQUENCE: 169

Phe Ala Lys Glu Phe Ala Lys Lys Phe Lys
1               5                   10
```

```
<210> SEQ ID NO 170
<211> LENGTH: 10
<212> TYPE: PRT
<213> ORGANISM: Artificial Sequence
<220> FEATURE:
<223> OTHER INFORMATION: Synthetic peptide

<400> SEQUENCE: 170

Lys Ala Arg Lys Ala Ala Lys Arg Ala Phe
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic peptide

<400> SEQUENCE: 171

Lys Ala Arg Lys Ala Ala Lys Arg Ala Ala
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic peptide

<400> SEQUENCE: 172

Ala Ala Glu Glu Ala Ala Glu Glu Ala Glu
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic peptide

<400> SEQUENCE: 173

Ala Ala Lys Lys Ala Ala Lys Lys Ala Lys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic peptide

<400> SEQUENCE: 174

Phe Val Lys Phe Val Lys Phe Val Lys Phe
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic peptide

<400> SEQUENCE: 175

Lys Arg Lys Ala Phe Arg Lys Phe Phe Phe
1               5                   10

<210> SEQ ID NO 176
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 176

Leu His Lys Met Tyr Asn Gln Val Trp
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic peptide

<400> SEQUENCE: 177

Trp Val Gln Asn Tyr Met Lys His Leu
1               5

<210> SEQ ID NO 178
<211> LENGTH: 10
<212> TYPE: PRT
<213> ORGANISM: Artificial Sequence
<220> FEATURE:
<223> OTHER INFORMATION: Synthetic peptide

<400> SEQUENCE: 178

Arg Leu Val Glu Met Met Arg Gln Ile Trp
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Synthetic peptide

<400> SEQUENCE: 179

Phe Leu Lys Arg Leu Leu Gln Glu Ile
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic peptide

<400> SEQUENCE: 180

Leu Arg Leu Leu His Arg Leu Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic peptide

<400> SEQUENCE: 181

Trp Val Arg Asp Ser Met Lys His Leu
1               5

<210> SEQ ID NO 182
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 182

Lys Phe Phe Arg Lys Lys Phe Arg Phe Ala
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic peptide

<400> SEQUENCE: 183

Trp Val Gln Arg Val Val Glu Lys Phe Leu
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic peptide

<400> SEQUENCE: 184

Ala Phe Phe Arg Arg Phe Lys Phe Lys Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic peptide

<400> SEQUENCE: 185

Leu Phe Lys Glu Val Val Arg Gln Val Trp
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide

<400> SEQUENCE: 186

Met Asp Lys Ile Tyr Asp Gln Val Trp Lys
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic peptide

<400> SEQUENCE: 187

Phe Val Lys Lys Phe Val Lys Lys Phe Val
1               5                   10

<210> SEQ ID NO 188
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 188

Lys Lys Phe Lys Phe Arg Arg Phe Phe Ala
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Synthetic peptide

<400> SEQUENCE: 189

Trp Val Arg Asp Val Val Arg Ser Met Asp
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Synthetic peptide

<400> SEQUENCE: 190

Glu Leu Ser Asn Ile Tyr Glu Arg Val Trp
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic peptide

<400> SEQUENCE: 191

Trp Ile Gln Arg Met Met Glu Val Leu Arg
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide

<400> SEQUENCE: 192

Phe Phe Phe Lys Arg Phe Ala Lys Arg Lys
1               5                   10

<210> SEQ ID NO 193
<211> LENGTH: 9
<212> TYPE: PRT
<213> ORGANISM: Artificial Sequence
<220> FEATURE:
<223> OTHER INFORMATION: Synthetic peptide

<400> SEQUENCE: 193

Leu His Lys Met Ser Asp Arg Val Trp
1               5

<210> SEQ ID NO 194
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 194

Phe Ala Lys Lys Phe Ala Lys Lys Phe
1               5

<210> SEQ ID NO 195
<211> LENGTH: 10
<212> TYPE: PRT
<213> ORGANISM: Artificial Sequence
<220> FEATURE:
<223> OTHER INFORMATION: Synthetic peptide

<400> SEQUENCE: 195

Trp Val Arg Glu Tyr Ile Asn Ser Leu Glu
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Synthetic peptide

<400> SEQUENCE: 196

Phe Phe Lys Lys Arg Phe Ala Phe Arg Lys
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Synthetic peptide

<400> SEQUENCE: 197

Lys Trp Val Gln Asp Tyr Ile Lys Asp Met
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Synthetic peptide

<400> SEQUENCE: 198

Ala Phe Arg Phe Lys Lys Arg Phe Phe Lys
1               5                   10

<210> SEQ ID NO 199
<211> LENGTH: 8
<212> TYPE: PRT
<213> ORGANISM: Artificial Sequence
<220> FEATURE:
<223> OTHER INFORMATION: Synthetic peptide

<400> SEQUENCE: 199

Leu Leu Arg His Leu Leu Arg Leu
1               5

<210> SEQ ID NO 200
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 200

Trp Ile Lys Lys Leu Leu Glu Ser Ser Gln
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Synthetic peptide

<400> SEQUENCE: 201

Asp Met Ser Arg Val Val Asp Arg Val Trp
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic peptide

<400> SEQUENCE: 202

Phe Glu Glu Glu Phe Glu Glu Glu Phe Glu
1               5                   10

<210> SEQ ID NO 203
<211> LENGTH: 9
<212> TYPE: PRT
<213> ORGANISM: Artificial Sequence
<220> FEATURE:
<223> OTHER INFORMATION: Synthetic peptide

<400> SEQUENCE: 203

Trp Val Lys Asn Ser Ile Asn His Leu
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic peptide

<400> SEQUENCE: 204

Leu Thr Lys Lys Gly Arg Arg Phe Cys
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic peptide

<400> SEQUENCE: 205

Ile Glu Gln Leu Leu Arg Lys Leu Phe
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic peptide

<400> SEQUENCE: 206

Leu His Asn Ile Ser Asn Lys Val Trp
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic peptide

<400> SEQUENCE: 207

Cys Phe Arg Arg Gly Lys Lys Thr Leu
1               5

<210> SEQ ID NO 208
<211> LENGTH: 10
<212> TYPE: PRT
<213> ORGANISM: Artificial Sequence
<220> FEATURE:
<223> OTHER INFORMATION: Synthetic peptide

<400> SEQUENCE: 208

Ile Val Arg Arg Ala Asp Arg Ala Ala Val
1               5                   10

<210> SEQ ID NO 209
<211> LENGTH: 9
<212> TYPE: PRT
<213> ORGANISM: Artificial Sequence
<220> FEATURE:
<223> OTHER INFORMATION: Synthetic peptide

<400> SEQUENCE: 209

Thr Val Glu Arg Phe Lys Asn Leu Ser
1               5

<210> SEQ ID NO 210
<211> LENGTH: 10
<212> TYPE: PRT
<213> ORGANISM: Artificial Sequence
<220> FEATURE:
<223> OTHER INFORMATION: Synthetic peptide

<400> SEQUENCE: 210

Gln Ser Ser Glu Leu Leu Lys Lys Ile Trp
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Synthetic peptide

<400> SEQUENCE: 211

Ser Leu Asn Lys Phe Arg Glu Val Thr
1               5

<210> SEQ ID NO 212
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 212

Leu Ile Lys Gln Ile Val Lys Lys Leu Phe
1               5                   10

<210> SEQ ID NO 213
<211> LENGTH: 6
<212> TYPE: PRT
<213> ORGANISM: Artificial Sequence
<220> FEATURE:
<223> OTHER INFORMATION: Synthetic peptide

<400> SEQUENCE: 213

Lys Lys Lys Phe Phe Phe
1               5

<210> SEQ ID NO 214
<211> LENGTH: 10
<212> TYPE: PRT
<213> ORGANISM: Artificial Sequence
<220> FEATURE:
<223> OTHER INFORMATION: Synthetic peptide

<400> SEQUENCE: 214

Leu Tyr Lys Lys Ile Ile Lys Lys Leu Leu
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic peptide

<400> SEQUENCE: 215

Phe Lys Lys Lys Phe Lys Lys Lys Phe Lys
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic peptide

<400> SEQUENCE: 216

Val Ala Ala Arg Asp Ala Arg Arg Val Ile
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Synthetic peptide

<400> SEQUENCE: 217

Phe Leu Lys Lys Val Ile Gln Lys Ile Leu
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Synthetic peptide

<400> SEQUENCE: 218
```

```
Leu Ile Lys Glu Ile Ile Lys Gln Val Met
1               5                   10
```

<210> SEQ ID NO 219
<211> LENGTH: 10
<212> TYPE: PRT
<213> ORGANISM: Artificial Sequence
<220> FEATURE:
<223> OTHER INFORMATION: Synthetic peptide

<400> SEQUENCE: 219

```
Leu Leu Lys Lys Ile Ile Lys Lys Tyr Leu
1               5                   10
```

<210> SEQ ID NO 220
<211> LENGTH: 10
<212> TYPE: PRT
<213> ORGANISM: Artificial Sequence
<220> FEATURE:
<223> OTHER INFORMATION: Synthetic peptide

<400> SEQUENCE: 220

```
Ala Phe Phe Glu Glu Glu Ala Glu Phe Glu
1               5                   10
```

<210> SEQ ID NO 221
<211> LENGTH: 9
<212> TYPE: PRT
<213> ORGANISM: Artificial Sequence
<220> FEATURE:
<223> OTHER INFORMATION: Synthetic peptide

<400> SEQUENCE: 221

```
Lys Lys Trp Val Gln Asp Ser Met Lys
1               5
```

<210> SEQ ID NO 222
<211> LENGTH: 10
<212> TYPE: PRT
<213> ORGANISM: Artificial Sequence
<220> FEATURE:
<223> OTHER INFORMATION: Synthetic peptide

<400> SEQUENCE: 222

```
Asn Phe Ala Asn Lys Val Gln Glu Val Ala
1               5                   10
```

<210> SEQ ID NO 223
<211> LENGTH: 10
<212> TYPE: PRT
<213> ORGANISM: Artificial Sequence
<220> FEATURE:
<223> OTHER INFORMATION: Synthetic peptide

<400> SEQUENCE: 223

```
Ala Val Glu Gln Val Lys Asn Ala Phe Asn
1               5                   10
```

<210> SEQ ID NO 224
<211> LENGTH: 10
<212> TYPE: PRT
<213> ORGANISM: Artificial Sequence
<220> FEATURE:
<223> OTHER INFORMATION: Synthetic peptide

<400> SEQUENCE: 224

```
Met Val Gln Lys Ile Ile Glu Lys Ile Leu
1               5                   10
```

<210> SEQ ID NO 225
<211> LENGTH: 9
<212> TYPE: PRT
<213> ORGANISM: Artificial Sequence
<220> FEATURE:
<223> OTHER INFORMATION: Synthetic peptide

<400> SEQUENCE: 225

```
Lys Met Ser Asp Gln Val Trp Lys Lys
1               5
```

<210> SEQ ID NO 226
<211> LENGTH: 9
<212> TYPE: PRT
<213> ORGANISM: Artificial Sequence
<220> FEATURE:
<223> OTHER INFORMATION: Synthetic peptide

<400> SEQUENCE: 226

```
Met Val Lys Lys Ile Ile Glu Lys Met
1               5
```

<210> SEQ ID NO 227
<211> LENGTH: 10
<212> TYPE: PRT
<213> ORGANISM: Artificial Sequence
<220> FEATURE:
<223> OTHER INFORMATION: Synthetic peptide

<400> SEQUENCE: 227

```
Ala Leu Lys Lys Gln Val Ile Lys Lys Ile
1               5                   10
```

<210> SEQ ID NO 228
<211> LENGTH: 10
<212> TYPE: PRT
<213> ORGANISM: Artificial Sequence
<220> FEATURE:
<223> OTHER INFORMATION: Synthetic peptide

<400> SEQUENCE: 228

```
Ile Lys Lys Ile Val Gln Lys Lys Leu Ala
1               5                   10
```

<210> SEQ ID NO 229
<211> LENGTH: 10
<212> TYPE: PRT
<213> ORGANISM: Artificial Sequence
<220> FEATURE:
<223> OTHER INFORMATION: Synthetic peptide

<400> SEQUENCE: 229

```
Ala Phe Phe Lys Lys Lys Ala Lys Phe Lys
1               5                   10
```

<210> SEQ ID NO 230
<211> LENGTH: 8
<212> TYPE: PRT
<213> ORGANISM: Artificial Sequence
<220> FEATURE:
<223> OTHER INFORMATION: Synthetic peptide

<400> SEQUENCE: 230

```
Met Lys Glu Ile Ile Lys Val Met
```

```
1               5
```

<210> SEQ ID NO 231
<211> LENGTH: 10
<212> TYPE: PRT
<213> ORGANISM: Artificial Sequence
<220> FEATURE:
<223> OTHER INFORMATION: Synthetic peptide

<400> SEQUENCE: 231

```
Ala Glu Glu Glu Ala Glu Glu Glu Ala Glu
1               5                   10
```

<210> SEQ ID NO 232
<211> LENGTH: 10
<212> TYPE: PRT
<213> ORGANISM: Artificial Sequence
<220> FEATURE:
<223> OTHER INFORMATION: Synthetic peptide

<400> SEQUENCE: 232

```
Ala Lys Lys Lys Ala Lys Lys Lys Ala Lys
1               5                   10
```

<210> SEQ ID NO 233
<211> LENGTH: 6
<212> TYPE: PRT
<213> ORGANISM: Artificial Sequence
<220> FEATURE:
<223> OTHER INFORMATION: Synthetic peptide

<400> SEQUENCE: 233

```
Lys Lys Lys Ala Ala Ala
1               5
```

<210> SEQ ID NO 234
<211> LENGTH: 10
<212> TYPE: PRT
<213> ORGANISM: Artificial Sequence
<220> FEATURE:
<223> OTHER INFORMATION: Synthetic peptide

<400> SEQUENCE: 234

```
Lys Arg Lys Lys Arg Phe Ala Phe Phe Phe
1               5                   10
```

<210> SEQ ID NO 235
<211> LENGTH: 10
<212> TYPE: PRT
<213> ORGANISM: Artificial Sequence
<220> FEATURE:
<223> OTHER INFORMATION: Synthetic peptide

<400> SEQUENCE: 235

```
Arg Lys Arg Lys Phe Phe Ala Phe Phe Lys
1               5                   10
```

<210> SEQ ID NO 236
<211> LENGTH: 10
<212> TYPE: PRT
<213> ORGANISM: Artificial Sequence
<220> FEATURE:
<223> OTHER INFORMATION: Synthetic peptide

<400> SEQUENCE: 236

```
Phe Phe Phe Ala Phe Arg Lys Lys Arg Lys
1               5                   10
```

<210> SEQ ID NO 237
<211> LENGTH: 10
<212> TYPE: PRT
<213> ORGANISM: Artificial Sequence
<220> FEATURE:
<223> OTHER INFORMATION: Synthetic peptide

<400> SEQUENCE: 237

Phe Arg Lys Lys Arg Phe Ala Phe Phe Lys
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Synthetic peptide

<400> SEQUENCE: 238

Phe Phe Phe Arg Arg Lys Lys Lys Phe Ala
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Synthetic peptide

<400> SEQUENCE: 239

Lys Phe Phe Ala Phe Arg Lys Lys Arg Phe
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Synthetic peptide

<400> SEQUENCE: 240

Lys Phe Phe Ala Phe Phe Lys Arg Lys Arg
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Synthetic peptide

<400> SEQUENCE: 241

Lys Lys Lys Lys Lys Phe Phe Phe Phe Phe
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Synthetic peptide

<400> SEQUENCE: 242

Ala Phe Lys Lys Lys Arg Arg Phe Phe Phe
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Synthetic peptide

<400> SEQUENCE: 243

Lys Arg Lys Lys Arg Ala Ala Phe Phe Phe
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Synthetic peptide

<400> SEQUENCE: 244

Lys Lys Phe Phe Ala Phe Phe Arg Lys Arg
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Synthetic peptide

<400> SEQUENCE: 245

Arg Lys Arg Phe Phe Ala Phe Phe Lys Lys
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Synthetic peptide

<400> SEQUENCE: 246

Lys Arg Lys Lys Arg Ala Ala Ala Phe Phe
1               5                   10

<210> SEQ ID NO 247
<211> LENGTH: 8
<212> TYPE: PRT
<213> ORGANISM: Artificial Sequence
<220> FEATURE:
<223> OTHER INFORMATION: Synthetic peptide

<400> SEQUENCE: 247

Lys Lys Lys Lys Phe Phe Phe Phe
1               5

<210> SEQ ID NO 248
<211> LENGTH: 10
<212> TYPE: PRT
<213> ORGANISM: Artificial Sequence
<220> FEATURE:
<223> OTHER INFORMATION: Synthetic peptide

<400> SEQUENCE: 248

Lys Arg Lys Lys Arg Ala Ala Ala Ala Phe
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Synthetic peptide

<400> SEQUENCE: 249

Lys Lys Lys Ala Phe Phe Phe Ala Lys Lys
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Synthetic peptide

<400> SEQUENCE: 250

Lys Arg Lys Lys Arg Ala Ala Ala Ala Ala
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Synthetic peptide

<400> SEQUENCE: 251

Lys Lys Lys Lys Lys Ala Ala Ala Ala Ala
1               5                   10

<210> SEQ ID NO 252
<211> LENGTH: 8
<212> TYPE: PRT
<213> ORGANISM: Artificial Sequence
<220> FEATURE:
<223> OTHER INFORMATION: Synthetic peptide

<400> SEQUENCE: 252

Lys Lys Lys Lys Ala Ala Ala Ala
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic peptide

<400> SEQUENCE: 253

Phe Lys Phe Lys Phe Lys Phe Lys Phe
1               5

<210> SEQ ID NO 254
<211> LENGTH: 8
<212> TYPE: PRT
<213> ORGANISM: Artificial Sequence
<220> FEATURE:
<223> OTHER INFORMATION: Synthetic peptide

<400> SEQUENCE: 254

Phe Arg Phe Lys Phe Lys Phe Arg
1               5

<210> SEQ ID NO 255

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 255

Arg Phe Gln Phe Lys Phe Arg Phe
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic peptide

<400> SEQUENCE: 256

Phe Arg Phe Lys Phe Lys Phe
1               5

<210> SEQ ID NO 257
<211> LENGTH: 6
<212> TYPE: PRT
<213> ORGANISM: Artificial Sequence
<220> FEATURE:
<223> OTHER INFORMATION: Synthetic peptide

<400> SEQUENCE: 257

Phe Arg Phe Lys Phe Ala
1               5

<210> SEQ ID NO 258
<211> LENGTH: 9
<212> TYPE: PRT
<213> ORGANISM: Artificial Sequence
<220> FEATURE:
<223> OTHER INFORMATION: Synthetic peptide

<400> SEQUENCE: 258

Arg Arg Phe Pro Arg Pro Pro Phe Phe
1               5

<210> SEQ ID NO 259
<211> LENGTH: 9
<212> TYPE: PRT
<213> ORGANISM: Artificial Sequence
<220> FEATURE:
<223> OTHER INFORMATION: Synthetic peptide

<400> SEQUENCE: 259

Phe Phe Pro Pro Arg Pro Phe Arg Arg
1               5

<210> SEQ ID NO 260
<211> LENGTH: 9
<212> TYPE: PRT
<213> ORGANISM: Artificial Sequence
<220> FEATURE:
<223> OTHER INFORMATION: Synthetic peptide

<400> SEQUENCE: 260

Leu Tyr Pro Pro Arg Pro Phe Arg Arg
1               5

<210> SEQ ID NO 261
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 261

Arg Arg Ile Pro Arg Pro Pro Tyr Leu
1               5

<210> SEQ ID NO 262
<211> LENGTH: 10
<212> TYPE: PRT
<213> ORGANISM: Artificial Sequence
<220> FEATURE:
<223> OTHER INFORMATION: Synthetic peptide

<400> SEQUENCE: 262

Pro Phe Arg Pro Pro Pro Arg Pro Arg Phe
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Synthetic peptide

<400> SEQUENCE: 263

Pro Arg Pro Arg Pro Pro Pro Arg Phe Phe
1               5                   10

<210> SEQ ID NO 264
<211> LENGTH: 9
<212> TYPE: PRT
<213> ORGANISM: Artificial Sequence
<220> FEATURE:
<223> OTHER INFORMATION: Synthetic peptide

<400> SEQUENCE: 264

Phe Phe Pro Pro Lys Pro Phe Lys Lys
1               5

<210> SEQ ID NO 265
<211> LENGTH: 9
<212> TYPE: PRT
<213> ORGANISM: Artificial Sequence
<220> FEATURE:
<223> OTHER INFORMATION: Synthetic peptide

<400> SEQUENCE: 265

Lys Lys Ile Pro Lys Pro Pro Tyr Leu
1               5

<210> SEQ ID NO 266
<211> LENGTH: 10
<212> TYPE: PRT
<213> ORGANISM: Artificial Sequence
<220> FEATURE:
<223> OTHER INFORMATION: Synthetic peptide

<400> SEQUENCE: 266

Pro Phe Lys Pro Pro Pro Lys Pro Lys Pro
1               5                   10

<210> SEQ ID NO 267
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 267

Pro Lys Pro Lys Pro Pro Pro Lys Phe Pro
1               5                   10

<210> SEQ ID NO 268
<211> LENGTH: 9
<212> TYPE: PRT
<213> ORGANISM: Artificial Sequence
<220> FEATURE:
<223> OTHER INFORMATION: Synthetic peptide

<400> SEQUENCE: 268

Leu Tyr Pro Pro Lys Pro Ile Lys Lys
1               5

<210> SEQ ID NO 269
<211> LENGTH: 9
<212> TYPE: PRT
<213> ORGANISM: Artificial Sequence
<220> FEATURE:
<223> OTHER INFORMATION: Synthetic peptide

<400> SEQUENCE: 269

Lys Lys Phe Pro Lys Pro Pro Phe Phe
1               5

<210> SEQ ID NO 270
<211> LENGTH: 23
<212> TYPE: PRT
<213> ORGANISM: Artificial Sequence
<220> FEATURE:
<223> OTHER INFORMATION: Synthetic peptide

<400> SEQUENCE: 270

Glu Phe Glu Phe Phe Phe Arg Phe Phe Phe Gly Gly Gly Glu Phe Glu
1               5                   10                  15

Phe Phe Phe Arg Phe Phe Phe
            20

<210> SEQ ID NO 271
<211> LENGTH: 23
<212> TYPE: PRT
<213> ORGANISM: Artificial Sequence
<220> FEATURE:
<223> OTHER INFORMATION: Synthetic peptide

<400> SEQUENCE: 271

Gln Phe Glu Phe Phe Phe Arg Phe Phe Phe Gly Gly Gly Gln Phe Glu
1               5                   10                  15

Phe Phe Phe Arg Phe Phe Phe
            20

<210> SEQ ID NO 272
<211> LENGTH: 23
<212> TYPE: PRT
<213> ORGANISM: Artificial Sequence
<220> FEATURE:
<223> OTHER INFORMATION: Synthetic peptide

<400> SEQUENCE: 272

Asp Phe Glu Phe Phe Phe Arg Phe Phe Phe Gly Gly Gly Asp Phe Glu
1               5                   10                  15
```

Phe Phe Phe Arg Phe Phe Phe
            20

<210> SEQ ID NO 273
<211> LENGTH: 23
<212> TYPE: PRT
<213> ORGANISM: Artificial Sequence
<220> FEATURE:
<223> OTHER INFORMATION: Synthetic peptide

<400> SEQUENCE: 273

Glu Phe Asn Phe Phe Phe Arg Phe Phe Phe Gly Gly Gly Glu Phe Asn
1               5                   10                  15

Phe Phe Phe Arg Phe Phe Phe
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Phe Phe Phe Arg Phe Phe Phe Glu Phe Gln Phe Phe Phe Arg Phe Phe
1               5                   10                  15

Phe Glu Phe Gln
            20

<210> SEQ ID NO 275
<211> LENGTH: 23
<212> TYPE: PRT
<213> ORGANISM: Artificial Sequence
<220> FEATURE:
<223> OTHER INFORMATION: Synthetic peptide

<400> SEQUENCE: 275

Phe Phe Phe Arg Phe Phe Phe Glu Phe Gln Gly Gly Gly Phe Phe Phe
1               5                   10                  15

Arg Phe Phe Phe Glu Phe Gln
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide

<400> SEQUENCE: 276

Arg Trp Arg Lys Phe Phe Lys Arg Phe Phe Gln Phe Glu Phe Phe Phe
1               5                   10                  15

Arg Phe Phe Phe
            20

<210> SEQ ID NO 277
<211> LENGTH: 23
<212> TYPE: PRT
<213> ORGANISM: Artificial Sequence
<220> FEATURE:
<223> OTHER INFORMATION: Synthetic peptide

<400> SEQUENCE: 277

Arg Trp Arg Lys Phe Phe Lys Arg Phe Phe Gly Gly Gly Phe Phe Phe

```
1               5                   10                  15
```
Arg Phe Phe Phe Asn Phe Asn
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

Arg Phe Arg Lys Phe Phe Lys Arg Phe Phe Gln Phe Glu Phe Phe Phe
1               5                   10                  15
Arg Phe Phe Phe
            20

<210> SEQ ID NO 279
<211> LENGTH: 23
<212> TYPE: PRT
<213> ORGANISM: Artificial Sequence
<220> FEATURE:
<223> OTHER INFORMATION: Synthetic peptide

<400> SEQUENCE: 279

Arg Phe Arg Lys Phe Phe Lys Arg Phe Phe Gly Gly Gly Phe Phe Phe
1               5                   10                  15
Arg Phe Phe Phe Asn Phe Asn
            20

<210> SEQ ID NO 280
<211> LENGTH: 23
<212> TYPE: PRT
<213> ORGANISM: Artificial Sequence
<220> FEATURE:
<223> OTHER INFORMATION: Synthetic peptide

<400> SEQUENCE: 280

Arg Trp Arg Lys Phe Phe Lys Arg Phe Phe Gly Gly Gly Phe Phe Phe
1               5                   10                  15
Arg Phe Phe Phe Glu Phe Gln
            20

<210> SEQ ID NO 281
<211> LENGTH: 23
<212> TYPE: PRT
<213> ORGANISM: Artificial Sequence
<220> FEATURE:
<223> OTHER INFORMATION: Synthetic peptide

<400> SEQUENCE: 281

Arg Phe Arg Lys Phe Phe Lys Arg Phe Phe Gly Gly Gly Phe Phe Phe
1               5                   10                  15
Arg Phe Phe Phe Glu Phe Gln
            20

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Glu Phe Glu Phe Phe Phe Arg Phe Phe Phe Glu Phe Glu Phe Phe Phe
1               5                   10                  15

Arg Phe Phe Phe
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Arg Trp Arg Lys Phe Phe Lys Arg Phe Phe Asn Phe Asn Phe Phe Phe
1               5                   10                  15

Arg Phe Phe Phe
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Gln Phe Glu Phe Phe Phe Arg Phe Phe Phe Gln Phe Glu Phe Phe Phe
1               5                   10                  15

Arg Phe Phe Phe
            20

<210> SEQ ID NO 285
<211> LENGTH: 23
<212> TYPE: PRT
<213> ORGANISM: Artificial Sequence
<220> FEATURE:
<223> OTHER INFORMATION: Synthetic peptide

<400> SEQUENCE: 285

Arg Trp Arg Lys Phe Phe Lys Arg Phe Phe Gly Gly Gly Asn Phe Asn
1               5                   10                  15

Phe Phe Phe Arg Phe Phe Phe
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide

<400> SEQUENCE: 286

Glu Phe Asn Phe Phe Phe Arg Phe Phe Phe Glu Phe Asn Phe Phe Phe
1               5                   10                  15

Arg Phe Phe Phe
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

```
Arg Phe Arg Lys Phe Phe Lys Arg Phe Phe Asn Phe Asn Phe Phe
1               5                   10                  15

Arg Phe Phe Phe
            20
```

<210> SEQ ID NO 288
<211> LENGTH: 23
<212> TYPE: PRT
<213> ORGANISM: Artificial Sequence
<220> FEATURE:
<223> OTHER INFORMATION: Synthetic peptide

<400> SEQUENCE: 288

```
Phe Phe Arg Lys Phe Phe Lys Arg Phe Arg Gly Gly Gly Asn Phe Asn
1               5                   10                  15

Phe Phe Phe Arg Phe Phe Phe
            20
```

<210> SEQ ID NO 289
<211> LENGTH: 23
<212> TYPE: PRT
<213> ORGANISM: Artificial Sequence
<220> FEATURE:
<223> OTHER INFORMATION: Synthetic peptide

<400> SEQUENCE: 289

```
Arg Phe Arg Lys Phe Phe Lys Arg Phe Gly Gly Gly Asn Phe Asn
1               5                   10                  15

Phe Phe Phe Arg Phe Phe Phe
            20
```

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide

<400> SEQUENCE: 290

```
Asp Phe Glu Phe Phe Phe Arg Phe Phe Phe Asp Phe Glu Phe Phe Phe
1               5                   10                  15

Arg Phe Phe Phe
            20
```

<210> SEQ ID NO 291
<211> LENGTH: 20
<212> TYPE: PRT
<213> ORGANISM: Artificial Sequence
<220> FEATURE:
<223> OTHER INFORMATION: Synthetic peptide

<400> SEQUENCE: 291

```
Arg Trp Arg Lys Phe Phe Lys Arg Phe Phe Phe Phe Arg Phe Phe
1               5                   10                  15

Phe Glu Phe Gln
            20
```

<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

Arg Phe Arg Lys Phe Phe Lys Arg Phe Phe Phe Phe Phe Arg Phe Phe
1               5                   10                  15

Phe Glu Phe Gln
        20

<210> SEQ ID NO 293
<211> LENGTH: 23
<212> TYPE: PRT
<213> ORGANISM: Artificial Sequence
<220> FEATURE:
<223> OTHER INFORMATION: Synthetic peptide

<400> SEQUENCE: 293

Phe Phe Arg Lys Phe Phe Lys Arg Phe Arg Gly Gly Gly Phe Phe Phe
1               5                   10                  15

Arg Phe Phe Phe Asn Phe Asn
        20

<210> SEQ ID NO 294
<211> LENGTH: 23
<212> TYPE: PRT
<213> ORGANISM: Artificial Sequence
<220> FEATURE:
<223> OTHER INFORMATION: Synthetic peptide

<400> SEQUENCE: 294

Phe Phe Arg Lys Phe Phe Lys Arg Trp Arg Gly Gly Gly Phe Phe Phe
1               5                   10                  15

Arg Phe Phe Phe Asn Phe Asn
        20

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide

<400> SEQUENCE: 295

Arg Phe Arg Lys Phe Phe Lys Arg Phe Phe Phe Phe Phe Arg Phe Phe
1               5                   10                  15

Phe Asn Phe Asn
        20

<210> SEQ ID NO 296
<211> LENGTH: 21
<212> TYPE: PRT
<213> ORGANISM: Artificial Sequence
<220> FEATURE:
<223> OTHER INFORMATION: Synthetic peptide

<400> SEQUENCE: 296

Phe Phe Arg Lys Phe Phe Lys Arg Phe Arg Phe Phe Phe Arg Phe Phe
1               5                   10                  15

Phe Glu Phe Gln Arg
        20

<210> SEQ ID NO 297
<211> LENGTH: 23
<212> TYPE: PRT
<213> ORGANISM: Artificial Sequence
<220> FEATURE:
<223> OTHER INFORMATION: Synthetic peptide

<400> SEQUENCE: 297

Phe Phe Glu His Phe Trp Lys Glu Phe Asn Gly Gly Gly Asn Phe Gln
1               5                   10                  15

Lys Trp Phe His Gln Phe Phe
            20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Phe Phe Arg Lys Phe Phe Lys Arg Trp Arg Gln Phe Glu Phe Phe
1               5                   10                  15

Arg Phe Phe Phe
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Arg Trp Arg Lys Phe Phe Lys Arg Phe Phe Phe Phe Phe Arg Phe Phe
1               5                   10                  15

Phe Asn Phe Asn
            20

<210> SEQ ID NO 300
<211> LENGTH: 23
<212> TYPE: PRT
<213> ORGANISM: Artificial Sequence
<220> FEATURE:
<223> OTHER INFORMATION: Synthetic peptide

<400> SEQUENCE: 300

Asn Phe Gln Lys Trp Phe His Gln Phe Phe Gly Gly Gly Phe Phe Glu
1               5                   10                  15

His Phe Trp Lys Glu Phe Asn
            20

<210> SEQ ID NO 301
<211> LENGTH: 23
<212> TYPE: PRT
<213> ORGANISM: Artificial Sequence
<220> FEATURE:
<223> OTHER INFORMATION: Synthetic peptide

<400> SEQUENCE: 301

Phe Phe Arg Lys Phe Phe Lys Arg Trp Arg Gly Gly Gly Asn Phe Asn
1               5                   10                  15

Phe Phe Phe Arg Phe Phe Phe
            20

<210> SEQ ID NO 302
<211> LENGTH: 21
<212> TYPE: PRT
<213> ORGANISM: Artificial Sequence
<220> FEATURE:

<223> OTHER INFORMATION: Synthetic peptide

<400> SEQUENCE: 302

Phe Phe Arg Lys Phe Phe Lys Arg Trp Arg Phe Phe Phe Arg Phe Phe
1               5                   10                  15

Phe Glu Phe Gln Arg
            20

<210> SEQ ID NO 303
<211> LENGTH: 20
<212> TYPE: PRT
<213> ORGANISM: Artificial Sequence
<220> FEATURE:
<223> OTHER INFORMATION: Synthetic peptide

<400> SEQUENCE: 303

Phe Phe Arg Lys Phe Phe Lys Arg Trp Arg Asn Phe Asn Phe Phe Phe
1               5                   10                  15

Arg Phe Phe Phe
            20

<210> SEQ ID NO 304
<211> LENGTH: 24
<212> TYPE: PRT
<213> ORGANISM: Artificial Sequence
<220> FEATURE:
<223> OTHER INFORMATION: Synthetic peptide

<400> SEQUENCE: 304

Phe Phe Arg Lys Phe Phe Lys Arg Phe Arg Gly Gly Gly Phe Phe Phe
1               5                   10                  15

Arg Phe Phe Phe Glu Phe Gln Arg
            20

<210> SEQ ID NO 305
<211> LENGTH: 20
<212> TYPE: PRT
<213> ORGANISM: Artificial Sequence
<220> FEATURE:
<223> OTHER INFORMATION: Synthetic peptide

<400> SEQUENCE: 305

Phe Phe Arg Lys Phe Phe Lys Arg Phe Arg Gln Phe Glu Phe Phe Phe
1               5                   10                  15

Arg Phe Phe Phe
            20

<210> SEQ ID NO 306
<211> LENGTH: 20
<212> TYPE: PRT
<213> ORGANISM: Artificial Sequence
<220> FEATURE:
<223> OTHER INFORMATION: Synthetic peptide

<400> SEQUENCE: 306

Phe Phe Arg Lys Phe Phe Lys Arg Phe Arg Asn Phe Asn Phe Phe Phe
1               5                   10                  15

Arg Phe Phe Phe
            20

<210> SEQ ID NO 307
<211> LENGTH: 23
<212> TYPE: PRT
<213> ORGANISM: Artificial Sequence

```
<220> FEATURE:
<223> OTHER INFORMATION: Synthetic peptide

<400> SEQUENCE: 307

Arg Phe Arg Lys Phe Phe Lys Arg Phe Phe Gly Gly Gly Gln Phe Glu
1               5                   10                  15
Phe Phe Phe Arg Phe Phe Phe
            20

<210> SEQ ID NO 308
<211> LENGTH: 24
<212> TYPE: PRT
<213> ORGANISM: Artificial Sequence
<220> FEATURE:
<223> OTHER INFORMATION: Synthetic peptide

<400> SEQUENCE: 308

Phe Phe Arg Lys Phe Phe Lys Arg Trp Arg Gly Gly Gly Phe Phe Phe
1               5                   10                  15
Arg Phe Phe Phe Glu Phe Gln Arg
            20

<210> SEQ ID NO 309
<211> LENGTH: 23
<212> TYPE: PRT
<213> ORGANISM: Artificial Sequence
<220> FEATURE:
<223> OTHER INFORMATION: Synthetic peptide

<400> SEQUENCE: 309

Phe Phe Arg Lys Phe Phe Lys Arg Phe Arg Gly Gly Gly Gln Phe Glu
1               5                   10                  15
Phe Phe Phe Arg Phe Phe Phe
            20

<210> SEQ ID NO 310
<211> LENGTH: 23
<212> TYPE: PRT
<213> ORGANISM: Artificial Sequence
<220> FEATURE:
<223> OTHER INFORMATION: Synthetic peptide

<400> SEQUENCE: 310

Phe Phe Arg Lys Phe Phe Lys Arg Trp Arg Gly Gly Gly Gln Phe Glu
1               5                   10                  15
Phe Phe Phe Arg Phe Phe Phe
            20

<210> SEQ ID NO 311
<211> LENGTH: 23
<212> TYPE: PRT
<213> ORGANISM: Artificial Sequence
<220> FEATURE:
<223> OTHER INFORMATION: Synthetic peptide

<400> SEQUENCE: 311

Arg Trp Arg Lys Phe Phe Lys Arg Phe Phe Gly Gly Gly Gln Phe Glu
1               5                   10                  15
Phe Phe Phe Arg Phe Phe Phe
            20

<210> SEQ ID NO 312
<211> LENGTH: 22
<212> TYPE: PRT
```

```
<213> ORGANISM: Artificial Sequence
<220> FEATURE:
<223> OTHER INFORMATION: Synthetic peptide

<400> SEQUENCE: 312

Gln Phe Asn His Phe Phe Lys Glu Phe Gly Gly Gly Gln Phe Asn His
1               5                   10                  15

Phe Phe Lys Glu Phe Phe
            20

<210> SEQ ID NO 313
<211> LENGTH: 20
<212> TYPE: PRT
<213> ORGANISM: Artificial Sequence
<220> FEATURE:
<223> OTHER INFORMATION: Synthetic peptide

<400> SEQUENCE: 313

Phe Phe Arg Lys Phe Phe Lys Arg Phe Arg Phe Phe Phe Arg Phe Phe
1               5                   10                  15

Phe Asn Phe Asn
            20

<210> SEQ ID NO 314
<211> LENGTH: 20
<212> TYPE: PRT
<213> ORGANISM: Artificial Sequence
<220> FEATURE:
<223> OTHER INFORMATION: Synthetic peptide

<400> SEQUENCE: 314

Phe Phe Arg Lys Phe Phe Lys Arg Trp Arg Phe Phe Phe Arg Phe Phe
1               5                   10                  15

Phe Asn Phe Asn
            20

<210> SEQ ID NO 315
<211> LENGTH: 23
<212> TYPE: PRT
<213> ORGANISM: Artificial Sequence
<220> FEATURE:
<223> OTHER INFORMATION: Synthetic peptide

<400> SEQUENCE: 315

Phe Phe Glu His Phe Trp Lys Glu Phe Asn Gly Gly Gly Phe Phe Glu
1               5                   10                  15

His Phe Trp Lys Glu Phe Asn
            20

<210> SEQ ID NO 316
<211> LENGTH: 22
<212> TYPE: PRT
<213> ORGANISM: Artificial Sequence
<220> FEATURE:
<223> OTHER INFORMATION: Synthetic peptide

<400> SEQUENCE: 316

Phe Phe Glu His Phe Trp Lys Glu Phe Gly Gly Gly Asn Phe Gln Lys
1               5                   10                  15

Trp Phe His Gln Phe Phe
            20

<210> SEQ ID NO 317
<211> LENGTH: 22
```

```
<212> TYPE: PRT
<213> ORGANISM: Artificial Sequence
<220> FEATURE:
<223> OTHER INFORMATION: Synthetic peptide

<400> SEQUENCE: 317

Asn Phe Gln Lys Trp Phe His Gln Phe Gly Gly Gly Phe Phe Glu His
1               5                   10                  15

Phe Trp Lys Glu Phe Asn
            20

<210> SEQ ID NO 318
<211> LENGTH: 22
<212> TYPE: PRT
<213> ORGANISM: Artificial Sequence
<220> FEATURE:
<223> OTHER INFORMATION: Synthetic peptide

<400> SEQUENCE: 318

Phe Phe Glu His Phe Trp Lys Glu Phe Asn Gly Gly Gly Leu His Lys
1               5                   10                  15

Met Tyr Asn Gln Val Trp
            20

<210> SEQ ID NO 319
<211> LENGTH: 23
<212> TYPE: PRT
<213> ORGANISM: Artificial Sequence
<220> FEATURE:
<223> OTHER INFORMATION: Synthetic peptide

<400> SEQUENCE: 319

Asn Phe Gln Lys Trp Phe His Gln Phe Phe Gly Gly Gly Asn Phe Gln
1               5                   10                  15

Lys Trp Phe His Gln Phe Phe
            20

<210> SEQ ID NO 320
<211> LENGTH: 23
<212> TYPE: PRT
<213> ORGANISM: Artificial Sequence
<220> FEATURE:
<223> OTHER INFORMATION: Synthetic peptide

<400> SEQUENCE: 320

Phe Ala Lys Lys Phe Ala Lys Lys Phe Lys Gly Gly Gly Asn Phe Gln
1               5                   10                  15

Lys Trp Phe His Gln Phe Phe
            20

<210> SEQ ID NO 321
<211> LENGTH: 23
<212> TYPE: PRT
<213> ORGANISM: Artificial Sequence
<220> FEATURE:
<223> OTHER INFORMATION: Synthetic peptide

<400> SEQUENCE: 321

Phe Phe Glu Lys Phe Phe His Asn Phe Gln Gly Gly Gly Phe Phe Glu
1               5                   10                  15

Lys Phe Phe His Asn Phe Gln
            20

<210> SEQ ID NO 322
```

<211> LENGTH: 23
<212> TYPE: PRT
<213> ORGANISM: Artificial Sequence
<220> FEATURE:
<223> OTHER INFORMATION: Synthetic peptide

<400> SEQUENCE: 322

Phe Phe Gln His Phe Trp Lys Gln Phe Asn Gly Gly Gly Phe Phe Gln
1               5                   10                  15

His Phe Trp Lys Gln Phe Asn
            20

<210> SEQ ID NO 323
<211> LENGTH: 20
<212> TYPE: PRT
<213> ORGANISM: Artificial Sequence
<220> FEATURE:
<223> OTHER INFORMATION: Synthetic peptide

<400> SEQUENCE: 323

Asn Phe Gln Lys Trp Phe His Gln Phe Asn Phe Gln Lys Trp Phe
1               5                   10                  15

His Gln Phe Phe
            20

<210> SEQ ID NO 324
<211> LENGTH: 23
<212> TYPE: PRT
<213> ORGANISM: Artificial Sequence
<220> FEATURE:
<223> OTHER INFORMATION: Synthetic peptide

<400> SEQUENCE: 324

Phe Ala Lys Lys Phe Ala Gln Lys Phe Lys Gly Gly Gly Asn Phe Gln
1               5                   10                  15

Lys Trp Phe His Gln Phe Phe
            20

<210> SEQ ID NO 325
<211> LENGTH: 23
<212> TYPE: PRT
<213> ORGANISM: Artificial Sequence
<220> FEATURE:
<223> OTHER INFORMATION: Synthetic peptide

<400> SEQUENCE: 325

Phe Ala Lys Lys Phe Ala Lys Lys Phe Lys Gly Gly Gly Gln Phe Glu
1               5                   10                  15

Phe Phe Phe Arg Phe Phe Phe
            20

<210> SEQ ID NO 326
<211> LENGTH: 19
<212> TYPE: PRT
<213> ORGANISM: Artificial Sequence
<220> FEATURE:
<223> OTHER INFORMATION: Synthetic peptide

<400> SEQUENCE: 326

Gln Phe Asn His Phe Phe Lys Glu Phe Gln Asn His Phe Phe Lys
1               5                   10                  15

Glu Phe Phe

<210> SEQ ID NO 327

```
<211> LENGTH: 23
<212> TYPE: PRT
<213> ORGANISM: Artificial Sequence
<220> FEATURE:
<223> OTHER INFORMATION: Synthetic peptide

<400> SEQUENCE: 327

Phe Ala Lys Lys Phe Ala Lys Lys Phe Lys Gly Gly Gly Asp Phe Glu
1               5                   10                  15

Phe Phe Phe Arg Phe Phe Phe
            20

<210> SEQ ID NO 328
<211> LENGTH: 22
<212> TYPE: PRT
<213> ORGANISM: Artificial Sequence
<220> FEATURE:
<223> OTHER INFORMATION: Synthetic peptide

<400> SEQUENCE: 328

Phe Phe Glu His Phe Trp Lys Glu Phe Asn Gly Gly Gly Trp Val Gln
1               5                   10                  15

Asn Tyr Met Lys His Leu
            20

<210> SEQ ID NO 329
<211> LENGTH: 20
<212> TYPE: PRT
<213> ORGANISM: Artificial Sequence
<220> FEATURE:
<223> OTHER INFORMATION: Synthetic peptide

<400> SEQUENCE: 329

Phe Ala Lys Lys Phe Ala Lys Lys Phe Lys Gln Phe Glu Phe Phe Phe
1               5                   10                  15

Arg Phe Phe Phe
            20

<210> SEQ ID NO 330
<211> LENGTH: 20
<212> TYPE: PRT
<213> ORGANISM: Artificial Sequence
<220> FEATURE:
<223> OTHER INFORMATION: Synthetic peptide

<400> SEQUENCE: 330

Phe Phe Gln His Phe Trp Lys Gln Phe Asn Phe Phe Gln His Phe Trp
1               5                   10                  15

Lys Gln Phe Asn
            20

<210> SEQ ID NO 331
<211> LENGTH: 20
<212> TYPE: PRT
<213> ORGANISM: Artificial Sequence
<220> FEATURE:
<223> OTHER INFORMATION: Synthetic peptide

<400> SEQUENCE: 331

Phe Phe Glu His Phe Trp Lys Glu Phe Asn Phe Phe Glu His Phe Trp
1               5                   10                  15

Lys Glu Phe Asn
            20
```

<210> SEQ ID NO 332
<211> LENGTH: 20
<212> TYPE: PRT
<213> ORGANISM: Artificial Sequence
<220> FEATURE:
<223> OTHER INFORMATION: Synthetic peptide

<400> SEQUENCE: 332

Asn Phe Glu Lys Trp Phe His Glu Phe Phe Asn Phe Glu Lys Trp Phe
1               5                   10                  15

His Glu Phe Phe
            20

<210> SEQ ID NO 333
<211> LENGTH: 23
<212> TYPE: PRT
<213> ORGANISM: Artificial Sequence
<220> FEATURE:
<223> OTHER INFORMATION: Synthetic peptide

<400> SEQUENCE: 333

Phe Ala Lys Lys Phe Ala Lys Lys Phe Lys Gly Gly Gly Gln Phe Asn
1               5                   10                  15

His Phe Phe Lys Glu Phe Phe
            20

<210> SEQ ID NO 334
<211> LENGTH: 23
<212> TYPE: PRT
<213> ORGANISM: Artificial Sequence
<220> FEATURE:
<223> OTHER INFORMATION: Synthetic peptide

<400> SEQUENCE: 334

Asn Phe Glu Lys Trp Phe His Glu Phe Phe Gly Gly Gly Asn Phe Glu
1               5                   10                  15

Lys Trp Phe His Glu Phe Phe
            20

<210> SEQ ID NO 335
<211> LENGTH: 23
<212> TYPE: PRT
<213> ORGANISM: Artificial Sequence
<220> FEATURE:
<223> OTHER INFORMATION: Synthetic peptide

<400> SEQUENCE: 335

Phe Ala Lys Lys Phe Ala Lys Lys Phe Lys Gly Gly Gly Phe Phe Phe
1               5                   10                  15

Arg Phe Phe Phe Glu Phe Gln
            20

<210> SEQ ID NO 336
<211> LENGTH: 20
<212> TYPE: PRT
<213> ORGANISM: Artificial Sequence
<220> FEATURE:
<223> OTHER INFORMATION: Synthetic peptide

<400> SEQUENCE: 336

Phe Ala Lys Lys Phe Ala Lys Lys Phe Lys Asp Phe Glu Phe Phe Phe
1               5                   10                  15

Arg Phe Phe Phe
            20

<210> SEQ ID NO 337
<211> LENGTH: 23
<212> TYPE: PRT
<213> ORGANISM: Artificial Sequence
<220> FEATURE:
<223> OTHER INFORMATION: Synthetic peptide

<400> SEQUENCE: 337

Gln Phe Asn His Phe Phe Lys Glu Phe Phe Gly Gly Gly Gln Phe Asn
1               5                   10                  15

His Phe Phe Lys Glu Phe Phe
            20

<210> SEQ ID NO 338
<211> LENGTH: 23
<212> TYPE: PRT
<213> ORGANISM: Artificial Sequence
<220> FEATURE:
<223> OTHER INFORMATION: Synthetic peptide

<400> SEQUENCE: 338

Phe Ala Lys Lys Phe Ala Lys Lys Phe Lys Gly Gly Gly Glu Phe Glu
1               5                   10                  15

Phe Phe Phe Arg Phe Phe Phe
            20

<210> SEQ ID NO 339
<211> LENGTH: 23
<212> TYPE: PRT
<213> ORGANISM: Artificial Sequence
<220> FEATURE:
<223> OTHER INFORMATION: Synthetic peptide

<400> SEQUENCE: 339

Phe Ala Lys Lys Phe Ala Lys Lys Phe Lys Gly Gly Gly Glu Phe Asn
1               5                   10                  15

Phe Phe Phe Arg Phe Phe Phe
            20

<210> SEQ ID NO 340
<211> LENGTH: 23
<212> TYPE: PRT
<213> ORGANISM: Artificial Sequence
<220> FEATURE:
<223> OTHER INFORMATION: Synthetic peptide

<400> SEQUENCE: 340

Phe Ala Lys Lys Phe Ala Lys Lys Phe Lys Gly Gly Gly Asn Phe Glu
1               5                   10                  15

Lys Trp Phe His Glu Phe Phe
            20

<210> SEQ ID NO 341
<211> LENGTH: 23
<212> TYPE: PRT
<213> ORGANISM: Artificial Sequence
<220> FEATURE:
<223> OTHER INFORMATION: Synthetic peptide

<400> SEQUENCE: 341

Phe Ala Lys Lys Phe Ala Lys Lys Phe Lys Gly Gly Gly Phe Phe Glu
1               5                   10                  15

Lys Phe Phe His Asn Phe Gln
            20

<210> SEQ ID NO 342
<211> LENGTH: 20
<212> TYPE: PRT
<213> ORGANISM: Artificial Sequence
<220> FEATURE:
<223> OTHER INFORMATION: Synthetic peptide

<400> SEQUENCE: 342

Gln Phe Asn His Phe Phe Lys Glu Phe Phe Gln Phe Asn His Phe Phe
1               5                   10                  15

Lys Glu Phe Phe
            20

<210> SEQ ID NO 343
<211> LENGTH: 20
<212> TYPE: PRT
<213> ORGANISM: Artificial Sequence
<220> FEATURE:
<223> OTHER INFORMATION: Synthetic peptide

<400> SEQUENCE: 343

Phe Phe Glu Lys Phe Phe His Asn Phe Gln Phe Phe Glu Lys Phe Phe
1               5                   10                  15

His Asn Phe Gln
            20

<210> SEQ ID NO 344
<211> LENGTH: 20
<212> TYPE: PRT
<213> ORGANISM: Artificial Sequence
<220> FEATURE:
<223> OTHER INFORMATION: Synthetic peptide

<400> SEQUENCE: 344

Phe Ala Lys Lys Phe Ala Lys Lys Phe Lys Glu Phe Glu Phe Phe Phe
1               5                   10                  15

Arg Phe Phe Phe
            20

<210> SEQ ID NO 345
<211> LENGTH: 20
<212> TYPE: PRT
<213> ORGANISM: Artificial Sequence
<220> FEATURE:
<223> OTHER INFORMATION: Synthetic peptide

<400> SEQUENCE: 345

Phe Ala Lys Lys Phe Ala Lys Lys Phe Lys Glu Phe Asn Phe Phe Phe
1               5                   10                  15

Arg Phe Phe Phe
            20

<210> SEQ ID NO 346
<211> LENGTH: 20
<212> TYPE: PRT
<213> ORGANISM: Artificial Sequence
<220> FEATURE:
<223> OTHER INFORMATION: Synthetic peptide

<400> SEQUENCE: 346

Phe Ala Lys Lys Phe Ala Lys Lys Phe Lys Phe Phe Glu His Phe Trp
1               5                   10                  15

Lys Glu Phe Asn

```
                20

<210> SEQ ID NO 347
<211> LENGTH: 20
<212> TYPE: PRT
<213> ORGANISM: Artificial Sequence
<220> FEATURE:
<223> OTHER INFORMATION: Synthetic peptide

<400> SEQUENCE: 347

Phe Ala Lys Lys Phe Ala Lys Lys Phe Lys Phe Phe Phe Arg Phe Phe
1               5                   10                  15

Phe Glu Phe Gln
            20

<210> SEQ ID NO 348
<211> LENGTH: 19
<212> TYPE: PRT
<213> ORGANISM: Artificial Sequence
<220> FEATURE:
<223> OTHER INFORMATION: Synthetic peptide

<400> SEQUENCE: 348

Phe Ala Lys Lys Phe Ala Lys Lys Phe Lys Leu His Lys Met Tyr Asn
1               5                   10                  15

Gln Val Trp

<210> SEQ ID NO 349
<211> LENGTH: 23
<212> TYPE: PRT
<213> ORGANISM: Artificial Sequence
<220> FEATURE:
<223> OTHER INFORMATION: Synthetic peptide

<400> SEQUENCE: 349

Phe Ala Lys Lys Phe Ala Lys Lys Phe Lys Gly Gly Gly Phe Phe Glu
1               5                   10                  15

His Phe Trp Lys Glu Phe Asn
            20

<210> SEQ ID NO 350
<211> LENGTH: 22
<212> TYPE: PRT
<213> ORGANISM: Artificial Sequence
<220> FEATURE:
<223> OTHER INFORMATION: Synthetic peptide

<400> SEQUENCE: 350

Phe Ala Lys Lys Phe Ala Lys Lys Phe Lys Gly Gly Gly Trp Val Gln
1               5                   10                  15

Asn Tyr Met Lys His Leu
            20

<210> SEQ ID NO 351
<211> LENGTH: 20
<212> TYPE: PRT
<213> ORGANISM: Artificial Sequence
<220> FEATURE:
<223> OTHER INFORMATION: Synthetic peptide

<400> SEQUENCE: 351

Phe Ala Lys Lys Phe Ala Lys Lys Phe Lys Asn Phe Gln Lys Trp Phe
1               5                   10                  15

His Gln Phe Phe
```

```
<210> SEQ ID NO 352
<211> LENGTH: 20
<212> TYPE: PRT
<213> ORGANISM: Artificial Sequence
<220> FEATURE:
<223> OTHER INFORMATION: Synthetic peptide

<400> SEQUENCE: 352

Phe Ala Lys Lys Phe Ala Lys Lys Phe Lys Phe Gln His Phe Trp
1               5                   10                  15

Lys Gln Phe Asn
            20

<210> SEQ ID NO 353
<211> LENGTH: 23
<212> TYPE: PRT
<213> ORGANISM: Artificial Sequence
<220> FEATURE:
<223> OTHER INFORMATION: Synthetic peptide

<400> SEQUENCE: 353

Phe Ala Lys Lys Phe Ala Lys Lys Phe Lys Gly Gly Gly Phe Gln
1               5                   10                  15

His Phe Trp Lys Gln Phe Asn
            20

<210> SEQ ID NO 354
<211> LENGTH: 19
<212> TYPE: PRT
<213> ORGANISM: Artificial Sequence
<220> FEATURE:
<223> OTHER INFORMATION: Synthetic peptide

<400> SEQUENCE: 354

Phe Ala Lys Lys Phe Ala Lys Lys Phe Lys Trp Val Gln Asn Tyr Met
1               5                   10                  15

Lys His Leu

<210> SEQ ID NO 355
<211> LENGTH: 20
<212> TYPE: PRT
<213> ORGANISM: Artificial Sequence
<220> FEATURE:
<223> OTHER INFORMATION: Synthetic peptide

<400> SEQUENCE: 355

Phe Ala Lys Lys Phe Ala Lys Lys Phe Lys Gln Phe Asn His Phe
1               5                   10                  15

Lys Glu Phe Phe
            20

<210> SEQ ID NO 356
<211> LENGTH: 22
<212> TYPE: PRT
<213> ORGANISM: Artificial Sequence
<220> FEATURE:
<223> OTHER INFORMATION: Synthetic peptide

<400> SEQUENCE: 356

Phe Ala Lys Lys Phe Ala Lys Lys Phe Lys Gly Gly Gly Leu His Lys
1               5                   10                  15

Met Tyr Asn Gln Val Trp
```

<210> SEQ ID NO 357
<211> LENGTH: 20
<212> TYPE: PRT
<213> ORGANISM: Artificial Sequence
<220> FEATURE:
<223> OTHER INFORMATION: Synthetic peptide

<400> SEQUENCE: 357

Phe Ala Lys Lys Phe Ala Lys Lys Phe Lys Asn Phe Glu Lys Trp Phe
1               5                   10                  15

His Glu Phe Phe
            20

<210> SEQ ID NO 358
<211> LENGTH: 20
<212> TYPE: PRT
<213> ORGANISM: Artificial Sequence
<220> FEATURE:
<223> OTHER INFORMATION: Synthetic peptide

<400> SEQUENCE: 358

Phe Ala Lys Lys Phe Ala Lys Lys Phe Lys Phe Phe Glu Lys Phe Phe
1               5                   10                  15

His Asn Phe Gln
            20

<210> SEQ ID NO 359
<211> LENGTH: 23
<212> TYPE: PRT
<213> ORGANISM: Artificial Sequence
<220> FEATURE:
<223> OTHER INFORMATION: Synthetic peptide

<400> SEQUENCE: 359

Phe Ala Lys Lys Phe Ala Lys Lys Phe Lys Gly Gly Gly Ala Phe Phe
1               5                   10                  15

Lys Lys Lys Ala Lys Phe Lys
            20

<210> SEQ ID NO 360
<211> LENGTH: 23
<212> TYPE: PRT
<213> ORGANISM: Artificial Sequence
<220> FEATURE:
<223> OTHER INFORMATION: Synthetic peptide

<400> SEQUENCE: 360

Ala Phe Phe Lys Lys Lys Ala Lys Phe Lys Gly Gly Gly Ala Phe Phe
1               5                   10                  15

Lys Lys Lys Ala Lys Phe Lys
            20

<210> SEQ ID NO 361
<211> LENGTH: 20
<212> TYPE: PRT
<213> ORGANISM: Artificial Sequence
<220> FEATURE:
<223> OTHER INFORMATION: Synthetic peptide

<400> SEQUENCE: 361

Lys Phe Lys Lys Ala Phe Lys Lys Ala Phe Lys Phe Lys Lys Ala Phe
1               5                   10                  15

```
Lys Lys Ala Phe
            20

<210> SEQ ID NO 362
<211> LENGTH: 23
<212> TYPE: PRT
<213> ORGANISM: Artificial Sequence
<220> FEATURE:
<223> OTHER INFORMATION: Synthetic peptide

<400> SEQUENCE: 362

Lys Phe Lys Lys Ala Phe Lys Lys Ala Phe Gly Gly Gly Lys Phe Lys
1               5                   10                  15

Lys Ala Phe Lys Lys Ala Phe
            20

<210> SEQ ID NO 363
<211> LENGTH: 23
<212> TYPE: PRT
<213> ORGANISM: Artificial Sequence
<220> FEATURE:
<223> OTHER INFORMATION: Synthetic peptide

<400> SEQUENCE: 363

Phe Ala Lys Lys Phe Ala Lys Lys Phe Lys Gly Gly Gly Phe Ala Lys
1               5                   10                  15

Lys Phe Ala Lys Lys Phe Lys
            20

<210> SEQ ID NO 364
<211> LENGTH: 20
<212> TYPE: PRT
<213> ORGANISM: Artificial Sequence
<220> FEATURE:
<223> OTHER INFORMATION: Synthetic peptide

<400> SEQUENCE: 364

Phe Ala Lys Lys Phe Ala Lys Lys Phe Lys Ala Phe Phe Lys Lys Lys
1               5                   10                  15

Ala Lys Phe Lys
            20

<210> SEQ ID NO 365
<211> LENGTH: 22
<212> TYPE: PRT
<213> ORGANISM: Artificial Sequence
<220> FEATURE:
<223> OTHER INFORMATION: Synthetic peptide

<400> SEQUENCE: 365

Pro Ser Arg Lys Ser Met Glu Lys Ser Val Ala Lys Leu Leu Asn Lys
1               5                   10                  15

Ile Ala Lys Ser Glu Pro
            20

<210> SEQ ID NO 366
<211> LENGTH: 20
<212> TYPE: PRT
<213> ORGANISM: Artificial Sequence
<220> FEATURE:
<223> OTHER INFORMATION: Synthetic peptide

<400> SEQUENCE: 366

Ala Phe Phe Lys Lys Lys Ala Lys Phe Lys Ala Phe Phe Lys Lys Lys
1               5                   10                  15
```

Ala Lys Phe Lys
        20

<210> SEQ ID NO 367
<211> LENGTH: 579
<212> TYPE: PRT
<213> ORGANISM: Homo sapiens

<400> SEQUENCE: 367

Met Leu Arg Ser Gly Pro Ala Ser Gly Pro Ser Val Pro Thr Gly Arg
1               5                   10                  15

Ala Met Pro Ser Arg Arg Val Ala Arg Pro Pro Ala Ala Pro Glu Leu
            20                  25                  30

Gly Ala Leu Gly Ser Pro Asp Leu Ser Ser Leu Ser Leu Ala Val Ser
        35                  40                  45

Arg Ser Thr Asp Glu Leu Glu Ile Ile Asp Glu Tyr Ile Lys Glu Asn
    50                  55                  60

Gly Phe Gly Leu Asp Gly Gly Gln Pro Gly Pro Gly Glu Gly Leu Pro
65                  70                  75                  80

Arg Leu Val Ser Arg Gly Ala Ala Ser Leu Ser Thr Val Thr Leu Gly
                85                  90                  95

Pro Val Ala Pro Pro Ala Thr Pro Pro Pro Trp Gly Cys Pro Leu Gly
            100                 105                 110

Arg Leu Val Ser Pro Ala Pro Gly Pro Gly Pro Gln Pro His Leu Val
        115                 120                 125

Ile Thr Glu Gln Pro Lys Gln Arg Gly Met Arg Phe Arg Tyr Glu Cys
    130                 135                 140

Glu Gly Arg Ser Ala Gly Ser Ile Leu Gly Glu Ser Ser Thr Glu Ala
145                 150                 155                 160

Ser Lys Thr Leu Pro Ala Ile Glu Leu Arg Asp Cys Gly Gly Leu Arg
                165                 170                 175

Glu Val Glu Val Thr Ala Cys Leu Val Trp Lys Asp Trp Pro His Arg
            180                 185                 190

Val His Pro His Ser Leu Val Gly Lys Asp Cys Thr Asp Gly Ile Cys
        195                 200                 205

Arg Val Arg Leu Arg Pro His Val Ser Pro Arg His Ser Phe Asn Asn
    210                 215                 220

Leu Gly Ile Gln Cys Val Arg Lys Lys Glu Ile Glu Ala Ala Ile Glu
225                 230                 235                 240

Arg Lys Ile Gln Leu Gly Ile Asp Pro Tyr Asn Ala Gly Ser Leu Lys
                245                 250                 255

Asn His Gln Glu Val Asp Met Asn Val Val Arg Ile Cys Phe Gln Ala
            260                 265                 270

Ser Tyr Arg Asp Gln Gln Gly Gln Met Arg Arg Met Asp Pro Val Leu
        275                 280                 285

Ser Glu Pro Val Tyr Asp Lys Lys Ser Thr Asn Thr Ser Glu Leu Arg
    290                 295                 300

Ile Cys Arg Ile Asn Lys Glu Ser Gly Pro Cys Thr Gly Gly Glu Glu
305                 310                 315                 320

Leu Tyr Leu Leu Cys Asp Lys Val Gln Lys Glu Asp Ile Ser Val Val
                325                 330                 335

Phe Ser Arg Ala Ser Trp Glu Gly Arg Ala Asp Phe Ser Gln Ala Asp
            340                 345                 350

Val His Arg Gln Ile Ala Ile Val Phe Lys Thr Pro Pro Tyr Glu Asp

```
        355                 360                 365
Leu Glu Ile Val Glu Pro Val Thr Val Asn Val Phe Leu Gln Arg Leu
370                 375                 380

Thr Asp Gly Val Cys Ser Glu Pro Leu Pro Phe Thr Tyr Leu Pro Arg
385                 390                 395                 400

Asp His Asp Ser Tyr Gly Val Asp Lys Lys Arg Lys Arg Gly Met Pro
            405                 410                 415

Asp Val Leu Gly Glu Leu Asn Ser Ser Asp Pro His Gly Ile Glu Ser
        420                 425                 430

Lys Arg Arg Lys Lys Pro Ala Ile Leu Asp His Phe Leu Pro Asn
    435                 440                 445

His Gly Ser Gly Pro Phe Leu Pro Pro Ser Ala Leu Leu Pro Asp Pro
    450                 455                 460

Asp Phe Phe Ser Gly Thr Val Ser Leu Pro Gly Leu Glu Pro Pro Gly
465                 470                 475                 480

Gly Pro Asp Leu Leu Asp Asp Gly Phe Ala Tyr Asp Pro Thr Ala Pro
            485                 490                 495

Thr Leu Phe Thr Met Leu Asp Leu Pro Pro Ala Pro Pro His Ala
        500                 505                 510

Ser Ala Val Val Cys Ser Gly Gly Ala Gly Ala Val Val Gly Glu Thr
        515                 520                 525

Pro Gly Pro Glu Pro Leu Thr Leu Asp Ser Tyr Gln Ala Pro Gly Pro
530                 535                 540

Gly Asp Gly Gly Thr Ala Ser Leu Val Gly Ser Asn Met Phe Pro Asn
545                 550                 555                 560

His Tyr Arg Glu Ala Ala Phe Gly Gly Gly Leu Leu Ser Pro Gly Pro
            565                 570                 575

Glu Ala Thr

<210> SEQ ID NO 368
<211> LENGTH: 390
<212> TYPE: PRT
<213> ORGANISM: Homo sapiens

<400> SEQUENCE: 368

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
            85                  90                  95

Pro Glu Pro Glu Ala Asp Tyr Tyr Ala Lys Glu Val Thr Arg Val Leu
        100                 105                 110

Met Val Glu Thr His Asn Glu Ile Tyr Asp Lys Phe Lys Gln Ser Thr
    115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
```

```
                145                 150                 155                 160
Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
        260                 265                 270

Ser Ser Arg His Arg Arg Ala Leu Asp Thr Asn Tyr Cys Phe Ser Ser
    275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
        340                 345                 350

Ala Pro Cys Cys Val Pro Gln Ala Leu Glu Pro Leu Pro Ile Val Tyr
    355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 369
<211> LENGTH: 2556
<212> TYPE: PRT
<213> ORGANISM: Homo sapiens
<220> FEATURE:
<221> NAME/KEY: MISC_FEATURE
<222> LOCATION: (891)..(891)
<223> OTHER INFORMATION: Xaa is denoted "X" in GenBank Sequence for Homo
      sapiens Notch1 (GenBank Acc. No. AAG33848.1)

<400> SEQUENCE: 369

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
```

-continued

```
                100                 105                 110
Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Arg Leu Cys Arg His Gly
            180                 185                 190

Gly Thr Cys His Asn Glu Val Gly Ser Tyr Arg Cys Val Cys Arg Ala
            195                 200                 205

Thr His Thr Gly Pro Asn Cys Glu Arg Pro Tyr Val Pro Cys Ser Pro
            210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Pro Cys Pro Pro Glu Trp Thr
            275                 280                 285

Gly Gln Tyr Cys Thr Glu Asp Val Asp Glu Cys Gln Leu Met Pro Asn
            290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
            370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
            435                 440                 445

Cys Glu Ile Asp Val Asn Glu Cys Val Ser Asn Pro Cys Gln Asn Asp
            450                 455                 460

Ala Thr Cys Leu Asp Gln Ile Gly Glu Phe Gln Cys Met Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
            515                 520                 525
```

```
Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg Leu Arg Gly Thr Cys Gln Asp Pro Asp Asn Ala
610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ser Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Ile Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Lys Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Ala Gly Ala Lys Gly
850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Xaa Tyr Arg Cys His Cys
                885                 890                 895

Gln Ala Gly Tyr Ser Gly Arg Asn Cys Glu Thr Asp Ile Asp Asp Cys
            900                 905                 910

Arg Pro Asn Pro Cys His Asn Gly Gly Ser Cys Thr Asp Gly Ile Asn
        915                 920                 925

Thr Ala Phe Cys Asp Cys Leu Pro Gly Phe Arg Gly Thr Phe Cys Glu
930                 935                 940
```

```
Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
            965                 970                 975

Ser Gly Ile His Cys Glu Asn Asn Thr Pro Asp Cys Thr Glu Ser Ser
        980                 985                 990

Cys Phe Asn Gly Gly Thr Cys Val Asp Gly Ile Asn Ser Phe Thr Cys
    995                 1000                1005

Leu Cys Pro Pro Gly Phe Thr Gly Ser Tyr Cys Gln His Val Val
1010            1015                1020

Asn Glu Cys Asp Ser Arg Pro Cys Leu Leu Gly Gly Thr Cys Gln
1025            1030                1035

Asp Gly Arg Gly Leu His Arg Cys Thr Cys Pro Gln Gly Tyr Thr
1040            1045                1050

Gly Pro Asn Cys Gln Asn Leu Val His Trp Cys Asp Ser Ser Pro
1055            1060                1065

Cys Lys Asn Gly Gly Lys Cys Trp Gln Thr His Thr Gln Tyr Arg
1070            1075                1080

Cys Glu Cys Pro Ser Gly Trp Thr Gly Leu Tyr Cys Asp Val Pro
1085            1090                1095

Ser Val Ser Cys Glu Val Ala Ala Gln Arg Gln Gly Val Asp Val
1100            1105                1110

Ala Arg Leu Cys Gln His Gly Gly Leu Cys Val Asp Ala Gly Asn
1115            1120                1125

Thr His His Cys Arg Cys Gln Ala Gly Tyr Thr Gly Ser Tyr Cys
1130            1135                1140

Glu Asp Leu Val Asp Glu Cys Ser Pro Ser Pro Cys Gln Asn Gly
1145            1150                1155

Ala Thr Cys Thr Asp Tyr Leu Gly Gly Tyr Ser Cys Lys Cys Val
1160            1165                1170

Ala Gly Tyr His Gly Val Asn Cys Ser Glu Glu Ile Asp Glu Cys
1175            1180                1185

Leu Ser His Pro Cys Gln Asn Gly Gly Thr Cys Leu Asp Leu Pro
1190            1195                1200

Asn Thr Tyr Lys Cys Ser Cys Pro Arg Gly Thr Gln Gly Val His
1205            1210                1215

Cys Glu Ile Asn Val Asp Asp Cys Asn Pro Pro Val Asp Pro Val
1220            1225                1230

Ser Arg Ser Pro Lys Cys Phe Asn Asn Gly Thr Cys Val Asp Gln
1235            1240                1245

Val Gly Gly Tyr Ser Cys Thr Cys Pro Pro Gly Phe Val Gly Glu
1250            1255                1260

Arg Cys Glu Gly Asp Val Asn Glu Cys Leu Ser Asn Pro Cys Asp
1265            1270                1275

Ala Arg Gly Thr Gln Asn Cys Val Gln Arg Val Asn Asp Phe His
1280            1285                1290

Cys Glu Cys Arg Ala Gly His Thr Gly Arg Arg Cys Glu Ser Val
1295            1300                1305

Ile Asn Gly Cys Lys Gly Lys Pro Cys Lys Asn Gly Gly Thr Cys
1310            1315                1320

Ala Val Ala Ser Asn Thr Ala Arg Gly Phe Ile Cys Lys Cys Pro
1325            1330                1335

Ala Gly Phe Glu Gly Ala Thr Cys Glu Asn Asp Ala Arg Thr Cys
```

```
            1340                1345                1350
Gly Ser Leu Arg Cys Leu Asn Gly Gly Thr Cys Ile Ser Gly Pro
    1355                1360                1365
Arg Ser Pro Thr Cys Leu Cys Leu Gly Pro Phe Thr Gly Pro Glu
    1370                1375                1380
Cys Gln Phe Pro Ala Ser Ser Pro Cys Leu Gly Gly Asn Pro Cys
    1385                1390                1395
Tyr Asn Gln Gly Thr Cys Glu Pro Thr Ser Glu Ser Pro Phe Tyr
    1400                1405                1410
Arg Cys Leu Cys Pro Ala Lys Phe Asn Gly Leu Leu Cys His Ile
    1415                1420                1425
Leu Asp Tyr Ser Phe Gly Gly Gly Ala Gly Arg Asp Ile Pro Pro
    1430                1435                1440
Pro Leu Ile Glu Glu Ala Cys Glu Leu Pro Glu Cys Gln Glu Asp
    1445                1450                1455
Ala Gly Asn Lys Val Cys Ser Leu Gln Cys Asn Asn His Ala Cys
    1460                1465                1470
Gly Trp Asp Gly Gly Asp Cys Ser Leu Asn Phe Asn Asp Pro Trp
    1475                1480                1485
Lys Asn Cys Thr Gln Ser Leu Gln Cys Trp Lys Tyr Phe Ser Asp
    1490                1495                1500
Gly His Cys Asp Ser Gln Cys Asn Ser Ala Gly Cys Leu Phe Asp
    1505                1510                1515
Gly Phe Asp Cys Gln Arg Ala Glu Gly Gln Cys Asn Pro Leu Tyr
    1520                1525                1530
Asp Gln Tyr Cys Lys Asp His Phe Ser Asp Gly His Cys Asp Gln
    1535                1540                1545
Gly Cys Asn Ser Ala Glu Cys Glu Trp Asp Gly Leu Asp Cys Ala
    1550                1555                1560
Glu His Val Pro Glu Arg Leu Ala Ala Gly Thr Leu Val Val Val
    1565                1570                1575
Val Leu Met Pro Pro Glu Gln Leu Arg Asn Ser Ser Phe His Phe
    1580                1585                1590
Leu Arg Glu Leu Ser Arg Val Leu His Thr Asn Val Val Phe Lys
    1595                1600                1605
Arg Asp Ala His Gly Gln Gln Met Ile Phe Pro Tyr Tyr Gly Arg
    1610                1615                1620
Glu Glu Glu Leu Arg Lys His Pro Ile Lys Arg Ala Ala Glu Gly
    1625                1630                1635
Trp Ala Ala Pro Asp Ala Leu Leu Gly Gln Val Lys Ala Ser Leu
    1640                1645                1650
Leu Pro Gly Gly Ser Glu Gly Gly Arg Arg Arg Arg Glu Leu Asp
    1655                1660                1665
Pro Met Asp Val Arg Gly Ser Ile Val Tyr Leu Glu Ile Asp Asn
    1670                1675                1680
Arg Gln Cys Val Gln Ala Ser Ser Gln Cys Phe Gln Ser Ala Thr
    1685                1690                1695
Asp Val Ala Ala Phe Leu Gly Ala Leu Ala Ser Leu Gly Ser Leu
    1700                1705                1710
Asn Ile Pro Tyr Lys Ile Glu Ala Val Gln Ser Glu Thr Val Glu
    1715                1720                1725
Pro Pro Pro Pro Ala Gln Leu His Phe Met Tyr Val Ala Ala Ala
    1730                1735                1740
```

```
Ala Phe Val Leu Leu Phe Phe Val Gly Cys Gly Val Leu Leu Ser
    1745              1750                1755

Arg Lys Arg Arg Arg Gln His Gly Gln Leu Trp Phe Pro Glu Gly
    1760              1765                1770

Phe Lys Val Ser Glu Ala Ser Lys Lys Lys Arg Arg Glu Pro Leu
    1775              1780                1785

Gly Glu Asp Ser Val Gly Leu Lys Pro Leu Lys Asn Ala Ser Asp
    1790              1795                1800

Gly Ala Leu Met Asp Asp Asn Gln Asn Glu Trp Gly Asp Glu Asp
    1805              1810                1815

Leu Glu Thr Lys Lys Phe Arg Phe Glu Glu Pro Val Val Leu Pro
    1820              1825                1830

Asp Leu Asp Asp Gln Thr Asp His Arg Gln Trp Thr Gln Gln His
    1835              1840                1845

Leu Asp Ala Ala Asp Leu Arg Met Ser Ala Met Ala Pro Thr Pro
    1850              1855                1860

Pro Gln Gly Glu Val Asp Ala Asp Cys Met Asp Val Asn Val Arg
    1865              1870                1875

Gly Pro Asp Gly Phe Thr Pro Leu Met Ile Ala Ser Cys Ser Gly
    1880              1885                1890

Gly Gly Leu Glu Thr Gly Asn Ser Glu Glu Glu Asp Ala Pro
    1895              1900                1905

Ala Val Ile Ser Asp Phe Ile Tyr Gln Gly Ala Ser Leu His Asn
    1910              1915                1920

Gln Thr Asp Arg Thr Gly Glu Thr Ala Leu His Leu Ala Ala Arg
    1925              1930                1935

Tyr Ser Arg Ser Asp Ala Ala Lys Arg Leu Leu Glu Ala Ser Ala
    1940              1945                1950

Asp Ala Asn Ile Gln Asp Asn Met Gly Arg Thr Pro Leu His Ala
    1955              1960                1965

Ala Val Ser Ala Asp Ala Gln Gly Val Phe Gln Ile Leu Ile Arg
    1970              1975                1980

Asn Arg Ala Thr Asp Leu Asp Ala Arg Met His Asp Gly Thr Thr
    1985              1990                1995

Pro Leu Ile Leu Ala Ala Arg Leu Ala Val Glu Gly Met Leu Glu
    2000              2005                2010

Asp Leu Ile Asn Ser His Ala Asp Val Asn Ala Val Asp Asp Leu
    2015              2020                2025

Gly Lys Ser Ala Leu His Trp Ala Ala Ala Val Asn Asn Val Asp
    2030              2035                2040

Ala Ala Val Val Leu Leu Lys Asn Gly Ala Asn Lys Asp Met Gln
    2045              2050                2055

Asn Asn Arg Glu Glu Thr Pro Leu Phe Leu Ala Ala Arg Glu Gly
    2060              2065                2070

Ser Tyr Glu Thr Ala Lys Val Leu Leu Asp His Phe Ala Asn Arg
    2075              2080                2085

Asp Ile Thr Asp His Met Asp Arg Leu Pro Arg Asp Ile Ala Gln
    2090              2095                2100

Glu Arg Met His His Asp Ile Val Arg Leu Leu Asp Glu Tyr Asn
    2105              2110                2115

Leu Val Arg Ser Pro Gln Leu His Gly Ala Pro Leu Gly Gly Thr
    2120              2125                2130
```

```
Pro Thr Leu Ser Pro Pro Leu Cys Ser Pro Asn Gly Tyr Leu Gly
    2135            2140            2145

Ser Leu Lys Pro Gly Val Gln Gly Lys Lys Val Arg Lys Pro Ser
    2150            2155            2160

Ser Lys Gly Leu Ala Cys Gly Ser Lys Glu Ala Lys Asp Leu Lys
    2165            2170            2175

Ala Arg Arg Lys Lys Ser Gln Asp Gly Lys Gly Cys Leu Leu Asp
    2180            2185            2190

Ser Ser Gly Met Leu Ser Pro Val Asp Ser Leu Glu Ser Pro His
    2195            2200            2205

Gly Tyr Leu Ser Asp Val Ala Ser Pro Pro Leu Pro Ser Pro
    2210            2215            2220

Phe Gln Gln Ser Pro Ser Val Pro Leu Asn His Leu Pro Gly Met
    2225            2230            2235

Pro Asp Thr His Leu Gly Ile Gly His Leu Asn Val Ala Ala Lys
    2240            2245            2250

Pro Glu Met Ala Ala Leu Gly Gly Gly Arg Leu Ala Phe Glu
    2255            2260            2265

Thr Gly Pro Pro Arg Leu Ser His Leu Pro Val Ala Ser Gly Thr
    2270            2275            2280

Ser Thr Val Leu Gly Ser Ser Gly Gly Ala Leu Asn Phe Thr
    2285            2290            2295

Val Gly Gly Ser Thr Ser Leu Asn Gly Gln Cys Glu Trp Leu Ser
    2300            2305            2310

Arg Leu Gln Ser Gly Met Val Pro Asn Gln Tyr Asn Pro Leu Arg
    2315            2320            2325

Gly Ser Val Ala Pro Gly Pro Leu Ser Thr Gln Ala Pro Ser Leu
    2330            2335            2340

Gln His Gly Met Val Gly Pro Leu His Ser Ser Leu Ala Ala Ser
    2345            2350            2355

Ala Leu Ser Gln Met Met Ser Tyr Gln Gly Leu Pro Ser Thr Arg
    2360            2365            2370

Leu Ala Thr Gln Pro His Leu Val Gln Thr Gln Val Gln Pro
    2375            2380            2385

Gln Asn Leu Gln Met Gln Gln Gln Asn Leu Gln Pro Ala Asn Ile
    2390            2395            2400

Gln Gln Gln Gln Ser Leu Gln Pro Pro Pro Pro Pro Gln Pro
    2405            2410            2415

His Leu Gly Val Ser Ser Ala Ser Gly His Leu Gly Arg Ser
    2420            2425            2430

Phe Leu Ser Gly Glu Pro Ser Gln Ala Asp Val Gln Pro Leu Gly
    2435            2440            2445

Pro Ser Ser Leu Ala Val His Thr Ile Leu Pro Gln Glu Ser Pro
    2450            2455            2460

Ala Leu Pro Thr Ser Leu Pro Ser Ser Leu Val Pro Pro Val Thr
    2465            2470            2475

Ala Ala Gln Phe Leu Thr Pro Pro Ser Gln His Ser Tyr Ser Ser
    2480            2485            2490

Pro Val Asp Asn Thr Pro Ser His Gln Leu Gln Val Pro Glu His
    2495            2500            2505

Pro Phe Leu Thr Pro Ser Pro Glu Ser Pro Asp Gln Trp Ser Ser
    2510            2515            2520

Ser Ser Pro His Ser Asn Val Ser Asp Trp Ser Glu Gly Val Ser
```

-continued

```
             2525                2530                2535
Ser Pro Pro Thr Ser Met Gln Ser Gln Ile Ala Arg Ile Pro Glu
    2540                2545                2550

Ala Phe Lys
    2555

<210> SEQ ID NO 370
<211> LENGTH: 390
<212> TYPE: PRT
<213> ORGANISM: Bos taurus

<400> SEQUENCE: 370

Met Glu Trp Gly Tyr Leu Leu Glu Val Thr Ser Leu Ala Ala Leu
1               5                   10                  15

Ala Leu Leu Gln Arg Ser Ser Gly Ala Ala Ala Ser Ala Lys Glu
                20                  25                  30

Leu Ala Cys Gln Glu Ile Thr Val Pro Leu Cys Lys Gly Ile Gly
                35                  40                  45

Tyr Asn Tyr Thr Tyr Met Pro Asn Gln Phe Asn His Asp Thr Gln
                50                  55                  60

Asp Glu Ala Gly Leu Glu Val His Gln Phe Trp Pro Leu Val Glu
65                  70                  75                  80

Ile Gln Cys Ser Pro Asp Leu Lys Phe Phe Leu Cys Ser Met Tyr
                85                  90                  95

Thr Pro Ile Cys Leu Glu Asp Tyr Lys Lys Pro Leu Pro Pro Cys
                100                 105                 110

Arg Ser Val Cys Glu Arg Ala Lys Ala Gly Cys Ala Pro Leu Met
                115                 120

Arg Gln Tyr Gly Phe Ala Trp Pro Asp Arg Met Arg Cys Asp Arg
            125                 130                 135

Leu Pro Glu Gln Gly Asn Pro Asp Thr Leu Cys Met Asp Tyr Asn
                140                 145                 150

Arg Thr Asp Leu Thr Thr Ala Ala Ser Ser Val Asp Gly Asp Pro
                155                 160                 165

Val Ala Gly Ile Cys Tyr Val Gly Asn Gln Ser Leu Asp Asn Leu
                170                 175                 180

Leu Gly Phe Val Leu Ala Pro Leu Val Ile Tyr Leu Phe Ile Gly
                185                 190                 195

Thr Met Phe Leu Leu Ala Gly Phe Val Ser Leu Phe Arg Ile Arg
            200                 205                 210

Ser Val Ile Lys Gln Gln Gly Gly Pro Thr Lys Thr His Lys Leu
                215                 220                 225

Glu Lys Leu Met Ile Arg Leu Gly Leu Phe Thr Val Leu Tyr Thr
                230                 235                 240

Val Pro Ala Ala Val Val Val Ala Cys Leu Phe Tyr Glu Gln His
                245                 250                 255

Asn Arg Pro Arg Trp Glu Ala Thr His Asn Cys Pro Cys Leu Arg
                260                 265                 270

Asp Leu Gln Pro Asp Gln Ala Arg Arg Pro Asp Tyr Ala Val Phe
                275                 280                 285

Met Leu Lys Tyr Phe Met Cys Leu Val Val Gly Ile Thr Ser Gly
                290                 295                 300

Val Trp Val Trp Ser Gly Lys Thr Leu Glu Ser Trp Arg Ala Leu
305                 310                 315                 320

Cys Thr Arg Cys Cys Trp Ala Ser Lys Gly Ala Gly Ala Gly Ala
                325                 330                 335
```

```
Gly Gly Gly Pro Gly Gly Gly Pro Gly Ala Gly Gly Gly
            340                 345                 350

Pro Gly Ala Gly Gly Ala Gly Ser Leu Tyr Ser Asp Val Ser Thr Gly
                355                 360                 365

Leu Thr Trp Arg Ser Gly Thr Ala Ser Ser Val Ser Tyr Pro Lys Gln
370                 375                 380

Met Pro Leu Ser Gln Val
385                 390

<210> SEQ ID NO 371
<211> LENGTH: 178
<212> TYPE: PRT
<213> ORGANISM: Homo sapiens

<400> SEQUENCE: 371

Lys Glu Lys Gln Gln Asn Ile Ser Pro Leu Val Arg Glu Arg Gly Pro
1               5                   10                  15

Gln Arg Val Ala Ala His Ile Thr Gly Thr Arg Gly Arg Ser Asn Thr
            20                  25                  30

Leu Ser Ser Pro Asn Ser Lys Asn Glu Lys Ala Leu Gly Arg Lys Ile
        35                  40                  45

Asn Ser Trp Glu Ser Ser Arg Ser Gly His Ser Phe Leu Ser Asn Leu
    50                  55                  60

His Leu Arg Asn Gly Glu Leu Val Ile His Lys Gly Phe Tyr Tyr
65                  70                  75                  80

Ile Tyr Ser Gln Thr Tyr Phe Arg Phe Gln Glu Glu Ile Lys Glu Asn
                85                  90                  95

Thr Lys Asn Asp Lys Gln Met Val Gln Tyr Ile Tyr Lys Tyr Thr Ser
            100                 105                 110

Tyr Pro Asp Pro Ile Leu Leu Met Lys Ser Ala Arg Asn Ser Cys Trp
        115                 120                 125

Ser Lys Asp Ala Glu Tyr Gly Leu Tyr Ser Ile Tyr Gln Gly Gly Ile
    130                 135                 140

Phe Glu Leu Lys Glu Asn Asp Arg Ile Phe Val Ser Val Thr Asn Glu
145                 150                 155                 160

His Leu Ile Asp Met Asp His Glu Ala Ser Phe Phe Gly Ala Phe Leu
                165                 170                 175

Val Gly

<210> SEQ ID NO 372
<211> LENGTH: 329
<212> TYPE: PRT
<213> ORGANISM: Homo sapiens

<400> SEQUENCE: 372

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
```

```
                    85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Glu Lys
            115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
                195                 200                 205

Ser Asp His Ile Asn Phe Asp Pro Val Tyr Lys Val Lys Pro Asn Pro
        210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                    245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Asn Ile Ala Ser Phe
                325

<210> SEQ ID NO 373
<211> LENGTH: 577
<212> TYPE: PRT
<213> ORGANISM: Homo sapiens

<400> SEQUENCE: 373

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125
```

```
Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
                260                 265                 270

Lys Lys Pro Ser Pro Phe Ile Phe Ile Ser Gln Arg Pro Ser Pro Glu
            275                 280                 285

Thr Gln Asp Thr Ile His Pro Leu Asp Glu Glu Ala Phe Leu Lys Val
        290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Arg Glu
                340                 345                 350

Pro Pro Val Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
        370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
                420                 425                 430

Pro Gly Glu Glu Asp Pro Ala Ala Val Ala Phe Gln Gly Tyr Leu Arg
            435                 440                 445

Gln Thr Arg Cys Ala Glu Glu Lys Ala Thr Lys Thr Gly Cys Leu Glu
        450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Ala Leu Ala Lys Gly Tyr
                485                 490                 495

Leu Lys Gln Asp Pro Leu Glu Met Thr Leu Ala Ser Ser Gly Ala Pro
            500                 505                 510

Thr Gly Gln Trp Asn Gln Pro Thr Glu Glu Trp Ser Leu Leu Ala Leu
        515                 520                 525

Ser Ser Cys Ser Asp Leu Gly Ile Ser Asp Trp Ser Phe Ala His Asp
530                 535                 540

Leu Ala Pro Leu Gly Cys Val Ala Ala Pro Gly Gly Leu Leu Gly Ser
```

```
                      545                 550                 555                 560
            Phe Asn Ser Asp Leu Val Thr Leu Pro Leu Ile Ser Ser Leu Gln Ser
                              565                 570                 575
            Ser

<210> SEQ ID NO 374
<211> LENGTH: 656
<212> TYPE: PRT
<213> ORGANISM: Drosophila melanogaster

<400> SEQUENCE: 374

Lys Ile Cys Ile Gly Thr Lys Ser Arg Leu Ser Val Pro Ser Asn Lys
1               5                   10                  15

Glu His His Tyr Arg Asn Leu Arg Asp Arg Tyr Thr Asn Cys Thr Tyr
            20                  25                  30

Val Asp Gly Asn Leu Glu Leu Thr Trp Leu Pro Asn Glu Asn Leu Asp
        35                  40                  45

Leu Ser Phe Leu Asp Asn Ile Arg Glu Val Thr Gly Tyr Ile Leu Ile
    50                  55                  60

Ser His Val Asp Val Lys Lys Val Val Phe Pro Lys Leu Gln Ile Ile
65                  70                  75                  80

Arg Gly Arg Thr Leu Phe Ser Leu Ser Val Glu Glu Lys Tyr Ala
                85                  90                  95

Leu Phe Val Thr Tyr Ser Lys Met Tyr Thr Leu Glu Ile Pro Asp Leu
            100                 105                 110

Arg Asp Val Leu Asn Gly Gln Val Gly Phe His Asn Asn Tyr Asn Leu
        115                 120                 125

Cys His Met Arg Thr Ile Gln Trp Ser Glu Ile Val Ser Asn Gly Thr
    130                 135                 140

Asp Ala Tyr Tyr Asn Tyr Asp Phe Thr Ala Pro Glu Arg Glu Cys Pro
145                 150                 155                 160

Lys Cys His Glu Ser Cys Thr His Gly Cys Trp Gly Glu Gly Pro Lys
                165                 170                 175

Asn Cys Gln Lys Phe Ser Lys Leu Thr Cys Ser Pro Gln Cys Ala Gly
            180                 185                 190

Gly Arg Cys Tyr Gly Pro Lys Pro Arg Glu Cys Cys His Leu Phe Cys
        195                 200                 205

Ala Gly Gly Cys Thr Gly Pro Thr Gln Lys Asp Cys Ile Ala Cys Lys
    210                 215                 220

Asn Phe Phe Asp Glu Gly Val Cys Lys Glu Cys Pro Pro Met Arg
225                 230                 235                 240

Lys Tyr Asn Pro Thr Thr Tyr Val Leu Glu Thr Asn Pro Glu Gly Lys
                245                 250                 255

Tyr Ala Tyr Gly Ala Thr Cys Val Lys Glu Cys Pro Gly His Leu Leu
            260                 265                 270

Arg Asp Asn Gly Ala Cys Val Arg Ser Cys Pro Gln Asp Lys Met Asp
        275                 280                 285

Lys Gly Gly Glu Cys Val Pro Cys Asn Gly Pro Cys Pro Lys Thr Cys
    290                 295                 300

Pro Gly Val Thr Val Leu His Ala Gly Asn Ile Asp Ser Phe Arg Asn
305                 310                 315                 320

Cys Thr Val Ile Asp Gly Asn Ile Arg Ile Leu Asp Gln Thr Phe Ser
                325                 330                 335

Gly Phe Gln Asp Val Tyr Ala Asn Tyr Thr Met Gly Pro Arg Tyr Ile
```

```
                    340                 345                 350
Pro Leu Asp Pro Glu Arg Leu Glu Val Phe Ser Thr Val Lys Glu Ile
            355                 360                 365

Thr Gly Tyr Leu Asn Ile Glu Gly Thr His Pro Gln Phe Arg Asn Leu
        370                 375                 380

Ser Tyr Phe Arg Asn Leu Glu Thr Ile His Gly Arg Gln Leu Met Glu
385                 390                 395                 400

Ser Met Phe Ala Ala Leu Ala Ile Val Lys Ser Ser Leu Tyr Ser Leu
                405                 410                 415

Glu Met Arg Asn Leu Lys Gln Ile Ser Ser Gly Ser Val Val Ile Gln
            420                 425                 430

His Asn Arg Asp Leu Cys Tyr Val Ser Asn Ile Arg Trp Pro Ala Ile
        435                 440                 445

Gln Lys Glu Pro Glu Gln Lys Val Trp Val Asn Glu Asn Leu Arg Ala
    450                 455                 460

Asp Leu Cys Glu Lys Asn Gly Thr Ile Cys Ser Asp Gln Cys Asn Glu
465                 470                 475                 480

Asp Gly Cys Trp Gly Ala Gly Thr Asp Gln Cys Leu Asn Cys Lys Asn
                485                 490                 495

Phe Asn Phe Asn Gly Thr Cys Ile Ala Asp Cys Gly Tyr Ile Ser Asn
            500                 505                 510

Ala Tyr Lys Phe Asp Asn Arg Thr Cys Lys Ile Cys His Pro Glu Cys
        515                 520                 525

Arg Thr Cys Asn Gly Ala Gly Ala Asp His Cys Gln Glu Cys Val His
    530                 535                 540

Val Arg Asp Gly Gln His Cys Val Ser Glu Cys Pro Lys Asn Lys Tyr
545                 550                 555                 560

Asn Asp Arg Gly Val Cys Arg Glu Cys His Ala Thr Cys Asp Gly Cys
                565                 570                 575

Thr Gly Pro Lys Asp Thr Ile Gly Ile Gly Ala Cys Thr Thr Cys Asn
            580                 585                 590

Leu Ala Ile Ile Asn Asn Asp Ala Thr Val Lys Arg Cys Leu Leu Lys
        595                 600                 605

Asp Asp Lys Cys Pro Asp Gly Tyr Phe Trp Glu Tyr Val His Pro Gln
    610                 615                 620

Glu Gln Gly Ser Leu Lys Pro Leu Ala Gly Arg Ala Val Cys Arg Lys
625                 630                 635                 640

Cys His Pro Leu Cys Glu Leu Cys Thr Asn Tyr Gly Tyr His Glu Gln
                645                 650                 655

<210> SEQ ID NO 375
<211> LENGTH: 326
<212> TYPE: PRT
<213> ORGANISM: Homo sapiens

<400> SEQUENCE: 375

Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Gly Glu Glu Gly Met Pro Leu Ser Thr Ile Arg Glu Val Ala Val
    50                  55                  60
```

```
Leu Arg His Leu Glu Thr Phe Glu His Pro Asn Val Val Arg Leu Phe
 65                  70                  75                  80

Asp Val Cys Thr Val Ser Arg Thr Asp Arg Glu Thr Lys Leu Thr Leu
                 85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 376
<211> LENGTH: 119
<212> TYPE: PRT
<213> ORGANISM: Paramecium bursaria Chlorella virus 1

<400> SEQUENCE: 376

Met Phe Asn Asp Arg Val Ile Val Lys Lys Ser Pro Leu Gly Gly Tyr
 1               5                  10                  15

Gly Val Phe Ala Arg Lys Ser Phe Glu Lys Gly Glu Leu Val Glu Glu
                20                  25                  30

Cys Leu Cys Ile Val Arg His Asn Asp Asp Trp Gly Thr Ala Leu Glu
            35                  40                  45

Asp Tyr Leu Phe Ser Arg Lys Asn Met Ser Ala Met Ala Leu Gly Phe
        50                  55                  60

Gly Ala Ile Phe Asn His Ser Lys Asp Pro Asn Ala Arg His Glu Leu
65                  70                  75                  80

Thr Ala Gly Leu Lys Arg Met Arg Ile Phe Thr Ile Lys Pro Ile Ala
                85                  90                  95

Ile Gly Glu Glu Ile Thr Ile Ser Tyr Gly Asp Asp Tyr Trp Leu Ser
            100                 105                 110
```

Arg Pro Arg Leu Thr Gln Asn
        115

<210> SEQ ID NO 377
<211> LENGTH: 293
<212> TYPE: PRT
<213> ORGANISM: Homo sapiens

<400> SEQUENCE: 377

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290

<210> SEQ ID NO 378
<211> LENGTH: 507
<212> TYPE: PRT
<213> ORGANISM: Homo sapiens

<400> SEQUENCE: 378

Met Glu Pro Ala Gly Pro Ala Pro Gly Arg Leu Gly Pro Leu Leu Cys
1               5                   10                  15

```
Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
 50                  55                  60

Pro Ile Gln Trp Phe Arg Gly Ala Gly Pro Ala Arg Glu Leu Ile Tyr
 65                  70                  75                  80

Asn Gln Lys Glu Gly His Phe Pro Arg Val Thr Val Ser Glu Ser
                 85                  90                  95

Thr Lys Arg Glu Asn Met Asp Phe Ser Ile Ser Ile Ser Asn Ile Thr
                100                 105                 110

Pro Ala Asp Ala Gly Thr Tyr Tyr Cys Val Lys Phe Arg Lys Gly Ser
             115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Val Gln Ser Leu Asp Thr Asn Asp Ile Thr Tyr
            420                 425                 430
```

```
Ala Asp Leu Asn Leu Pro Lys Gly Lys Lys Pro Ala Pro Gln Ala Ala
        435                 440                 445

Glu Pro Asn Asn His Thr Glu Tyr Ala Ser Ile Gln Thr Ser Pro Gln
450                 455                 460

Pro Ala Ser Glu Asp Thr Leu Thr Tyr Ala Asp Leu Asp Met Val His
465                 470                 475                 480

Leu Asn Arg Thr Pro Lys Gln Pro Ala Pro Lys Pro Glu Pro Ser Phe
                485                 490                 495

Ser Glu Tyr Ala Ser Val Gln Val Pro Arg Lys
                500                 505

<210> SEQ ID NO 379
<211> LENGTH: 1456
<212> TYPE: PRT
<213> ORGANISM: Homo sapiens

<400> SEQUENCE: 379

Met Arg Leu Pro Leu Leu Val Phe Ala Ser Val Ile Pro Gly Ala
1               5                   10                  15

Val Leu Leu Leu Asp Thr Arg Gln Phe Leu Ile Tyr Asn Glu Asp His
                20                  25                  30

Lys Arg Cys Val Asp Ala Val Ser Pro Ser Ala Val Gln Thr Ala Ala
            35                  40                  45

Cys Asn Gln Asp Ala Glu Ser Gln Lys Phe Arg Trp Val Ser Glu Ser
        50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
290                 295                 300
```

```
Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
            325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
        355                 360                 365

Tyr Ala Gly His Cys Tyr Lys Ile His Arg Asp Glu Lys Lys Ile Gln
370                 375                 380

Arg Asp Ala Leu Thr Thr Cys Arg Lys Glu Gly Gly Asp Leu Thr Ser
385                 390                 395                 400

Ile His Thr Ile Glu Glu Leu Asp Phe Ile Ile Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
        435                 440                 445

Leu Arg Gly Glu Pro Ser His Glu Asn Asn Arg Gln Glu Asp Cys Val
450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
            500                 505                 510

Phe Tyr Cys Tyr Met Ile Gly His Thr Leu Ser Thr Phe Ala Glu Ala
        515                 520                 525

Asn Gln Thr Cys Asn Asn Glu Asn Ala Tyr Leu Thr Thr Ile Glu Asp
    530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
        595                 600                 605

Gly Gly Leu Trp Asp Val Leu Lys Cys Asp Glu Lys Ala Lys Phe Val
    610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
        675                 680                 685

Ser Ile Asn Asn Lys Glu Glu Gln Gln Thr Ile Trp Arg Leu Ile Thr
    690                 695                 700

Ala Ser Gly Ser Tyr His Lys Leu Phe Trp Leu Gly Leu Thr Tyr Gly
705                 710                 715                 720
```

Ser Pro Ser Glu Gly Phe Thr Trp Ser Asp Gly Ser Pro Val Ser Tyr
            725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Thr Met Ser Trp Asn Asp Ile Asn
            755                 760                 765

Cys Glu His Leu Asn Asn Trp Ile Cys Gln Ile Gln Lys Gly Gln Thr
            770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
                805                 810                 815

Glu Lys Glu Thr Met Asp Asn Ala Arg Ala Phe Cys Lys Arg Asn Phe
                820                 825                 830

Gly Asp Leu Val Ser Ile Gln Ser Glu Ser Glu Lys Lys Phe Leu Trp
                835                 840                 845

Lys Tyr Val Asn Arg Asn Asp Ala Gln Ser Ala Tyr Phe Ile Gly Leu
            850                 855                 860

Leu Ile Ser Leu Asp Lys Lys Phe Ala Trp Met Asp Gly Ser Lys Val
865                 870                 875                 880

Asp Tyr Val Ser Trp Ala Thr Gly Glu Pro Asn Phe Ala Asn Glu Asp
                885                 890                 895

Glu Asn Cys Val Thr Met Tyr Ser Asn Ser Gly Phe Trp Asn Asp Ile
                900                 905                 910

Asn Cys Gly Tyr Pro Asn Ala Phe Ile Cys Gln Arg His Asn Ser Ser
            915                 920                 925

Ile Asn Ala Thr Thr Val Met Pro Thr Met Pro Ser Val Pro Ser Gly
        930                 935                 940

Cys Lys Glu Gly Trp Asn Phe Tyr Ser Asn Lys Cys Phe Lys Ile Phe
945                 950                 955                 960

Gly Phe Met Glu Glu Glu Arg Lys Asn Trp Gln Glu Ala Arg Lys Ala
                965                 970                 975

Cys Ile Gly Phe Gly Gly Asn Leu Val Ser Ile Gln Asn Glu Lys Glu
            980                 985                 990

Gln Ala Phe Leu Thr Tyr His Met  Lys Asp Ser Thr Phe  Ser Ala Trp
        995                 1000                1005

Thr Gly  Leu Asn Asp Val Asn  Ser Glu His Thr Phe  Leu Trp Thr
1010                1015                1020

Asp Gly  Arg Gly Val His Tyr  Thr Asn Trp Gly Lys  Gly Tyr Pro
1025                1030                1035

Gly Gly  Arg Arg Ser Ser Leu  Ser Tyr Glu Asp Ala  Asp Cys Val
1040                1045                1050

Val Ile  Ile Gly Gly Ala Ser  Asn Glu Ala Gly Lys  Trp Met Asp
1055                1060                1065

Asp Thr  Cys Asp Ser Lys Arg  Gly Tyr Ile Cys Gln  Thr Arg Ser
1070                1075                1080

Asp Pro  Ser Leu Thr Asn Pro  Ala Thr Ile Gln  Thr Asp Gly
1085                1090                1095

Phe Val Lys Tyr Gly Lys Ser  Ser Tyr Ser Leu Met  Arg Gln Lys
1100                1105                1110

Phe Gln  Trp His Glu Ala Glu  Thr Tyr Cys Lys Leu  His Asn Ser
1115                1120                1125

Leu Ile  Ala Ser Ile Leu Asp  Pro Tyr Ser Asn Ala  Phe Ala Trp 1130                1135                1140

Leu Gln Met Glu Thr Ser Asn Glu Arg Val Trp Ile Ala Leu Asn
    1145                1150                1155

Ser Asn Leu Thr Asp Asn Gln Tyr Thr Trp Thr Asp Lys Trp Arg
    1160                1165                1170

Val Arg Tyr Thr Asn Trp Ala Ala Asp Glu Pro Lys Leu Lys Ser
    1175                1180                1185

Ala Cys Val Tyr Leu Asp Leu Asp Gly Tyr Trp Lys Thr Ala His
    1190                1195                1200

Cys Asn Glu Ser Phe Tyr Phe Leu Cys Lys Arg Ser Asp Glu Ile
    1205                1210                1215

Pro Ala Thr Glu Pro Pro Gln Leu Pro Gly Arg Cys Pro Glu Ser
    1220                1225                1230

Asp His Thr Ala Trp Ile Pro Phe His Gly His Cys Tyr Tyr Ile
    1235                1240                1245

Glu Ser Ser Tyr Thr Arg Asn Trp Gly Gln Ala Ser Leu Glu Cys
    1250                1255                1260

Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
    1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 380
<211> LENGTH: 684
<212> TYPE: PRT
<213> ORGANISM: Homo sapiens

<400> SEQUENCE: 380

Met Met Asp Ala Ser Lys Glu Leu Gln Val Leu His Ile Asp Phe Leu
1               5                   10                  15

Asn Gln Asp Asn Ala Val Ser His Thr Trp Glu Phe Gln Thr Ser
            20                  25                  30

```
Ser Pro Val Phe Arg Arg Gly Gln Val Phe His Leu Arg Leu Val Leu
     35                  40                  45
Asn Gln Pro Leu Gln Ser Tyr His Gln Leu Lys Leu Glu Phe Ser Thr
 50                  55                  60
Gly Pro Asn Pro Ser Ile Ala Lys His Thr Leu Val Leu Asp Pro
 65                  70                  75                  80
Arg Thr Pro Ser Asp His Tyr Asn Trp Gln Ala Thr Leu Gln Asn Glu
                 85                  90                  95
Ser Gly Lys Glu Val Thr Val Ala Val Thr Ser Ser Pro Asn Ala Ile
                100                 105                 110
Leu Gly Lys Tyr Gln Leu Asn Val Lys Thr Gly Asn His Ile Leu Lys
            115                 120                 125
Ser Glu Glu Asn Ile Leu Tyr Leu Leu Phe Asn Pro Trp Cys Lys Glu
130                 135                 140
Asp Met Val Phe Met Pro Asp Glu Asp Glu Arg Lys Glu Tyr Ile Leu
145                 150                 155                 160
Asn Asp Thr Gly Cys His Tyr Val Gly Ala Ala Arg Ser Ile Lys Cys
                165                 170                 175
Lys Pro Trp Asn Phe Gly Gln Phe Glu Lys Asn Val Leu Asp Cys Cys
            180                 185                 190
Ile Ser Leu Leu Thr Glu Ser Ser Leu Lys Pro Thr Asp Arg Arg Asp
            195                 200                 205
Pro Val Leu Val Cys Arg Ala Met Cys Ala Met Met Ser Phe Glu Lys
210                 215                 220
Gly Gln Gly Val Leu Ile Gly Asn Trp Thr Gly Asp Tyr Glu Gly Gly
225                 230                 235                 240
Thr Ala Pro Tyr Lys Trp Thr Gly Ser Ala Pro Ile Leu Gln Gln Tyr
                245                 250                 255
Tyr Asn Thr Lys Gln Ala Val Cys Phe Gly Gln Cys Trp Val Phe Ala
            260                 265                 270
Gly Ile Leu Thr Thr Val Leu Arg Ala Leu Gly Ile Pro Ala Arg Ser
            275                 280                 285
Val Thr Gly Phe Asp Ser Ala His Asp Thr Glu Arg Asn Leu Thr Val
290                 295                 300
Asp Thr Tyr Val Asn Glu Asn Gly Glu Lys Ile Thr Ser Met Thr His
305                 310                 315                 320
Asp Ser Val Trp Asn Phe His Val Trp Thr Asp Ala Trp Met Lys Arg
                325                 330                 335
Pro Asp Leu Pro Lys Gly Tyr Asp Gly Trp Gln Ala Val Asp Ala Thr
            340                 345                 350
Pro Gln Glu Arg Ser Gln Gly Val Phe Cys Cys Gly Pro Ser Pro Leu
            355                 360                 365
Thr Ala Ile Arg Lys Gly Asp Ile Phe Ile Val Tyr Asp Thr Arg Phe
370                 375                 380
Val Phe Ser Glu Val Asn Gly Asp Arg Leu Ile Trp Leu Val Lys Met
385                 390                 395                 400
Val Asn Gly Gln Glu Glu Leu His Val Ile Ser Met Glu Thr Thr Ser
                405                 410                 415
Ile Gly Lys Asn Ile Ser Thr Lys Ala Val Gly Gln Asp Arg Arg Arg
            420                 425                 430
Asp Ile Thr Tyr Glu Tyr Lys Tyr Pro Glu Gly Ser Ser Glu Glu Arg
            435                 440                 445
Gln Val Met Asp His Ala Phe Leu Leu Leu Ser Ser Glu Arg Glu His
```

```
            450                 455                 460
Arg Arg Pro Val Lys Glu Asn Phe Leu His Met Ser Val Gln Ser Asp
465                 470                 475                 480

Asp Val Leu Leu Gly Asn Ser Val Asn Phe Thr Val Ile Leu Lys Arg
                485                 490                 495

Lys Thr Ala Ala Leu Gln Asn Val Asn Ile Leu Gly Ser Phe Glu Leu
            500                 505                 510

Gln Leu Tyr Thr Gly Lys Lys Met Ala Lys Leu Cys Asp Leu Asn Lys
                515                 520                 525

Thr Ser Gln Ile Gln Gly Gln Val Ser Glu Val Thr Leu Thr Leu Asp
530                 535                 540

Ser Lys Thr Tyr Ile Asn Ser Leu Ala Ile Leu Asp Asp Glu Pro Val
545                 550                 555                 560

Ile Arg Gly Phe Ile Ile Ala Glu Ile Val Glu Ser Lys Glu Ile Met
                565                 570                 575

Ala Ser Glu Val Phe Thr Ser Phe Gln Tyr Pro Glu Phe Ser Ile Glu
            580                 585                 590

Leu Pro Asn Thr Gly Arg Ile Gly Gln Leu Leu Val Cys Asn Cys Ile
        595                 600                 605

Phe Lys Asn Thr Leu Ala Ile Pro Leu Thr Asp Val Lys Phe Ser Leu
610                 615                 620

Glu Ser Leu Gly Ile Ser Ser Leu Gln Thr Ser Asp His Gly Thr Val
625                 630                 635                 640

Gln Pro Gly Glu Thr Ile Gln Ser Gln Ile Lys Cys Thr Pro Ile Lys
                645                 650                 655

Thr Gly Pro Lys Lys Phe Ile Val Lys Leu Ser Ser Lys Gln Val Lys
                660                 665                 670

Glu Ile Asn Ala Gln Lys Ile Val Leu Ile Thr Lys
                675                 680

<210> SEQ ID NO 381
<211> LENGTH: 585
<212> TYPE: PRT
<213> ORGANISM: Homo sapiens

<400> SEQUENCE: 381

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
```

```
                    565                 570                 575

Ala Ala Ser Gln Ala Ala Leu Gly Leu
            580                 585

<210> SEQ ID NO 382
<211> LENGTH: 10
<212> TYPE: PRT
<213> ORGANISM: Artificial Sequence
<220> FEATURE:
<223> OTHER INFORMATION: Synthetic peptide

<400> SEQUENCE: 382

Ile Glu Ser Lys Arg Arg Lys Lys Lys Pro
1               5                   10

<210> SEQ ID NO 383
<211> LENGTH: 10
<212> TYPE: PRT
<213> ORGANISM: Artificial Sequence
<220> FEATURE:
<223> OTHER INFORMATION: Synthetic peptide

<400> SEQUENCE: 383

Ala Pro Gly Pro Gly Asp Gly Gly Thr Ala
1               5                   10

<210> SEQ ID NO 384
<211> LENGTH: 11
<212> TYPE: PRT
<213> ORGANISM: Artificial Sequence
<220> FEATURE:
<223> OTHER INFORMATION: Synthetic peptide

<400> SEQUENCE: 384

Phe Ala Lys Lys Phe Ala Lys Lys Phe Lys Cys
1               5                   10

<210> SEQ ID NO 385
<211> LENGTH: 11
<212> TYPE: PRT
<213> ORGANISM: Artificial Sequence
<220> FEATURE:
<223> OTHER INFORMATION: Synthetic peptide

<400> SEQUENCE: 385

Lys Phe Arg Lys Ala Phe Lys Arg Phe Phe Cys
1               5                   10

<210> SEQ ID NO 386
<211> LENGTH: 4
<212> TYPE: PRT
<213> ORGANISM: Artificial Sequence
<220> FEATURE:
<223> OTHER INFORMATION: Synthetic peptide

<400> SEQUENCE: 386

Lys Phe Phe Lys
1

<210> SEQ ID NO 387
<211> LENGTH: 4
<212> TYPE: PRT
<213> ORGANISM: Artificial Sequence
<220> FEATURE:
<223> OTHER INFORMATION: Synthetic peptide

<400> SEQUENCE: 387
```

Lys Trp Trp Lys
1

<210> SEQ ID NO 388
<211> LENGTH: 4
<212> TYPE: PRT
<213> ORGANISM: Artificial Sequence
<220> FEATURE:
<223> OTHER INFORMATION: Synthetic peptide

<400> SEQUENCE: 388

Lys Tyr Tyr Lys
1

<210> SEQ ID NO 389
<211> LENGTH: 4
<212> TYPE: PRT
<213> ORGANISM: Artificial Sequence
<220> FEATURE:
<223> OTHER INFORMATION: Synthetic peptide

<400> SEQUENCE: 389

Lys Phe Trp Lys
1

<210> SEQ ID NO 390
<211> LENGTH: 4
<212> TYPE: PRT
<213> ORGANISM: Artificial Sequence
<220> FEATURE:
<223> OTHER INFORMATION: Synthetic peptide

<400> SEQUENCE: 390

Lys Trp Phe Lys
1

<210> SEQ ID NO 391
<211> LENGTH: 4
<212> TYPE: PRT
<213> ORGANISM: Artificial Sequence
<220> FEATURE:
<223> OTHER INFORMATION: Synthetic peptide

<400> SEQUENCE: 391

Lys Phe Tyr Lys
1

<210> SEQ ID NO 392
<211> LENGTH: 4
<212> TYPE: PRT
<213> ORGANISM: Artificial Sequence
<220> FEATURE:
<223> OTHER INFORMATION: Synthetic peptide

<400> SEQUENCE: 392

Lys Tyr Phe Lys
1

<210> SEQ ID NO 393
<211> LENGTH: 4
<212> TYPE: PRT
<213> ORGANISM: Artificial Sequence
<220> FEATURE:
<223> OTHER INFORMATION: Synthetic peptide

<400> SEQUENCE: 393

Lys Trp Tyr Lys
1

<210> SEQ ID NO 394
<211> LENGTH: 4
<212> TYPE: PRT
<213> ORGANISM: Artificial Sequence
<220> FEATURE:
<223> OTHER INFORMATION: Synthetic peptide

<400> SEQUENCE: 394

Lys Tyr Trp Lys
1

<210> SEQ ID NO 395
<211> LENGTH: 4
<212> TYPE: PRT
<213> ORGANISM: Artificial Sequence
<220> FEATURE:
<223> OTHER INFORMATION: Synthetic peptide

<400> SEQUENCE: 395

Arg Phe Phe Arg
1

<210> SEQ ID NO 396
<211> LENGTH: 4
<212> TYPE: PRT
<213> ORGANISM: Artificial Sequence
<220> FEATURE:
<223> OTHER INFORMATION: Synthetic peptide

<400> SEQUENCE: 396

Arg Trp Trp Arg
1

<210> SEQ ID NO 397
<211> LENGTH: 4
<212> TYPE: PRT
<213> ORGANISM: Artificial Sequence
<220> FEATURE:
<223> OTHER INFORMATION: Synthetic peptide

<400> SEQUENCE: 397

Arg Tyr Tyr Arg
1

<210> SEQ ID NO 398
<211> LENGTH: 4
<212> TYPE: PRT
<213> ORGANISM: Artificial Sequence
<220> FEATURE:
<223> OTHER INFORMATION: Synthetic peptide

<400> SEQUENCE: 398

Arg Phe Trp Arg
1

<210> SEQ ID NO 399
<211> LENGTH: 4
<212> TYPE: PRT
<213> ORGANISM: Artificial Sequence
<220> FEATURE:
<223> OTHER INFORMATION: Synthetic peptide

<400> SEQUENCE: 399

Arg Trp Phe Arg

<210> SEQ ID NO 400
<211> LENGTH: 4
<212> TYPE: PRT
<213> ORGANISM: Artificial Sequence
<220> FEATURE:
<223> OTHER INFORMATION: Synthetic peptide

<400> SEQUENCE: 400

Arg Phe Tyr Arg
1

<210> SEQ ID NO 401
<211> LENGTH: 4
<212> TYPE: PRT
<213> ORGANISM: Artificial Sequence
<220> FEATURE:
<223> OTHER INFORMATION: Synthetic peptide

<400> SEQUENCE: 401

Arg Tyr Phe Arg
1

<210> SEQ ID NO 402
<211> LENGTH: 4
<212> TYPE: PRT
<213> ORGANISM: Artificial Sequence
<220> FEATURE:
<223> OTHER INFORMATION: Synthetic peptide

<400> SEQUENCE: 402

Arg Trp Tyr Arg
1

<210> SEQ ID NO 403
<211> LENGTH: 4
<212> TYPE: PRT
<213> ORGANISM: Artificial Sequence
<220> FEATURE:
<223> OTHER INFORMATION: Synthetic peptide

<400> SEQUENCE: 403

Arg Tyr Trp Arg
1

<210> SEQ ID NO 404
<211> LENGTH: 4
<212> TYPE: PRT
<213> ORGANISM: Artificial Sequence
<220> FEATURE:
<223> OTHER INFORMATION: Synthetic peptide

<400> SEQUENCE: 404

His Phe Phe His
1

<210> SEQ ID NO 405
<211> LENGTH: 4
<212> TYPE: PRT
<213> ORGANISM: Artificial Sequence
<220> FEATURE:
<223> OTHER INFORMATION: Synthetic peptide

<400> SEQUENCE: 405

His Trp Trp His
1

```
<210> SEQ ID NO 406
<211> LENGTH: 4
<212> TYPE: PRT
<213> ORGANISM: Artificial Sequence
<220> FEATURE:
<223> OTHER INFORMATION: Synthetic peptide

<400> SEQUENCE: 406

His Tyr Tyr His
1

<210> SEQ ID NO 407
<211> LENGTH: 4
<212> TYPE: PRT
<213> ORGANISM: Artificial Sequence
<220> FEATURE:
<223> OTHER INFORMATION: Synthetic peptide

<400> SEQUENCE: 407

His Phe Trp His
1

<210> SEQ ID NO 408
<211> LENGTH: 4
<212> TYPE: PRT
<213> ORGANISM: Artificial Sequence
<220> FEATURE:
<223> OTHER INFORMATION: Synthetic peptide

<400> SEQUENCE: 408

His Trp Phe His
1

<210> SEQ ID NO 409
<211> LENGTH: 4
<212> TYPE: PRT
<213> ORGANISM: Artificial Sequence
<220> FEATURE:
<223> OTHER INFORMATION: Synthetic peptide

<400> SEQUENCE: 409

His Phe Tyr His
1

<210> SEQ ID NO 410
<211> LENGTH: 4
<212> TYPE: PRT
<213> ORGANISM: Artificial Sequence
<220> FEATURE:
<223> OTHER INFORMATION: Synthetic peptide

<400> SEQUENCE: 410

His Tyr Phe His
1

<210> SEQ ID NO 411
<211> LENGTH: 4
<212> TYPE: PRT
<213> ORGANISM: Artificial Sequence
<220> FEATURE:
<223> OTHER INFORMATION: Synthetic peptide

<400> SEQUENCE: 411

His Trp Tyr His
1
```

```
<210> SEQ ID NO 412
<211> LENGTH: 4
<212> TYPE: PRT
<213> ORGANISM: Artificial Sequence
<220> FEATURE:
<223> OTHER INFORMATION: Synthetic peptide

<400> SEQUENCE: 412

Gly Gly Gly Arg
1

<210> SEQ ID NO 413
<211> LENGTH: 4
<212> TYPE: PRT
<213> ORGANISM: Artificial Sequence
<220> FEATURE:
<223> OTHER INFORMATION: Synthetic peptide

<400> SEQUENCE: 413

Gly Pro Gly Arg
1
```

PEPTIDES HAVING ANTI-INFLAMMATORY PROPERTIES

CROSS-REFERENCE TO RELATED APPLICATIONS

Pursuant to 35 U.S.C. §119 (e), this application claims the benefit of priority to U.S. Provisional Patent Application Ser. No. 62/063,909, filed Oct. 14, 2014, the disclosure of which application is hereby incorporated by reference herein in its entirety.

FIELD OF THE INVENTION

Aspects of the present invention relate to peptides having anti-inflammatory activity, compositions containing one or more of the peptides, and use of the peptides to treat conditions associated with excessive inflammation in animals, particularly humans and other mammals.

BACKGROUND OF THE INVENTION

Under normal conditions, inflammation is a process that helps an animal recover from injury. Acute inflammation is the initial response of a tissue to harmful stimuli. It involves a complex, highly regulated process that begins when cells present in the injured tissue, including macrophages, dendritic cells, histiocytes, Kupffer cells, and mastocytes, sense molecules associated with the injury and become activated. Upon activation, these cells release inflammatory mediators, such as vasodilators. The vasodilators induce increased blood flow and permeability of the blood vessels in the vicinity of the injury. This, in turn, results in the increased movement of plasma and leukocytes (including neutrophils and macrophages) from the blood into the injured tissue. Because inflammatory mediators are, in general, rapidly degraded, acute inflammation requires constant stimulation in order to be sustained. As a result, acute inflammation ends once the harmful stimulus is removed.

Various agents, including but not limited to bacteria, viruses, physical injury, chemical injury, cancer, chemotherapy, and radiation therapy, can, depending on the specific agent and the genetic makeup of the animal exposed to it, cause prolonged and excessive inflammation. Such inflammation, known as chronic inflammation, is believed to be a contributing factor to many widespread and debilitating diseases, including heart disease, cancer, respiratory disease, stroke, neurological diseases such as Alzheimer's disease, diabetes, and kidney disease. The result of chronic inflammation is the destruction of normal tissue and its replacement with collagen-rich connective tissue. Collagen-rich connective tissue, also known as scar tissue, exhibits diminished tissue function as compared to normal tissue. Persistent and prolonged formation of scar tissue, in turn, leads to fibrosis. Fibrosis is among the common symptoms of diseases affecting the lungs, skin, liver, heart, and bone marrow, and is a critical factor in diseases such as idiopathic pulmonary fibrosis, scleroderma, keloids, liver cirrhosis, myocardial fibrosis, diabetic kidney disease, myelodysplastic syndrome, and other disorders.

Studies of chronic inflammation and fibrosis have indicated that, regardless of the activating agent and the tissue affected, a common network of signaling proteins tend to function together to establish the pro-inflammatory state. This network of signaling proteins includes a number of different cytokines, cytokine receptors, transcription factors, and micro RNAs, including TGFβ, TGFβRII, and miRNA19b.

Despite growing knowledge about conditions that involve excessive inflammation, such as chronic inflammation and fibrosis, treatments for such conditions remain elusive. Many drugs and other substances have been shown to have anti-inflammatory activity, either in vitro or in vivo, but for many indications caused or potentiated by inflammation, there are still no therapies. In addition, many anti-inflammatory therapies are associated with harmful side effects. Thus, there remains a critical need to identify therapeutic agents that reduce inflammation without harmful side effects.

SUMMARY OF THE INVENTION

The present invention is based, in part, on the discovery of novel peptides that have powerful anti-inflammatory activities in vitro and in vivo. The present invention is also based, in part, on the discovery that peptides of the invention specifically bind to key functional regions on one or more signaling proteins, particularly pro-inflammatory cytokines, macrophage inhibition proteins, and histone regulation proteins. The present invention is also based, in part, on the discovery that the peptides of the invention are sufficiently stable in the circulation to allow for intravenous administration.

Accordingly, in one aspect, the invention provides a composition comprising an anti-inflammatory polypeptide. In certain embodiments, the anti-inflammatory polypeptide is 3 to 24 amino acids residues in length and includes a striapathic region consisting of alternating hydrophobic and hydrophilic modules. In certain embodiments, each hydrophilic module is made up of a sequence of one or more (e.g., 1-5, 1-4, 1-3) hydrophilic amino acid residues. In certain embodiments, each hydrophobic module is made up of a sequence of one or more (e.g., 1-5, 1-4, 1-3) hydrophobic amino acid residues.

In certain embodiments, the striapathic region of an anti-inflammatory peptide includes m hydrophilic modules and n hydrophobic modules, with m and n each being a positive integer. For example, in certain embodiments, the striapathic region includes two hydrophilic modules and two hydrophobic modules (2:2), two hydrophilic modules and three hydrophobic modules (2:3), three hydrophilic modules and two hydrophobic modules (3:2), three hydrophilic modules and three hydrophobic modules (3:3), three hydrophilic modules and four hydrophobic modules (3:4), or four hydrophilic modules and three hydrophobic modules (4:3).

In certain embodiments, the striapathic region of an anti-inflammatory polypeptide is at least 5, 6, 7, 8, 9, or 10 amino acid residues in length. In preferred embodiments, the length of the striapathic region is between 7 and 12 amino acid residues. In certain embodiments, the striapathic region makes up at least 25% of the length of the polypeptide. For example, in certain embodiments, the striapathic region comprises at least 30%, 35%, 40%, 45%, 50%, 60%, 65%, 70%, 75%, 80%, 85%, 90%, 95%, or 100% of the length of the polypeptide.

In certain embodiments, the striapathic region of an anti-inflammatory polypeptide adopts a helical secondary structure. Examples of helical secondary structures include $3_{10}$-helices, α-helices, π-helices, and poly-proline helices. In other embodiments, the striapathic region of an anti-inflammatory polypeptide adopts a beta-strand secondary structure. In preferred embodiments, the striapathic region of an anti-inflammatory polypeptides has an amphipathic conformation.

In certain embodiments, an anti-inflammatory polypeptide comprises, consists essentially of, or consists of a striapathic region having a sequence that conforms to any one of the structural formulas disclosed herein (e.g., any one of Formulas I-LIII). In certain embodiments, the anti-inflammatory polypeptide is one of the polypeptides listed in Tables 3-9. In other embodiments, the anti-inflammatory polypeptide has at least 70%, 80%, or 90% homology with any one of the polypeptides disclosed in Tables 3-9.

In certain embodiments, an anti-inflammatory polypeptide binds to at least one signaling protein. In preferred embodiments, the anti-inflammatory polypeptide binds to at least one signaling protein in vitro and/or in vivo, with sufficient affinity to modulate the activity of the signaling protein. Examples of signaling proteins that the anti-inflammatory polypeptides bind to include proteins that function as pro-inflammatory cytokines, proteins that inhibit macrophage activity, or protein that regulate histone function. In certain embodiments, the anti-inflammatory polypeptide binds to a protein target selected from the group consisting of NFkB class II proteins (e.g., Rel A, Rel B, cRel, NF-kB1, and NF-kB2), TGFβ, Notch receptors (e.g., Notch1), Wnt receptors (e.g., Wnt8R), TRAIL, EGFR, interleukin receptors (e.g., IL6R, IL10R), cyclin dependent kinases (e.g., CDK6), CD47, SIRP-α, transglutaminases (e.g., TGM2), LEGUMAIN, CD209, FAS, programmed cell death protein 1 (PD-1/CD279), mitogen-activated protein kinase kinase 7 (MKK7), ribonucleotide reductase (RNR), and histone methyl transferase. In preferred embodiments, the anti-inflammatory polypeptide binds to two, three, four, or more such signaling proteins. For example, in certain embodiments, an anti-inflammatory polypeptide binds to an NF-kB Class II protein (e.g., RelB) and at least one other signaling protein that functions as a pro-inflammatory cytokine, an inhibitor of macrophage activity, or a regulator of histone function. In preferred embodiments, the anti-inflammatory polypeptide binds to the NF-kB Class II protein and at least one other protein target, with sufficient binding affinity to each target to modulate the activity of both targets in vivo. In preferred embodiments, an anti-inflammatory polypeptide binds to the dimerization site of an NFkB Class II protein (e.g., RelB).

In certain embodiments, an anti-inflammatory polypeptides binds to a carrier protein in the blood (e.g., serum albumin).

In certain embodiments, an anti-inflammatory polypeptide is modified to include, for example, a linker, a carbohydrate, a lipid, or a polymer (e.g., PEG). In certain embodiments, a first anti-inflammatory polypeptide is linked to a second anti-inflammatory polypeptide so as to form a multimer, such as a dimer. In certain embodiments, the dimer is a homodimer. In other embodiments, the dimer is a heterodimer. In certain embodiments, the linker is a peptide linker. In preferred embodiments, the peptide linker forms a peptide bond with the C-terminus of the first anti-inflammatory polypeptide and a peptide bond with the N-terminus of the second anti-inflammatory polypeptide. In certain embodiments, the linker is a biodegradeable linker. In certain embodiments, the linker is a disulfide bond. In certain embodiments, the disulfide linkage is formed by a pair of cysteine residues (e.g., one cysteine residue from each of the polypeptides being linked).

In certain embodiments, the anti-inflammatory polypeptide is linked to a molecule other than another anti-inflammatory polypeptide. For example, the anti-inflammatory polypeptide can be linked to a label or a chemotherapeutic agent. In certain embodiments, the linker is a biodegradable linker. In certain embodiments, the linker is a di-sulfide bond (e.g., involving the sulfhydryl group of a cysteine residue located at the C-terminus or N-terminus of the anti-inflammatory polypeptide).

In another aspect, the invention provides pharmaceutical compositions that comprise an anti-inflammatory polypeptide and a pharmaceutically acceptable carrier. In certain embodiments, the pharmaceutical composition comprises a single type of anti-inflammatory polypeptide. In other embodiments, the pharmaceutical composition comprises a combination of two or more anti-inflammatory polypeptides. In preferred embodiments, the pharmaceutical composition is substantially free of blood proteins and/or metabolites found in the blood. In other embodiments, the pharmaceutical composition includes serum albumin (e.g., human serum albumin). In preferred embodiments, any serum albumin present in a pharmaceutical composition is recombinantly produced and/or substantially free of other blood proteins and/or metabolites found in the blood. In certain embodiments, the pharmaceutical composition comprises 1 mg to 1000 mg (e.g., 10 to 400 mg, 20 to 300 mg, or about 25 to 250 mg) of an anti-inflammatory polypeptide.

In another aspect, the invention provides methods of treating a subject by administering to the subject a composition (e.g., a pharmaceutical composition) comprising an anti-inflammatory polypeptide. In certain embodiments, the subject is an animal, such as a mammal (e.g., a human). In certain embodiments, the subject has elevated levels of inflammatory cytokines, is suffering from a chronic inflammatory condition, or is likely to develop a chronic inflammatory condition. In certain embodiments, the chronic inflammatory condition can be irritable bowel disease, ulcerative colitis, colitis, Crohn's disease, fibrosis, idiopathic pulmonary fibrosis, asthma, keratitis, arthritis, osteoarthritis, rheumatoid arthritis, an auto-immune disease, a feline or human immunodeficiency virus (FIV or HIV) infection, or cancer. In certain embodiments, the cancer is colon cancer, breast cancer, leukemia, lymphoma, ovarian cancer, prostate cancer, liver cancer, lung cancer, testicular cancer, cervical cancer, bladder cancer, endometrial cancer, kidney cancer, melanoma, or a cancer of the thyroid or brain. In certain embodiments, the composition is administered in combination with a chemotherapeutic agent, immunotherapeutic agent, and/or radiation therapy.

These and other features and advantages of the compositions and methods of the invention will be set forth or will become more fully apparent in the description that follows and in the appended claims. For example, suitable anti-inflammatory polypeptides may be identified by use of the Structural Algorithm described herein. Furthermore, features and advantages of the described compositions and methods may be learned by practicing the methods or will be obvious from the description.

DETAILED DESCRIPTION OF THE INVENTION

Figure 1:
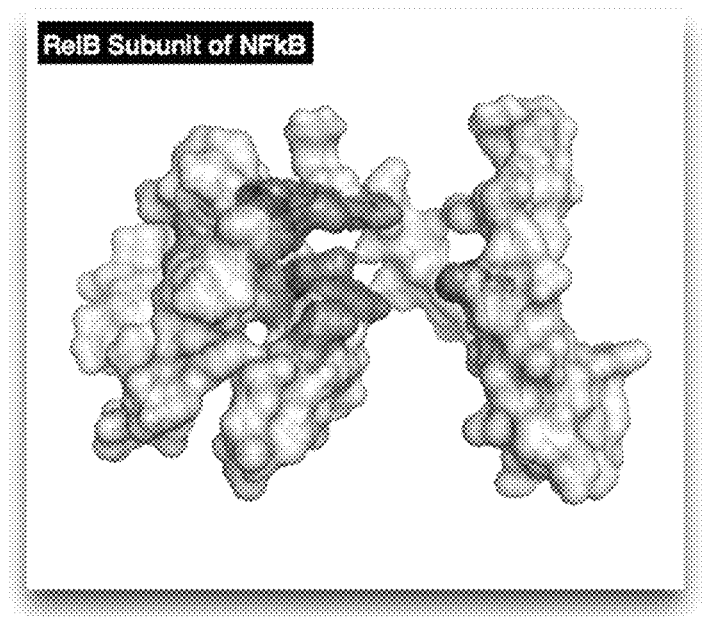
FIG. 1 depicts a structural model of human RelB, an NF-kB Class II protein.

The following description supplies specific details in order to provide a thorough understanding of the present invention. That said, to avoid obscuring aspects of the described anti-inflammatory polypeptides and related methods of treating a subject, well-known structures, materials, processes, techniques, and operations are not shown or described in detail. Additionally, the skilled artisan will understand that the described anti-inflammatory polypeptides and related methods of treating a subject can be implemented and used without employing these specific details. Indeed, the described anti-inflammatory polypeptides and methods can be placed into practice by modifying the illustrated polypeptides, compositions, and methods, and can be used in conjunction with other treatments, apparatuses, and techniques conventionally used in the industry.

As discussed above, the invention disclosed herein relates to immune-modulatory polypeptides, particularly peptides that have immunosuppressive properties, and methods of administering such immune-modulatory polypeptides to a subject, particularly a subject suffering from a medical condition associated with persistent inflammation or at risk developing such a medical condition.

The invention provides anti-inflammatory polypeptides, sometimes referred to as "RP peptides," that satisfy the requirements of the Structural Algorithm described below. The invention also provides anti-inflammatory polypeptides that share a minimum degree of homology with any of the exemplary RP peptides disclosed herein. Thus, a peptide or polypeptide of the invention is an anti-inflammatory polypeptide that satisfies the Structural Algorithm described below or shares a minimum degree of homology with any of the exemplary RP peptides disclosed herein (e.g., in Tables 3-9).

The terms "peptide" and "polypeptide" are used synonymously herein to refer to polymers constructed from amino acid residues.

The term "amino acid residue," as used herein, refers to any naturally occurring amino acid (L or D form), non-naturally occurring amino acid, or amino acid mimetic (such as a peptoid monomer).

The "length" of a polypeptide is the number of amino acid residues linked end-to-end that constitute the polypeptide, excluding any non-peptide linkers and/or modifications that the polypeptide may contain.

The term "striapathic region," as used herein, refers to an alternating sequence of hydrophobic and hydrophilic modules. A "hydrophobic module" is made up of a peptide sequence consisting of one to five hydrophobic amino acid residues. Likewise, a hydrophilic module is made up of a peptide sequence consisting of one to five hydrophilic amino acid residues.

Hydrophobic amino acid residues are characterized by a functional group ("side chain") that has predominantly non-polar chemical properties. Such hydrophobic amino acid residues can be naturally occurring (L or D form) or non-naturally occurring. Alternatively, hydrophobic amino acid residues can be amino acid mimetics characterized by a functional group ("side chain") that has predominantly non-polar chemical properties. Conversely, hydrophilic amino acid residues are characterized by a functional group ("side chain") that has predominantly polar (charged or uncharged) chemical properties. Such hydrophilic amino acid residues can be naturally occurring (L or D form) or non-naturally occurring. Alternatively, hydrophilic amino acid residues can be amino acid mimetics characterized by a functional group ("side chain") that has predominantly polar (charged or uncharged) chemical properties. Examples of hydrophilic and hydrophobic amino acid residues are shown in Table 1, below. Suitable non-naturally occurring amino acid residues and amino acid mimetics are known in the art. See, e.g., Liang et al. (2013), "An Index for Characterization of Natural and Non-Natural Amino Acids for Peptidomimetics," PLoS ONE 8(7):e67844.

Although most amino acid residues can be considered as either hydrophobic or hydrophilic, a few, depending on their context, can behave as either hydrophobic or hydrophilic. For example, due to their relatively weak non-polar characteristics, glycine, proline, and/or cysteine can sometimes function as hydrophilic amino acid residues. Conversely, due to their bulky, slightly hydrophobic side chains, histidine and arginine can sometimes function as hydrophobic amino acid residues.

TABLE 1

Hydrophobic and Hydrophilic Amino Acid Residues

| Hydrophilic Residues (X) | Hydrophobic Residues (Y) |
|---|---|
| Arginine | Tryptophan |
| Histidine | Phenylalanine |
| Lysine | Tyrosine |
| Aspartic Acid | Isoleucine |
| Glutamic Acid | Leucine |
| Asparagine | Valine |
| Glutamine | Methionine |
| Pyrrolysine | Cysteine |
| | Threonine |
| | Serine |
| | Alanine |
| | Proline |
| | Glycine |
| | Selenocysteine |
| | N-formylmethionine |
| | Norleucine |
| | Norvaline |

The term "anti-inflammatory property," as used herein, refers to any property of a polypeptide that can be evaluated in silico, in vitro, and/or in vivo, that reduces or inhibits, or would be expected to reduce or inhibit, a pro-inflammatory signal mediated by a protein target and/or reduces or inhibits inflammation in a subject.

Structural Algorithm

In its most basic form, the Structural Algorithm requires an anti-inflammatory peptide to have the following characteristics:

a length of 3 to 24 amino acid residues;

a striapathic region that comprises at least 25% of the length of the polypeptide; and at least one anti-inflammatory property.

The anti-inflammatory peptide and/or its striapathic region can have a length that is greater than 3 amino acid residues and/or less than 24 amino acid residues. Thus, the requisite length of the polypeptide can be, for example, 3 to 20, 3 to 18, 3 to 16, 3 to 14, 3 to 12, 4 to 20, 4 to 18, 4 to 16, 4 to 14, 4 to 12, 5 to 20, 5 to 18, 5 to 16, 5 to 14, 5 to 12, 6 to 20, 6 to 18, 6 to 16, 6 to 14, 6 to 12, 7 to 20, 7 to 18, 7 to 16, 7 to 14, or in certain embodiments 7 to 12 amino acid residues. For an anti-inflammatory polypeptide that is longer than 12 amino acid residues, it can be advantageous to design a kink in the secondary structure (e.g., such as produced by a proline residue) such that the polypeptide has a striapathic region that is 12 or fewer amino acid residues in length. The striapathic region of an anti-inflammatory peptide can comprise at least 30%, 35%, 40%, 45%, 50%, 60%, 65%, 70%, 75%, 80%, 85%, 90%, 95%, or 100% of the length of the polypeptide.

An anti-inflammatory polypeptide can have a striapathic region that includes at least two hydrophobic modules and one or more (e.g., two or three) hydrophilic modules. Alternatively, an anti-inflammatory polypeptide can have a striapathic region that includes at least three hydrophobic modules and two or more (e.g., three or four) hydrophilic modules; a striapathic region that includes at least two hydrophilic modules and one or more (e.g., two or three) hydrophilic modules; or a striapathic region that includes at least three hydrophilic modules and two or more (e.g., three or four) hydrophobic modules.

As discussed above, a striapathic region consists of alternating hydrophilic ($X_m$) and hydrophobic ($Y_n$) modules. In this context, the subscripts m and n are positive integers that identify different modules. Each $X_m$ module consists of a sequence according to the formula $X_{ma}$-$X_{mb}$-$X_{mc}$-$X_{md}$-$X_{me}$. $X_{ma}$ is selected from the group consisting of a naturally occurring hydrophilic amino acid, a non-naturally occurring hydrophilic amino acid, and a hydrophilic amino acid mimetic; and $X_{mb}$, $X_{mc}$, $X_{md}$ and $X_{me}$ are each individually absent or selected from the group consisting of a naturally occurring hydrophilic amino acid, a non-naturally occurring hydrophilic amino acid, and a hydrophilic amino acid mimetic. Each $Y_n$ module consists of a sequence according to the formula $Y_{na}$-$Y_{nb}$-$Y_{nc}$-$Y_{nd}$-$Y_{ne}$. $Y_{na}$ is selected from the group consisting of a naturally occurring hydrophobic amino acid, a non-naturally occurring hydrophobic amino acid, and a hydrophobic amino acid mimetic; $Y_{nb}$, $Y_{nc}$, $Y_{nd}$, and $Y_{ne}$ are each individually absent or selected from the group consisting of a naturally occurring hydrophobic, a non-naturally occurring hydrophobic amino acid, and a hydrophobic amino acid mimetic.

In certain anti-inflammatory polypeptides, each $X_m$ module consists of a sequence according to the formula $X_{ma}$-$X_{mb}$-$X_{mc}$-$X_{md}$ or $X_{ma}$-$X_{mb}$-$X_{mc}$. Similarly, in certain anti-inflammatory polypeptides, each $Y_n$ module consists of a sequence according to the formula $Y_{na}$-$Y_{nb}$-$Y_{nc}$-$Y_{nd}$ or $Y_{na}$-$Y_{nb}$-$Y_{nc}$.

Anti-inflammatory peptides can include a striapathic region corresponding to a formula selected from the group consisting of:

$$Y_{1a}\text{-}Y_{1b}\text{-}Y_{1c}\text{-}X_{1a}\text{-}Y_{2a}\text{-}Y_{2b}\text{-}Y_{2c} \quad \text{(Formula I)};$$

$$Y_{1a}\text{-}Y_{1b}\text{-}Y_{1c}\text{-}X_{1a}\text{-}Y_{2a}\text{-}Y_{2b}\text{-}Y_{2c}\text{-}X_{2a}\text{-}Y_{3a}\text{-}X_{3a} \quad \text{(Formula II)};$$

$$X_{2a}\text{-}Y_{3a}\text{-}X_{3a}\text{-}Y_{1a}\text{-}Y_{1b}\text{-}Y_{1c}\text{-}X_{1a}\text{-}Y_{2a}\text{-}Y_{2b}\text{-}Y_{2c} \quad \text{(Formula III)};$$

$$X_{1a}\text{-}X_{1b}\text{-}X_{1c}\text{-}Y_{2a}\text{-}X_{2a}\text{-}X_{2b}\text{-}X_{2c} \quad \text{(Formula IV)};$$

$$Y_{1a}\text{-}X_{1a}\text{-}X_{1b}\text{-}X_{1c}\text{-}Y_{2a}\text{-}X_{2a}\text{-}X_{2b}\text{-}X_{2c}\text{-}Y_{3a}\text{-}X_{3a} \quad \text{(Formula V)};$$

$$X_{1a}\text{-}X_{1b}\text{-}Y_{2a}\text{-}Y_{2b}\text{-}X_{2a}\text{-}X_{2b} \quad \text{(Formula VI)};$$

$$Y_{1a}\text{-}X_{1a}\text{-}X_{1b}\text{-}Y_{2a}\text{-}Y_{2b}\text{-}X_{2a}\text{-}X_{2b}\text{-}Y_{3a} \quad \text{(Formula VII)};$$

$$Y_{1a}\text{-}X_{1a}\text{-}X_{1b}\text{-}Y_{2a}\text{-}Y_{2b}\text{-}X_{2a}\text{-}X_{2b}\text{-}Y_{3a}\text{-}Y_{3b}\text{-}X_{3a} \quad \text{(Formula VIII)};$$

$$Y_{1a}\text{-}Y_{1b}\text{-}X_{1a}\text{-}X_{1b}\text{-}Y_{2a}\text{-}Y_{2b}\text{-}X_{2a}\text{-}X_{2b}\text{-}Y_{3a}\text{-}Y_{3b} \quad \text{(Formula IX)};$$

$$Y_{1a}\text{-}Y_{1b}\text{-}X_{1a}\text{-}X_{1b}\text{-}Y_{2a}\text{-}Y_{2b}\text{-}X_{2a}\text{-}X_{2b}\text{-}Y_{3a}\text{-}X_{3a} \quad \text{(Formula X)};$$

$$X_{1a}\text{-}Y_{1a}\text{-}X_{2a}\text{-}X_{2b}\text{-}Y_{2a}\text{-}Y_{2b}\text{-}X_{3a}\text{-}X_{3b}\text{-}Y_{3a}\text{-}Y_{3b} \quad \text{(Formula XI)};$$

$$X_{1a}\text{-}Y_{1a}\text{-}Y_{1b}\text{-}X_{2a}\text{-}X_{2b}\text{-}Y_{2a}\text{-}Y_{2b}\text{-}X_{3a}\text{-}X_{3b}\text{-}Y_{3a} \quad \text{(Formula XII)};$$

$$Y_{1a}\text{-}X_{1a}\text{-}X_{1b}\text{-}Y_{2a}\text{-}Y_{2b}\text{-}X_{2a}\text{-}X_{2b}\text{-}X_{2c}\text{-}Y_{3a}\text{-}Y_{3b} \quad \text{(Formula XIII)};$$

$$X_{1a}\text{-}X_{1b}\text{-}X_{1c}\text{-}Y_{1a}\text{-}Y_{1b}\text{-}X_{2a}\text{-}X_{2b}\text{-}Y_{2a}\text{-}Y_{2b}\text{-}Y_{2c} \quad \text{(Formula XIV)};$$

$$Y_{1a}\text{-}Y_{1b}\text{-}Y_{1c}\text{-}X_{1a}\text{-}X_{1b}\text{-}Y_{2a}\text{-}Y_{2b}\text{-}X_{2a}\text{-}X_{2b}\text{-}X_{2c} \quad \text{(Formula XV)};$$

$$Y_{1a}\text{-}Y_{1b}\text{-}X_{1a}\text{-}X_{1b}\text{-}X_{1c}\text{-}Y_{2a}\text{-}Y_{2b}\text{-}X_{2a}\text{-}X_{2b}\text{-}Y_{3a} \quad \text{(Formula XVI)};$$

$$Y_{1a}\text{-}Y_{1b}\text{-}X_{1a}\text{-}X_{1b}\text{-}Y_{2a}\text{-}Y_{2b} \quad \text{(Formula XVII)};$$

$$X_{1a}\text{-}Y_{1a}\text{-}Y_{1b}\text{-}X_{2a}\text{-}X_{2b}\text{-}Y_{2a}\text{-}Y_{2b}\text{-}X_{3a} \quad \text{(Formula XVIII)};$$

$$Y_{1a}\text{-}Y_{1b}\text{-}X_{1a}\text{-}X_{1b}\text{-}Y_{2a}\text{-}Y_{2b}\text{-}X_{2a}\text{-}Y_{3a}\text{-}Y_{3b}\text{-}X_{3a} \quad \text{(Formula XIX)};$$

$$X_{1a}\text{-}Y_{1a}\text{-}Y_{1b}\text{-}X_{2a}\text{-}Y_{2a}\text{-}Y_{2b}\text{-}X_{3a}\text{-}X_{3b}\text{-}Y_{3a}\text{-}Y_{3b} \quad \text{(Formula XX)};$$

$$Y_{1a}\text{-}Y_{1b}\text{-}X_{1a}\text{-}X_{1b}\text{-}Y_{2a}\text{-}X_{2a}\text{-}X_{2b}\text{-}Y_{3a}\text{-}Y_{3b} \quad \text{(Formula XXI)};$$

$$X_{1a}\text{-}Y_{1a}\text{-}Y_{1b}\text{-}X_{2a}\text{-}X_{2b}\text{-}X_{2c}\text{-}Y_{2a}\text{-}X_{3a}\text{-}Y_{3a}\text{-}Y_{3b} \quad \text{(Formula XXII)};$$

$$Y_{1a}\text{-}Y_{1b}\text{-}X_{1a}\text{-}Y_{2a}\text{-}X_{2a}\text{-}X_{2b}\text{-}X_{2c}\text{-}Y_{3a}\text{-}Y_{3b}\text{-}X_{3a} \quad \text{(Formula XXIII)};$$

$$X_{1a}\text{-}X_{1b}\text{-}Y_{1a}\text{-}X_{2a}\text{-}Y_{2a}\text{-}X_{3a}\text{-}X_{3b} \quad \text{(Formula XXIV)};$$

$$Y_{1a}\text{-}Y_{1b}\text{-}Y_{1c}\text{-}X_{1a}\text{-}X_{1b}\text{-}Y_{2a}\text{-}X_{2a}\text{-}Y_{3a}\text{-}X_{3a}\text{-}X_{3b} \quad \text{(Formula XXV)};$$

$$X_{1a}\text{-}X_{1b}\text{-}Y_{1a}\text{-}X_{2a}\text{-}Y_{2a}\text{-}X_{3a}\text{-}X_{3b}\text{-}Y_{3a}\text{-}Y_{3b}\text{-}Y_{3c} \quad \text{(Formula XXVI)};$$

$$X_{1a}\text{-}X_{1b}\text{-}X_{1c}\text{-}Y_{1a}\text{-}Y_{1b}\text{-}Y_{1c} \quad \text{(Formula XXVII)};$$

$$X_{1a}\text{-}X_{1b}\text{-}X_{1c}\text{-}X_{1d}\text{-}Y_{1a}\text{-}Y_{1b}\text{-}Y_{1c}\text{-}Y_{1d} \quad \text{(Formula XXVIII)};$$

$$Y_{1a}\text{-}X_{1a}\text{-}X_{1b}\text{-}X_{1c}\text{-}X_{1d}\text{-}Y_{2a}\text{-}Y_{2b}\text{-}Y_{2c}\text{-}Y_{2d}\text{-}X_{2a} \quad \text{(Formula XXIX)};$$

$$X_{1a}\text{-}X_{1b}\text{-}X_{1c}\text{-}X_{1d}\text{-}X_{1e}\text{-}Y_{1a}\text{-}Y_{1b}\text{-}Y_{1c}\text{-}Y_{1d}\text{-}Y_{1e} \quad \text{(Formula XXX)};$$

$$Y_{1a}\text{-}Y_{1b}\text{-}X_{1a}\text{-}X_{1b}\text{-}X_{1c}\text{-}Y_{2a}\text{-}Y_{2b}\text{-}Y_{2c}\text{-}X_{2a}\text{-}X_{2b} \quad \text{(Formula XXXI)};$$

$$X_{1a}\text{-}Y_{1a}\text{-}X_{2a}\text{-}Y_{2a}\text{-}X_{3a}\text{-}X_{3b}\text{-}X_{3c}\text{-}Y_{3a}\text{-}Y_{3b}\text{-}Y_{3c} \quad \text{(Formula XXXII)};$$

$$Y_{1a}\text{-}Y_{1b}\text{-}Y_{1c}\text{-}X_{1a}\text{-}X_{1b}\text{-}X_{1c} \quad \text{(Formula XXXIII)};$$

$$Y_{1a}\text{-}Y_{1b}\text{-}Y_{1c}\text{-}Y_{1d}\text{-}X_{1a}\text{-}X_{1b}\text{-}X_{1c}\text{-}X_{1d} \quad \text{(Formula XXXIV)};$$

$$X_{1a}\text{-}Y_{1a}\text{-}Y_{1b}\text{-}Y_{1c}\text{-}Y_{1d}\text{-}X_{2a}\text{-}X_{2b}\text{-}X_{2c}\text{-}X_{2d}\text{-}Y_{2a} \quad \text{(Formula XXXV)};$$

$$Y_{1a}\text{-}Y_{1b}\text{-}Y_{1c}\text{-}Y_{1d}\text{-}Y_{1e}\text{-}X_{1a}\text{-}X_{1b}\text{-}X_{1c}\text{-}X_{1d}\text{-}X_{1e} \quad \text{(Formula XXXVI)};$$

$$X_{1a}\text{-}X_{1b}\text{-}Y_{1a}\text{-}Y_{1b}\text{-}Y_{1c}\text{-}X_{2a}\text{-}X_{2b}\text{-}X_{2c}\text{-}Y_{2a}\text{-}Y_{2b} \quad \text{(Formula XXXVII)};$$

$$Y_{1a}\text{-}Y_{1b}\text{-}Y_{1c}\text{-}X_{1a}\text{-}X_{1a}\text{-}X_{1c}\text{-}Y_{2a}\text{-}Y_{2a}\text{-}Y_{3a}\text{-}X_{3a} \quad \text{(Formula XXXVIII)};$$

$$Y_{1a}\text{-}X_{1a}\text{-}X_{1b}\text{-}X_{1c}\text{-}X_{1d}\text{-}X_{1e}\text{-}Y_{2a} \quad \text{(Formula XXXIX)};$$

$$Y_{1a}\text{-}X_{1a}\text{-}X_{1b}\text{-}X_{1c}\text{-}X_{1d}\text{-}X_{1e}\text{-}Y_{2a}\text{-}Y_{2b}\text{-}Y_{2c}\text{-}Y_{2d} \quad \text{(Formula XL)};$$

$$Y_{1a}\text{-}Y_{1b}\text{-}X_{1a}\text{-}X_{1b}\text{-}X_{1c}\text{-}X_{1d}\text{-}X_{1e}\text{-}Y_{2a}\text{-}Y_{2b}\text{-}Y_{2c} \quad \text{(Formula XLI)};$$

$$Y_{1a}\text{-}Y_{1b}\text{-}Y_{1c}\text{-}X_{1a}\text{-}X_{1b}\text{-}X_{1c}\text{-}X_{1d}\text{-}X_{1e}\text{-}Y_{2a}\text{-}Y_{2b} \quad \text{(Formula XLII)};$$

$$Y_{1a}\text{-}Y_{1b}\text{-}Y_{1c}\text{-}Y_{1e}\text{-}X_{1a}\text{-}X_{1b}\text{-}X_{1c}\text{-}X_{1d}\text{-}X_{1e}\text{-}Y_{2a} \quad \text{(Formula XLIII)};$$

$$X_{1a}\text{-}Y_{1a}\text{-}Y_{1b}\text{-}Y_{1c}\text{-}Y_{1d}\text{-}Y_{1e}\text{-}X_{2a} \quad \text{(Formula XLIV)};$$

$$X_{1a}\text{-}Y_{1a}\text{-}Y_{1b}\text{-}Y_{1c}\text{-}Y_{1d}\text{-}Y_{1e}\text{-}X_{2a}\text{-}X_{2b}\text{-}X_{2c}\text{-}X_{2d} \quad \text{(Formula XLV)};$$

$$X_{1a}\text{-}X_{1b}\text{-}Y_{1a}\text{-}Y_{1b}\text{-}Y_{1c}\text{-}Y_{1d}\text{-}Y_{1e}\text{-}X_{2a}\text{-}X_{2b}\text{-}X_{2c} \quad \text{(Formula XLVI)};$$

$$X_{1a}\text{-}X_{1b}\text{-}X_{1c}\text{-}Y_{1a}\text{-}Y_{1b}\text{-}Y_{1c}\text{-}Y_{1d}\text{-}Y_{1e}\text{-}X_{2a}\text{-}X_{2b} \quad \text{(Formula XLVII)};$$

$$X_{1a}\text{-}X_{1b}\text{-}X_{1c}\text{-}X_{1d}\text{-}Y_{1a}\text{-}Y_{1b}\text{-}Y_{1c}\text{-}Y_{1d}\text{-}Y_{1e}\text{-}X_{2a} \quad \text{(Formula XLVIII)};$$

$$Y_{1a}\text{-}X_{1a}\text{-}Y_{2a}\text{-}X_{2a}\text{-}Y_{3a}\text{-}X_{3a} \quad \text{(Formula XLIX)};$$

$$Y_{1a}\text{-}Y_{1b}\text{-}X_{1a}\text{-}Y_{2a}\text{-}Y_{2b}\text{-}X_{2a}\text{-}Y_{3a}\text{-}Y_{3b}\text{-}X_{3a}\text{-}Y_{4a} \quad \text{(Formula L)};$$

$$X_{1a}\text{-}X_{1b}\text{-}Y_{1a}\text{-}Y_{1b}\text{-}X_{2a}\text{-}Y_{2a}\text{-}Y_{2b}\text{-}Y_{2c}\text{-}Y_{2d} \quad \text{(Formula LI)};$$

$$Y_{1a}\text{-}Y_{1b}\text{-}Y_{1c}\text{-}Y_{1d}\text{-}X_{1a}\text{-}Y_{2a}\text{-}Y_{2b}\text{-}X_{2a}\text{-}X_{2b} \quad \text{(Formula LII)};$$

$$Y_{1a}\text{-}Y_{1b}\text{-}X_{1a}\text{-}Y_{2a}\text{-}Y_{2b}\text{-}Y_{2c}\text{-}X_{2b}\text{-}Y_{3a}\text{-}X_{3a}\text{-}Y_{4a} \quad \text{(Formula LIII)};$$

and $$Y_{1a}\text{-}X_{1a}\text{-}Y_{2a}\text{-}X_{2a}\text{-}Y_{3a}\text{-}Y_{3b}\text{-}Y_{3c}\text{-}X_{3a}\text{-}Y_{4a}\text{-}Y_{4b} \quad \text{(Formula LIV)}.$$

Typically, the striapathic region (or a portion thereof) of an anti-inflammatory polypeptide will have an amphipathic conformation (e.g., under physiological conditions). To be considered amphipathic, the striapathic region (or portion thereof) need not be in the amphipathic conformation at all times. Rather, it is sufficient that the amphipathic conformation be present at least 50%, 60%, 70%, 80%, or more of the time, or when the anti-inflammatory polypeptide is binding to a target molecule, such as an NF-kB Class II protein (e.g., Rel B). Often, the amphipathic conformation will be associated with a particular secondary structure, such as a helical structure. Thus, the striapathic region (or a portion thereof) of the anti-inflammatory polypeptide can have an amphipathic $3_{10}$-helical conformation, an amphipathic α-helical conformation, an amphipathic π-helical conformation, or an amphipathic poly-proline helical conformation. Alternatively, the striapathic region (or a portion thereof) of the anti-inflammatory polypeptide can have an amphipathic β-strand conformation.

For anti-inflammatory peptides that comprise a striapathic region that includes or has an amphipathic helical conformation (e.g., $3_{10}$-helical, α-helical, π-helical, or polyproline helical conformation), the hydrophobic surface ("side") can have a facial arc of at least 100°. In certain embodiments, the facial arc of the hydrophobic surface or side is at least 125°, 150°, 175°, 200°, 225°, 250°, 275°, or 300°.

Anti-inflammatory polypeptides in certain embodiments have a striapathic region that has a relatively large hydrophobic volume. Accordingly, the striapathic region can optimally contain hydrophobic amino acid residues having a total side-chain volume of at least 600 cubic angstroms. In certain embodiments, the hydrophobic amino acid residues of the striapathic region have a hydrophobic side-chain volume of at least 650, 700, 750, 800, 850, 900, 950, 1000, or more cubic angstroms. Alternatively, or in addition, the striapathic region can be characterized by a ratio of the sum of the side-chain volume of hydrophobic amino acid residues to the sum of the side-chain volume of hydrophilic amino acid residues, wherein the ratio is at least 0.75 or higher. For example, the ratio can be at least 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, or greater.

Because of the desirability of a striapathic region having a relatively large hydrophobic side-chain volume, it is generally preferable to include one or more (e.g., 2, 3, 4, 5, or more) large hydrophobic amino acid residues in the sequence of the striapathic region. Conversely, it is generally preferable to have two or fewer (e.g., 1 or 0) small hydrophobic amino acid residues in the sequence of the striapathic region. Examples of large hydrophobic amino acid residues include tryptophan, phenylalanine, and tyrosine. In addition, under certain circumstances, histidine or arginine can be considered a large hydrophobic amino acid residue. Examples of small hydrophobic residues include glycine, alanine, serine, cysteine, valine, threonine, and proline. Accordingly, an anti-inflammatory polypeptide can have a striapathic region that includes one or more (e.g., 2, 3, 4, 5, or more) hydrophobic residues selected from the group consisting of tryptophan, phenylalanine, and tyrosine. Alternatively, the anti-inflammatory polypeptide can have a striapathic region that includes one or more (e.g., 2, 3, 4, 5, or more) hydrophobic residues selected from (i) the group consisting of tryptophan, phenylalanine, tyrosine, and histidine, or (ii) the group consisting of tryptophan, phenylalanine, tyrosine, and arginine. In certain embodiments, the anti-inflammatory polypeptide has a striapathic region that includes two or fewer (e.g., 1 or 0) hydrophobic residues selected from the group consisting of glycine, alanine, serine, cysteine, valine, threonine, and proline. Alternatively, the anti-inflammatory polypeptide can have a striapathic region that includes no more than one hydrophobic residue selected from the group consisting of glycine, alanine, serine, cysteine, valine, threonine, and proline. In other alternatives, the anti-inflammatory polypeptide can have a striapathic region that includes no glycine residues, no alanine residues, no serine residues, no cysteine residues, no valine residues, no threonine residues, and/or no proline residues.

It is also preferable that an anti-inflammatory polypeptide have a striapathic region characterized by a moderate level of cationicity (i.e., a striapathic region that does not contain an excessive number of amino acid residues having positively charged side chains). Examples of amino acid residues having positively charged side groups (assuming physiological conditions) includes lysine, typically arginine, and sometimes histidine. Examples of amino acid residues having negatively charged side chains (assuming physiological conditions) include aspartic acid and glutamic acid. Examples of hydrophilic amino acid residues having uncharged side chains (assuming physiological conditions) include asparagine and glutamine. Accordingly, an anti-inflammatory polypeptide can have a striapathic region that includes five or fewer (e.g., 4, 3, 2) lysine residues. Alternatively, an anti-inflammatory polypeptide can have a striapathic region that includes five or fewer (e.g., 4, 3, 2) amino acid residues selected from the group consisting of lysine and arginine. In other alternatives, an anti-inflammatory polypeptide can have a striapathic region that includes five or fewer (e.g., 4, 3, 2) amino acid residues selected from the group consisting of lysine, arginine, and histidine. For anti-inflammatory polypeptides that have a striapathic region that includes one or more (e.g., two or more) positively charged amino acid residues, it can be advantageous for the striapathic region to also include some negatively charged or polar, uncharged amino acid residues. For example, the anti-inflammatory polypeptide can have a striapathic region that includes both positively and negatively charged amino acid residues, such that the net charge on the polypeptide is no more than +2 or +1 (e.g., the number of positively charged amino acid residues does not exceed the number of negatively charged amino acid residues by more than one or two). Alternatively, the anti-inflammatory polypeptide can have a striapathic region that includes both positively charged and polar, uncharged amino acid residues, such that the net charge on the polypeptide is no more than +2 or +1 (e.g., the number of positively charged amino acid residues does not exceed one or two). In other alternatives, the anti-inflammatory polypeptide can have a striapathic region that includes both positively charged, negatively charged, and hydrophilic uncharged charged amino acid residues, such that the net charge on the polypeptide is no more than +2.

To avoid certain undesired interactions between RP peptides and other molecules (whether another RP peptide, a metal ion, etc.) it can be advantageous to limit the number of certain types of amino acid residues in the polypeptide. For example, because cysteine residues form di-sulfide bonds under certain conditions (e.g., oxidative environments), it can be useful to limit the number of cysteine residues in a polypeptide of the invention to no more than one or two, or even none. Because histidine residues chelate metals under certain conditions (e.g., alkaline environments), it can be useful to limit the number of histidine residues in a polypeptide of the invention to no more than one or two, or even none. In addition, because proline residues tend to introduce kinks into secondary structure elements (e.g., α-helices and β-strands), it can be useful to exclude proline residues in the striapathic region of a polypeptide of the invention, or limit their number to no more than one.

Class I Polypeptides

An anti-inflammatory polypeptide of the invention can be a Class I polypeptide. Class I polypeptides comprise, consist essentially of, or consist of a striapathic region that includes a sequence selected from the group of sequences defined by Formula I:

$$Y_{1a}\text{-}Y_{1b}\text{-}Y_{1c}\text{-}X_{1a}\text{-}Y_{2a}\text{-}Y_{2b}\text{-}Y_{2c} \qquad \text{(Formula I)}.$$

Each of amino acid residues $Y_{1a}$, $Y_{1b}$, $Y_{1c}$, $Y_{2a}$, $Y_{2b}$, and $Y_{2c}$ in Formula I can be selected from the group consisting of Phe (F), Trp (W), Tyr (Y), His (H), Leu (L), Cys (C), Met (M), Val (V), Ile (I), Pro (P), Thr (T), Ser (S), Ala (A), and Gly (G). In certain embodiments, at least 3, 4, 5, or 6 of amino acid residues $Y_{1a}$, $Y_{1b}$, $Y_{1c}$, $Y_{2a}$, $Y_{2b}$, and $Y_{2c}$ in Formula I are selected from the group consisting of Phe (F), Trp (W), Tyr (Y), His (H), and Leu (L). In certain embodiments, at least 3, 4, 5, or 6 of amino acid residues $Y_{1a}$, $Y_{1b}$, $Y_{1c}$, $Y_{2a}$, $Y_{2b}$, and $Y_{2c}$ in Formula I are selected from the group consisting of Phe (F), Trp (W), and Tyr (Y). In certain embodiments, less than two (and in certain embodiments 1 or none) of amino acid residues $Y_{1a}$, $Y_{1b}$, $Y_{1c}$, $Y_{2a}$, $Y_{2b}$, and $Y_{2c}$ in Formula I are selected from the group consisting of Pro (P), Thr (T), Ser (S), Ala (A), and Gly (G).

The module $Y_{1a}\text{-}Y_{1b}\text{-}Y_{1c}$ in Formula I can have a sequence selected from the group consisting of Phe-Phe-Phe (FFF), Trp-Trp-Trp (WWW), Tyr-Tyr-Tyr (YYY), Leu-Leu-Leu (LLL), Cys-Cys-Cys (CCC), Met-Met-Met (MMM), Val-Val-Val (VVV), Ile-Ile-Ile (III). Alternatively, the module $Y_{1a}\text{-}Y_{1b}\text{-}Y_{1c}$ in Formula I can have a sequence selected from the group consisting of Pro-Pro-Pro (PPP), Thr-Thr-Thr (TTT), and Ala-Ala-Ala (AAA). In certain embodiments, module $Y_{1a}\text{-}Y_{1b}\text{-}Y_{1c}$ in Formula I has a sequence selected from the group consisting of Phe-Phe-Phe (FFF), Trp-Trp-Trp (WWW), Tyr-Tyr-Tyr (YYY), and combinations thereof (e.g., Phe-Phe-Trp (FFW), Phe-Trp-Trp (FWW), Trp-Phe-Trp (WFW), Trp-Trp-Phe (WWF), Phe-Phe-Tyr (FFY), Phe-Tyr-Tyr (FYY), Tyr-Phe-Tyr (YFY), Tyr-Tyr-Phe (YYF), Trp-Trp-Tyr (WWY), Trp-Tyr-Tyr (WYY), Tyr-Trp-Tyr (YWY), Tyr-Tyr-Trp (YYW), Phe-Trp-Tyr (FWY), Phe-Tyr-Trp (FYW), Trp-Phe-Tyr (WFY), Trp-Tyr-Phe (WYF), Tyr-Trp-Phe (YWF), or Tyr-Phe-Trp (YFW)).

The module $Y_{2a}\text{-}Y_{2b}\text{-}Y_{2c}$ in Formula I can have a sequence selected from the group consisting of Phe-Phe-Phe (FFF), Trp-Trp-Trp (WWW), Tyr-Tyr-Tyr (YYY), Leu-Leu-Leu (LLL), Cys-Cys-Cys (CCC), Met-Met-Met (MMM), Val-Val-Val (VVV), and Ile-Ile-Ile (III). Alternatively, the module $Y_{2a}\text{-}Y_{2b}\text{-}Y_{2c}$ in Formula I can have a sequence selected from the group consisting of Pro-Pro-Pro (PPP), Thr-Thr-Thr (TTT), and Ala-Ala-Ala (AAA). In certain embodiments, module $Y_{2a}\text{-}Y_{2b}\text{-}Y_{2c}$ in Formula I has a sequence selected from the group consisting of Phe-Phe-Phe (FFF), Trp-Trp-Trp (WWW), Tyr-Tyr-Tyr (YYY), and combinations thereof (e.g., Phe-Phe-Trp (FFW), Phe-Trp-Trp (FWW), Trp-Phe-Trp (WFW), Trp-Trp-Phe (WWF), Phe-Phe-Tyr (FFY), Phe-Tyr-Tyr (FYY), Tyr-Phe-Tyr (YFY), Tyr-Tyr-Phe (YYF), Trp-Trp-Tyr (WWY), Trp-Tyr-Tyr (WYY), Tyr-Trp-Tyr (YWY), Tyr-Tyr-Trp (YYW), Phe-Trp-Tyr (FWY), Phe-Tyr-Trp (FYW), Trp-Phe-Tyr (WFY), Trp-Tyr-Phe (WYF), Tyr-Trp-Phe (YWF), or Tyr-Phe-Trp (YFW)).

Thus, a Class I anti-inflammatory polypeptide can comprise, consist essentially of, or consist of a striapathic region having a sequence selected from the group consisting of FFF-$X_{1a}$-FFF (SEQ ID NO: 1), WWW-$X_{1a}$-WWW (SEQ ID NO: 2), YYY-$X_{1a}$-YYY (SEQ ID NO: 3), and combinations thereof. Alternatively, a Class I anti-inflammatory polypeptide can comprise, consist essentially of, or consist of a striapathic region having a sequence selected from the group consisting of LLL-$X_{1a}$-LLL (SEQ ID NO: 4), CCC-$X_{1a}$-CCC (SEQ ID NO: 5), MMM-$X_{1a}$-MMM (SEQ ID NO: 6), VVV-$X_{1a}$-VVV (SEQ ID NO: 7), and III-$X_{1a}$-III (SEQ ID NO: 8). In such peptides, $X_{1a}$ can be selected from the group consisting of Arg (R), His (H), and Lys (K); or $X_{1a}$ can be selected from the group consisting of Glu (E), Gln (Q), Asn (N), and Asp (D).

A Class I anti-inflammatory polypeptide can comprise, consist essentially of, or consist of a striapathic region having a sequence selected from the group of sequences defined by Formula II or the group of sequences defined by Formula III:

$$Y_{1a}\text{-}Y_{1b}\text{-}Y_{1c}\text{-}X_{1a}\text{-}Y_{2a}\text{-}Y_{2b}\text{-}Y_{2c}\text{-}X_{2a}\text{-}Y_{3a}\text{-}X_{3a} \quad \text{(Formula II);}$$

$$X_{2a}\text{-}Y_{3a}\text{-}X_{3a}\text{-}Y_{1a}\text{-}Y_{1b}\text{-}Y_{1c}\text{-}X_{1a}\text{-}Y_{2a}\text{-}Y_{2b}\text{-}Y_{2c} \quad \text{(Formula III).}$$

The $Y_{1a}$-$Y_{1b}$-$Y_{1c}$-$X_{1a}$-$Y_{2a}$-$Y_{2b}$-$Y_{2c}$ sequences defined by Formulas II and III can be any of the sequences described above in connection with Formula I. $X_{2a}$ and $X_{3a}$ in Formulas II and III can be each individually selected from the group consisting of Arg (R), His (H), Lys (K), Glu (E), Gln (Q), Asn (N), and Asp (D). Alternatively, $X_{2a}$ and $X_{3a}$ in Formulas II and III can be each individually selected from the group consisting of Arg (R), His (H), and Lys (K). In other alternatives, $X_{2a}$ and $X_{3a}$ in Formulas II and III can be each individually selected from the group consisting of Arg (R), His (H), Lys (K), and Gln (Q). In other alternatives, $X_{2a}$ and $X_{3a}$ in Formulas II and III can be each individually selected from the group consisting Glu (E), Gln (Q), Asn (N), and Asp (D). In other alternatives, $X_{2a}$ in Formulas II and III can be selected from the group consisting of Arg (R), His (H), and Lys (K), and $X_{3a}$ in Formulas II and III can be selected from the group consisting of Glu (E), Gln (Q), Asn (N), and Asp (D). Y3a in Formulas II and III can be selected from the group consisting of Phe (F), Trp (W), Tyr (Y), Leu (L), Cys (C), Met (M), Val (V), and Ile (I). In certain embodiments, Y3a in Formulas II and III is selected from the group consisting of Phe (F), Trp (W), Tyr (Y), and Leu (L).

The modules $X_{2a}$-$Y_{3a}$-$X_{3a}$ in Formulas II and III can be selected from the group consisting of EFQ, EFE, EFN, EFD, NFQ, NFE, NFN, NFD, QFQ, QFE, QFN, QFD, DFQ, DFE, DFN, DFD, EWQ, EWE, EWN, EWD, NWQ, NWE, NWN, NWD, QWQ, QWE, QWN, QWD, DWQ, DWE, DWN, DWD, EYQ, EYE, EFN, EYD, NYQ, NYE, NYN, NYD, QYQ, QYE, QYN, QYD, DYQ, DYE, DYN, DYD, ELQ, ELE, ELN, ELD, NLQ, NLE, NLN, NLD, QLQ, QLE, QLN, QLD, DLQ, DLE, DLN, DLD, RFR, RFQ, RFE, RFN, RFD, RWR, RWQ, RWE, RWN, and RWD.

A Class I anti-inflammatory polypeptide can comprise, consist essentially of, or consist of a striapathic region comprising, consisting essentially of, or consisting of a sequence selected from the group of sequences listed in Table 3, e.g., RP394, RP108-RP123, RP125-131, RP133, RP135-RP141, RP143-RP146, RP148-RP150, RP152-RP165, RP179, RP395, RP211, RP230, RP232, RP258, RP267, RP268, RP271, RP273, RP280-281, and RP287. In certain embodiments, the Class I anti-inflammatory polypeptide can comprise, consist essentially of, or consist of a striapathic region that comprises, consists essentially of, or consists of a sequence selected from the group of sequences consisting of RP113 (SEQ ID NO: 39), RP118 (SEQ ID NO: 44), and RP394 (SEQ ID NO: 33).

Class II Polypeptides

An anti-inflammatory polypeptide of the invention can be a Class II polypeptide. Class II anti-inflammatory polypeptides can comprise, consist essentially of, or consist of a striapathic region that includes a sequence selected from the group of sequences defined by Formula VII:

$$Y_{1a}\text{-}X_{1a}\text{-}X_{1b}\text{-}Y_{2a}\text{-}Y_{2b}\text{-}X_{2a}\text{-}X_{2b}\text{-}Y_{3a} \quad \text{(Formula VII).}$$

Amino acid residue $Y_{2a}$ in Formula VII can be selected from the group consisting of Phe (F), Trp (W), Tyr (Y), Leu (L), Cys (C), Met (M), Val (V), Ile (I), Pro (P), Thr (T), Ser (S), Ala (A), and Gly (G). In certain embodiments, amino acid residue $Y_{2a}$ in Formula VII is selected from the group consisting of Phe (F), Trp (W), and Tyr (Y). Alternatively, amino acid residue $Y_{2a}$ in Formula VII can be selected from the group consisting of Leu (L), Cys (C), Met (M), Val (V), Ile (I).

Amino acid residue $Y_{2b}$ in Formula VII can be selected from the group consisting of Phe (F), Trp (W), Tyr (Y), Leu (L), Cys (C), Met (M), Val (V), Ile (I), Pro (P), Thr (T), Ser (S), Ala (A), and Gly (G). In certain embodiments, amino acid residue $Y_{2b}$ in Formula VII is selected from the group consisting of Phe (F), Trp (W), and Tyr (Y). Alternatively, amino acid residue $Y_{2b}$ in Formula VII can be selected from the group consisting of Leu (L), Cys (C), Met (M), Val (V), Ile (I).

Amino acid residue $X_{1b}$ in Formula VII can be selected from the group consisting of Arg (R), Lys (K), and His (H). Alternatively amino acid residue $X_{1b}$ in Formula VII can be selected from the group consisting of Asn (N), Gln (Q), Asp (D), and Glu (E).

Amino acid residue $X_{2a}$ in Formula VII can be selected from the group consisting of Arg (R), Lys (K), and His (H). Alternatively, amino acid residue $X_{2a}$ can be selected from the group consisting of Asn (N), Gln (Q), Asp (D), and Glu (E).

The sequence $X_{1b}$-$Y_{2a}$-$Y_{2b}$-$X_{2a}$ in Formula VII can be selected from the group consisting of Lys-Phe-Phe-Lys (KFFK; SEQ ID NO: 386), Lys-Trp-Trp-Lys (KWWK; SEQ ID NO: 387), Lys-Tyr-Try-Lys (KYYK; SEQ ID NO: 388), Lys-Phe-Trp-Lys (KFWK; SEQ ID NO: 389), Lys-Trp-Phe-Lys (KWFK; SEQ ID NO: 390), Lys-Phe-Tyr-Lys (KFYK; SEQ ID NO: 391), Lys-Tyr-Phe-Lys (KYFK; SEQ ID NO: 392), Lys-Trp-Tyr-Lys (KWYK; SEQ ID NO: 393), and Lys-Tyr-Trp-Lys (KYWK; SEQ ID NO: 394). Alternatively, the sequence $X_{1b}$-$Y_{2a}$-$Y_{2b}$-$X_{2a}$ in Formula VII can be selected from the group consisting of Arg-Phe-Phe-Arg (RFFR; SEQ ID NO: 395), Arg-Trp-Trp-Arg (RWWR; SEQ ID NO: 396), Arg-Tyr-Try-Arg (RYYR; SEQ ID NO: 397), Arg-Phe-Trp-Arg (RFWR; SEQ ID NO: 398), Arg-Trp-Phe-Arg (RWFR; SEQ ID NO: 399), Arg-Phe-Tyr-Arg (RFYR; SEQ ID NO: 400), Arg-Tyr-Phe-Arg (RYFR; SEQ ID NO: 401), Arg-Trp-Tyr-Arg (RWYR; SEQ ID NO: 402), and Arg-Tyr-Trp-Arg (RYWR; SEQ ID NO: 403). In other alternatives, the sequence $X_{1b}$-$Y_{2a}$-$Y_{2b}$-$X_{2a}$ in Formula VII can be selected from the group consisting of His-Phe-Phe-His (HFFH; SEQ ID NO: 404), His-Trp-Trp-His (HWWH; SEQ ID NO: 405), His-Tyr-Try-His (HYYH; SEQ ID NO: 406), His-Phe-Trp-His (HFWH; SEQ ID NO: 407), His-Trp-Phe-His (HWFH; SEQ ID NO: 408), His-Phe-Tyr-His (HFYH; SEQ ID NO: 409), His-Tyr-Phe-His (HYFH; SEQ ID NO: 410), His-Trp-Tyr-His (HWYH; SEQ ID NO: 411), and His-Tyr-Trp-His (HYWH;SEQ ID NO:132).

Amino acid residue $X_{1a}$ in Formula VII can be selected from the group consisting of Arg (R), Lys (K), His (H), Asn (N), Gln (Q), Asp (D), and Glu (E). In certain embodiments, amino acid residue $X_{1a}$ is selected from the group consisting of Arg (R) and Gln (Q). In certain embodiments, amino acid residue $X_{1a}$ in Formula VII is Arg (R). Alternatively, amino acid residue $X_{1a}$ in Formula VII can be selected from the group consisting of Lys (K), Gln (Q), Glu (E), and Asn (N).

Amino acid resiude $X_{2b}$ in Formula VII can be selected from the group consisting of Arg (R), Lys (K), His (H), Asn (N), Gln (Q), Asp (D), and Glu (E). In certain embodiments, amino acid residue $X_{2b}$ is selected from the group consisting of Arg (R) and Gln (Q). In certain embodiments, amino acid residue $X_{2b}$ in Formula VII is Arg (R). Alternatively, amino acid residue $X_{2b}$ in Formula VII can be selected from the group consisting of Lys (K), Gln (Q), Glu (E), and Asn (N).

Amino acid residue $Y_{1a}$ in Formula VII can be selected from the group consisting of Phe (F), Trp (W), Tyr (Y), Leu (L), Cys (C), Met (M), Val (V), Ile (I), Thr (T), Pro (P), Ser (S), Ala (A), and Gly (G). In certain embodiments, amino acid residue $Y_{1a}$ in Formula VII is selected from the group consisting of Phe (F), Trp (W), and Tyr (Y). Alternatively, amino acid residue $Y_{1a}$ in Formula VII can be selected from the group consisting of Leu (L), Cys (C), Met (M), Val (V), Ile (I).

Amino acid residue $Y_{3a}$ in Formula VII can be selected from the group consisting of Phe (F), Trp (W), Tyr (Y), Leu (L), Cys (C), Met (M), Val (V), Ile (I), Thr (T), Pro (P), Ser (S), Ala (A), and Gly (G). In certain embodiments, amino acid residue $Y_{3a}$ in Formula VII is selected from the group consisting of Phe (F), Trp (W), and Tyr (Y). Alternatively, amino acid residue $Y_{3a}$ in Formula VII can be selected from the group consisting of Leu (L), Cys (C), Met (M), Val (V), Ile (I).

Thus, a Class II anti-inflammatory polypeptide can comprise, consist essentially of, or consist of a striapathic region having a sequence selected from the group consisting of F-$X_{1a}$-$X_{1b}$-FF-$X_{2a}$-$X_{2b}$-F (SEQ ID NO: 9), F-$X_{1a}$-$X_{1b}$-FF-$X_{2a}$-$X_{2b}$-W (SEQ ID NO: 10), W-$X_{1a}$-$X_{1b}$-FF-$X_{2a}$-$X_{2b}$-F (SEQ ID NO: 11), F-$X_{1a}$-$X_{1b}$-FW-$X_{2a}$-$X_{2b}$-F (SEQ ID NO: 12), F-$X_{1a}$-$X_{1b}$-WF-$X_{2a}$-$X_{2b}$-F (SEQ ID NO: 13), F-$X_{1a}$-$X_{1b}$-WW-$X_{2a}$-$X_{2b}$-F (SEQ ID NO: 14), W-$X_{1a}$-$X_{1b}$-WW-$X_{2a}$-$X_{2b}$-F (SEQ ID NO: 15), F-$X_{1a}$-$X_{1b}$-WW-$X_{2a}$-$X_{2b}$-W (SEQ ID NO: 16), W-$X_{1a}$-$X_{1b}$-WW-$X_{2a}$-$X_{2b}$-W (SEQ ID NO: 17), F-$X_{1a}$-$X_{1b}$-FF-$X_{2a}$-$X_{2b}$-Y (SEQ ID NO: 18), Y-$X_{1a}$-$X_{1b}$-FF-$X_{2a}$-$X_{2b}$-F (SEQ ID NO: 19), F-$X_{1a}$-$X_{1b}$-FY-$X_{2a}$-$X_{2b}$-F (SEQ ID NO: 20), F-$X_{1a}$-$X_{1b}$-YF-$X_{2a}$-$X_{2b}$-F (SEQ ID NO: 21), F-$X_{1a}$-$X_{1b}$-YY-$X_{2a}$-$X_{2b}$-F (SEQ ID NO: 22), Y-$X_{1a}$-$X_{1b}$-YY-$X_{2a}$-$X_{2b}$-F (SEQ ID NO: 23), F-$X_{1a}$-$X_{1b}$-YY-$X_{2a}$-$X_{2b}$-Y (SEQ ID NO: 24), and Y-$X_{1a}$-$X_{1b}$-YY-$X_{2a}$-$X_{2b}$-Y (SEQ ID NO: 25), Y-$X_{1a}$-$X_{1b}$-YY-$X_{2a}$-$X_{2b}$-W (SEQ ID NO: 26), W-$X_{1a}$-$X_{1b}$-YY-$X_{2a}$-$X_{2b}$-Y (SEQ ID NO: 27), Y-$X_{1a}$-$X_{1b}$-YW-$X_{2a}$-$X_{2b}$-Y (SEQ ID NO: 28), Y-$X_{1a}$-$X_{1b}$-WY-$X_{2a}$-$X_{2b}$-Y (SEQ ID NO: 29), Y-$X_{1a}$-$X_{1b}$-WW-$X_{2a}$-$X_{2b}$-Y (SEQ ID NO: 30), W-$X_{1a}$-$X_{1b}$-WW-$X_{2a}$-$X_{2b}$-Y (SEQ ID NO: 31), and Y-$X_{1a}$-$X_{1b}$-WW-$X_{2a}$-$X_{2b}$-W (SEQ ID NO: 32). Amino acid residues $X_{1a}$, $X_{1b}$, $X_{2a}$, and $X_{2b}$ in the foregoing sequences can be selected as discussed above.

A Class II anti-inflammatory polypeptide can comprise, consist essentially of, or consist of a striapathic region that further includes a first additional amino acid residue directly bound to amino acid residue $Y_{1a}$ of Formula VII. The first additional amino acid residue can be a hydrophobic amino acid residue (e.g., a residue selected from the group consisting of Phe (F), Trp (W), Tyr (Y), Leu (L), Cys (C), Met (M), Val (V), Ile (I), Thr (T), Pro (P), Ser (S), Ala (A), and Gly (G); a residue selected from the group consisting of Phe (F), Trp (W), and Tyr (Y); a residue selected from the group consisting of Phe (F), Trp (W), Tyr (Y), and Leu (L); or, a residue selected from the group consisting of Leu (L), Cys (C), Met (M), Val (V), and Be (I)). Alternatively, the first additional amino acid residue can be a hydrophilic amino acid residue (e.g., a residue selected from the group consisting of Arg (R), Lys (K), His (H), Asn (N), Gln (Q), Asp (D), and Glu (E); a residue selected from the group consisting of Arg (R), Lys (K), and His (H); a residue selected from the group consisting Arg (R), Lys (K), His (H), and Gln (Q); or a residue selected from the group consisting of Asn (N), Gln (Q), Asp (D), and Glu (E)).

A Class II anti-inflammatory polypeptide can comprise, consist essentially of, or consist of a striapathic region that further includes a first additional amino acid residue directly bound to amino acid residue $Y_{3a}$ of Formula VII. The first additional amino acid residue can be a hydrophobic amino acid residue (e.g., a residue selected from the group consisting of Phe (F), Trp (W), Tyr (Y), Leu (L), Cys (C), Met (M), Val (V), Ile (I), Thr (T), Pro (P), Ser (S), Ala (A), and Gly (G); a residue selected from the group consisting of Phe (F), Trp (W), and Tyr (Y); a residue selected from the group consisting of Phe (F), Trp (W), Tyr (Y), and Leu (L); or, a residue selected from the group consisting of Leu (L), Cys (C), Met (M), Val (V), and Be (I)). Alternatively, the first additional amino acid residue can be a hydrophilic amino acid residue (e.g., a residue selected from the group consisting of Arg (R), Lys (K), His (H), Asn (N), Gln (Q), Asp (D), and Glu (E); a residue selected from the group consisting of Arg (R), Lys (K), and His (H); a residue selected from the group consisting Arg (R), Lys (K), His (H), and Gln (Q); or a residue selected from the group consisting of Asn (N), Gln (Q), Asp (D), and Glu (E)).

A Class II anti-inflammatory polypeptide can comprise, consist essentially of, or consist of a striapathic region that further includes a first additional amino acid residue directly bound to amino acid residue $Y_{1a}$ of Formula VII and a second additional amino acid reside directly bound to amino acid residue $Y_{3a}$ of Formula VII. The first additional amino acid residue can be a hydrophobic amino acid residue and the second additional amino acid residue can be a hydrophilic amino acid residue. Alternatively, the first additional amino acid residue can be a hydrophilic amino acid residue and the second amino acid residue can be a hydrophobic amino acid residue. Regardless, the additional hydrophobic amino acid residue can be selected from the group consisting of Phe (F), Trp (W), Tyr (Y), Leu (L), Cys (C), Met (M), Val (V), Be (I), Thr (T), Pro (P), Ser (S), Ala (A), and Gly (G); and in certain embodiments from the group consisting of Phe (F), Trp (W), and Tyr (Y); and in additional embodiments from the group consisting of Phe (F). The additional hydrophilic amino acid residue can be selected from the group consisting of Arg (R), Lys (K), His (H), Asn (N), Gln (Q), Asp (D), and Glu (E); and in certain embodiments, a residue selected from the group consisting of Arg (R), Lys (K), and His (H); or a residue selected from the group consisting of Asn (N), Gln (Q), Asp (D), and Glu (E).

A Class II anti-inflammatory polypeptide can comprise, consist essentially of, or consist of a striapathic region comprising, consisting essentially of, or consisting of a sequence selected from the group of sequences listed in Table 5, e.g., RP124, RP132, RP134, RP142, RP147, RP151, RP166-RP172, RP175, RP177, RP182, RP183, RP185, RP186, RP 424, RP190, RP194, RP198, RP199-RP202, RP204, RP206, RP207, RP209, RP210, RP212-RP216, RP218, RP219, RP425, RP225, RP227, RP233-RP239, RP398, RP241-RP247, RP250-RP256, RP426, RP427, RP285, and RP387. In certain embodiments, the Class II anti-inflammatory polypeptide comprises, consists essentially of, or consists of a striapathic region comprising, consisting essentially of, or consisting of a sequence selected from the group consisting of RP124 (SEQ ID NO: 106), RP166 (SEQ ID NO: 112), RP182 (SEQ ID NO: 121), and RP183 (SEQ ID NO: 122).

Class XII Polypeptides

An anti-inflammatory polypeptide of the invention can be a Class XII polypeptide. Class XII anti-inflammatory polypeptides can comprise, consist essentially of, or consist of a striapathic region that includes a sequence selected from the group of sequences defined by Formula XLIX:

$$Y_{1a}\text{-}X_{1a}\text{-}Y_{2a}\text{-}X_{2a}\text{-}Y_{3a}\text{-}X_{3a} \qquad \text{(Formula XLIX)}.$$

Amino acid residues $Y_{1a}$, $Y_{2a}$, and $Y_{3a}$ of Formula XLIX can be each independently selected from the group consisting of Phe (F), Trp (W), Tyr (Y), Leu (L), Ile (I), Cys (C), Met (M), Val (V), Pro (P), Thr (T), Ser (S), Ala (A), and Gly (G). In certain embodiments, amino acid residues $Y_{1a}$, $Y_{2a}$, and $Y_{3a}$ of Formula XLIX are each independently selected from: the group consisting of Phe (F), Trp (W), and Tyr (Y); the group consisting of Phe (F), Trp (W), Tyr (Y), and Leu (L); or the group consisting of Phe (F), Trp (W), Tyr (Y), Leu (L), Ile (I), Cys (C), Met (M), Val (V), and Ala (A).

Amino acid residues $X_{1a}$, $X_{2a}$, and $X_{3a}$ of Formula XLIX can be each independently selected from the group consisting of Arg (R), Lys (K), His (H), Gln (Q), Glu (E), Asn (N), and Asp (D). In certain embodiments, amino acid residues $X_{1a}$, $X_{2a}$, and $X_{3a}$ are each independently selected from the group consisting of Arg (R), Lys (K), and His (H). Alternatively, amino acid residues $X_{1a}$, $X_{2a}$, and $X_{3a}$ are each independently selected from the group consisting of Arg (R), Lys (K), His (H), and Gln (Q).

A Class XII anti-inflammatory polypeptide can comprise, consist essentially of, or consist of a striapathic region that further includes a first additional amino acid residue. The first additional amino acid residue can be a hydrophilic amino acid residue directly bound to amino acid residue $Y_{1a}$ of Formula XLIX. Thus, the first additional amino acid residue can be, for example, a residue selected from the group consisting of Arg (R), Lys (K), His (H), Asn (N), Gln (Q), Asp (D), and Glu (E); a residue selected from the group consisting of Arg (R), Lys (K), and His (H); a residue selected from the group consisting Arg (R), Lys (K), His (H), and Gln (Q); or a residue selected from the group consisting of Asn (N), Gln (Q), Asp (D), and Glu (E)). Alternatively, the first amino acid residue can be a hydrophobic amino acid residue directly bound to amino acid residue $X_{3a}$ of Formula XLIX. Thus, the first additional amino acid residue can be, for example, a residue selected from the group consisting of Phe (F), Trp (W), and Tyr (Y); a residue selected from the group consisting of Phe (F), Trp (W), Tyr (Y), and Leu (L); or a residue selected from the group consisting of Phe (F), Trp (W), Tyr (Y), Leu (L), Ile (I), Cys (C), Met (M), Val (V), and Ala (A)).

A Class XII anti-inflammatory polypeptide can comprise, consist essentially of, or consist of a striapathic region that further includes first and second additional amino acid residues. The first additional amino acid residue can be a hydrophilic amino acid residue, as discussed above, which is directly bound to amino acid residue $Y_{1a}$ of Formula XLIX. The second additional amino acid residue can be directly bound to the first additional amino acid residue. Thus, the second additional amino acid residue can be a hydrophobic amino acid residue, e.g., a residue selected from the group consisting of Phe (F), Trp (W), Tyr (Y), Leu (L), Cys (C), Met (M), Val (V), Ile (I), Thr (T), Pro (P), Ser (S), Ala (A), and Gly (G); a residue selected from the group consisting of Phe (F), Trp (W), and Tyr (Y); a residue selected from the group consisting of Phe (F), Trp (W), Tyr (Y), and Leu (L); or, a residue selected from the group consisting of Leu (L), Cys (C), Met (M), Val (V), and Ile (I)). Alternatively, the second additional amino acid residue can be a hydrophobic amino acid residue directly bound to amino acid residue $X_{3a}$ of Formula XLIX, as discussed above.

A Class XII anti-inflammatory polypeptide can comprise, consist essentially of, or consist of a striapathic region that further includes first, second, and third additional amino acid residues. The first additional amino acid residue can be a hydrophilic amino acid residue which is directly bound to amino acid residue $Y_{1a}$ of Formula XLIX and the second additional amino acid residue can be a hydrophobic amino acid residue which is directly bound to the first additional amino acid residue, as discussed above. The third additional amino acid residue can be a hydrophilic amino acid residue that is directly bound to the second additional amino acid residue. Thus, the third additional amino acid residue can be, for example, a residue selected from the group consisting of Arg (R), Lys (K), His (H), Asn (N), Gln (Q), Asp (D), and Glu (E); a residue selected from the group consisting of Arg (R), Lys (K), and His (H); a residue selected from the group consisting Arg (R), Lys (K), His (H), and Gln (Q); or a residue selected from the group consisting of Asn (N), Gln (Q), Asp (D), and Glu (E)). Alternatively, the third amino acid residue can be a hydrophobic amino acid residue directly bound to amino acid residue $X_{3a}$ of Formula XLIX. Thus, the third additional amino acid residue can be, for example, a residue selected from the group consisting of Phe (F), Trp (W), and Tyr (Y); a residue selected from the group consisting of Phe (F), Trp (W), Tyr (Y), and Leu (L); or a residue selected from the group consisting of Phe (F), Trp (W), Tyr (Y), Leu (L), Ile (I), Cys (C), Met (M), Val (V), and Ala (A)).

A Class XII anti-inflammatory polypeptide can comprise, consist essentially of, or consist of a striapathic region that further includes four, five, six, or more additional amino acid residues. The additional amino acid residue can be added in a manner that continues the alternating patter of a hydrophobic amino acid residue followed by a hydrophilic amino acid residue followed by a hydrophobic amino acid residue, as shown in Formula XLIX. In this manner, Class XII anti-inflammatory polypeptides can be expanded to comprise, consist essentially of, or consist of a striapathic region having 10, 11, 12, or more amino acid residues.

An anti-inflammatory polypeptide of Class XII can comprise, consist essentially of, or consist of a striapathic region comprising, consisting essentially of, or consisting of a sequence selected from the group consisting of RP393, RP391, PR392, RP390, and RP389.

Class XIV Polypeptides

An anti-inflammatory polypeptide of the invention can be a Class XIV polypeptide. Class XIV anti-inflammatory polypeptides can comprise, consist essentially of, or consist of a striapathic region that includes a sequence selected from the group of sequences defined by any one of Formulas LI through LIV:

$$X_{1a}\text{-}X_{1b}\text{-}Y_{1a}\text{-}Y_{1b}\text{-}X_{2a}\text{-}Y_{2a}\text{-}Y_{2b}\text{-}Y_{2c}\text{-}Y_{2d} \qquad \text{(Formula LI)};$$

$$Y_{1a}\text{-}Y_{1b}\text{-}Y_{1c}\text{-}Y_{1d}\text{-}X_{1a}\text{-}Y_{2a}\text{-}Y_{2b}\text{-}X_{2a}\text{-}X_{2b} \qquad \text{(Formula LII)};$$

$$Y_{1a}\text{-}Y_{1b}\text{-}X_{1a}\text{-}Y_{2a}\text{-}Y_{2b}\text{-}Y_{2c}\text{-}X_{2b}\text{-}Y_{3a}\text{-}X_{3a}\text{-}Y_{4a} \qquad \text{(Formula LIII)};$$

and $$Y_{1a}\text{-}X_{1a}\text{-}Y_{2a}\text{-}X_{2a}\text{-}Y_{3a}\text{-}Y_{3b}\text{-}Y_{3c}\text{-}X_{3a}\text{-}Y_{4a}\text{-}Y_{4b} \qquad \text{(Formula LIV)}.$$

The striapathic region of a Class XIV polypeptide can include at least 3 (e.g., 3 to 6) proline amino acid residues.

For example, amino acid residues $Y_{1a}$, $Y_{2a}$, and $Y_{2b}$ in Formula LI can be proline amino acid residues. Alternatively, amino acid residues $Y_{1c}$, $Y_{1d}$, and $Y_{2b}$ in Formula LII can be proline amino acid residues. In other alternatives, amino acid residues $Y_{1a}$, $Y_{2a}$, $Y_{2b}$, $Y_{2c}$, $Y_{3a}$, and $Y_{4a}$ in Formula LIII can be proline amino acid residues. In still other alternatives, amino acid residues $Y_{1a}$, $Y_{2b}$, $Y_{3a}$, $Y_{3b}$, $Y_{3c}$, and $Y_{4b}$ in Formula LIV can be proline amino acid residues.

Hydrophobic amino acid residues (e.g., $Y_{1a}$, $Y_{1b}$, $Y_{1c}$, $Y_{1d}$, $Y_{2a}$, $Y_{2b}$, $Y_{2c}$, $Y_{2d}$, $Y_{3a}$, $Y_{3b}$, $Y_{3c}$, $Y_{4a}$, and $Y_{4b}$) not designated as proline residues in Formulas LI through LIV can be each individually selected from the group consisting of Phe (F), Trp (W), Tyr (Y), Leu (L), Cys (C), Met (M), Val (V), Ile (I), Thr (T), Pro (P), Ser (S), Ala (A), and Gly (G). In certain embodiments, such hydrophobic amino acid residues are each individually selected from: the group consisting of Phe (F), Trp (W), and Tyr (Y); the group consisting of Phe (F), Trp (W), Tyr (Y), and Leu (L); or, the group consisting of Leu (L), Cys (C), Met (M), Val (V), and Ile (I)).

Hydrophilic amino acid residues in Formulas LI through LIV (e.g., $X_{1a}$, $X_{1b}$, $X_{2a}$, $X_{2b}$, and $X_{3a}$) can be each individually selected from the group consisting of Arg (R), Lys (K), His (H), Asn (N), Gln (Q), Asp (D), and Glu (E). In certain embodiments, such hydrophilic amino acid residues are each individually selected from the group consisting of Arg (R), Lys (K), and His (H). Alternatively, such hydrophilic amino acid residues are each individually selected from: the group consisting of Arg (R), Lys (K), His (H), and Gln (Q); or the group consisting of Asn (N), Gln (Q), Asp (D), and Glu (E).

An anti-inflammatory polypeptide of Class XIV can comprise, consist essentially of, or consist of a striapathic region that comprises, consists essentially of, or consists of a sequence selected from the group consisting of RP449, RP450, RP448, RP447, RP452, RP451, RP444, RP441, RP446, RP445, RP442, and RP443.

Other Classes of Polypeptides

An anti-inflammatory polypeptide of the invention can be from any of Classes II through XI and XIII. Such anti-inflammatory polypeptides can comprise, consist essentially of, or consist of a striapathic region that includes a sequence selected from the group of sequences defined by any one of Formulas IV through XLVIII and L.

Hydrophobic amino acid residues in Formulas IV through XLVIII and L (e.g., $Y_{1a}$, $Y_{1b}$, $Y_{1c}$, $Y_{1d}$, $Y_{1e}$, $Y_{2a}$, $Y_{2b}$, $Y_{2c}$, $Y_{2d}$, $Y_{2e}$, $Y_{3a}$, $Y_{3b}$, $Y_{3c}$, $Y_{4a}$, and $Y_{4b}$) can be each individually selected from the group consisting of Phe (F), Trp (W), Tyr (Y), Leu (L), Cys (C), Met (M), Val (V), Ile (I), Thr (T), Pro (P), Ser (S), Ala (A), and Gly (G). In certain embodiments, such hydrophobic amino acid residues are each individually selected from: the group consisting of Phe (F), Trp (W), and Tyr (Y); the group consisting of Phe (F), Trp (W), Tyr (Y), and Leu (L); or, the group consisting of Leu (L), Cys (C), Met (M), Val (V), and Ile (I)).

Hydrophilic amino acid residues in Formulas IV through XLVIII and L (e.g., $X_{1a}$, $X_{1b}$, $X_{1c}$, $X_{1d}$, $X_{2a}$, $X_{2b}$, $X_{2c}$, $X_{2d}$, $X_{3a}$, $X_{3b}$, $X_{3c}$, $X_{4a}$, and $X_{4b}$) can be each individually selected from the group consisting of Arg (R), Lys (K), His (H), Asn (N), Gln (Q), Asp (D), and Glu (E). In certain embodiments, such hydrophilic amino acid residues are each individually selected from the group consisting of Arg (R), Lys (K), and His (H). Alternatively, such hydrophilic amino acid residues are each individually selected from: the group consisting of Arg (R), Lys (K), His (H), and Gln (Q); or the group consisting of Asn (N), Gln (Q), Asp (D), and Glu (E).

An anti-inflammatory polypeptide of any one of Formulas IV through XLVIII and L can comprise, consist essentially of, or consist of a striapathic region that further includes a first additional amino acid residue directly bound to the first amino acid residue of the Formula (e.g., $Y_{1a}$ or $X_{1a}$) or to the last amino acid residue in the formula. The first additional amino acid residue can be a hydrophilic amino acid residue (e.g., a residue selected from the group consisting of Arg (R), Lys (K), His (H), Asn (N), Gln (Q), Asp (D), and Glu (E); a residue selected from the group consisting of Arg (R), Lys (K), and His (H); a residue selected from the group consisting Arg (R), Lys (K), His (H), and Gln (Q); or a residue selected from the group consisting of Asn (N), Gln (Q), Asp (D), and Glu (E)). Alternatively, the first additional amino acid residue can be a hydrophobic amino acid residue (e.g., a residue selected from the group consisting of Phe (F), Trp (W), Tyr (Y), Leu (L), Cys (C), Met (M), Val (V), Ile (I), Thr (T), Pro (P), Ser (S), Ala (A), and Gly (G); a residue selected from the group consisting of Phe (F), Trp (W), and Tyr (Y); a residue selected from the group consisting of Phe (F), Trp (W), Tyr (Y), and Leu (L); or, a residue selected from the group consisting of Leu (L), Cys (C), Met (M), Val (V), and Ile (I)).

An anti-inflammatory polypeptide of any one of Formulas IV through XLVIII and L can comprise, consist essentially of, or consist of a striapathic region that further includes first and second additional amino acid residues, with the first additional amino acid residue directly bound to the first amino acid residue of the Formula (e.g., $Y_{1a}$ or $X_1$) or the last amino acid residue in the formula, and the second additional amino acid residue directly bound to the first amino acid residue in the formula, the last amino acid residue in the formula, or the first additional amino acid residue. The first additional amino acid residue can be a hydrophilic or hydrophobic amino acid residue, as discussed above. The second additional amino acid residue likewise can be a hydrophilic or hydrophobic amino acid residue, as discussed above.

An anti-inflammatory polypeptide of any one of Formulas IV through XLVIII and L can comprise, consist essentially of, or consist of a striapathic region that comprises, consists essentially of, or consists of a sequence selected from the group consisting of RP396, RP405, RP174, RP176, RP178, RP180-181, RP184, RP408, RP187, RP416, RP188, RP189, RP388, RP417, RP191-RP193, RP404, RP196, RP397, RP197, RP402, RP203, RP409, RP205, RP208, RP217, RP220-RP224, RP226, RP229, RP231, RP240, RP248, RP249, RP415, RP257, RP259-RP266, RP269, RP272, RP274, RP277-RP279, RP282, RP283, RP286, RP289, and RP414.

Variant Polypeptides

The exemplary anti-inflammatory polypeptide sequences shown in Tables 3-9 (below) are merely examples and are not the only anti-inflammatory polypeptides provided herein. Indeed, fragments and variants of the sequences of the disclosed peptides are within the scope of the invention.

A "fragment" of the invention includes at least 6, 7, 8, 9, 10, 11, 12, 13, 14, 15, 16, 17, 18, 19, 20, 21, 22, or 23 contiguous amino acid residues of a polypeptide disclosed herein (or up to one less than the number of amino acid residues in the subject polypeptide) and retains at least one anti-inflammatory property of the subject polypeptide. Thus, fragments of the invention include polypeptides that are missing one, two, three, four, or more amino acids from the N-terminus and/or the C-terminus relative to a polypeptide disclosed herein.

A "variant" of the invention is a polypeptide that is substantially similar to a polypeptide disclosed herein and retains at least one anti-inflammatory property of the subject polypeptide. Variants can include deletions (i.e., truncations) of one or more amino acid residues at the N-terminus or the C-terminus of a subject polypeptide disclosed herein; deletion and/or addition of one or more amino acid residues at one or more internal sites in the subject polypeptide disclosed herein; and/or substitution of one or more amino acid residues at one or more positions in the subject polypeptide disclosed herein. For subject polypeptides that are 12 amino acid residues in length or shorter, variant polypeptides can include three or fewer (e.g., two, one, or none) deleted amino acid residues, whether located internally, at the N-terminal end, and/or at the C-terminal end.

Accordingly, the invention further provides anti-inflammatory polypeptides that are at least 50% identical (e.g., at least 60%, 70%, 80%, 90%, or more) to any one of the anti-inflammatory polypeptides disclosed in Tables 3-9 and still retain at least one anti-inflammatory property. For example, the invention provides anti-inflammatory polypeptides that are 3 to 24 amino acids residues in length and comprise, consist essentially of, or consist of a striapathic region sharing at least 50% identity (e.g., at least 60%, 70%, 80%, 90%, or more identity) with a Class I anti-inflammatory polypeptide (e.g., any one of the sequences of Table 3). Such identity can be shared, for example, with RP-394 (SEQ ID NO: 33), RP-108 (SEQ ID NO: 34), RP-113 (SEQ ID NO: 39), RP-118 (SEQ ID NO: 44), RP-129 (SEQ ID NO: 54), or RP-179 (SEQ ID NO: 86). Alternatively, the invention provides anti-inflammatory polypeptides that are 3 to 24 amino acid residues in length and comprise, consist essentially of, or consist of a striapathic region sharing at least 50% identity (e.g., at least 60%, 70%, 80%, 90%, or more identity) with a Class II, Sub-class 1 anti-inflammatory polypeptide (e.g., any one of the sequences of Table 5). Such identity can be shared, for example, with RP-124 (SEQ ID NO: 106), RP-134 (SEQ ID NO: 108), RP-166 (SEQ ID NO: 112), RP-168 (SEQ ID NO: 114), RP-182 (SEQ ID NO: 121), or RP-183 (SEQ ID NO: 122). In other alternatives, the invention provides anti-inflammatory polypeptides that are 3 to 24 amino acid residues in length and comprise, consist essentially of, or consist of a striapathic region sharing at least 50% identity (e.g., at least 60%, 70%, 80%, 90%, or more identity) with any Class II through Class IX or Class XIII anti-inflammatory polypeptide (e.g., any one of the sequences of Table 6). In other alternatives, the invention provides anti-inflammatory polypeptides that are 3 to 24 amino acid residues in length and comprise, consist essentially of, or consist of a striapathic region sharing at least 50% identity (e.g., at least 60%, 70%, 80%, 90%, or more identity) with any Class VIII to Class XI anti-inflammatory polypeptide (e.g., any one of the sequences of Table 7). In other alternatives, the invention provides anti-inflammatory polypeptides that are 3 to 24 amino acid residues in length and comprise, consist essentially of, or consist of a striapathic region sharing at least 50% identity (e.g., at least 60%, 70%, 80%, 90%, or more identity) with a Class XII or Class XIV anti-inflammatory polypeptide (e.g., any one of the sequences of Table 8). In still other alternatives, the invention provides anti-inflammatory polypeptides that are 3 to 24 amino acid residues in length and comprise, consist essentially of, or consist of a striapathic region sharing at least 50% identity (e.g., at least 60%, 70%, 80%, 90%, or more identity) with any one of the combination sequences of Table 9.

The differences between the striapathic region of a homologous anti-inflammatory polypeptide and any one of the anti-inflammatory polypeptides of Tables 3-9 can include deletions, additions, and/or substitutions of amino acid residues, as discussed above. Substituted amino acid residues can be unrelated to the amino acid residue being replaced (e.g., unrelated in terms or hydrophobicity/hydrophilicity, size, charge, polarity, etc.), or the substituted amino acid residues can constitute similar, conservative, or highly conservative amino acid substitutions. As used herein, "similar," "conservative," and "highly conservative" amino acid substitutions are defined as shown in Table 2, below. The determination of whether an amino acid residue substitution is similar, conservative, or highly conservative is based exclusively on the side chain of the amino acid residue and not the peptide backbone, which may be modified to increase peptide stability, as discussed below.

TABLE 2

Classification of Amino Acid Substitutions

| Amino Acid in Subject Polypeptide | Similar Amino Acid Substitutions | Conservative Amino Acid Substitutions | Highly Conservative Amino Acid Substitutions |
|---|---|---|---|
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T, K | A | n/a |
| Methionine (M) | L, I, V, F | L, I, V | L, I |
| Valine (V) | I, L, M, T, A | I, L, M | I |
| Leucine (L) | M, I, V, F, T, A | M, I, V, F | M, I |
| Isoleucine (I) | V, L, M, F, T, C | V, L, M, F | V, L, M |
| Phenylalanine (F) | W, L, M, I, V | W, L | n/a |
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K | R, K | R, K |
| Lysine (K) | R, H | R, H | R, H |
| Arginine (R) | KH | K, H | K, H |

In certain embodiments, a variant polypeptide of the invention binds to two or more targets (e.g., pro-inflammatory targets). In some embodiments, a variant polypeptide binds to three, four, five, or more pro-inflammatory targets. For example, a variant polypeptide can bind to any combination of targets disclosed herein (e.g., an NF-kB Class II protein and human serum albumin (HSA)), as discussed below. Such binding can be based on in silico, in vitro, or in vivo data.

Modeling Polypeptide Binding to Target Molecules

The determination of whether a polypeptide has anti-inflammatory properties can be performed in silico. For example, the binding of a polypeptide (e.g., a polypeptide that has a length of 3 to 24 amino acid residues and includes a striapathic region comprising at least 25% of the length of the polypeptide) to a putative target molecule can be modeled in silico, using any of the numerous molecular modeling and docking platforms available in the art, to thereby assess whether the polypeptide is an anti-inflammatory polypeptide. The on-line ClusPro™ algorithm, version 2.0 (developed at Boston University) is particularly useful for modeling the conformation of polypeptides and their binding to target molecules, such as signaling proteins, as described in the Examples set forth below. Modeling algorithms, such as the ClusPro™ algorithm, that allow for docking of polypeptides on target molecules can be used, for example, to predict the binding energy associated with the polypeptide-target interaction. Such predictions provide reasonable estimates for the binding energies, but they are not necessarily equal to the binding energies that would be calculated by testing the polypeptides and protein targets in vitro. In that regard, the binding energies identified herein were all generated using the ClusPro™ algorithm. Accordingly, absent indication to the contrary, any numerical reference to the binding energy associated with a peptide binding to a particular target is a reference to a binding energy determined by modeling the interaction using the ClusPro™ algorithm.

As detailed in the Examples below, the exemplary RP peptides have been shown to interact with various signaling molecules associated with inflammation, including NF-kB Class II subunit RelB, TGFβ, Notch1, Wnt8R, TRAIL, IL6R, IL10R, EGFR, and CDK6, as well as other membrane associated signaling molecules, including CD206, CD47 and SIRP-α, translational modification protein transglutaminase 2 (TGM2), and histone modification enzyme histone methyl transferase (HMT). Upon folding of these protein targets to their normal 3-dimensional conformations, an amphipathic cleft is often generated that has high affinity for the immune-modulating peptides herein described.

For modeling interactions between potential anti-inflammatory polypeptides and NF-kB Class II subunits, any Class II subunit sequence can be used (e.g., RelA, RelB, cRel, NF-kB1, or NF-kB2). In certain embodiments, the Class II subunit sequence folds into a functional Class II subunit or a functional fragment thereof. The particular Class II subunit used for modeling can be selected based on the type of subject that the anti-inflammatory polypeptide is intended to treat (e.g., a human NF-kB Class II subunit is selected if the intended subject is a human, a bovine NF-kB Class II subunit is selected if the intended subject is a cow, etc.). The NF-kB Class II subunit sequence used for modeling can be the human RelB sequence (NCBI Accession No. NP-006500), which is as follows:

(SEQ ID NO: 367)
MLRSGPASGPSVPTGRAMPSRRVARPPAAPELGALGSPDLSSLSLAVSRSTDELEIIDEYIKENG

FGLDGGQPGPGEGLPRLVSRGAASLSTVTLGPVAPPATPPPWGCPLGRLVSPAPGPGPQPHLVIT

EQPKQRGMRFRYECEGRSAGSILGESSTEASKTLPAIELRDCGGLREVEVTACLVWKDWPHRVHP

HSLVGKDCTDGICRVRLRPHVSPRHSFNNLGIQCVRKKEIEAAIERKIQLGIDPYNAGSLKNHQE

VDMNVVRICFQASYRDQQGQMRRMDPV<u>LSEPVYDKKSTNTSELRICRINKESGPCIGGEELYLLC</u>

<u>DKVQKEDISVVFSRASWEGRADFSQADVHRQIAIVFKTPPYEDLEIVEPVTVNVFLQRLTDGVCS</u>

<u>EPLPFTYLPRDHDSYGVDKKRKRGMPDVLGELNSSDPHGIESKRRKKKPAILDHFLPNHGSGPFL</u>

PPSALLPDPDFFSGTVSLPGLEPPGGPDLLDDGFAYDPTAPTLFTMLDLLPPAPPHASAVVCSGG

AGAVVGETPGPEPLTLDSYQAPGPGDGGTASLVGSNMFPNHYREAAFGGGLLSPGPEAT.

The underlined sequence in human RelB (above) has been identified as the dimerization domain. The highlighted amino acid residues (Tyr-300, Leu-302, and His-332) are believed to be particularly important in the dimerization interaction.

An anti-inflammatory polypeptide can be identified based on its ability to bind (e.g., in silico) to the dimerization pocket of the Class II subunit and/or interfere with or block the ability of the Class II subunit to dimerize. For example, the anti-inflammatory polypeptide can bind to at least one amino acid residue of human RelB (SEQ ID NO: 367) selected from the group consisting of Leu-281, Ile-283, Cys-284, Glu-298, Tyr-300, Leu-301, Leu-302, Cys-303, Ile-311, Ser-312, Ala-329, Asp-330, Val-331, His-332, Gln-334, and Leu-371, or the equivalent amino acid residue(s) in a different human NF-kB Class II protein or an NF-kB Class II protein of another species. Alternatively, the anti-inflammatory polypeptide can bind to at least one amino acid residue of human RelB (SEQ ID NO: 367) selected from the group consisting of Glu-298, Tyr-300, Leu-302, Asp-330, Gln-334, and Leu-371 or the equivalent amino acid residue(s) in a different human NF-kB Class II protein or an NF-kB Class II protein of another species.

In certain embodiments, an anti-inflammatory polypeptide binds to human RelB (SEQ ID NO: 367) with an affinity of at least −650 kcal/mol, and in certain embodiments at least −700, −750, −800, −850, −900, −925, −950, −975, −1000, −1025, −1050, −1075, −1100, −1125, −1150, −1200 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and TGFβ, any TGFβ protein sequence can be used. The TGFβ sequence generally folds into a functional TGFβ protein or a functional fragment thereof. The TGFβ protein sequence used for modeling can be selected based on the type of subject that the anti-inflammatory polypeptide is intended to treat (e.g., a human TGFβ is selected if the intended subject is a human, a bovine TGFβ is selected if the intended subject is a cow, etc.). The sequence used for modeling can be the human TGFβ sequence (NCBI Acc. No. NP_000651.3), which is as follows:

(SEQ ID NO: 368)
MPPSGLRLLPLLLPLLWLLVLTPGRPAAGLSTCKTIDMELVKRKRIE

AIRGQILSKLRLASPPSQGEVPPGPLPEAVLALYNSTRDRVAGESAE

-continued

PEPEPEADYYAKEVTRVLMVETHNEIYDKFKQSTHSIYMFFNTSELR

EAVPEPVLLSRAELRLLRLKLKVEQHVELYQKYSNNSWRYLSNRLLA

PSDSPEWLSFDVTGVVRQWLSRGGEIEGFRLSAHCSCDSRDNTLQVD

INGFTTGRRGDLATIHGMNRPFLLLMATPLERAQHLQSSRHRRALDT

NYCFSSTEKNCCVRQLYIDFRKDLGWKWIHEPKGYHANFCLGPCPYI

WSLDTQYSKVLALYNQHNPGASAAPCCVPQALEPLPIVYYVGRKPKV

EQLSNMIVRSCKCS.

An anti-inflammatory polypeptide can be identified, for example, based on its ability to bind to the receptor binding site on TGFβ and/or interfere with or block the ability of TGFβ to bind to its receptor. For example, the anti-inflammatory polypeptide can bind to at least one amino acid residue of human TGFβ (SEQ ID NO: 368) selected from the group consisting of Arg-25, Gly-29, Trp-30, Lys-31, Trp-32, Ile-33, His-34, Tyr-91, Val-92, Val-93, Gly-94, Arg-95, Lys-96, and Pro-97, or the equivalent amino acid residue(s) in a TGFβ protein of another species. Alternatively, the anti-inflammatory polypeptide can bind to at least one amino acid residue of human TGFβ (SEQ ID NO: 368) selected from the group consisting of Leu-20, Ile-22, Phe-24, Asp-27, Leu-28, Trp-30, Trp-32, Tyr-39, Phe-43, Pro-80, Leu-83, Leu-101 and Ser-112, or the equivalent amino acid residue(s) in a TGFβ protein of another species. In other alternatives, the anti-inflammatory polypeptide can bind to at least one amino acid residue of human TGFβ (SEQ ID NO: 368) selected from the group consisting of Asp-27, Leu-28, Trp-30, and Trp-32, or the equivalent amino acid residue(s) in a TGFβ protein of another species.

In certain embodiments, an anti-inflammatory polypeptide can bind to human TGFβ (SEQ ID NO: 368) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and Notch1, any Notch1 protein sequence can be used. The Notch1 sequence used for modeling generally folds into a functional Notch1 protein or a calcium-binding fragment thereof. The Notch1 sequence used for modeling can be selected based on the type of subject that the anti-inflammatory polypeptide is intended to treat (e.g., a human Notch1 is selected if the intended subject is a human, a bovine Notch1 is selected if the intended subject is a cow, etc.). The sequence used for modeling can be the human Notch1 sequence (GenBank Acc. No. AAG33848.1), which is as follows:

```
                                           (SEQ ID NO: 369)
MPPLLAPLLCLALLPALAARGPRCSQPGETCLNGGKCEAANGTEACV

CGGAFVGPRCQDPNPCLSTPCKNAGTCHVVDRRGVADYACSCALGFS

GPLCLTPLDNACLTNPCRNGGTCDLLTLTEYKCRCPPGWSGKSCQQA

DPCASNPCANGGQCLPFEASYICHCPPSFHGPTCRQDVNECGQKPRL

CRHGGTCHNEVGSYRCVCRATHTGPNCERPYVPCSPSPCQNGGTCRP

TGDVTHECACLPGFTGQNCEENIDDCPGNNCKNGGACVDGVNTYNCP

CPPEWTGQYCTEDVDECQLMPNACQNGGTCHNTHGGYNCVCVNGWTG

EDCSENIDDCASAACFHGATCHDRVASFYCECPHGRTGLLCHLNDAC

ISNPCNEGSNCDTNPVNGKAICTCPSGYTGPACSQDVDECSLGANPC

EHAGKCINTLGSFECQCLQGYTGPRCEIDVNECVSNPCQNDATCLDQ

IGEFQCMCMPGYEGVHCEVNTDECASSPCLHNGRCLDKINEFQCECP

TGFTGHLCQYDVDECASTPCKNGAKCLDGPNTYTCVCTEGYTGTHCE

VDIDECDPDPCHYGSCKDGVATFTCLCRPGYTGHHCETNINECSSQP

CRLRGTCQDPDNAYLCFCLKGTTGPNCEINLDDCASSPCDSGTCLDK

IDGYECACEPGYTGSMCNSNIDECAGNPCHNGGTCEDGINGFTCRCP

EGYHDPTCLSEVNECNSNPCVHGACRDSLNGYKCDCDPGWSGTNCDI
```

```
-continued
NNNECESNPCVNGGTCKDMTSGIVCTCREGFSGPNCQTNINECASNP

CLNKGTCIDDVAGYKCNCLLPYTGATCEVVLAPCAPSPCRNGGECRQ

SEDYESFSCVCPTAGAKGQTCEVDINECVLSPCRHGASCQNTHGXYR

CHCQAGYSGRNCETDIDDCRPNPCHNGGSCTDGINTAFCDCLPGFRG

TFCEEDINECASDPCRNGANCTDCVDSYTCTCPAGFSGIHCENNTPD

CTESSCFNGGTCVDGINSFTCLCPPGFTGSYCQHVVNECDSRPCLLG

GTCQDGRGLHRCTCPQGYTGPNCQNLVHWCDSSPCKNGGKCWQTHTQ

YRCECPSGWTGLYCDVPSVSCEVAAQRQGVDVARLCQHGGLCVDAGN

THHCRCQAGYTGSYCEDLVDECSPSPCQNGATCTDYLGGYSCKCVAG

YHGVNCSEEIDECLSHPCQNGGTCLDLPNTYKCSCPRGTQGVHCEIN

VDDCNPPVDPVSRSPKCFNNGTCVDQVGGYSCTCPPGFVGERCEGDV

NECLSNPCDARGTQNCVQRVNDFHCECRAGHTGRRCESVINGCKGKP

CKNGGTCAVASNTARGFICKCPAGFEGATCENDARTCGSLRCLNGGT

CISGPRSPTCLCLGPFTGPECQFPASSPCLGGNPCYNQGTCEPTSES

PFYRCLCPAKFNGLLCHILDYSFGGGAGRDIPPPLIEEACELPECQE

DAGNKVCSLQCNNHACGWDGGDCSLNFNDPWKNCTQSLQCWKYFSDG

HCDSQCNSAGCLFDGFDCQRAEGQCNPLYDQYCKDHFSDGHCDQGCN

SAECEWDGLDCAEHVPERLAAGTLVVVVLMPPEQLRNSSFHFLRELS

RVLHTNVVFKRDAHGQQMIFPYYGREEELRKHPIKRAAEGWAAPDAL

LGQVKASLLPGGSEGGRRRRELDPMDVRGSIVYLEIDNRQCVQASSQ

CFQSATDVAAFLGALASLGSLNIPYKIEAVQSETVEPPPPAQLHFMY

VAAAAFVLLFFVGCGVLLSRKRRRQHGQLWFPEGFKVSEASKKKRRE

PLGEDSVGLKPLKNASDGALMDDNQNEWGDEDLETKKFRFEEPVVLP

DLDDQTDHRQWTQQHLDAADLRMSAMAPTPPQGEVDADCMDVNVRGP

DGFTPLMIASCSGGGLETGNSEEEEDAPAVISDFIYQGASLHNQTDR

TGETALHLAARYSRSDAAKRLLEASADANIQDNMGRTPLHAAVSADA

QGVFQILIRNRATDLDARMHDGTTPLILAARLAVEGMLEDLINSHAD

VNAVDDLGKSALHWAAAVNNVDAAVVLLKNGANKDMQNNREETPLFL

AAREGSYETAKVLLDHFANRDITDHMDRLPRDIAQERMHHDIVRLLD

EYNLVRSPQLHGAPLGGTPTLSPPLCSPNGYLGSLKPGVQGKKVRKP

SSKGLACGSKEAKDLKARRKKSQDGKGCLLDSSGMLSPVDSLESPHG

YLSDVASPPLLPSPFQQSPSVPLNHLPGMPDTHLGIGHLNVAAKPEM

AALGGGGRLAFETGPPRLSHLPVASGTSTVLGSSSGGALNFTVGGST

SLNGQCEWLSRLQSGMVPNQYNPLRGSVAPGPLSTQAPSLQHGMVGP

LHSSLAASALSQMMSYQGLPSTRLATQPHLVQTQQVQPQNLQMQQQN

LQPANIQQQQSLQPPPPPPQPHLGVSSAASGHLGRSFLSGEPSQADV

QPLGPSSLAVHTILPQESPALPTSLPSSLVPPVTAAQFLTPPSQHSY

SSPVDNTPSHQLQVPEHPFLTPSPESPDQWSSSSPHSNVSDWSEGVS

SPPTSMQSQIARIPEAFK.
```

An anti-inflammatory polypeptide can be identified based on its ability to bind to the calcium-binding site on Notch1 and/or interfere with or block the ability of Notch1 to bind to calcium. For example, the anti-inflammatory polypeptide can bind to at least one amino acid residue of human Notch1 (SEQ ID NO: 369) selected from the group consisting of Phe-1520, Gln-1523, Arg-1524, Glu-1526, Ala-1553, Glu-1556, Trp-1557, Cys-1562, His-1602, Arg-1684, Gln-1685, Cys-1686, Ser-1691, Cys-1693, Phe-1694, and Phe-1703, or the equivalent amino acid residue(s) in a Notch1 protein of another species. Alternatively, the anti-inflammatory polypeptide can bind to at least one amino acid residue of human Notch1 (SEQ ID NO: 369) selected from the group consisting of Phe-1520, Trp-1557, Cys-1562, and Phe-1703, or the equivalent amino acid residue(s) in a Notch1 protein of another species.

In certain embodiments, a polypeptide of the invention binds to human Notch1 (SEQ ID NO: 369) with an affinity of at least −650 kcal/mol, and in certain embodiments at least −700, −750, −800, −850, −900, −925, −950, −975, −1000, −1025, −1050, −1075 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and Wnt8R, any Wnt8R protein sequence can be used. The Wnt8R sequence used for modeling generally folds into a functional Wnt8R protein or a Wnt8-binding fragment thereof. The Wnt8R protein sequence used for modeling can be selected based on the type of subject that the anti-inflammatory polypeptide is intended to treat (e.g., a human Wnt8R is selected if the intended subject is a human, a bovine Wnt8R is selected if the intended subject is a cow, etc.). The sequence used for modeling can be, for example, the bovine Wnt8R sequence (NCBI Acc. No. XP_005214377.1), which is as follows:

```
                                        (SEQ ID NO: 370)
MEWGYLLEVTSLLAALALLQRSSGAAAASAKELACQEITVPLCKGIG

YNYTYMPNQFNHDTQDEAGLEVHQFWPLVEIQCSPDLKFFLCSMYTP

ICLEDYKKPLPPCRSVCERAKAGCAPLMRQYGFAWPDRMRCDRLPEQ

GNPDTLCMDYNRTDLTTAASSVDGDPVAGICYVGNQSLDNLLGFVLA

PLVIYLFIGTMFLLAGFVSLFRIRSVIKQQGGPTKTHKLEKLMIRLG

LFTVLYTVPAAVVVACLFYEQHNRPRWEATHNCPCLRDLQPDQARRP

DYAVFMLKYFMCLVVGITSGVWVWSGKTLESWRALCTRCCWASKGAG

AAGAGAAGGGPGGGGPGAGGGGPGAGGAGSLYSDVSTGLTWRSGTA

SSVSYPKQMPLSQV.
```

An anti-inflammatory polypeptide can be identified based on its ability to bind to a Wnt ligand-binding site on Wnt8R and/or interfere with or block the ability of Wnt8R to bind to a Wnt ligand (e.g., Wnt8). For example, the anti-inflammatory polypeptide can bind to at least one amino acid residue of bovine Wnt8R (SEQ ID NO: 370) selected from the group consisting of Tyr-52, Gln-56, Phe-57, Asn-58, Met-91, Tyr-100, Lys-101, Pro-103, Pro-105, Pro-106, Arg-137 and Asp-145, or the equivalent amino acid residue(s) in a Wnt8R protein of another species. Alternatively, the anti-inflammatory polypeptide can bind to at least one amino acid residue of bovine Wnt8R (SEQ ID NO: 370) selected from the group consisting of Tyr-52, Phe-57, Tyr-100, and Asp-145, or the equivalent amino acid residue(s) in a Wnt8R protein of another species.

In certain embodiments, a polypeptide of the invention binds to bovine Wnt8R (SEQ ID NO: 370) with an affinity of at least −600 kcal/mol, and in certain embodiments at least −650, −700, −750, −800, −850, −875, −900, −925, −950, −975 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and TRAIL, any TRAIL protein sequence can be used. The TRAIL sequence used for modeling in certain embodiments folds into a function TRAIL protein or a functional fragment thereof. The TRAIL protein sequence used for modeling can be selected based on the type of subject that the anti-inflammatory polypeptide is intended to treat (e.g., a human TRAIL is selected if the intended subject is a human, a bovine TRAIL is selected if the intended subject is a cow, etc.). The sequence used for modeling can be the human TRAIL sequence (GenBank Acc. No. EAW78466.1), which is as follows:

```
                                        (SEQ ID NO: 371)
KEKQQNISPLVRERGPQRVAAHITGTRGRSNTLSSPNSKNEKALGRK

INSWESSRSGHSFLSNLHLRNGELVIHEKGFYYIYSQTYFRFQEEIK

ENTKNDKQMVQYIYKYTSYPDPILLMKSARNSCWSKDAEYGLYSIYQ

GGIFELKENDRIFVSVTNEHLIDMDHEASFFGAFLVG.
```

An anti-inflammatory polypeptide can be identified, for example, based on its ability to bind to the receptor binding site on TRAIL and/or interfere with or block the ability of TRAIL to bind to its receptor. For example, the anti-inflammatory polypeptide can bind to at least one amino acid residue of human TRAIL (SEQ ID NO: 371) selected from the group consisting of Arg-130, Arg-158, Ser-159, Gly-160, His-161, Phe-163, Tyr-189, Arg-189, Gln-193, Glu-195, Glu-236, Tyr-237, Leu-239, Asp-267, Asp-269, His-270, and Glu-271, or the equivalent amino acid residue(s) in a TRAIL protein of another species. Alternatively, the anti-inflammatory polypeptide can bind to at least one amino acid residue of human TRAIL (SEQ ID NO: 371) selected from the group consisting of Ala-123, His-161, Ser-162, Phe-163, Tyr-183, Tyr-185, Tyr-243, His-270, Glu-271, Phe-274, Phe-278, Leu-279, and Val-280, or the equivalent amino acid residue(s) in a TRAIL protein of another species. In other alternatives, the anti-inflammatory polypeptide can bind to at least one amino acid residue of human TRAIL (SEQ ID NO: 371) selected from the group consisting of Phe-163, Tyr-243, Glu-271, and Phe-278, or the equivalent amino acid residue(s) in a TRAIL protein of another species.

In certain embodiments, an anti-inflammatory polypeptide can bind to human TRAIL (SEQ ID NO: 371) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and IL6R, any IL6R protein sequence can be used. The IL6R sequence used for modeling generally folds into a functional IL6R protein or a IL6-binding fragment thereof. The IL6R protein sequence used for modeling can be selected based on the type of subject that the anti-inflammatory polypeptide is intended to treat (e.g., a human IL6R is selected if the intended subject is a human, a bovine IL6R is selected if the intended subject is a cow, etc.). The sequence used for modeling can be the human IL6R sequence (NCBI Acc. No. NP_786943.1), which is as follows:

(SEQ ID NO: 372)
MLTLQTWLVQALFIFLTTESTGELLDPCGYISPESPVVQLHSNFTAV

CVLKEKCMDYFHVNANYIVWKTNHFTIPKEQYTIINRTASSVTFTDI

ASLNIQLTCNILTFGQLEQNVYGITIISGLPPEKPKNLSCIVNEGKK

MRCEWDGGRETHLETNFTLKSEWATHKFADCKAKRDTPTSCTVDYST

VYFVNIEVWVEAENALGKVTSDHINFDPVYKVKPNPPHNLSVINSEE

LSSILKLTWTNPSIKSVIILKYNIQYRTKDASTWSQIPPEDTASTRS

SFTVQDLKPFTEYVFRIRCMKEDGKGYWSDWSEEASGITYEDNIASF.

An anti-inflammatory polypeptide can be identified, for example, based on its ability to bind to the IL6-binding site on IL6R and/or interfere with or block the ability of IL6R to bind to its ligand, IL6. For example, the anti-inflammatory polypeptide can bind to at least one amino acid residue of human IL6R (SEQ ID NO: 372) selected from the group consisting of Glu-163, Gly-164, Phe-168, Gln-190, Phe-229, Tyr-230, Phe-279 and Gln-281, or the equivalent amino acid residue(s) in a IL6R protein of another species. Alternatively, the anti-inflammatory polypeptide can bind to at least one amino acid residue of human IL6R (SEQ ID NO: 372) selected from the group consisting of Leu-108, Glu-140, Pro-162, Phe-229, Tyr-230, and Phe-279, or the equivalent amino acid residue(s) in a IL6R protein of another species. In other alternatives, the anti-inflammatory polypeptide can bind to at least one amino acid residue of human IL6R (SEQ ID NO: 372) selected from the group consisting of Glu-140, Phe-229, Tyr-230, Phe-279, or the equivalent amino acid residue(s) in a IL6R protein of another species.

In certain embodiments, an anti-inflammatory polypeptide can bind to human IL6R (SEQ ID NO: 372) with an affinity of at least −600 kcal/mol, and in certain embodiments at least −650, −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and IL10R, any appropriate IL10R protein sequence can be used. The IL10R sequence used for modeling generally folds into a functional IL10R protein or a IL10-binding fragment thereof. The IL10R protein sequence used for modeling can be selected based on the type of subject that the anti-inflammatory polypeptide is intended to treat (e.g., a human IL10R is selected if the intended subject is a human, a bovine IL10R is selected if the intended subject is a cow, etc.). The sequence used for modeling can be the human IL10R sequence (NCBI Acc. No. NP_001549.2), which is as follows:

(SEQ ID NO: 373)
MLPCLVVLLAALLSLRLGSDAHGTELPSPPSVWFEAEFFHHILHWTP

IPNQSESTCYEVALLRYGIESWNSISNCSQTLSYDLTAVTLDLYHSN

GYRARVRAVDGSRHSNWTVTNTRFSVDEVTLTVGSVNLEIHNGFILG

KIQLPRPKMAPANDTYESIFSHFREYEIAIRKVPGNFTFTHKKVKHE

NFSLLTSGEVGEFCVQVKPSVASRSNKGMWSKEECISLTRQYFTVTN

VIIFFAFVLLLSGALAYCLALQLYVRRRKKLPSVLLFKKPSPFIFIS

QRPSPETQDTIHPLDEEAFLKVSPELKNLDLHGSTDSGFGSTKPSLQ

TEEPQFLLPDPHPQADRTLGNREPPVLGDSCSSGSSNSTDSGICLQE

PSLSPSTGPTWEQQVGSNSRGQDDSGIDLVQNSEGRAGDTQGGSALG

HHSPPEPEVPGEEDPAAVAFQGYLRQTRCAEEKATKTGCLEEESPLT

DGLGPKFGRCLVDEAGLHPPALAKGYLKQDPLEMTLASSGAPTGQWN

QPTEEWSLLALSSCSDLGISDWSFAHDLAPLGCVAAPGGLLGSFNSD

LVTLPLISSLQSSE.

An anti-inflammatory polypeptide can be identified, for example, based on its ability to bind to the IL10-binding site on IL10R and/or interfere with or block the ability of IL10R to bind to its ligand, IL10. For example, the anti-inflammatory polypeptide can bind to at least one amino acid residue of human IL10R (SEQ ID NO: 373) selected from the group consisting of Tyr-43, Ile-45, Glu-46, Asp-61, Asn-73, Arg-76, Asn-94, Arg-96, Phe-143, Ala-189, Ser-190, and Ser-191, or the equivalent amino acid residue(s) in a IL6R protein of another species. Alternatively, the anti-inflammatory polypeptide can bind to at least one amino acid residue of human IL10R (SEQ ID NO: 373) selected from the group consisting of Leu-41, Arg-42, Tyr-43, Ile-45, Glu-46, Ser-47, Trp-48, Arg-76, and Arg-78, or the equivalent amino acid residue(s) in a IL10R protein of another species. In other alternatives, the anti-inflammatory polypeptide can bind to at least one amino acid residue of human IL10R (SEQ ID NO: 373) selected from the group consisting of Tyr-43, Ile-45, Glu-46, Trp-48, or the equivalent amino acid residue(s) in a IL10R protein of another species.

In certain embodiments, an anti-inflammatory polypeptide can bind to human IL10R (SEQ ID NO: 373) with an affinity of at least −600 kcal/mol, and in certain embodiments at least −650, −700, −750, −775, −800, −825, −850, −875, −900 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and EGFR, any EGFR protein sequence can be used. The EGFR sequence used for modeling generally folds into a functional EGFR protein or a ligand-binding fragment thereof. The EGFR protein sequence used for modeling can be selected based on the type of subject that the anti-inflammatory polypeptide is intended to treat (e.g., a human EGFR is selected if the intended subject is a human, a bovine EGFR is selected if the intended subject is a cow, etc.). Alternatively, the sequence used for modeling can be the drosophila EGFR sequence (GenBank Acc. No. AAR85273.1), which is as follows:

(SEQ ID NO: 374)
KICIGTKSRLSVPSNKEHHYRNLRDRYTNCTYVDGNLELTWLPNENL

DLSFLDNIREVTGYILISHVDVKKVVFPKLQIIRGRTLFSLSVEEEK

YALFVTYSKMYTLEIPDLRDVLNGQVGFHNNYNLCHMRTIQWSEIVS

NGTDAYYNYDFTAPERECPKCHESCTHGCWGEGPKNCQKFSKLTCSP

QCAGGRCYGPKPRECCHLFCAGGCTGPTQKDCIACKNFFDEGVCKEE

CPPMRKYNPTTYVLETNPEGKYAYGATCVKECPGHLLRDNGACVRSC

PQDKMDKGGECVPCNGPCPKTCPGVTVLHAGNIDSFRNCTVIDGNIR

ILDQTFSGFQDVYANYTMGPRYIPLDPERLEVFSTVKEITGYLNIEG

THPQFRNLSYFRNLETIHGRQLMESMFAALAIVKSSLYSLEMRNLKQ

ISSGSVVIQHNRDLCYVSNIRWPAIQKEPEQKVWVNENLRADLCEKN

GTICSDQCNEDGCWGAGTDQCLNCKNFNFNGTCIADCGYISNAYKFD

NRTCKICHPECRTCNGAGADHCQECVHVRDGQHCVSECPKNKYNDRG

VCRECHATCDGCTGPKDTIGIGACTTCNLAIINNDATVKRCLLKDDK

CPDGYFWEYVHPQEQGSLKPLAGRAVCRKCHPLCELCTNYGYHEQ.

An anti-inflammatory polypeptide can be identified, for example, based on its ability to bind to the ligand-binding site on EGFR and/or interfere with or block the ability of at least one ligand to bind to EGFR. For example, the anti-inflammatory polypeptide can bind to at least one amino acid residue of drosophila EGFR (SEQ ID NO: 374) selected from the group consisting of Leu-10, Thr-40, Trp-41, Asp-48, Phe-51, Leu-63, His-66, Asp-68, Leu-88, and Tyr-101, or the equivalent amino acid residue(s) in a EGFR protein of another species. Alternatively, the anti-inflammatory polypeptide can bind to at least one amino acid residue of drosophila EGFR (SEQ ID NO: 374) selected from the group consisting of Trp-41, Asp-48, Phe-51, Asp-68, and Tyr-101, or the equivalent amino acid residue(s) in a EGFR protein of another species.

In certain embodiments, an anti-inflammatory polypeptide can bind to drosophila EGFR (SEQ ID NO: 374) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and CDK6, any CDK6 protein sequence can be used. The CDK6 sequence used for modeling generally folds into a functional CDK6 protein or a functional fragment thereof. The CDK6 protein sequence used for modeling can be selected based on the type of subject that the anti-inflammatory polypeptide is intended to treat (e.g., a human CDK6 is selected if the intended subject is a human, a bovine CDK6 is selected if the intended subject is a cow, etc.). The sequence used for modeling can be the human CDK6 sequence (NCBI Acc. No. NP_001250.1), which is as follows:

(SEQ ID NO: 375)
MEKDGLCRADQQYECVAEIGEGAYGKVFKARDLKNGGRFVALKRVRV

QTGEEGMPLSTIREVAVLRHLETFEHPNVVRLFDVCTVSRTDRETKL

TLVFEHVDQDLTTYLDKVPEPGVPTETIKDMMFQLLRGLDFLHSHRV

VHRDLKPQNILVTSSGQIKLADFGLARIYSFQMALTSVVVTLWYRAP

EVLLQSSYATPVDLWSVGCIFAEMFRRKPLFRGSSDVDQLGKILDVI

GLPGEEDWPRDVALPRQAFHSKSAQPIEKFVTDIDELGKDLLLKCLT

FNPAKRISAYSALSHPYFQDLERCKENLDSHLPPSQNTSELNTA.

An anti-inflammatory polypeptide can be identified, for example, based on its ability to bind to the active site on CDK6 and/or interfere with or block the kinase activity of CDK6 or the ability of CDK6 to phosphorylate one or more CDK6 substrates. For example, the anti-inflammatory polypeptide can bind to at least one amino acid residue of human CDK6 (SEQ ID NO: 375) selected from the group consisting of Val-142, Arg-144, Asp-145, Ser-171, Val-180, Val-181, Leu-183, Arg-186, Val-190, Gln-193, Tyr-196, and Val-200, or the equivalent amino acid residue(s) in a CDK6 protein of another species. Alternatively, the anti-inflammatory polypeptide can bind to at least one amino acid residue of human CDK6 (SEQ ID NO: 375) selected from the group consisting of Asp-145, Val-180, and Tyr-196, or the equivalent amino acid residue(s) in a CDK6 protein of another species.

In certain embodiments, an anti-inflammatory polypeptide can bind to human CDK6 (SEQ ID NO: 375) with an affinity of at least −600 kcal/mol, and in certain embodiments at least −650, −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and histone methyl transferase (HMT), any HMT protein sequence can be used. The HMT sequence used for modeling generally folds into a functional HMT protein or a functional fragment thereof. The HMT protein sequence used for modeling can be selected based on the type of subject that the anti-inflammatory polypeptide is intended to treat (e.g., a human HMT is selected if the intended subject is a human, a bovine HMT is selected if the intended subject is a cow, etc.). The sequence used for modeling can be, for example, the Paramecium bursaria Chlorella virus 1 HMT sequence (NCBI Acc. No. NP_048968.1), which is as follows:

(SEQ ID NO: 376)
MFNDRVIVKKSPLGGYGVFARKSFEKGELVEECLCIVRHNDDWGTAL

EDYLFSRKNMSAMALGFGAIFNHSKDPNARHELTAGLKRMRIFTIKP

IAIGEEITISYGDDYWLSRPRLTQN.

An anti-inflammatory polypeptide can be identified, for example, based on its ability to bind to the active site on HMT and/or interfere with or block the methyl transferase activity of HMT or the ability of HMT to methylate histone substrates. For example, the anti-inflammatory polypeptide can bind to at least one amino acid residue of Paramecium bursaria HMT (SEQ ID NO: 376) selected from the group consisting of Asn-69, His-70, Ser-71, Lys-72, Asp-73, Pro-74, and Asn-75, or the equivalent amino acid residue(s) in a HMT protein of another species. Alternatively, the anti-inflammatory polypeptide can bind to at least one amino acid residue of Paramecium bursaria HMT (SEQ ID NO: 376) selected from the group consisting of Tyr-16, Glu-48, Tyr-50, Leu-51, Phe-52, and Asn-69, or the equivalent amino acid residue(s) in a HMT protein of another species.

In certain embodiments, an anti-inflammatory polypeptide can bind to Paramecium bursaria HMT (SEQ ID NO: 376) with an affinity of at least −600 kcal/mol, and in certain embodiments at least −650, −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and CD47, any CD47 protein sequence can be used. The CD47 sequence used for modeling generally folds into a functional CD47 protein or a SIRP-α-binding portion thereof. The CD47 protein sequence used for modeling can be selected based on the type of subject that the anti-inflammatory polypeptide is intended to treat (e.g., a human CD47 is selected if the intended subject is a human, a bovine CD47 is selected if the intended subject is a cow, etc.). The sequence used for modeling can be the human CD47 sequence (NCBI Acc. No. XP_005247966.1), which is as follows:

(SEQ ID NO: 377)
MWPLVAALLLGSACCGSAQLLFNKTKSVEFTFCNDTVVIPCFVTNME

AQNTTEVYVKWKFKGRDIYTFDGALNKSTVPTDFSSAKIEVSQLLKG

DASLKMDKSDAVSHTGNYTCEVTELTREGETIIELKYRVVSWFSPNE

NILIVIFPIFAILLFWGQFGIKTLKYRSGGMDEKTIALLVAGLVITV

IVIVGAILFVPGEYSLKNATGLGLIVTSTGILILLHYYVFSTAIGLT

SFVIAILVIQVIAYILAVVGLSLCIAACIPMHGPLLISGLSILALAQ

LLGLVYMKFVE.

An anti-inflammatory polypeptide can be identified, for example, based on its ability to bind to the SIRP-α-binding site on HMT and/or interfere with or block the binding of CD47 to SIRP-α. For example, the anti-inflammatory polypeptide can bind to at least one amino acid residue of CD47 (SEQ ID NO: 377) selected from the group consisting of Glu-29, Ala-30, Glu-35, Val-36, Tyr-37, Lys-39, Thr-49, Asp-51, Glu-97, Thr-99, Leu-101, Thr-102, Arg-103, Glu-104, and Glu-106, or the equivalent amino acid residue(s) in a CD47 protein of another species. In certain embodiments, the anti-inflammatory polypeptide can bind to at least one amino acid residue of CD47 (SEQ ID NO: 377) selected from the group consisting of Glu-29, Glu-35, Lys-39, Glu-97, Leu-101, Thr-102, Arg-103, Glu-104, and Glu-106, or the equivalent amino acid residue(s) in a CD47 protein of another species. Alternatively, the anti-inflammatory polypeptide can bind to at least one amino acid residue of human CD47 (SEQ ID NO: 377) selected from the group consisting of Tyr-16, Glu-48, Tyr-50, Leu-51, Phe-52, and Asn-6 Tyr-37, Thr-49, Phe-50, Asp-51, Ala-53, Glu-97, Val-98, Glu-100, Leu-101, Thr-102, Glu-104, Glu-106, Gly-107, or the equivalent amino acid residue(s) in a CD47 protein of another species. In certain embodiments, the anti-inflammatory polypeptide can bind to at least one amino acid residue of CD47 (SEQ ID NO: 377) selected from the group consisting of Tyr-37, Glu-97, Glu-100, Leu-101, Glu-104, Glu-106, or the equivalent amino acid residue(s) in a CD47 protein of another species.

In certain embodiments, an anti-inflammatory polypeptide can bind to human CD47 (SEQ ID NO: 377) with an affinity of at least −550 kcal/mol, and in certain embodiments at least −600, −650, −675, −700, −725, −750, −775, −800 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and SIRP-α, any SIRP-α protein sequence can be used. The SIRP-α sequence used for modeling generally folds into a functional SIRP-α protein or a CD47-binding fragment thereof. The SIRP-α protein sequence used for modeling can be selected based on the type of subject that the anti-inflammatory polypeptide is intended to treat (e.g., a human SIRP-α is selected if the intended subject is a human, a bovine SIRP-α is selected if the intended subject is a cow, etc.). The sequence used for modeling can be the human SIRP-α sequence (GenBank Acc. No. AAH26692.1), which is as follows:

(SEQ ID NO: 378)
MEPAGPAPGRLGPLLCLLLAASCAWSGVAGEEELQVIQPDKSVSVAA

GESAILHCTVTSLIPVGPIQWFRGAGPARELIYNQKEGHFPRVTTVS

ESTKRENMDFSISISNITPADAGTYYCVKFRKGSPDTEFKSGAGTEL

SVRAKPSAPVVSGPAARATPQHTVSFTCESHGFSPRDITLKWFKNGN

ELSDFQTNVDPVGESVSYSIHSTAKVVLTREDVHSQVICEVAHVTLQ

GDPLRGTANLSETIRVPPTLEVTQQPVRAENQVNVTCQVRKFYPQRL

QLTWLENGNVSRTETASTVTENKDGTYNWMSWLLVNVSAHRDDVKLT

CQVEHDGQPAVSKSHDLKVSAHPKEQGSNTAAENTGSNERNIYIVVG

VVCTLLVALLMAALYLVRIRQKKAQGSTSSTRLHEPEKNAREITQVQ

SLDTNDITYADLNLPKGKKPAPQAAEPNNHTEYASIQTSPQPASEDT

LTYADLDMVHLNRTPKQPAPKPEPSFSEYASVQVPRK.

An anti-inflammatory polypeptide can be identified, for example, based on its ability to bind to the HMT-binding site on SIRP-α and/or interfere with or block the binding of SIRP-α to HMT. For example, the anti-inflammatory polypeptide can bind to at least one amino acid residue of SIRP-α (SEQ ID NO: 378) selected from the group consisting of Leu-30, Gln-37, Gln-52, Lys-53, Ser-66, Thr-67, Arg-69, Met-72, Phe-74, Lys-96 and Asp-100, or the equivalent amino acid residue(s) in a SIRP-α protein of another species. Alternatively, the anti-inflammatory polypeptide can bind to at least one amino acid residue of human SIRP-α (SEQ ID NO: 378) selected from the group consisting of Tyr-50, Gln-52, Pro-58, Ser-66, Thr-67, and Ser-77, or the equivalent amino acid residue(s) in a SIRP-α protein of another species. In certain embodiments, the anti-inflammatory polypeptide can bind to at least one amino acid residue of SIRP-α (SEQ ID NO: 378) selected from the group consisting of Tyr-50, Gln-52, Ser-66, and Thr-67, or the equivalent amino acid residue(s) in a SIRP-α protein of another species.

In certain embodiments, an anti-inflammatory polypeptide can bind to human SIRP-α (SEQ ID NO: 378) with an affinity of at least −600 kcal/mol, and in certain embodiments at least −650, −700, −750, −800, −825, −850, −875, −900, −925, −950, −975, −1000 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and CD206, any CD206 protein sequence can be used. The CD206 sequence used for modeling generally folds into a functional CD206 protein or a mannose-binding fragment thereof. The CD206 protein sequence used for modeling can be selected based on the type of subject that the anti-inflammatory polypeptide is intended to treat (e.g., a human CD206 is selected if the intended subject is a human, a bovine CD206 is selected if the intended subject is a cow, etc.). The sequence used for modeling can be the human CD206 sequence (NCBI Acc. No. NP_002429.1), which is as follows:

```
                                       (SEQ ID NO: 379)
MRLPLLLVFASVIPGAVLLLDTRQFLIYNEDHKRCVDAVSPSAVQTA

ACNQDAESQKFRWVSESQIMSVAFKLCLGVPSKTDWVAITLYACDSK

SEFQKWECKNDTLLGIKGEDLFFNYGNRQEKNIMLYKGSGLWSRWKI

YGTTDNLCSRGYEAMYTLLGNANGATCAFPFKFENKWYADCTSAGRS

DGWLWCGTTTDYDTDKLFGYCPLKFEGSESLWNKDPLTSVSYQINSK

SALTWHQARKSCQQQNAELLSITEIHEQTYLTGLTSSLTSGLWIGLN

SLSFNSGWQWSDRSPFRYLNWLPGSPSAEPGKSCVSLNPGKNAKWEN

LECVQKLGYICKKGNTTLNSFVIPSESDVPTHCPSQWWPYAGHCYKI

HRDEKKIQRDALTTCRKEGGDLTSIHTIEELDFIISQLGYEPNDELW

IGLNDIKIQMYFEWSDGTPVTFTKWLRGEPSHENNRQEDCVVMKGKD

GYWADRGCEWPLGYICKMKSRSQGPEIVEVEKGCRKGWKKHHFYCYM

IGHTLSTFAEANQTCNNENAYLTTIEDRYEQAFLTSFVGLRPEKYFW

TGLSDIQTKGTFQWTIEEEVRFTHWNSDMPGRKPGCVAMRTGIAGGL

WDVLKCDEKAKFVCKHWAEGVTHPPKPTTTPEPKCPEDWGASSRTSL

CFKLYAKGKHEKKTWFESRDFCRALGGDLASINNKEEQQTIWRLITA

SGSYHKLFWLGLTYGSPSEGFTWSDGSPVSYENWAYGEPNNYQNVEY

CGELKGDPTMSWNDINCEHLNNWICQIQKGQTPKPEPTPAPQDNPPV

TEDGWVIYKDYQYYFSKEKETMDNARAFCKRNFGDLVSIQSESEKKF

LWKYVNRNDAQSAYFIGLLISLDKKFAWMDGSKVDYVSWATGEPNFA

NEDENCVTMYSNSGFWNDINCGYPNAFICQRHNSSINATTVMPTMPS

VPSGCKEGWNFYSNKCFKIFGFMEEERKNWQEARKACIGFGGNLVSI

QNEKEQAFLTYHMKDSTFSAWTGLNDVNSEHTFLWTDGRGVHYTNWG

KGYPGGRRSSLSYEDADCVVIIGGASNEAGKWMDDTCDSKRGYICQT

RSDPSLTNPPATIQTDGFVKYGKSSYSLMRQKFQWHEAETYCKLHNS

LIASILDPYSNAFAWLQMETSNERVWIALNSNLTDNQYTWTDKWRVR

YTNWAADEPKLKSACVYLDLDGYWKTAHCNESFYFLCKRSDEIPATE
```

-continued

```
PPQLPGRCPESDHTAWIPFHGHCYYIESSYTRNWGQASLECLRMGSS

LVSIESAAESSFLSYRVEPLKSKTNFWIGLFRNVEGTWLWINNSPVS

FVNWNTGDPSGERNDCVALHASSGFWSNIHCSSYKGYICKRPKIIDA

KPTHELLTTKADTRKMDPSKPSSNVAGVVIIVILLILTGAGLAAYFF

YKKRRVHLPQEGAFENTLYFNSQSSPGTSDMKDLVGNIEQNEHSVI.
```

An anti-inflammatory polypeptide can be identified, for example, based on its ability to bind to the mannose-binding site on CD206 and/or interfere with or block the binding of SIRP-mannose to CD206. For example, the anti-inflammatory polypeptide can bind to at least one amino acid residue of CD206 (SEQ ID NO: 379) selected from the group consisting of Glu-725, Tyr-729, Glu-733, Asn-747, and Asp-748, or the equivalent amino acid residue(s) in a CD206 protein of another species. Alternatively, the anti-inflammatory polypeptide can bind to at least one amino acid residue of human CD206 (SEQ ID NO: 379) selected from the group consisting of Phe-708, Thr-709, Trp-710, Pro-714. Glu-719, Asn-720, Trp-721, Ala-722, Glu-725, Tyr-729, Glu-733, Asn-747, Asp-748, Ser-1691, Cys-1693, Phe-1694, and Phe-1703, or the equivalent amino acid residue(s) in a CD206 protein of another species. In certain embodiments, the anti-inflammatory polypeptide can bind to at least one amino acid residue of CD206 (SEQ ID NO: 379) selected from the group consisting of Phe-708, Trp-710, Trp-721, Glu-725, Tyr-729, Glu-733, or the equivalent amino acid residue(s) in a CD206 protein of another species.

In certain embodiments, an anti-inflammatory polypeptide can bind to human CD206 (SEQ ID NO: 379) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and TGM2, any TGM2 protein sequence can be used. The TGM2 sequence used for modeling generally folds into a functional TGM2 protein or acyl-transferase catalytic fragment thereof. The TGM2 protein sequence used for modeling can be selected based on the type of subject that the anti-inflammatory polypeptide is intended to treat (e.g., a human TGM2 is selected if the intended subject is a human, a bovine TGM2 is selected if the intended subject is a cow, etc.). The sequence used for modeling can be the human TGM2 sequence (GenBank Acc. No. AAB95430.1), which is as follows:

```
                                       (SEQ ID NO: 380)
MMDASKELQVLHIDFLNQDNAVSHHTWEFQTSSPVFRRGQVFHLRLV

LNQPLQSYHQLKLEFSTGPNPSIAKHTLVVLDPRTPSDHYNWQATLQ

NESGKEVTVAVTSSPNAILGKYQLNVKTGNHILKSEENILYLLFNPW

CKEDMVFMPDEDERKEYILNDTGCHYVGAARSIKCKPWNFGQFEKNV

LDCCISLLTESSLKPTDRRDPVLVCRAMCAMMSFEKGQGVLIGNWTG

DYEGGTAPYKWTGSAPILQQYYNTKQAVCFGQCWVFAGILTTVLRAL

GIPARSVTGFDSAHDTERNLTVDTYVNENGEKITSMTHDSVWNFHVW
```

-continued

```
TDAWMKRPDLPKGYDGWQAVDATPQERSQGVFCCGPSPLTAIRKGDI

FIVYDTRFVFSEVNGDRLIWLVKMVNGQEELHVISMETTSIGKNIST

KAVGQDRRRDITYEYKYPEGSSEERQVMDHAFLLLSSEREHRRPVKE

NFLHMSVQSDDVLLGNSVNFTVILKRKTAALQNVNILGSFELQLYTG

KKMAKLCDLNKTSQIQGQVSEVTLTLDSKTYINSLAILDDEPVIRGF

IIAEIVESKEIMASEVFTSFQYPEFSIELPNTGRIGQLLVCNCIFKN

TLAIPLTDVKFSLESLGISSLQTSDHGTVQPGETIQSQIKCTPIKTG

PKKFIVKLSSKQVKEINAQKIVLITK.
```

An anti-inflammatory polypeptide can be identified, for example, based on its ability to bind to the active site on TGM2 and/or interfere with or block the acyl-transferase activity of TGM2. For example, the anti-inflammatory polypeptide can bind to at least one amino acid residue of TGM2 (SEQ ID NO: 380) selected from the group consisting of Cys-277, His-335, and Asp-358, or the equivalent amino acid residue(s) in a TGM2 protein of another species.

In certain embodiments, an anti-inflammatory polypeptide can bind to human TGM2 (SEQ ID NO: 380) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and serum albumin, any serum albumin protein sequence can be used. The serum albumin sequence used for modeling generally folds into a functional serum albumin protein or a functional fragment thereof. The serum albumin protein sequence used for modeling can be selected based on the type of subject that the anti-inflammatory polypeptide is intended to treat (e.g., a human serum albumin (HSA) is selected if the intended subject is a human, a bovine serum albumin (BSA) is selected if the intended subject is a cow, etc.). The sequence used for modeling can be the human serum albumin (HSA) sequence (NCBI Acc. No. NP_000468.1), which is as follows:

```
                                    (SEQ ID NO: 381)
DAHKSEVAHRFKDLGEENFKALVLIAFAQYLQQCPFEDHVKLVNEVT

EFAKTCVADESAENCDKSLHTLFGDKLCTVATLRETYGEMADCCAKQ

EPERNECFLQHKDDNPNLPRLVRPEVDVMCTAFHDNEETFLKKYLYE

IARRHPYFYAPELLFFAKRYKAAFTECCQAADKAACLLPKLDELRDE

GKASSAKQRLKCASLQKFGERAFKAWAVARLSQRFPKAEFAEVSKLV

TDLTKVHTECCHGDLLECADDRADLAKYICENQDSISSKLKECCEKP

LLEKSHCIAEVENDEMPADLPSLAADFVESKDVCKNYAEAKDVFLGM

FLYEYARRHPDYSVVLLLRLAKTYETTLEKCCAAADPHECYAKVFDE

FKPLVEEPQNLIKQNCELFEQLGEYKFQNALLVRYTKKVPQVSTPTL

VEVSRNLGKVGSKCCKHPEAKRMPCAEDYLSVVLNQLCVLHEKTPVS

DRVTKCCTESLVNRRPCFSALEVDETYVPKEFNAETFTFHADICTLS

EKERQIKKQTALVELVKHKPKATKEQLKAVMDDFAAFVEKCCKADDK

ETCFAEEGKKLVAASQAALGL.
```

An anti-inflammatory polypeptide can be identified, for example, based on its ability to bind to HSA under physiological conditions (e.g., in the blood stream).

In certain embodiments, an anti-inflammatory polypeptide can bind to HSA (SEQ ID NO: 381) with an affinity of at least −650 kcal/mol, and in certain embodiments at least −700, −750, −800, −850, −900, −925, −950, −975, −1000, −1025, −1050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

In certain embodiments, an anti-inflammatory polypeptide binds to two or more targets (e.g., pro-inflammatory targets). In some embodiments, an anti-inflammatory polypeptide binds to three, four, five, or more pro-inflammatory targets. For example, an anti-inflammatory polypeptide can bind to any combination of targets disclosed herein. Such binding can be based on in silico, in vitro, or in vivo data. Thus, an anti-inflammatory polypeptide can bind to two or more NF-kB Class II subunits (e.g., RelB and at least one other NF-kB Class II subunit, such as RelA, cRel, NF-kB1, or NF-kB2). Alternatively (or in addition), an anti-inflammatory polypeptide can bind to an NF-kB Class II subunit (e.g., RelB) and at least one other signaling molecule (e.g., at least one signaling molecule selected from the group consisting of TGFβ, Notch1, Wnt8R, TRAIL, IL6R, IL10R, EGFR, CDK6, CD206, CD47, SIRP-α, HMT, and TGM2). For example, an anti-inflammatory polypeptide can bind to an NF-kB Class II subunit (e.g., RelB) and at least one signaling molecule selected from the group consisting of TGFβ, Notch1, Wnt8R, TRAIL, IL6R, IL10R, EGFR, and CDK6. Alternatively, an anti-inflammatory polypeptide can bind to an NF-kB Class II subunit (e.g., RelB) and at least one signaling molecule selected from the group consisting of CD206, CD47, SIRP-α, and TGM2. In other alternatives, an anti-inflammatory polypeptide can bind to an NF-kB Class II subunit (e.g., RelB) and HMT. In other alternatives, an anti-inflammatory polypeptide can bind to at least one signaling molecule selected from the group consisting of TGFβ, Notch1, Wnt8R, TRAIL, IL6R, IL10R, EGFR, and CDK6, and at least one signaling molecule selected from the group consisting of CD206, CD47, SIRP-α, and TGM2. In other alternatives, an anti-inflammatory polypeptide can bind to at least one signaling molecule selected from the group consisting of TGFβ, Notch1, Wnt8R, TRAIL, IL6R, IL10R, EGFR, and CDK6, and also bind to HMT. In still other embodiments, an anti-inflammatory polypeptide can bind to an NF-kB Class II subunit (e.g., RelB), at least one signaling molecule selected from the group consisting of TGFβ, Notch1, Wnt8R, TRAIL, IL6R, IL10R, EGFR, and CDK6, at least one signaling molecule selected from the group consisting of CD206, CD47, SIRP-α, and TGM2, and also HMT. In certain embodiments, an anti-inflammatory polypeptide binds to two or more pro-inflammatory targets and also serum albumin (e.g., human serum albumin).

For modeling interactions between potential anti-inflammatory polypeptides and LEGUMAIN, any LEGUMAIN protein sequence can be used. The LEGUMAIN sequence used for modeling generally folds into a functional LEGUMAIN protein or a functional fragment thereof. The LEGUMAIN protein sequence used for modeling can be selected based on the type of subject that the anti-inflammatory polypeptide is intended to treat (e.g., a human LEGUMAIN is selected if the intended subject is a human, a bovine LEGUMAIN is selected if the intended subject is a cow, etc.). The sequence used for modeling can be the human LEGUMAIN sequence (GenBank Acc. No. AAH03061.1).

eling generally folds into a functional CD209 protein or a functional fragment thereof. The CD209 protein sequence used for modeling can be selected based on the type of subject that the anti-inflammatory polypeptide is intended to treat (e.g., a human CD209 is selected if the intended subject is a human, a bovine CD209 is selected if the intended (SEQ ID NO: 413)
MVWKVAVFLSVALGIGAIPIDDPEDGGKHWVVIVAGSNGWYNYRHQADACHAYQIIHRNGIPDEQ

IVVMMYDDIAYSEDNPTPGIVINRPNGTDVYQGVPKDYTGEDVTPQNFLAVLRGDAEAVKGIGSG

KVLKSGPQDHVFIYFTDHGSTGILVFPNEDLHVKDLNETIHYMYKHKMYRKMVFYIEACESGSMM

NHLPDNINVYATTAANPRESSYACYYDEKRSTYLGDWYSVNWMEDSDVEDLTKETLHKQYHLVKSS

HTNTSHVMQYGNKTISTMKVMQFQGMKRKASSPVPLPPVTHLDLTPSPDVPLTIMKRKLMNTNDL

EESRQLTEEIQRHLDARHLIEKSVRKIVSLLAASEAEVEQLLSERAPLTGHSCYPEALLHFRTHC

FNWHSPTYEYALRHLYVLVNLCEKPYPLHRIKLSMDHVCLGHY.

An anti-inflammatory polypeptide can be identified, for example, based on its ability to bind to the active site on LEGUMAIN and/or interfere with or block the ability of subject is a cow, etc.). The sequence used for modeling can be the human CD209 sequence (GenBank Acc. No. NP_001138366.1).

(SEQ ID NO: 414)
MSDSKEPRLQQLGLLVSKVPSSISQEQSRQDAIYQNLTQLKAAVGELSEKSKLQEIYQELTQLKA

AVGELPEKSKLQEIYQELTRLKAAVGELPEKSKLQEIYQELTWLKAAVGELPEKSKMQEIYQELT

RLKAAVGELPEKSKQQEIYQELTRLKAAVGELPEKSKQQEIYQELTRLKAAVGELPEKSKQQEIY

QELTQLKAAVERLCHPCPWEWTFFQGNCYFMSNSQRNWHDSITACKEVGAQLVVIKSAEEQNFLQ

LQSSRSNRFTWMGLSDLNQEGTWQWVDGSPLLPSFKQYWNRGEPNNVGEEEDCAEFSGNGWNDDKC

NLAKFWICKKSAASCSRDEEQFLSPAPATPNPPPA

LEGUMAIN to bind to its target. For example, the anti-inflammatory polypeptide can bind to at least one amino acid residue of human LEGUMAIN (SEQ ID NO: 137) selected from the group consisting of Asn-44, Arg-46, His-159, Glu-189, Cys-191, Ser-217, Ser-218 and Asp-233, or the equivalent amino acid residue(s) in a LEGUMAIN protein of another species. Alternatively, the anti-inflammatory polypeptide can bind to at least one amino acid residue of human LEGUMAIN (SEQ ID NO: 137) selected from the group consisting of Asn-44, Glu-189 and Asp-233, or the equivalent amino acid residue(s) in a LEGUMAIN protein of another species.

In certain embodiments, an anti-inflammatory polypeptide can bind to human LEGUMAIN (SEQ ID NO: 137) with an affinity of at least −600 kcal/mol, and in certain embodiments at least −650, −700, −750, −800, −850, −900, −925, −950 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and CD209, any CD209 protein sequence can be used. The CD209 sequence used for mod- An anti-inflammatory polypeptide can be identified, for example, based on its ability to bind to the active site on CD209 and/or interfere with or block the ability of CD209 to bind to its receptor. For example, the anti-inflammatory polypeptide can bind to at least one amino acid residue of human CD209 (SEQ ID NO: 140) selected from the group consisting of Phe-269, Glu-280, Glu-303, Asn-305, Asn-306, Glu-310, Asp-311, Ser-316, Gly-317, Asn-321 and Lys-324 or the equivalent amino acid residue(s) in a CD209 protein of another species. Alternatively, the anti-inflammatory polypeptide can bind to at least one amino acid residue of human CD209 (SEQ ID NO: 140) selected from the group consisting of Phe-269, Glu-280, Glu-303, Glu-310, Asp-311, Asn-321 and Lys-324, or the equivalent amino acid residue(s) in a CD209 protein of another species.

In certain embodiments, an anti-inflammatory polypeptide can bind to human CD209 (SEQ ID NO: 140) with an affinity of at least −600 kcal/mol, and in certain embodiments at least −650, −700, −750, −800, −850, −900, −925, −950, −1,000, −1,050 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and FAS, any FAS protein sequence can be used. The FAS sequence used for modeling generally folds into a functional FAS protein or a functional fragment thereof. The FAS protein sequence used for modeling can be selected based on the type of subject that the anti-inflammatory polypeptide is intended to treat (e.g., a human FAS is selected if the intended subject is a human, a bovine FAS is selected if the intended subject is a cow, etc.). The sequence used for modeling can be the human FAS sequence (NCBI Reference Sequence: NP_000034.1).

motes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

For modeling interactions between potential anti-inflammatory polypeptides and PD-1, any PD-1 protein sequence can be used. The PD-1 sequence used for modeling gener- (SEQ ID NO: 415)
MLGIWTLLPLVLTSVARLSSKSVNAQVTDINSKGLELRKTVTTVETQNLEGLHHDGQFCHKPCPP

GERKARDCTVNGDEPDCVPCQEGKEYTDKAHFSSKCRRCRLCDEGHGLEVEINCTRTQNTKCRCK

PNFFCNSTVCEHCDPCTKCEHGIIKECTLTSNTKCKEEGSRSNLGWLCLLLLPIPLIVWVKRKEV

QKTCRKHRKENQGSHESPTLNPETVAINLSDVDLSKYITTIAGVMTLSQVKGFVRKNGVNEAKID

EIKNDNVQDTAEQKVQLLRNWHQLHGKKEAYDTLIKDLKKANLCTLAEKIQTIILKDITSDSENS

NFRNEIQSLV.

An anti-inflammatory polypeptide can be identified, for example, based on its ability to bind to the active site on FAS and/or interfere with or block the ability of FAS to bind to its ligand. For example, the anti-inflammatory polypeptide can bind to at least one amino acid residue of human FAS (SEQ ID NO: 152) selected from the group consisting of Lys-251, Lys-296, Lys-299, Leu-303, Leu-306, Ala-307, Glu-308, Lys-309, Gln-311, Ile-314, Leu-315, Asp-317, Ile-318 and Thr-319, or the equivalent amino acid residue(s)

ally folds into a functional PD-1 protein or a functional fragment thereof. The PD-1 protein sequence used for modeling can be selected based on the type of subject that the anti-inflammatory polypeptide is intended to treat (e.g., a human PD-1 is selected if the intended subject is a human, a bovine PD-1 is selected if the intended subject is a cow, etc.). The sequence used for modeling can be the human PD-1 sequence (Locus: XP_006712636.1).

(SEQ ID NO: 416)
MQIPQAPWPVVWAVLQLGWRPGWFLDSPDRPWNPPTFSPALLVVTEGDNATFTCSFSNTSESFVL

NWYRMSPSNQTDKLAAFPEDRSQPGQDCRFRVTQLPNGRDFHMSVVRARRNDSGTYLCGAISLAP

KAQIKESLRAELRVTERRAEVPTAHPSPSPRPAGQFQTLVVGVVGGLLGSLVLLVWVLAVICSRA

ARG.

in a FAS protein of another species. Alternatively, the anti-inflammatory polypeptide can bind to at least one amino acid residue of human FAS (SEQ ID NO: 152) selected from the group consisting of Lys-296, Lys-299, Leu-306, Ala-307, Glu-308, Ile-314, Leu-315, Asp-317 and Ile-318, or the equivalent amino acid residue(s) in a FAS protein of another species.

In certain embodiments, an anti-inflammatory polypeptide can bind to human FAS (SEQ ID NO: 152) with an affinity of at least −600 kcal/mol, and in certain embodiments at least −650, −700, −750, −800, −850, −900, −925, −950 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2. PD-1, functioning as an immune checkpoint plays an important role in down regulating the immune system by preventing the activation of T-cells, which in turn reduces autoimmunity and pro- An anti-inflammatory polypeptide can be identified, for example, based on its ability to bind to the active site on PD-1 and/or interfere with or block the ability of PD-1 to bind to its receptor. For example, the anti-inflammatory polypeptide can bind to at least one amino acid residue of human PD-1 (SEQ ID NO: 159) selected from the group consisting of Val-64, Asn-66, Tyr-68, Met-70, Thr-76, Lys-78, Thr-120, Leu-122, Ala-125, Ser-127, or the equivalent amino acid residue(s) in a PD-1 protein of another species. Alternatively, the anti-inflammatory polypeptide can bind to at least one amino acid residue of human PD-1 (SEQ ID NO: 159) selected from the group consisting of Tyr-68, Met-70, Lys-78 and Leu-122, or the equivalent amino acid residue(s) in a PD-1 protein of another species.

In certain embodiments, an anti-inflammatory polypeptide can bind to human PD-1 (SEQ ID NO: 159) with an affinity of at least −600 kcal/mol, and in certain embodiments at least −650, −700, −750, −800, −850, −900, −925, −950, −1,000 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

Dual specificity mitogen-activated protein kinase kinase 7, also known as MAP kinase kinase 7 or MKK7, is an enzyme that in humans is encoded by the MAP2K7 gene. This protein is a member of the mitogen-activated protein kinase kinase family. The MKK7 protein exists as six different isoforms with three possible N-termini (α, β, and γ isoforms) and two possible C-termini (1 and 2 isoforms). MKK7 is involved in signal transduction mediating the cell responses to proinflammatory cytokines, and environmental stresses. This kinase specifically activates MAPK8/JNK1 and MAPK9/JNK2, and this kinase itself is phosphorylated and activated by MAP kinase kinase kinases including MAP3K1/MEKK1, MAP3K2/MEKK2, MAP3K3/MEKK5, and MAP4K2/GCK.

For modeling interactions between potential anti-inflammatory polypeptides and MKK7, any MKK7 protein sequence can be used. The MKK7 sequence used for modeling generally folds into a functional MKK7 protein or a functional fragment thereof. The MKK7 protein sequence used for modeling can be selected based on the type of subject that the anti-inflammatory polypeptide is intended to treat (e.g., a human MKK7 is selected if the intended subject is a human, a bovine MKK7 is selected if the intended subject is a cow, etc.). The sequence used for modeling can be the human MKK7 sequence (NCBI Reference Sequence: NP_001284484.1).

consisting of Met-142, Val-150, Lys-152, Lys-165, Met-212, Met-215, Thr-217, Lys-221, Leu-266, Cys-276 and Asp-277, or the equivalent amino acid residue(s) in a MKK7 protein of another species. Alternatively, the anti-inflammatory polypeptide can bind to at least one amino acid residue of human MKK7 (SEQ ID NO: 166) selected from the group consisting of Met-142, Val-150, Lys-165, Met-212, Met-215, Leu-266 and Asp-277, or the equivalent amino acid residue(s) in a MKK7 protein of another species.

In certain embodiments, an anti-inflammatory polypeptide can bind to human MKK7 (SEQ ID NO: 166) with an affinity of at least −600 kcal/mol, and in certain embodiments at least −650, −700, −750, −800, −850, −900, −925, −950, −1,000 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

For modeling interactions between potential anti-inflammatory polypeptides and ribonucleotide reductase (RNR), any RNR protein sequence can be used. The RNR sequence used for modeling generally folds into a functional RNR protein or a functional fragment thereof. The RNR protein sequence used for modeling can be selected based on the (SEQ ID NO: 417)
MAASSLEQKLSRLEAKLKQENREARRRIDLNLDISPQRPRPIIVITLSPAPAPSQRAALQLPLAN

DGGSRSPSSESSPQHPTPPARPRHMLGLPSTLFTPRSMESIEIDQKLQEIMKQTGYLTIGGQRYQ

AEINDLENLGEMGSGTCGQVWKMRFRKTGHVIAVKQMRRSGNKEENKRILMDLDVVLKSHDCPYI

VQCFGTFITNTDVFIAMELMGTCAEKLKKRMQGPIPERILGKMTVAIVKALYYLKEKHGVIHRDV

KPSNILLDERGQIKLCDFGISGRLVDSKAKTRSAGCAAYMAPERIDPPDPTKPDYDIRADVWSLG

ISLVELATGQFPYKNCKTDFEVLTKVLQEEPPLLPGHMGFSGDFQSFVKDCLTKDHRKRPKYNKL

LEHSFIKRYETLEVDVASWFKDVMAKTESPRTSGVLSQPHLPFFR.

An anti-inflammatory polypeptide can be identified, for example, based on its ability to bind to the active site on MKK7 and/or interfere with or block the ability of MKK7 to bind to its receptor. For example, the anti-inflammatory polypeptide can bind to at least one amino acid residue of human MKK7 (SEQ ID NO: 166) selected from the group type of subject that the anti-inflammatory polypeptide is intended to treat (e.g., a human RNR is selected if the intended subject is a human, a bovine RNR is selected if the intended subject is a cow, etc.). The sequence used for modeling can be the yeast RNR sequence (GenBank: AJV34160.1).

(SEQ ID NO: 418)
MYVYKRDGRKEPVQFDKITARISRLCYGLDPKHIDAVKVTQRIISGVYEGVTTIELDNLAAETCA

YMTTVHPDYATLAARIAISNLHKQTTKQFSKVVEDLYRYVNAATGKPAPMISDDVYNIVMENKDK

LNSAIVYDRDFQYSYFGFKTLERSYLLRINGQVAERPQHLIMRVALGIHGRDIEAALETYNLMSL

KYYTHASPTLFNAGTPKPQMSSCFLVAMKEDSIEGIYDTLKECALISKTAGGIGLHIHNIRSTGS

YIAGTNGTSNGLIPMIRVFNNTARYVDQGGNKRPGAFALYLEPWHADIFDFIDIRKNHGKEEIRA

RDLFPALWIPDLFMKRVEENGTWTLFSPTSAPGLSDCYGDEFEALYTRYEKEGRGKTIKAQKLWY

SILEAQTETGTPFVVYKDACNRKSNQKNLGVIKSSNLCCEIVEYSAPDETAVCNLASVALPAFIE

TSEDGKTSTYNFKKLHEIAKVVTRNLNRVIDRNYYPVEEARKSNMRHRPIALGVQGLADTFMLLR

LPFDSEEARLLNIQIFETIYHASMEASCELAQKDGPYETFQGSPASQGILQFDMWDQKPYGMWDW

DTLRKDIMKHGIRNSLTMAPMPTASTSQILGYNECFEPVTSNMYSRRVLSGEFQVVNPYLLRDLV

DLGIWDEGMKQYLITQNGSIQGLPNVPQELKDLYKTVWEISQKTIINMAADRSVYIDQSHSLNLF

-continued

```
LRAPTMGKLTSMHFYGWKKGLKTGMYYLRTQAASAAIQFTIDQKIADQATENVADISNLKRPSYM

PSSASYAASDFVPAAVTANATIPSLDSSSEASREASPAPTGSHSLTKGMAELNVQESKVEVPEVP

APTKNEEKAAPIVDDEETEFDIYNSKVIACAIDNPEACEMCSG.
```

An anti-inflammatory polypeptide can be identified, for example, based on its ability to bind to the active site on RNR and/or interfere with or block the ability of RNR to bind to its receptor. For example, the anti-inflammatory polypeptide can bind to at least one amino acid residue of human RNR (SEQ ID NO: 168) selected from the group consisting of Asn-426, Leu-427, Cys-428, Glu-430, Met-606, Pro-608 and Ala-610, or the equivalent amino acid residue(s) in a RNR protein of another species.

In certain embodiments, an anti-inflammatory polypeptide can bind to human RNR (SEQ ID NO: 168) with an affinity of at least −600 kcal/mol, and in certain embodiments at least −650, −700, −750, −800, −850, −900, −925, −950, −1,000 kcal/mol, or greater. The requisite binding affinity can correspond to a binding affinity that can be detected in vitro or in vivo. Alternatively, the requisite binding affinity can correspond to a binding affinity that can be detected in silico, e.g., using the ClusPro™ algorithm.

Excluded Polypeptides

Compositions of the invention optionally exclude polypeptides that satisfy the Structural Algorithm described herein which may have been known in the art prior to the filing of the present application. Various publications have discussed synthetic and naturally occurring anti-inflammatory polypeptides and/or polypeptides having a striapathic sequence including, for example, US Patent Application Nos. 2012/0270770 and 2003/0109452, and U.S. Pat. No. 6,559,281. Accordingly, one or more polypeptides and/or uses of such polypeptides described in such publications can be excluded from the scope of the presently disclosed composition and/or methods. For example, peptide RP-398 (SEQ ID NO: 155) is optionally excluded from compositions disclosed herein and/or methods of using such compositions. Moreover, any of the polypeptides disclosed in Tables 3-9, below, can be optionally excluded from compositions disclosed herein and/or methods of using such compounds.

Linked Anti-Inflammatory Polypeptide Combinations

The invention further includes any two anti-inflammatory polypeptides which have been linked together. The linkage can be formed by a peptide linker, such as a Gly-Gly-Gly (GGG), Gly-Gly-Gly-Arg (GGGR; SEQ ID NO: 412), Gly-Pro-Gly (GPG), or Gly-Pro-Gly-Arg (GPGR; SEQ ID NO: 413) sequence, that links the C-terminal end of a first anti-inflammatory polypeptide to the N-terminal end of a second anti-inflammatory polypeptide. Alternatively, the linkage can be a peptoid linker (e.g., a poly N-substituted version of any of the foregoing peptide linkers), a polymer containing g-amino acids (e.g., corresponding to any of the foregoing peptide linkers), or a non-peptide, chemical linker. The linked anti-inflammatory polypeptides can be any of the polypeptides disclosed herein (e.g., in Tables 3-9), and can include the same polypeptide being linked to form a homodimer or different polypeptides being linked to form a heterodimer. Techniques for linking peptides via peptide and non-peptide linkers are well known in the art, and the inventive polypeptide combinations are intended to encompass all such linkages.

Anti-inflammatory polypeptides can be linked to another molecule via a biodegradable linkage, such as a disulfide bond. The disulfide bond can be mediated by the sulfhydryl group of a cysteine residue found in the anti-inflammatory polypeptide and a sulfhydryl group in the other molecule. The cysteine residue can be, e.g., located at either the C-terminal or N-terminal end of anti-inflammatory polypeptide. Specific examples include RP-433 (FAKKFAKKFKC, SEQ ID NO: 384) and RP-434 (KFRKAFKRFFC; SEQ ID NO: 385), though any of the peptides disclosed herein could be similarly modified. Using a disulfide linkage of this sort, polypeptides of the invention can be conveniently linked to various types of useful molecules. For example, the linkage can be with another anti-inflammatory polypeptide (which optionally includes a C-terminal or N-terminal cysteine residue), a fluorescent label (e.g., Dylight 350), a chemotherapeutic agent (e.g., a taxol derivative formed by adding a sulfhydral group to an appropriate site on the taxol ring structure, followed by oxidation with a cysteine-containing peptide of the invention), or the like.

Linked anti-inflammatory polypeptides (e.g., homo- or heterodimers) can bind to a target molecule (e.g., a target protein, such as a pro-inflammatory signaling protein) with a binding energy that is greater than that of either monomer polypeptide alone. Thus, for example, the energy of binding of linked anti-inflammatory polypeptides to an NF-kB Class II protein (e.g., RelB) can be at least −700 kcal/mol, and in certain embodiments at least −750, −800, −900, −1000, −1100, −1200, −1250, −1300, −1350, −1400, −1425, −1450, −1475, −1500, −1525, −1550, −1575, −1600 kcal/mol, or greater. The energy of binding can be determined, e.g., in silico, in vitro, or in vivo, using methods well-known in the art (e.g., using the ClusPro™ algorithm).

Modified Polypeptides

Embodiments of the invention include the modification of any of the anti-inflammatory polypeptides of the invention, by chemical or genetic means. Examples of such modification include construction of peptides of partial or complete sequence with non-natural amino acids and/or natural amino acids in L or D forms. For example, any of the peptides disclosed herein and any variants thereof could be produced in an all-D form. Furthermore, polypeptides of the invention can be modified to contain carbohydrate or lipid moieties, such as sugars or fatty acids, covalently linked to the side chains or the N- or C-termini of the amino acids. In addition, the polypeptides of the invention can be modified to enhance solubility and/or half-life upon being administered. For example, polyethylene glycol (PEG) and related polymers have been used to enhance solubility and the half-life of protein therapeutics in the blood. Accordingly, the polypeptides of the invention can be modified by PEG polymers and the like. Polypeptides of the invention can also be modified to contain sulfur, phosphorous, halogens, metals, etc. And amino acid mimics can be used to produce polypeptides of the invention (e.g., having a structure based on the Structural Algorithm or a structure similar to any of the anti-inflammatory polypeptides disclosed herein). In certain embodiments, polypeptides of the invention that include amino acid mimics have enhanced properties, such as resistance to degradation. For example, polypeptides of the invention can include one or more (e.g., all) peptoid monomers.

Compositions

Compositions of the invention include an anti-inflammatory polypeptide that satisfies the structural algorithm described herein. For example, the anti-inflammatory polypeptide can have a striapathic region having a sequence that conforms with any one of Formulas I-LIV. In particular, the anti-inflammatory polypeptide can be any of the polypeptides listed in Table 3-9, or a fragment or variant thereof. Typically, the anti-inflammatory polypeptide included in the compositions of the invention will be a synthetic polypeptide (e.g., made by chemical synthesis and/or produced recombinantly).

The compositions of the invention can include a single anti-inflammatory polypeptide, or combinations thereof. The compositions can be substantially free of proteins and other polypeptides that do not satisfy the structural algorithm disclosed herein. As used herein, the term "substantially free of proteins and other polypeptides" means that less than 5% of the protein content of the composition is made up of proteins and other polypeptides that are not an anti-inflammatory polypeptide of the invention. A composition that is substantially free of non-anti-inflammatory polypeptides of the invention can have less than 4%, 3%, 2%, 1%, 0.5%, 0.1%, 0.05%, 0.01%, or less of proteins or other polypeptides that do not satisfy the structural algorithm disclosed herein. Thus, the compositions can be substantially free of blood proteins, such as serum albumin, globulins, fibrinogen, and clotting factors. Alternatively, the compositions can be substantially free of globulins, fibrinogen, and clotting factors, but can include purified or recombinantly produced serum albumin.

The compositions of the invention in certain embodiments contain an anti-inflammatory polypeptide that is not naturally found in a human or other mammal or animal. However, compositions of the invention can include an anti-inflammatory polypeptide that is naturally found in a human or other mammal or animal, provided that the composition is substantially free of biological molecules (such as non-anti-inflammatory polypeptides, nucleic acids, lipids, carbohydrates, and metabolites) that are associated with the anti-inflammatory polypeptide in vivo or co-purify with the anti-inflammatory polypeptide. As used herein, the term "substantially free of biological molecules" means that less than 5% of the dry weight of the composition is made up of biological molecules that are not anti-inflammatory polypeptides. A composition that is substantially free of such biological molecules can have less than 4%, 3%, 2%, 1%, 0.5%, 0.1%, 0.05%, 0.01%, or less of biological molecules that are not anti-inflammatory polypeptides. Thus, for example, the composition can be substantially free of biological molecules that are abundant in the blood, such the proteins discussed above, fatty acids, cholesterol, non-protein clotting factors, metabolites, and the like. In addition, the composition can be substantially free of cells, including red blood cells, white blood cells, and platelets, and cell fragments.

The compositions of the invention can include at least 1 mg (e.g., at least 5, 10, 20, 30, 40, 50, 75, 100, 150, 200, 250, 300, 400, 500, 600, 700, 800, 900, 1000 mg, or more) of anti-inflammatory polypeptide. Thus, for example, the compositions can include an amount of anti-inflammatory polypeptide equal to about 1 mg to about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints).

The compositions of the invention can include a solution that contains at least 1 mg/ml (e.g., at least 5, 10, 15, 20, 25, 30, 35, 40, 45, 50, 55, 60, 65, 70, 75, 80, 85, 90, 95, 100 mg/ml or more) of an anti-inflammatory polypeptide. Thus, for example, the compositions can include a solution having an anti-inflammatory polypeptide concentration of about 1 mg/ml to about 1000 mg/ml (e.g., about 5 mg/ml to about 900 mg/ml, about 5 mg/ml to about 800 mg/ml, about 5 mg/ml to about 700 mg/ml, about 5 mg/ml to about 600 mg/ml, about 5 mg/ml to about 500 mg/ml, about 10 mg/ml to about 500 mg/ml, about 10 mg/ml to about 400 mg/ml, about 10 mg/ml to about 300 mg/ml, about 10 mg/ml to about 250 mg/ml, about 10 mg/ml to about 200 mg/ml, about 10 mg/ml to about 150 mg/ml, about 10 mg/ml to about 100 mg/ml, about 50 mg/ml to about 500 mg/ml, about 50 mg/ml to about 400 mg/ml, about 50 mg/ml to about 300 mg/ml, about 50 mg/ml to about 250 mg/ml, about 50 mg/ml to about 200 mg/ml, about 50 mg/ml to about 150 mg/ml, about 50 mg/ml to about 100 mg/ml, about 75 mg/ml to about 500 mg/ml, about 75 mg/ml to about 400 mg/ml, about 75 mg/ml to about 300 mg/ml, about 75 mg/ml to about 250 mg/ml, about 75 mg/ml to about 200 mg/ml, about 75 mg/ml to about 150 mg/ml, about 75 mg/ml to about 100 mg/ml, about 100 mg/ml to about 500 mg/ml, about 100 mg/ml to about 400 mg/ml, about 100 mg/ml to about 300 mg/ml, about 100 mg/ml to about 250 mg/ml, about 100 mg/ml to about 200 mg/ml, about 10 mg/ml to about 150 mg/ml, or any other range containing two of the foregoing endpoints).

The compositions of the invention include pharmaceutical compositions. Such pharmaceutical compositions can comprise one or more anti-inflammatory polypeptides and a pharmaceutically acceptable carrier. Pharmaceutical compositions can further include a protein other than an anti-inflammatory polypeptide of the invention and/or a chemotherapeutic agent. The other protein can be a therapeutic agent, such as a therapeutic antibody. The therapeutic protein or antibody can have anti-inflammatory properties or other properties that the anti-inflammatory polypeptides of the invention augment or are augmented by. Alternatively, the other protein can be a carrier protein, such as serum albumin (e.g., HSA). The serum albumin (e.g., HAS, BSA, etc.) can be purified or recombinantly produced. By mixing the anti-inflammatory polypeptide(s) in the pharmaceutical composition with serum album, the anti-inflammatory polypeptides can be effectively "loaded" onto the serum albumin, allowing a greater amount of anti-inflammatory polypeptide to be successfully delivered to a site of inflammation. The chemotherapeutic agent can be, for example, an anti-cancer chemotherapeutic agent. Such chemotherapeutic agents include, but are not limited to, Gemcitabine, Docetaxel, Bleomycin, Erlotinib, Gefitinib , Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

Methods

The anti-inflammatory polypeptides of the invention provide powerful tools for reducing inflammation and/or treating conditions associated with excessive inflammation (whether acute or chronic). As used herein, the terms "treat," "treating," and similar words shall mean stabilizing, reducing the symptoms of, preventing the occurrence of, or curing a medical condition.

Accordingly, the invention provides methods of reducing the expression level and/or activity of at least one (e.g., 2, 3, 4, 5, or more) pro-inflammatory cytokine(s) at a site of inflammation in a subject. The methods include administering an anti-inflammatory polypeptide of the invention (or, for example, a pharmaceutical composition comprising an anti-inflammatory polypeptide) to the subject. The pro-inflammatory cytokine can be selected from the group consisting of NF-kB, TNF α, IL-1, IL-6, IL-8, IL-12, IL-17, IL-23, MCP-1, MMP-1, and MMP-9. The reduction can be a reduction of at least 10% (e.g., 15%, 20%, 25%, 30%, 35%, 40%, 45%, 50%, or more) in the expression or activity of the cytokine.

The invention also provides methods of inhibiting an increase in the expression level and/or activity of at least one (e.g., 2, 3, 4, 5, or more) pro-inflammatory cytokine(s) at a potential site of inflammation in a subject. The methods include administering an anti-inflammatory polypeptide of the invention (or, for example, a pharmaceutical composition comprising an anti-inflammatory polypeptide) to the subject. The pro-inflammatory cytokine can be selected from the group consisting of NF-kB, TNFα, IL-1, IL-6, IL-8, IL-12, IL-17, IL-23, MCP-1, MMP-1, and MMP-9. The methods can inhibit increased cytokine expression and/or activity by limiting such increases to no more than 20% (e.g., 15%, 12.5%, 10%, 7.5%, 5%, 4%, 3%, 2%, 1%, or less).

The invention also provides a method of treating or preventing a condition associated with chronic inflammation. The condition associated with chronic inflammation can be irritable bowel disease, ulcerative colitis, colitis, Crohn's disease, idiopathic pulmonary fibrosis, asthma, keratitis, arthritis, osteoarthritis, rheumatoid arthritis, autoimmune diseases, a feline or human immunodeficiency virus (FIV or HIV) infection, cancer, age-related inflammation and/or stem cell dysfunction (e.g., age-related increases in Nlrp3 expression, age-related elevation of SOCS3 in muscle stem cells, etc.), graft-versus-host disease (GVHD), keloids, scleroderma, obesity, diabetes, diabetic wounds, other chronic wounds, atherosclerosis, multiple sclerosis, Parkinson's disease, Alzheimer's disease, macular degeneration, gout, gastric ulcers, gastritis, mucositis, toxoplasmosis, and chronic viral or microbial infections (e.g., such as chronic bacterial or protozoan infections). The methods includes administering an anti-inflammatory polypeptide of the invention (or, for example, a pharmaceutical composition comprising an anti-inflammatory polypeptide) to a subject suffering from or likely to develop the condition.

The invention also provides methods of treating or preventing fibrosis. The fibrosis can be, for example, pulmonary fibrosis, dermal fibrosis, hepatic fibrosis, renal fibrosis, or fibrosis caused by ionizing radiation. The methods include administering an anti-inflammatory polypeptide of the invention (or, for example, a pharmaceutical composition comprising an anti-inflammatory polypeptide) to a subject suffering from or likely to develop fibrosis.

The invention also provides methods of treating cancer. The cancer can be colon cancer, breast cancer, leukemia, lymphoma, ovarian cancer, prostate cancer, liver cancer, lung cancer, testicular cancer, cervical cancer, bladder cancer, endometrial cancer, kidney cancer, melanoma, cancers of the thyroid or brain, or ophthalmic cancer. The methods include administering an anti-inflammatory polypeptide of the invention (or, for example, a pharmaceutical composition comprising an anti-inflammatory polypeptide) to a subject suffering from cancer.

For any of the foregoing methods, the subject can be an animal, such as a domesticated animal (e.g., a horse, cow, pig, goat, sheep, rabbit, chicken, turkey, duck, etc.), a pet (e.g., a dog, cat, rabbit, hamster, gerbil, bird, fish, etc.), a lab animal (e.g., a mouse, rat, monkey, chimpanzee, owl, fish, etc.), a zoo animal (e.g., a gorilla, orangutan, chimpanzee, monkey, elephant, camel, zebra, boar, lion, tiger, giraffe, bear, bird, etc.), a wild animal (e.g., a deer, wolf, mountain lion, bird, etc.), or a human.

In conjunction with any of the foregoing methods, the anti-inflammatory polypeptide(s) can be administered at a dose and frequency that depends on the type of animal, the size of the animal, and the condition being treated. Typically, the anti-inflammatory polypeptide is administered daily (or every other day, or weekly), in an amount between about 1 mg and about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints). The daily dose can be administered once during the day, or broken up into smaller doses that are taken at multiple time points during the day. For a human (and other similarly-sized mammals), a dose of 5 mg/kg every other day can be administered. The anti-inflammatory polypeptide can be administered for a fixed period of time (e.g., for 2-3 weeks), at intervals (e.g., administer polypeptide for 2-3 weeks, wait 2-3 weeks, then repeat the cycle), or until such time as the pro-inflammatory cytokine levels have been reduced or stabilized, the chronic inflammatory condition or fibrosis has ameliorated, or the cancer has gone into remission.

The administration of the anti-inflammatory polypeptides (or pharmaceutical compositions comprising such polypeptides) in conjunction with any of the foregoing methods can be performed intravenously, intraperitoneally, parenteral, orthotopically, subcutaneously, topically, nasally, orally, sublingually, intraocularly, by means of an implantable depot, using nanoparticle-based delivery systems, microneedle patch, microspheres, beads, osmotic or mechanical pumps, and/or other mechanical means.

In conjunction with any of the foregoing methods, the anti-inflammatory polypeptides (or pharmaceutical compositions comprising such polypeptides) can be administered in combination with another drug designed to reduce or prevent inflammation, treat or prevent chronic inflammation or fibrosis, or treat cancer. In each case, the anti-inflammatory polypeptide can be administered prior to, at the same time as, or after the administration of the other drug. For the treatment of cancer, the anti-inflammatory polypeptide(s) can be administered in combination with a chemotherapeutic agent selected from the group consisting of steroids, anthracyclines, thyroid hormone replacement drugs, thymidylate-targeted drugs, Chimeric Antigen Receptor/T cell therapies, and other cell therapies. Specific chemotherapeutic agents include, for example, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

Alternatively, for the methods of treating cancer, the anti-inflammatory polypeptide(s) (or pharmaceutical compositions comprising such polypeptides) can be administered in combination with radiation therapy. Again, the anti-inflammatory polypeptide(s) can be administered prior to, or after the administration of the radiation therapy.

Any of the foregoing methods of the invention further include a step of assessing the efficacy of the therapeutic treatment. Because the anti-inflammatory polypeptides of the invention have a demonstrable ability to reduce tissue inflammation and suppress the excessive production of inflammatory mediators such as IL-1, IL-6, IL-12, and TNFα, both in tissues and in serum (data not shown), the efficacy of the therapeutic treatment can be assessed by measuring the levels of such cytokines (e.g., in the serum) to determine whether the levels have responded appropriately to the treatment. Depending on the cytokine levels, the dosage of anti-inflammatory polypeptide(s) can be adjusted up or down, as needed.

EXAMPLES

Example 1

Peptide Designs

Polypeptides were designed in silico to include a striapathic region of alternating $X_m$ and $Y_n$ modules, with each $X_m$ module having one to five hydrophilic amino acid residues and each $Y_n$ module having one to five hydrophobic residues.

Initial designs focused on polypeptides consisting of a striapathic region having a total length of around 10 amino acid residues, with each $X_m$ module having one or two hydrophilic amino acid residues and each $Y_n$ module having one or two hydrophobic residues, and with the ratio of hydrophobic to hydrophilic amino acid residues being around 1:1. Such polypeptides were predicted to have an amphipathic, helical secondary structure, with a hydrophobic surface on one side of the helix and a hydrophilic surface on the opposite side of the helix.

Additional peptide designs were subsequently generated that maintained a total length of around 10 amino acid residues, but expanded the number of possible amino acid residues in a hydrophilic or hydrophobic module from two to three and varied the hydrophobic to hydrophilic ratio. For example, larger hydrophobic modules having three hydrophobic amino acid residues were coupled with shorter hydrophilic modules having one hydrophilic amino acid residue, giving rise to polypeptides predicted to have a stronger hydrophobic character. Such peptides were predicted to maintain an amphipathic, helical secondary structure, but have a larger hydrophobic surface on one side of the helix and a correspondingly smaller hydrophilic surface on the other side. Similarly, larger hydrophilic modules having three hydrophilic amino acid residues were coupled with shorter hydrophobic modules having one hydrophobic amino acid residue, giving rise to peptides having a stronger hydrophilic character. Such peptides were also predicted to maintain an amphipathic, helical secondary structure, but have a larger hydrophilic surface on one side of the helix and a correspondingly smaller hydrophobic surface on the other side.

Other peptide designs included: polypeptides having modules of four or five hydrophilic amino acid residues and/or four or five hydrophobic; polypeptides having a total length of around 10 amino acid residues but lacking hydrophobic amino acid residues; polypeptides having hydrophilic and hydrophobic modules each consisting of a single amino acid residue; and proline-rich polypeptides. Finally, larger polypeptides comprising two of the smaller peptide designs were also generated.

Exemplary polypeptides designed as described above are presented in Tables 3-9, below. To provide greater clarity into the types of polypeptides that have been developed, the peptides have been organized into Classes. Typically, the striapathic region of a specific Class of polypeptides shares a common sequence of hydrophobic and hydrophilic modules that is at least six or seven amino acid residues long. However, because the data indicates that polypeptides that have the same sequence but reversed N-terminal to C-terminal orientation have surprisingly similar anti-inflammatory activities, efforts have been made to keep such polypeptides in the same Class. Accordingly, some polypeptides have been grouped into the same Class even though the common sequence of hydrophobic and hydrophilic modules is less than six amino acid residues long. In addition, some of the polypeptides could have been grouped differently because they contain the common sequence of hydrophobic and hydrophilic modules of more than one Class. Thus, while providing a helpful framework for organizing the polypeptides around structural and functional similarities, the classification system does not capture all aspects of the relationships between different polypeptides.

Table 3 presents various Class I polypeptides, which have a striapathic region that includes a sequence corresponding to Formula I (i.e., $Y_{1a}$-$Y_{1b}$-$Y_{1c}$-$X_{1a}$-$Y_{2a}$-$Y_{2b}$-$Y_{2c}$). Two different types of Class I polypeptides are presented in Table 3: peptides that have a striapathic region consisting of a sequence corresponding to Formula II (i.e., $Y_{1a}$-$Y_{1b}$-$Y_{1c}$-$X_{1a}$-$Y_{2a}$-$Y_{2b}$-$Y_{2c}$-$X_{2a}$-$Y_{3a}$-$X_{3a}$); and peptide that have a striapathic region consisting of a sequence corresponding to Formula III (i.e., $X_{2a}$-$Y_{3a}$-$X_{3a}$-$Y_{1a}$-$Y_{1b}$-$Y_{1c}$-$X_{1a}$-$Y_{2a}$-$Y_{2b}$-$Y_{2c}$). In addition, a peptide having a striapathic region having a sequence corresponding to Formula I, but not Formulas II or III, is presented.

TABLE 3

Class I Polypeptides

| RP # | Sequence | RelB Binding E (kCal/mol) | Formula | SEQ ID NO: |
|---|---|---|---|---|
| 394 | NFNFFFRFFF | −1,286.6 | III | 33 |

TABLE 3 -continued

Class I Polypeptides

| RP # | Sequence | RelB Binding E (kCal/mol) | Formula | SEQ ID NO: |
|---|---|---|---|---|
| 108 | WWWRWWWEWQ | -1,278.0 | II | 34 |
| 109 | EFNFFFRFFF | -1,247.7 | III | 35 |
| 110 | DFEFFFRFFF | -1,232.0 | III | 36 |
| 111 | QFEFFFRFFF | -1,226.8 | III | 37 |
| 112 | EFEFFFRFFF | -1,216.0 | III | 38 |
| 113 | FFFRFFFEFQ | -1,208.9 | II | 39 |
| 114 | FFFRFFFEFE | -1,176.3 | II | 40 |
| 115 | FFFRFFFEFD | -1,172.3 | II | 41 |
| 116 | FFFRFFFNFE | -1,162.6 | II | 42 |
| 117 | FFFRFFFDFE | -1,147.7 | II | 43 |
| 118 | FFFRFFFNFN | -1,139.9 | II | 44 |
| 119 | FFFHFFFEFQ | -1,135.4 | II | 45 |
| 120 | FFFHFFFNFE | -1,126.4 | II | 46 |
| 121 | FFFHFFFEFN | -1,126.4 | II | 47 |
| 122 | EFNFFFHFFF | -1,125.1 | III | 48 |
| 123 | FFFRFFFEFN | -1,124.5 | II | 49 |
| 125 | FFFHFFFEFE | -1,115.4 | II | 50 |
| 126 | QFEFFFHFFF | -1,114.4 | III | 51 |
| 127 | FFFHFFFEFD | -1,114.3 | II | 52 |
| 128 | FFFHFFFDFE | -1,111.4 | II | 53 |
| 129 | YYYRYYYEYQ | -1,110.2 | II | 54 |
| 130 | NFEFFFHFFF | -1,109.1 | III | 55 |
| 131 | FFFKFFFKFE | -1,107.0 | II | 56 |
| 133 | EFDFFFRFFF | -1,103.4 | III | 57 |
| 135 | FFFHFFFDFD | -1,102.4 | II | 58 |
| 136 | FFFHFFFNFN | -1,100.4 | II | 59 |
| 137 | FFFRFFFDFD | -1,100.3 | II | 60 |
| 138 | FFFKFFFKFN | -1,098.2 | II | 61 |
| 139 | FFFKFFFEFE | -1,095.1 | II | 62 |
| 140 | FFFEFFFKFE | -1,091.8 | II | 63 |
| 141 | FFFQFFFQFQ | -1,088.8 | II | 64 |
| 143 | FFFKFFFQFQ | -1,084.4 | II | 65 |
| 144 | FFFKFFFNFN | -1,083.5 | II | 66 |
| 145 | FFFNFFFNFN | -1,083.3 | II | 67 |
| 146 | FFFKFFFEFQ | -1,082.6 | II | 68 |
| 148 | FFFKFFFKFQ | -1,080.0 | II | 69 |
| 149 | FFFKFFFQFK | -1,079.6 | II | 70 |
| 150 | FFFKFFFKFD | -1,077.4 | II | 71 |
| 152 | FFFKFFFDFD | -1,074.5 | II | 72 |
| 153 | FFFNFFFKFN | -1,074.2 | II | 73 |
| 154 | FFFDFFFDFD | -1,073.5 | II | 74 |
| 155 | FFFKFFFEFK | -1,073.3 | II | 75 |
| 156 | FFFKFFFDFK | -1,072.6 | II | 76 |
| 157 | FFFEFFFEFE | -1,070.8 | II | 77 |
| 158 | FFFDFFFKFD | -1,070.7 | II | 78 |
| 159 | FFFKFFFKFK | -1,070.7 | II | 79 |
| 160 | FFFEFFFKFK | -1,069.7 | II | 80 |
| 161 | FFFQFFFKFK | -1,069.6 | II | 81 |
| 162 | FFFKFFFNFK | -1,069.2 | II | 82 |
| 163 | FFFNFFFKFK | -1,066.7 | II | 83 |
| 164 | FFFQFFFKFQ | -1,062.5 | II | 84 |
| 165 | FFFDFFFKFK | -1,061.9 | II | 85 |
| 179 | LLLRLLLELQ | -966.7 | II | 86 |
| 395 | FVFKFVFKFV | -917.2 | I | 87 |
| 211 | CCCRCCCECQ | -818.2 | II | 88 |
| 230 | MMMRMMMEMQ | -774.6 | II | 89 |
| 232 | VVVRVVVEVQ | -771.6 | II | 90 |
| 258 | IIIRIIIEIQ | -699.2 | II | 91 |
| 267 | GGGRGGGEGQ | -640.4 | II | 92 |
| 268 | PPPRPPPEPQ | -627.1 | II | 93 |
| 271 | TTTRTTTETQ | -614.4 | II | 94 |
| 273 | AAARAAAEAQ | -609.4 | II | 95 |
| 280 | AAAKAAAKAA | -556.0 | II | 96 |
| 281 | AAAEAAAEAE | -541.6 | II | 97 |
| 287 | SSSRSSSESQ | -499.3 | II | 98 |

Table 4 presents some quasi-Class I polypeptides. These peptides include a sequence similar to the striapathic sequence of Formula II (i.e., $Y_{1a}$-$Y_{1b}$-$Y_{1c}$-$X_{1a}$-$Y_{2a}$-$Y_{2b}$-$Y_{2c}$-$X_{2a}$-$Y_{3a}$-$X_{3a}$), but the hydrophobic amino acid residues have all been replaced with a particular hydrophilic amino acid residue.

TABLE 4

Quasi-Class I Polypeptides

| RP # | Sequence | RelB Binding E (kCal/mol) | Formula | SEQ ID NO: |
|---|---|---|---|---|
| 173 | HHHRHHHEHQ | −1,002.2 | II* | 99 |
| 195 | RRRRRRRERQ | −855.2 | II* | 100 |
| 275 | QQQRQQQEQQ | −575.6 | II* | 101 |
| 276 | EEEREEEEEQ | −569.5 | II* | 102 |
| 284 | NNNRNNNENQ | −522.7 | II* | 103 |
| 288 | DDDRDDDEDQ | −463.6 | II* | 104 |
| 290 | KKKRKKKEKQ | −423.7 | II* | 105 |

*These peptides do not comply with the sequence requirements of Formula II, but instead represent an "all hydrophilic" variation on the sequence requirements of Formula II.

Table 5 presents various Class II, Sub-class 1 polypeptides. The presented peptides have a striapathic region consisting of a sequence corresponding to Formula X (i.e., $Y_{1a}$-$Y_{1b}$-$X_{1a}$-$X_{1b}$-$Y_{2a}$-$Y_{2b}$-$X_{2a}$-$X_{2b}$-$Y_{3a}$-$X_{3a}$), or a striapathic region consisting of a sequence corresponding to Formula XI (i.e., $X_{1a}$-$Y_{1a}$-$X_{2a}$-$X_{2b}$-$Y_{2a}$-$Y_{2b}$-$X_{3a}$-$X_{3b}$-$Y_{3a}$-$Y_{3b}$).

TABLE 5

Class II, Sub-class 1 Polypeptides

| RP # | Sequence | RelB Binding E (kCal/mol) | Formula | SEQ ID NO: |
|---|---|---|---|---|
| 124 | FFQKFFKRWR | −1,121.3 | X | 106 |
| 132 | FFRKFFKRFR | −1,104.8 | X | 107 |
| 134 | RFRKFFKRFF | −1,103.3 | XI | 108 |
| 142 | RFRKFFKQFF | −1,085.5 | XI | 109 |
| 147 | FFQKFFKRFR | −1,080.3 | X | 110 |
| 151 | RWRKFFKQFF | −1,077.0 | XI | 111 |
| 166 | FFEHFWKEFN | −1,044.8 | X | 112 |
| 167 | FFQHFWKQFN | −1,024.9 | X | 113 |
| 168 | QFNHFFKEFF | −1,022.8 | XI | 114 |
| 169 | FFDKFFHDFQ | −1,014.2 | X | 115 |
| 170 | QFDHFFKDFF | −1,011.9 | XI | 116 |
| 171 | FFEKFFHNFQ | −1,009.9 | X | 117 |
| 172 | NFEKWFHEFF | −1,007.9 | XI | 118 |
| 175 | LFRRAFKQLD | −989.5 | X | 119 |
| 177 | NFQKWFHQFF | −976.3 | XI | 120 |
| 182 | KFRKAFKRFF | −944.8 | XI | 121 |
| 183 | FFRKFAKRFK | −933.2 | X | 122 |
| 185 | FFKKFFKKFK | −920.6 | X | 123 |
| 186 | KFKKFFKKFF | −919.6 | XI | 124 |
| 424 | KARKAFKRFF | −910.2 | XI | 125 |
| 190 | WVKDAMQHLD | −888.7 | X | 126 |
| 194 | FFKKFAKKFK | −859.1 | X | 127 |
| 198 | FAEKFFKNFK | −850.4 | X | 128 |
| 199 | KFNKFFKEAF | −847.1 | XI | 129 |
| 200 | FAKQFFNKFK | −846.0 | X | 130 |
| 201 | KFNKAFKQAF | −837.8 | XI | 131 |
| 202 | KFNKAFKQAF | −837.8 | XI | 132 |
| 204 | FAQKFFKDFK | −835.9 | X | 133 |
| 206 | FAEEFAEEFE | −823.1 | X | 134 |
| 207 | KFKKFFKKAF | −820.7 | XI | 135 |
| 209 | KFKNFFQKAF | −819.1 | XI | 136 |
| 210 | KFKNFFQKAF | −819.1 | XI | 137 |
| 212 | FAKQFANKFK | −817.9 | X | 138 |
| 213 | KFKNAFQKAF | −815.2 | XI | 139 |
| 214 | KFKNAFQKAF | −815.2 | XI | 140 |
| 215 | FAKKFFKKFK | −814.0 | X | 141 |
| 216 | KFKKAFKKFF | −811.2 | XI | 142 |
| 218 | FAEKFAEKFE | −807.6 | X | 143 |
| 219 | DLHQMADKVW | −807.6 | XI | 144 |
| 425 | KARKAAKRFF | −800.3 | XI | 145 |
| 225 | FAKNFAKKFK | −794.0 | X | 146 |
| 227 | FAEKFAKNFK | −786.6 | X | 147 |
| 233 | KFKKAFKKAF | −771.2 | XI | 148 |
| 234 | FAKNFAKNFK | −769.8 | X | 149 |
| 235 | FAKEFAKEFE | −768.9 | X | 150 |
| 236 | KFDKAFKQAF | −766.2 | XI | 151 |
| 237 | KFDKAFKQAF | −766.2 | XI | 152 |
| 238 | FAEKFAKKFK | −765.1 | X | 153 |
| 239 | FAEKFAEKFK | −764.2 | X | 154 |
| 398 | FAKKFAKKFK | −760.3 | X | 155 |
| 241 | FAKNFAKNFN | −758.7 | X | 156 |
| 242 | FAQKFAKNFK | −758.6 | X | 157 |
| 243 | FANNFANNFN | −755.2 | X | 158 |
| 244 | FANNFANNFN | −755.2 | X | 159 |
| 245 | FANKFANKFN | −754.0 | X | 160 |
| 246 | FANKFAKKFK | −752.2 | X | 161 |
| 247 | FAQKFAKDFK | −750.7 | X | 162 |

TABLE 5 -continued

Class II, Sub-class 1 Polypeptides

| RP # | Sequence | RelB Binding E (kCal/mol) | Formula | SEQ ID NO: |
|---|---|---|---|---|
| 250 | FAKEFAKEFK | −745.7 | X | 163 |
| 251 | FANKFANKFK | −739.7 | X | 164 |
| 252 | KFDKFFKQAF | −739.1 | XI | 165 |
| 253 | KFDKFFKQAF | −739.1 | XI | 166 |
| 254 | KFNKAFKEAF | −738.4 | XI | 167 |
| 255 | KFNKAFKEAF | −738.4 | XI | 168 |
| 256 | FAKEFAKKFK | −702.8 | X | 169 |
| 426 | KARKAAKRAF | −634.5 | XI | 170 |
| 427 | KARKAAKRAA | −578.1 | XI | 171 |
| 285 | AAEEAAEEAE | −511.6 | X | 172 |
| 387 | AAKKAAKKAK | −301.6 | X | 173 |

Table 6 presents polypeptides that fall into a variety of different Classes, including: Class II peptides (having a striapathic region that includes a sequence corresponding to any of Formulas VI to XVI); Class II, Sub-class 2 (having a striapathic region that includes a sequence corresponding to Formulas VIII and XII); Class II, Sub-class 3 (having a striapathic region that includes a sequence corresponding to Formula IX); Class II, Sub-class 4 (having a striapathic region that includes a sequence corresponding to Formulas XIV and XV); Class II, Sub-class 5 (having a striapathic region that includes a sequence corresponding to Formulas XIII and XVI); Class III peptides (having a striapathic region that includes a sequence corresponding to any of Formulas XVII to XX); Class III, Sub-class 1 peptides (having a striapathic region that includes a sequence corresponding to Formulas XIX or XX); Class IV peptides (having a striapathic region that includes a sequence corresponding to Formulas IV and V); Class V peptides (having a striapathic region that includes a sequence corresponding to Formula XXI); Class VI peptides (having a striapathic region that includes a sequence corresponding to Formulas XXII and XXIII); Class VII peptides (having a striapathic region that includes a sequence corresponding to any of Formulas XXIV to XXVI); Class VIII peptides (having a striapathic region that includes a sequence corresponding to any of Formulas XXVII to XXXII); Class VIII, Sub-class 3 and 4 peptides (having a striapathic region that includes a sequence corresponding to Formulas XXXI and XXXII, respectively); Class IX peptides (having a striapathic region that includes a sequence corresponding to any of Formulas XXXIII to XXXVIII); Class IX, Sub-class 3 and 4 peptides (having striapathic regions that include a sequence corresponding to Formulas XXXVII and XXXVIII, respectively); and Class XIII (having a striapathic region that includes a sequence corresponding to Formula L). Because polypeptides of Class VIII, Sub-class 3 and Class IX, Sub-class 3 share the same sequence of hydrophobic and hydrophilic modules, but reversed N-terminal to C-terminal orientation, they could have been grouped into the same Class and Sub-class. Similarly, because polypeptides of Class VIII, Sub-class 4 and Class IX, Sub-class 4 share the same sequence of hydrophobic and hydrophilic modules, but reversed N-terminal to C-terminal orientation, they could have been grouped into the same Class and Sub-class.

TABLE 6

Class II to Class IX and Class XIII Polypeptides

| RP # | Sequence | RelB Binding E (kCal/mol) | Formula | SEQ ID NO: |
|---|---|---|---|---|
| 396 | FVKFVKFVKF | −1,039.7 | L | 174 |
| 405 | KRKAFRKFFF | −1,026.6 | XIV | 175 |
| 174 | LHKMYNQVW | −1,000.2 | VII | 176 |
| 176 | WVQNYMKHL | −979.3 | VII | 177 |
| 178 | RLVEMMRQIW | −972.2 | XX | 178 |
| 180 | FLKRLLQEI | −955.9 | VII | 179 |
| 181 | LRLLHRLL | −950.2 | XVII | 180 |
| 184 | WVRDSMKHL | −925.6 | VII | 181 |
| 408 | KFFRKKFRFA | −917.4 | XXII | 182 |
| 187 | WVQRVVEKFL | −906.4 | IX | 183 |
| 416 | AFFRRFKFKK | −904.1 | XXV | 184 |
| 188 | LFKEVVRQVW | −902.9 | IX | 185 |
| 189 | MDKIYDQVWK | −893.3 | VIII | 186 |
| 388 | FVKKFVKKFV | −891.9 | X | 187 |
| 417 | KKFKFRRFFA | −888.8 | XXVI | 188 |
| 191 | WVRDVVRSMD | −874.1 | XIX | 189 |
| 192 | ELSNIYERVW | −872.4 | XX | 190 |
| 193 | WIQRMMEVLR | −866.9 | XIX | 191 |
| 404 | FFFKRFAKRK | −856.7 | XV | 192 |
| 196 | LHKMSDRVW | −852.4 | VII | 193 |
| 197 | WVREYINSLE | −851.2 | XIX | 195 |
| 402 | FFKKRFAFRK | −851.0 | XXXI | 196 |
| 203 | KWVQDYIKDM | −837.0 | XII | 197 |
| 409 | AFRFKKRFFK | −832.7 | XXIII | 198 |
| 205 | LLRHLLRL | −830.0 | XVII | 199 |
| 208 | WIKKLLESSQ | −819.7 | XIX | 200 |
| 217 | DMSRVVDRVW | −810.4 | XX | 201 |
| 220 | FEEEFEEEFE | −804.8 | V | 202 |
| 221 | WVKNSINHL | −803.7 | VII | 203 |
| 222 | LTKKGRRFC | −799.7 | XXI | 204 |
| 223 | IEQLLRKLF | −796.8 | VII | 205 |
| 224 | LHNISNKVW | −794.5 | VII | 206 |
| 226 | CFRRGKKTL | −786.7 | XXI | 207 |
| 229 | IVRRADRAAV | −781.5 | XXI | 208 |
| 231 | TVERFKNLS | −771.8 | XXI | 209 |

TABLE 6 -continued

Class II to Class IX and Class XIII Polypeptides

| RP # | Sequence | RelB Binding E (kCal/mol) | Formula | SEQ ID NO: |
|---|---|---|---|---|
| 240 | QSSELLKKIW | −761.9 | XX | 210 |
| 248 | SLNKFREVT | −750.5 | XXI | 211 |
| 249 | LIKQIVKKLF | −750.5 | IX | 212 |
| 397 | FAKKFAKKF | −739.3 | VII | 194 |
| 415 | KKKFFF | −706.8 | XXVII | 213 |
| 257 | LYKKIIKKLL | −699.8 | IX | 214 |
| 259 | FKKKFKKKFK | −686.5 | V | 215 |
| 260 | VAARDARRVI | −684.6 | XXI | 216 |
| 261 | FLKKVIQKIL | −679.4 | IX | 217 |
| 262 | LIKEIIKQVM | −668.4 | IX | 218 |
| 263 | LLKKIIKKYL | −666.7 | IX | 219 |
| 264 | AFFEEEAEFE | −652.2 | XXXVIII | 220 |
| 265 | KKWVQDSMK | −650.1 | XVIII | 221 |
| 266 | NFANKVQEVA | −644.1 | XXI | 222 |
| 269 | AVEQVKNAFN | −621.1 | XXI | 223 |
| 272 | MVQKIIEKIL | −613.1 | IX | 224 |
| 274 | KMSDQVWKK | −595.9 | XVIII | 225 |
| 277 | MVKKIIEKM | −569.2 | VII | 226 |
| 278 | ALKKQVIKKI | −559.1 | XVI | 227 |
| 279 | IKKIVQKKLA | −556.7 | XIII | 228 |
| 282 | AFFKKKAKFK | −537.6 | XXXVIII | 229 |
| 283 | MKEIIKVM | −533.1 | VII | 230 |
| 286 | AEEEAEEEAE | −504.4 | V | 231 |
| 289 | AKKKAKKKAK | −431.6 | V | 232 |
| 414 | KKKAAA | 0.0 | XXVII | 233 |

Table 7 presents polypeptide of Classes VIII through XI. All of the peptides presented in Table 7 have a striapathic region that includes a hydrophilic module having four or five hydrophilic amino acid residues and/or a hydrophobic module having four or five hydrophobic amino acid residues. Class VIII, Sub-class 1 peptides have a striapathic region that includes a sequence corresponding to Formulas XXVIII or XXIX; Class VIII, Sub-class 2 peptides have a striapathic region that includes a sequence corresponding to Formula XXX; Class IX, Sub-class 1 peptides have a striapathic region that includes a sequence corresponding to Formulas XXXIV or XXXV; Class IX, Sub-class 2 peptides have a striapathic region that includes a sequence corresponding to Formula XXXVI; Class X peptides have a striapathic region that includes a sequence corresponding to any of Formulas XXXIX to XLIII; and Class XI peptides have a striapathic region that includes a sequence corresponding to any of Formulas XLIV to XLVIII. Because polypeptides of Class VIII, Sub-class 1 and Class IX, Sub-class 1 share the same sequence of hydrophobic and hydrophilic modules, but reversed N-terminal to C-terminal orientation, they could have been grouped into the same Class and Sub-class. Similarly, because polypeptides of Class VIII, Sub-class 2 and Class IX, Sub-class 2 share the same sequence of hydrophobic and hydrophilic modules, but reversed N-terminal to C-terminal orientation, they could have been grouped into the same Class and Sub-class.

TABLE 7

Class VIII to XI Polypeptides

| RP # | Sequence | RelB Binding E (kCal/mol) | Formula | SEQ ID NO: |
|---|---|---|---|---|
| 406 | KRKKRFAFFF | −993.5 | XXX | 234 |
| 422 | RKRKFFAFFK | −948.2 | XLVIII | 235 |
| 407 | FFFAFRKKRK | −914.7 | XXXVI | 236 |
| 400 | FRKKRFAFFK | −900.5 | XXIX | 237 |
| 419 | FFFRRKKKFA | −881.9 | XLII | 238 |
| 401 | KFFAFRKKRF | −880.1 | XXXV | 239 |
| 423 | KFFAFFKRKR | −877.1 | XLV | 240 |
| 411 | KKKKKFFFFF | −863.7 | XXX | 241 |
| 418 | AFKKKRRFFF | −854.1 | XLI | 242 |
| 428 | KRKKRAAFFF | −842.0 | XXX | 243 |
| 420 | KKFFAFFRKR | −840.2 | XLVI | 244 |
| 421 | RKRFFAFFKK | −835.5 | XLVII | 245 |
| 429 | KRKKRAAAFF | −758.1 | XXX | 246 |
| 413 | KKKKFFFF | −715.8 | XXVIII | 247 |
| 430 | KRKKRAAAAF | −676.7 | XXX | 248 |
| 270 | KKKAFFFAKK | −614.4 | XLVII | 249 |
| 431 | KRKKRAAAAA | −544.9 | XXX | 250 |
| 410 | KKKKKAAAAA | −385.3 | XXX | 251 |
| 412 | KKKKAAAA | −382.8 | XXVIII | 252 |

Table 8 presents polypeptides of Class XII and Class XIV. Class XII peptides have a striapathic region that includes a sequence corresponding to Formula XLIX (i.e., $Y_{1a}$-$X_{1a}$-$Y_{2a}$-$X_{2a}$-$Y_{3a}$-$X_{3a}$). Class XII peptides are predicted to adopt a beta-strand secondary structure. Class XIV peptides are proline-rich peptides that have a striapathic region that includes a sequence corresponding to one of Formulas LI-LIV.

TABLE 8

Beta-Strand and Proline-Rich Polypeptides

| RP # | Sequence | RelB Binding E (kCal/mol) | Formula | SEQ ID NO: |
|---|---|---|---|---|
| 393 | FKFKFKFKF | −1,193.2 | XLIX | 253 |
| 391 | FRFKFKFR | −1,190.8 | XLIX | 254 |

TABLE 8 -continued

Beta-Strand and Proline-Rich Polypeptides

| RP # | Sequence | RelB Binding E (kCal/mol) | Formula | SEQ ID NO: |
|---|---|---|---|---|
| 392 | RFQFKFRF | -1,170.3 | XLIX | 255 |
| 390 | FRFKFKF | -1,083.3 | XLIX | 256 |
| 389 | FRFKFA | -1,009.8 | XLIX | 257 |
| 449 | RRFPRPPFF | -1,116.8 | LI | 258 |
| 450 | FFPPRPFRR | -1,100.0 | LII | 259 |
| 448 | LYPPRPFRR | -1,059.3 | LII | 260 |
| 447 | RRIPRPPYL | -1,050.5 | LI | 261 |
| 452 | PFRPPPRPRF | -1,012.2 | LIII | 262 |
| 451 | PRPRPPPRFF | -1,002.1 | LIV | 263 |
| 444 | FFPPKPFKK | -954.8 | LII | 264 |
| 441 | KKIPKPPYL | -922.1 | LI | 265 |
| 446 | PFKPPPKPKP | -882.3 | LIII | 266 |
| 445 | PKPKPPPKFP | -866.3 | LIV | 267 |
| 442 | LYPPKPIKK | -846.6 | LII | 268 |
| 443 | KKFPKPPFF | -802.8 | LI | 269 |

Table 9 presents fusion peptides, which include combinations of Class I, Class II, and/or Class III peptides linked together by a peptide bond and, optionally, a short peptide linker (e.g., a tri-glycine (GGG) linker).

TABLE 9

Peptide Combinations

| RP # | Sequence | RelB Binding E (kCal/mol) | Formula | SEQ ID NO: |
|---|---|---|---|---|
| 292 | EFEFFFRFFFGGGEFEFFFRFFF | -1,606.1 | III + III | 270 |
| 293 | QFEFFFRFFFGGGQFEFFFRFFF | -1,602.0 | III + III | 271 |
| 294 | DFEFFFRFFFGGGDFEFFFRFFF | -1,591.8 | III + III | 272 |
| 295 | EFNFFFRFFFGGGEFNFFFRFFF | -1,591.8 | III + III | 273 |
| 296 | FFFRFFFEFQFFFRFFFEFQ | -1,511.6 | II + II | 274 |
| 297 | FFFRFFFEFQGGGFFFRFFFEFQ | -1,511.5 | II + II | 275 |
| 298 | RWRKFFKRFFQFEFFFRFFF | -1,505.2 | XI + III | 276 |
| 299 | RWRKFFKRFFGGGFFFRFFFNFN | -1,501.3 | XI + II | 277 |
| 300 | RFRKFFKRFFQFEFFFRFFF | -1,486.0 | XI + III | 278 |
| 301 | RFRKFFKRFFGGGFFFRFFFNFN | -1,485.0 | XI + II | 279 |
| 302 | RWRKFFKRFFGGGFFFRFFFEFQ | -1,479.6 | XI + II | 280 |
| 303 | RFRKFFKRFFGGGFFFRFFFEFQ | -1,476.8 | XI + II | 281 |
| 304 | EFEFFFRFFFEFEFFFRFFF | -1,476.0 | III + III | 282 |
| 305 | RWRKFFKRFFNFNFFFRFFF | -1,474.2 | XI + III | 283 |
| 306 | QFEFFFRFFFQFEFFFRFFF | -1,467.0 | III + III | 284 |
| 307 | RWRKFFKRFFGGGNFNFFFRFFF | -1,464.2 | XI + III | 285 |
| 308 | EFNFFFRFFFEFNFFFRFFF | -1,460.5 | III + III | 286 |
| 309 | RFRKFFKRFFNFNFFFRFFF | -1,458.4 | XI + III | 287 |
| 310 | FFRKFFKRFRGGGNFNFFFRFFF | -1,447.1 | X + III | 288 |
| 311 | RFRKFFKRFFGGGNFNFFFRFFF | -1,432.1 | XI + III | 289 |
| 312 | DFEFFFRFFFDFEFFFRFFF | -1,430.0 | III + III | 290 |
| 313 | RWRKFFKRFFFFFRFFFEFQ | -1,427.4 | XI + II | 291 |
| 314 | RFRKFFKRFFFFFRFFFEFQ | -1,425.6 | XI + II | 292 |

TABLE 9-continued

Peptide Combinations

| RP # | Sequence | RelB Binding E (kCal/mol) | Formula | SEQ ID NO: |
| --- | --- | --- | --- | --- |
| 315 | FFRKFFKRFRGGGFFFRFFFNFN | -1,420.6 | X + II | 293 |
| 316 | FFRKFFKRWGGGFFFRFFFNFN | -1,417.5 | X + II | 294 |
| 317 | RFRKFFKRFFFFRFFFNFN | -1,406.6 | XI + II | 295 |
| 318 | FFRKFFKRFRFFFFRFFFEFQR | -1,402.0 | X + II | 296 |
| 291 | FFEHFWKEFNGGGNFQKWFHQFF | -1,401.6 | X + XI | 297 |
| 319 | FFRKFFKRWRQFEFFFRFFF | -1,400.7 | X + III | 298 |
| 320 | RWRKFFKRFFFFRFFFNFN | -1,397.9 | XI + II | 299 |
| 321 | NFQKWFHQFFGGGFFEHFWKEFN | -1,396.0 | XI + X | 300 |
| 322 | FFRKFFKRWRGGGNFNFFFRFFF | -1,394.4 | X + III | 301 |
| 323 | FFRKFFKRWRFFFRFFFEFQR | -1,394.3 | X + II | 302 |
| 324 | FFRKFFKRWRNFNFFFRFFF | -1,393.7 | X + III | 303 |
| 325 | FFRKFFKRFRGGGFFFRFFFEFQR | -1,386.8 | X + II | 304 |
| 326 | FFRKFFKRFRQFEFFFRFFF | -1,382.8 | X + III | 305 |
| 327 | FFRKFFKRFRNFNFFFRFFF | -1,378.2 | X + III | 306 |
| 328 | RFRKFFKRFFGGGQFEFFFRFFF | -1,368.5 | XI + III | 307 |
| 329 | FFRKFFKRWRGGGFFFRFFFEFQR | -1,354.5 | X + II | 308 |
| 330 | FFRKFFKRFRGGGQFEFFFRFFF | -1,352.8 | X + III | 309 |
| 331 | FFRKFFKRWRGGGQFEFFFRFFF | -1,352.2 | X + III | 310 |
| 332 | RWRKFFKRFFGGGQFEFFFRFFF | -1,349.8 | XI + III | 311 |
| 333 | QFNHFFKEFGGGQFNHFFKEFF | -1,340.0 | VII + XI | 312 |
| 334 | FFRKFFKRFRFFFFRFFFNFN | -1,337.5 | X + II | 313 |
| 335 | FFRKFFKRWRFFFRFFFNFN | -1,337.0 | X + II | 314 |
| 336 | FFEHFWKEFNGGGFFEHFWKEFN | -1,325.5 | X + X | 315 |
| 337 | FFEHFWKEFGGGNFQKWFHQFF | -1,324.8 | VII + XI | 316 |
| 338 | NFQKWFHQFGGGFFEHFWKEFN | -1,317.9 | VII + X | 317 |
| 339 | FFEHFWKEFNGGGLHKMYNQVW | -1,315.4 | X + VII | 318 |
| 340 | NFQKWFHQFFGGGNFQKWFHQFF | -1,309.9 | XI + XI | 319 |
| 341 | FAKKFAKKFKGGGNFQKWFHQFF | -1,308.3 | X + XI | 320 |
| 342 | FFEKFFHNFQGGGFFEKFFHNFQ | -1,304.6 | X + X | 321 |
| 343 | FFQHFWKQFNGGGFFQHFWKQFN | -1,300.2 | X + X | 322 |
| 344 | NFQKWFHQFFNFQKWFHQFF | -1,293.5 | XI + XI | 323 |
| 345 | FAKKFAQKFKGGGNFQKWFHQFF | -1,291.9 | X + XI | 324 |
| 346 | FAKKFAKKFKGGGQFEFFFRFFF | -1,290.9 | X + III | 325 |
| 347 | QFNHFFKEFQFNHFFKEFF | -1,279.8 | VII + XI | 326 |
| 348 | FAKKFAKKFKGGGDFEFFFRFFF | -1,278.4 | X + III | 327 |
| 349 | FFEHFWKEFNGGGWVQNYMKHL | -1,268.8 | X + VII | 328 |
| 350 | FAKKFAKKFKQFEFFFRFFF | -1,268.5 | X + III | 329 |

TABLE 9-continued

Peptide Combinations

| RP # | Sequence | RelB Binding E (kCal/mol) | Formula | SEQ ID NO: |
|---|---|---|---|---|
| 351 | FFQHFWKQFNFFQHFWKQFN | -1,263.2 | X + X | 330 |
| 352 | FFEHFWKEFNFFEHFWKEFN | -1,251.5 | X + X | 331 |
| 353 | NFEKWFHEFFNFEKWFHEFF | -1,247.0 | XI + XI | 332 |
| 354 | FAKKFAKKFKGGGQFNHFFKEFF | -1,244.6 | X + XI | 333 |
| 355 | NFEKWFHEFFGGGNFEKWFHEFF | -1,241.4 | XI + XI | 334 |
| 356 | FAKKFAKKFKGGGFFFRFFFEFQ | -1,237.9 | X + II | 335 |
| 357 | FAKKFAKKFKDFEFFFRFFF | -1,235.3 | X + III | 336 |
| 358 | QFNHFFKEFFGGGQFNHFFKEFF | -1,230.0 | XI + XI | 337 |
| 359 | FAKKFAKKFKGGGEFEFFFRFFF | -1,221.7 | X + III | 338 |
| 360 | FAKKFAKKFKGGGEFNFFFRFFF | -1,221.0 | X + III | 339 |
| 361 | FAKKFAKKFKGGGNFEKWFHEFF | -1,212.3 | X + XI | 340 |
| 362 | FAKKFAKKFKGGGFFEKFFHNFQ | -1,210.8 | X + X | 341 |
| 363 | QFNHFFKEFFQFNHFFKEFF | -1,208.6 | XI + XI | 342 |
| 364 | FFEKFFHNFQFFEKFFHNFQ | -1,207.5 | X + X | 343 |
| 365 | FAKKFAKKFKEFEFFFRFFF | -1,204.2 | X + III | 344 |
| 366 | FAKKFAKKFKEFNFFFRFFF | -1,187.6 | X + III | 345 |
| 367 | FAKKFAKKFKFFEHFWKEFN | -1,168.1 | X + X | 346 |
| 368 | FAKKFAKKFKFFFRFFFEFQ | -1,166.4 | X + II | 347 |
| 369 | FAKKFAKKFKLHKMYNQVW | -1,159.5 | X + VII | 348 |
| 370 | FAKKFAKKFKGGGFFEHFWKEFN | -1,140.4 | X + X | 349 |
| 371 | FAKKFAKKFKGGGWVQNYMKHL | -1,130.4 | X + VII | 350 |
| 372 | FAKKFAKKFKNFQKWFHQFF | -1,126.1 | X + XI | 351 |
| 373 | FAKKFAKKFKFFQHFWKQFN | -1,119.8 | X + X | 352 |
| 374 | FAKKFAKKFKGGGFFQHFWKQFN | -1,119.6 | X + X | 353 |
| 375 | FAKKFAKKFKWVQNYMKHL | -1,119.2 | X + VII | 354 |
| 376 | FAKKFAKKFKQFNHFFKEFF | -1,108.3 | X + XI | 355 |
| 377 | FAKKFAKKFKGGGLHKMYNQVW | -1,100.3 | X + VII | 356 |
| 378 | FAKKFAKKFKNFEKWFHEFF | -1,081.4 | X + XI | 357 |
| 379 | FAKKFAKKFKFFEKFFHNFQ | -1,046.8 | X + X | 358 |
| 380 | FAKKFAKKFKGGGAFFKKKAKFK | -950.9 | X + XXXVIII | 359 |
| 381 | AFFKKKAKFKGGGAFFKKKAKFK | -935.5 | XXXVIII + XXXVIII | 360 |
| 382 | KFKKAFKKAFKFKKAFKKAF | -925.2 | XI + XI | 361 |
| 383 | KFKKAFKKAFGGGKFKKAFKKAF | -923.8 | XI + XI | 362 |
| 384 | FAKKFAKKFKGGGFAKKFAKKFK | -909.2 | X + X | 363 |
| 385 | FAKKFAKKFKAFFKKKAKFK | -839.9 | X + XXXVIII | 364 |

TABLE 9-continued

Peptide Combinations

| RP # | Sequence | RelB Binding E (kCal/mol) | Formula | SEQ ID NO: |
|---|---|---|---|---|
| 228 | PSRKSMEKSVAKLLNKIAKSEP | −782.4 | IX + XVIII | 365 |
| 386 | AFFKKKAKFKAFFKKKAKFK | −716.0 | XXXVIII + XXXVIII | 366 |

In each of Tables 3-9, the RP# is a randomly assigned designation used to identify specific peptide sequences. The "Binding E" (see column 3 in each of the Tables) corresponds to a predicted measure of the energy released when individual peptides bind to the protein dimerization domain of RelB, an NFkB Class II protein (see Example 2, below).

Example 2

Predicted Binding of Peptides to Rel B

To identify peptides having anti-inflammatory activity, the NF-kB complex was selected as a target, since it is known to be a key component in the signaling pathways that regulate inflammation. Dimerization of NF-kB (either homologous or heterologous), which is mediated by the dimerization domains found in NF-kB Class II proteins (e.g., RelA, RelB, cRel, NF-kB1, and NF-kB2), is essential for activation of the NF-kB complex and its generation of pro-inflammatory signals. Accordingly, peptide designs were selected for their ability to specifically bind to the dimerization domain of RelB (NCBI Acc. No. NP_033072.2), with the goal that such binding would inhibit NF-kB dimerization and activation.

Peptide binding to the dimerization domain of Rel B was evaluated in silico, using the web-based ClusPro™ algorithm developed at Boston University. The ClusPro™ algorithm filters docked conformations between a protein target and a putative ligand and determines surface complementarity, ranking the conformations based on their clustering properties. The free energy filters select complexes with the lowest desolvation and electrostatic energies. Clustering is then used to smooth the local minima and to select the ones with the broadest energy wells, a property associated with the free energy at the binding site. Using this method, it is possible to evaluate the affinity a ligand possesses for a particular target, whereupon the ligands can be ranked and then tested for biological activity in vitro or in vivo.

The binding energies calculated by the ClusPro™ algorithm are shown for each of the peptides in Tables 3-9, in the third columns of the tables. In each of Tables 3-9, the peptides are ranked according to the calculated RelB binding energy, from highest to lowest binding energy. The RelB binding energies were used to explore the structure-function relationship of the peptides, particularly with regard to (i) increasing or decreasing hydrophobicity, (ii) positive/negative charge density, and (iii) altering the arc of the hydrophobic and hydrophilic faces of the peptides. The peptides shown in Table 10 (below) will be used to illustrate the results of the study.

TABLE 10

Predicted Binding of Select Peptides to RelB

| RP # | Sequence | RelB Binding E (kCal/mol)* | Formula | SEQ ID NO: |
|---|---|---|---|---|
| RP-182 | KFRKAFKRFF | −944.8 | XI | 121 |
| RP-166 | FFEHFWKEFN | −1,044.8 | X | 112 |
| RP-113 | FFFRFFFEFQ | −1,208.9 | II | 39 |
| RP-289 | AKKKAKKKAK | −431.6 | V | 232 |
| RP-387 | AAKKAAKKAK | −338.3 | X | 173 |
| NF-CONTR2 | IESKRRKKKP | −476.6 | N/A | 382 |
| NF-CONTR3 | APGPGDGGTA | −621.1 | N/A | 383 |

*The lower the energy value, the greater affinity the ligand possesses for the binding site on the target protein.

A structural model of the RelB subunit of NF-kB is shown in FIG. 1. Amino acids with the dimerization site are shaded to indicate their hydrophobic or hydrophilic character. In particular, the amino acid residues colored light grey are hydrophilic, while the amino acid residues colored dark grey are hydrophobic. Given the distinct locations of the hydrophilic and hydrophobic amino acid residues within the binding pocket of the dimerization domain, it is evident that striapathic peptides having an amphipathic secondary structure have the potential to bind site-specifically to the dimerization domain binding pocket.

Figure 2:
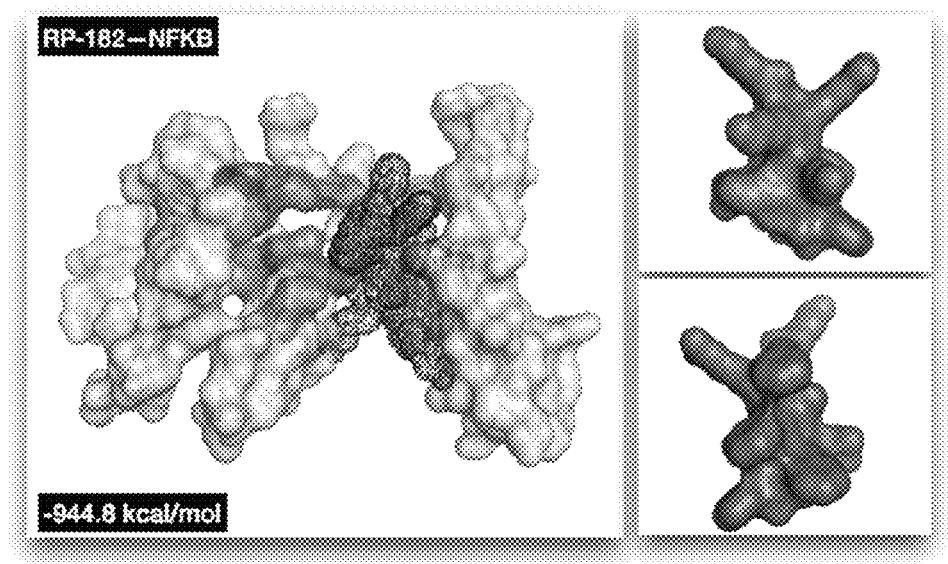
FIG. 2 depicts a structural model of human RelB bound by RP-182.

The secondary structure of RP-182 (SEQ ID NO: 121) and its binding to RelB (SEQ ID NO: 367) is modeled in FIG. 2. As can be seen in the panels on the right, RP-182's predicted secondary structure has distinct hydrophobic and hydrophilic sides that comprise approximately equal facial arcs (see also FIG. 9) and are of high volume. Overall, the structure of RP-182 possesses high hydrophobicity and high cationicity (with a total of five cationic amino acid residues). These characteristics of RP-182 are summarized in Table 11, below. Based on the structural modeling, RP-182 binds with high affinity to the RelB dimerization domain binding pocket, with an estimated binding energy of −944.8 kcal/mol.

Figure 3:
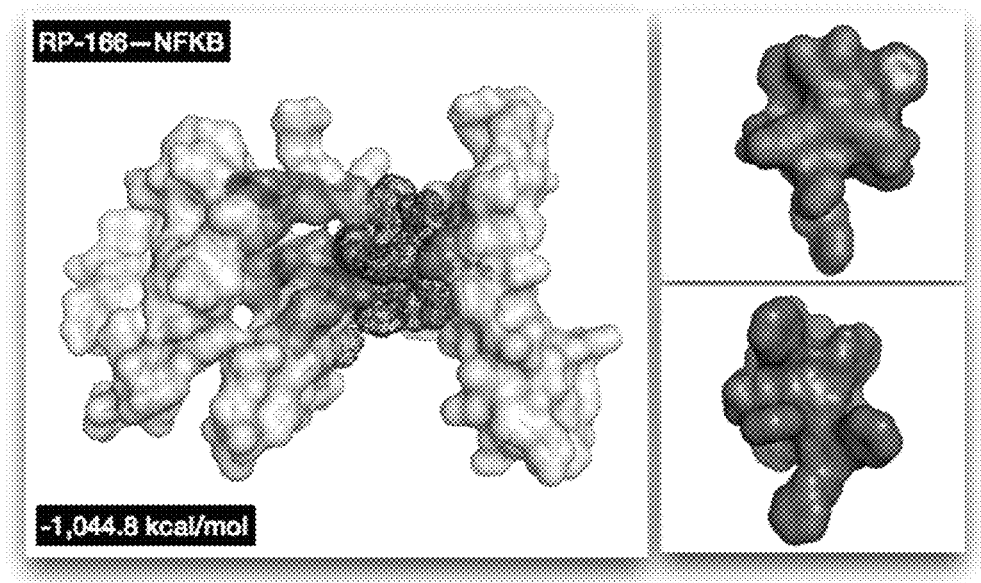
FIG. 3 depicts a structural model of human RelB bound by RP-166.

The secondary structure of RP-166 (SEQ ID NO: 112) and its binding to RelB (SEQ ID NO: 367) is modeled in FIG. 3. As can be seen in the panels on the right, RP-166's predicted secondary structure also has distinct hydrophobic and hydrophilic sides that comprise approximately equal facial arcs (see also FIG. 9). These characteristics are not surprising, as the striapathic region of RP-166 has a modular structure that is identical (albeit reversed) to that of RP-182's (compare Formulas X and XI). As with RP-182, the hydrophobic and hydrophilic surfaces of RP-166 are of high volume, but RP-166 has a greater ratio of hydrophobic volume to hydrophilic volume as compared to RP-182. In addition, the cationicity of RP-166 is significantly reduced relative to that of RP-182, since RP-166 has an equal number of cationic amino acid residues and anionic amino acid residues. These characteristics of RP-166 are summarized in Table 11, below. Based on the structural modeling, RP-166 binds to the RelB dimerization domain binding pocket with even higher affinity than RP-182, having an estimated binding energy of −1,044.8 kcal/mol.

Figure 4:
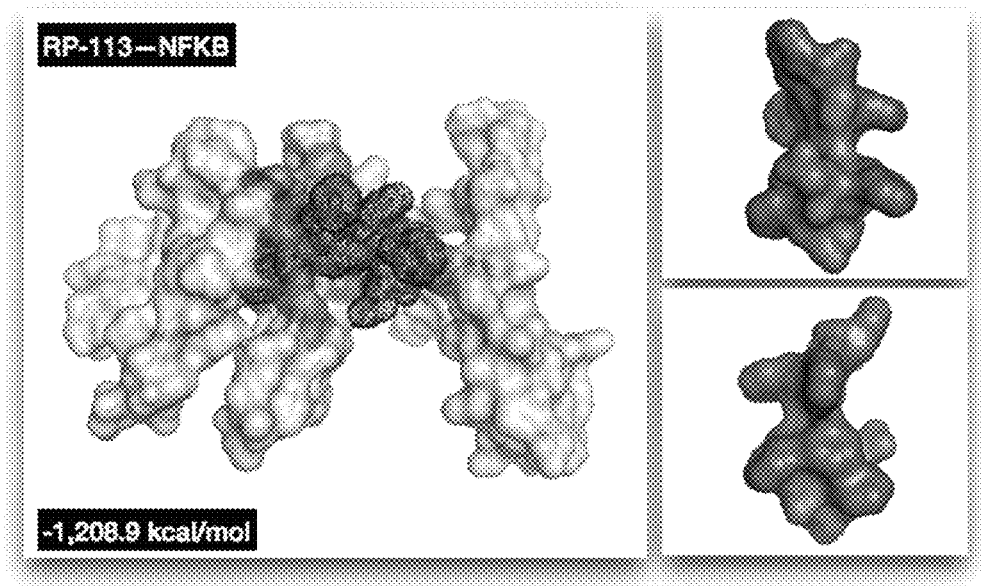
FIG. 4 depicts a structural model of human RelB bound by RP-113.
Figure 9:
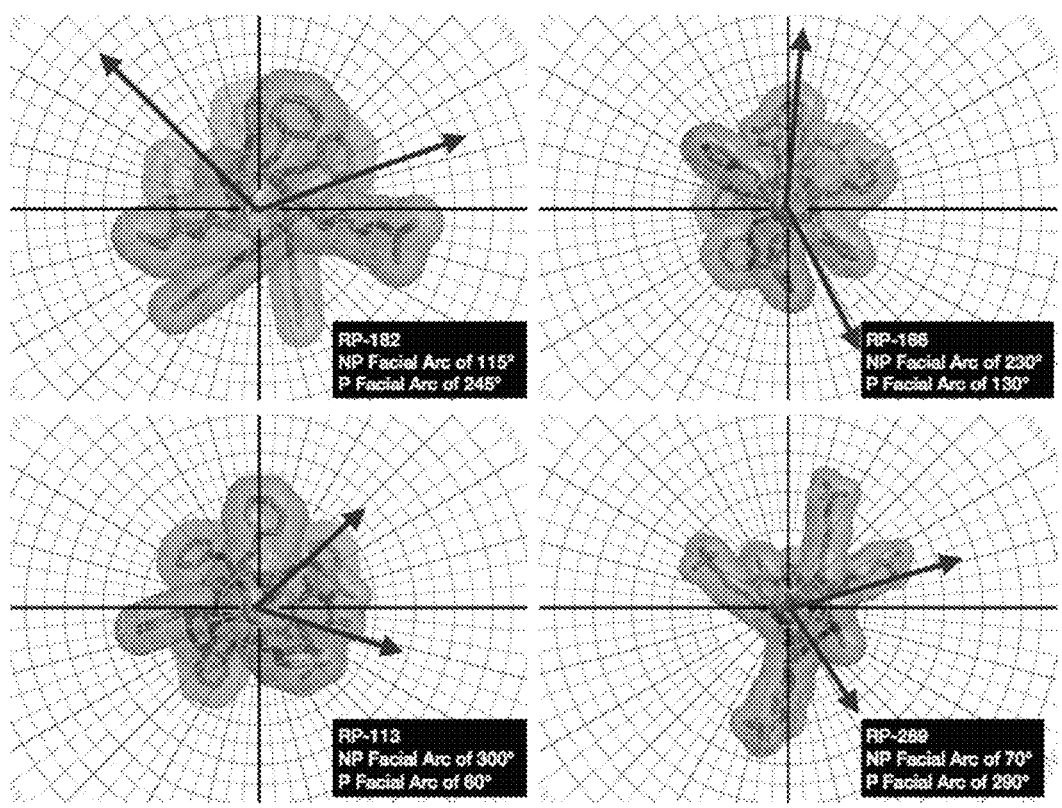
FIG. 9 depicts structural models of polypeptides RP-182, RP-166, RP-113, and RP-289, with each model showing the polar and non-polar facial arc associated with the helices formed by the polypeptides.

The secondary structure of RP-113 (SEQ ID NO: 39) and its binding to RelB (SEQ ID NO: 367) is modeled in FIG. 4. As can be seen in the panels on the right, RP-113's predicted secondary structure also has distinct hydrophobic and hydrophilic sides, but the hydrophobic side comprises a much larger facial arc than the hydrophilic side. As shown in FIG. 9, the facial arc of the polar side of RP-113 is only 60°, while the facial arc of the non-polar side is 300°. Consistent with this shift toward a larger hydrophobic surface, RP-113 has a larger hydrophobic volume than either RP-182 or RP-166, as well as a significantly larger ratio of hydrophobic to hydrophilic volume. See Table 11, below. Like RP-166, the cationicity of RP-113 is significantly reduced relative to that of RP-182, since RP-113 has an equal number of cationic amino acid residues and anionic amino acid residues. Based on the structural modeling, RP-113 binds to the RelB dimerization domain binding pocket with one of the highest affinities predicted for the peptides of the invention, having an estimated binding energy of −1,208.9 kcal/mol.

Figure 5:
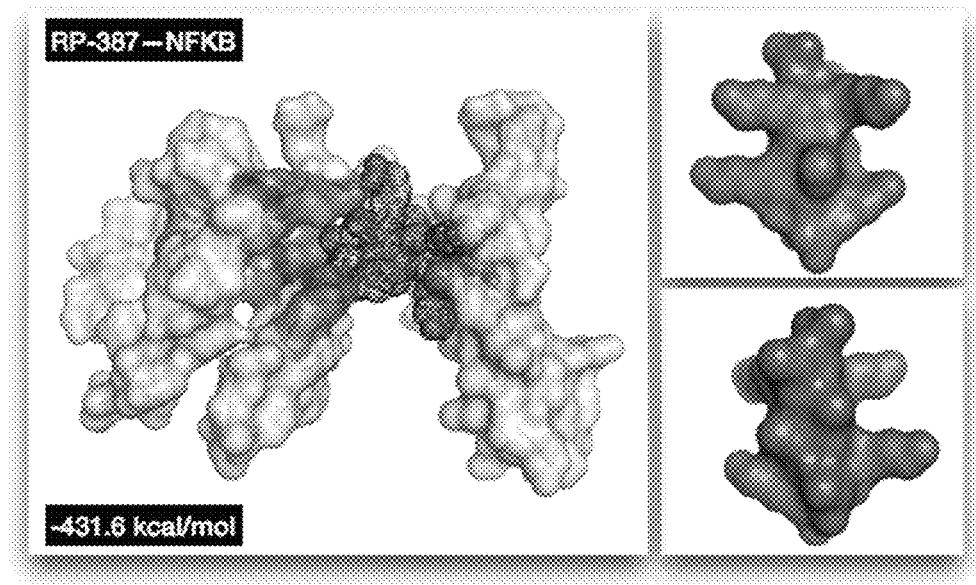
FIG. 5 depicts a structural model of human RelB bound by RP-387.
Figure 10:
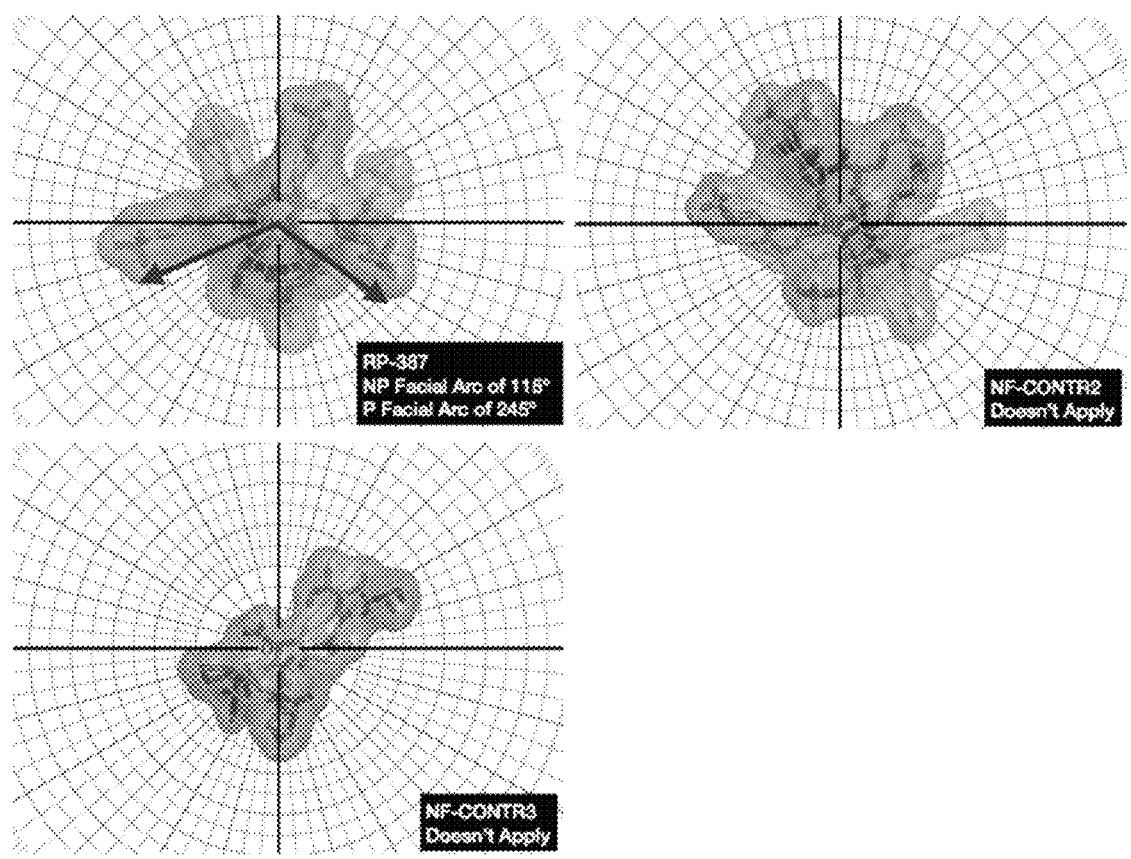
FIG. 10 depicts structural models of polypeptides RP-387, NF-Contr2, and NF-Contr3, with each model showing the polar and non-polar amino acid residues. The facial arc associated with the helix formed by RP-387 is also shown.

The secondary structure of RP-387 (SEQ ID NO: 173) and its binding to RelB (SEQ ID NO: 367) is modeled in FIG. 5. As can be seen in the panels on the right, RP-387's predicted secondary structure has distinct hydrophobic and hydrophilic sides. However, in contrast to RP-113, the hydrophilic side of RP-387 comprises a much larger facial arc than the hydrophobic side. As shown in FIG. 10, the facial arc of the polar side of RP-387 is 245°, while the facial arc of the non-polar side is 115°. Consistent with this shift toward a larger hydrophilic surface, RP-387 has a smaller hydrophobic volume than any of RP-182, RP-166, and RP-113, as well as a significantly smaller ratio of hydrophobic to hydrophilic volume. See Table 11, below. With regard to cationicity, RP-387 is similar to RP-182, having a total of five cationic amino acid residues. Based on the structural modeling, RP-387 binds to the RelB dimerization domain binding pocket, but is does so relatively poorly, having an estimated binding energy of only −338.3 kcal/mol.

Figure 6:
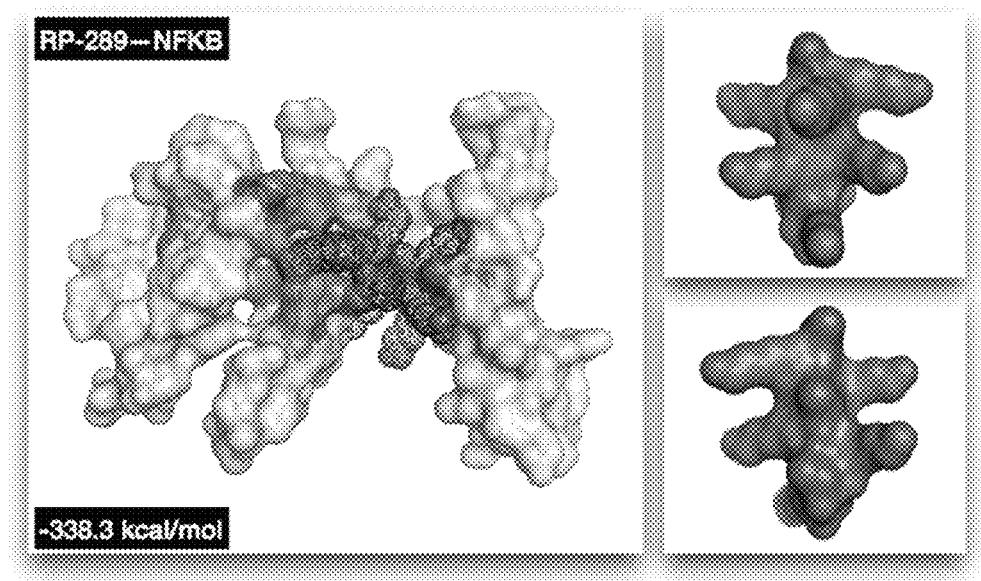
FIG. 6 depicts a structural model of human RelB bound by RP-289.

The secondary structure of RP-289 (SEQ ID NO: 232) and its binding to RelB (SEQ ID NO: 367) is modeled in FIG. 6. As can be seen in the panels on the right, RP-289's predicted secondary structure has distinct hydrophobic and hydrophilic sides. However, RP-289's hydrophobic side is one of the smallest of the peptides screened. As shown in FIG. 9, the facial arc of the polar side of RP-289 is 290°, while the facial arc of the non-polar side is only 70°. Of the peptides listed in Table 11, RP-289 has the smallest hydrophobic volume and the smallest ratio of hydrophobic to hydrophilic volume. RP-289 also has the highest cationicity of the peptides listed in Table 11, having a total of seven cationic amino acid residues. Based on the structural modeling, RP-289 binds to the RelB dimerization domain, though comparatively much more weakly than RP-182, RP-166, and RP-113, having an estimated binding energy of only −431.6 kcal/mol.

Figure 7:
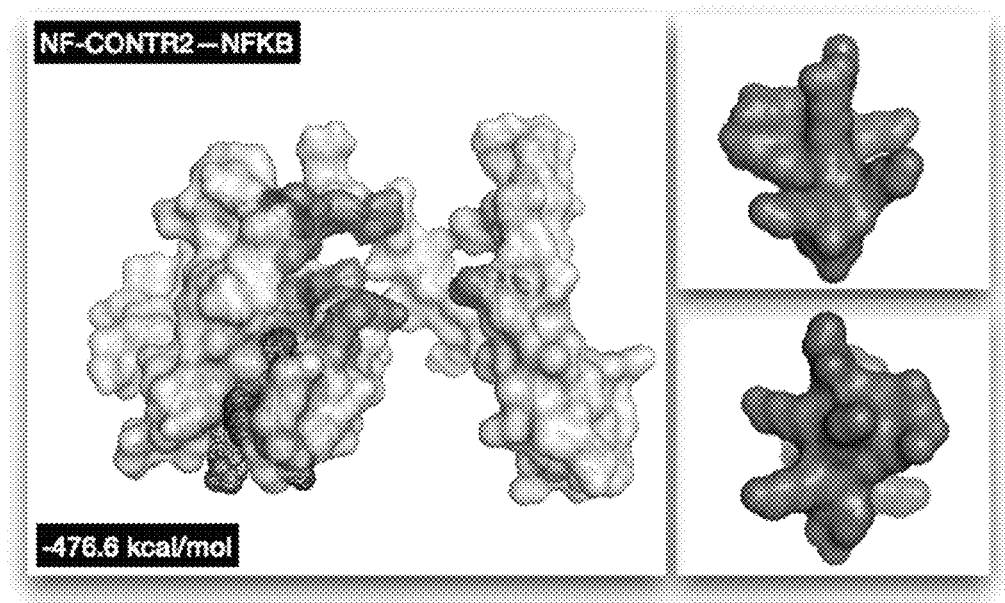
FIG. 7 depicts a structural model of human RelB bound by NF-Contr2.
Figure 8:
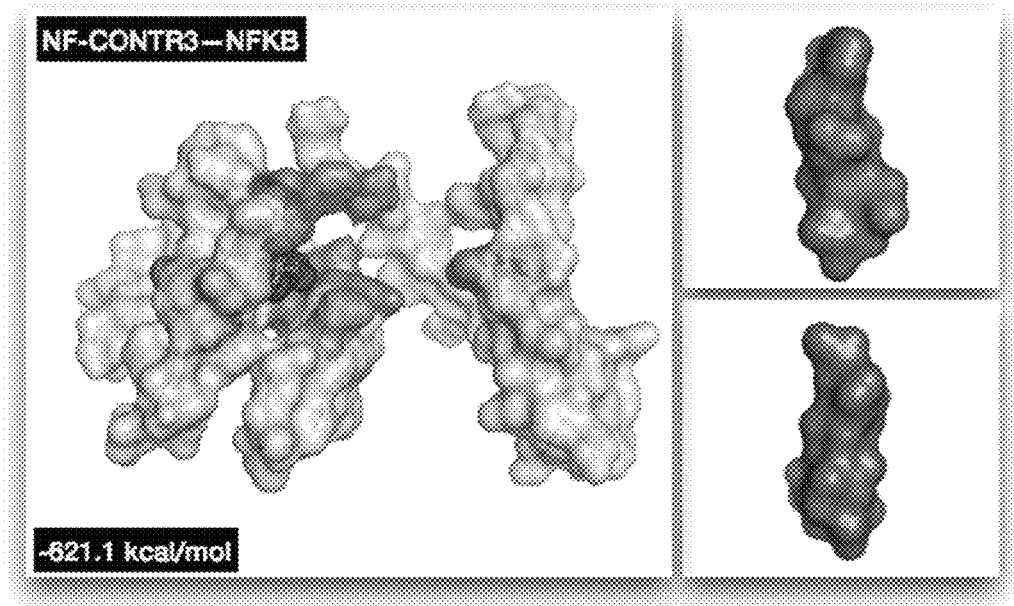
FIG. 8 depicts a structural model of human RelB bound by NF-Contr3.

Tables 10 and 11 also identify two control peptides, NF-CONTR2 and NF-CONTR3, which are fragments of the RelB subunit of NF-kB. The sequences of NF-CONTR2 and NF-CONTR3 do not conform to any of structural Formulas I-LIII. The secondary structure of NF-CONTR2 (SEQ ID NO: 382) and its binding to RelB (SEQ ID NO: 367) is modeled in FIG. 7. The secondary structure of NF-CONTR3 (SEQ ID NO: 383) and its binding to RelB (SEQ ID NO: 367) is modeled in FIG. 8. Neither peptide is predicted to adopt a clearly amphipathic secondary structure throughout the length of the peptide. Moreover, although the ClusPro™ algorithm identifies a binding interaction between each of NF-CONTR2 and NF-CONTR3 and RelB, the binding energies are not very strong and neither peptide displays a preference for binding to the RelB dimerization domain binding pocket.

TABLE 11

Physical Characteristics of Select Peptides

| RP# | Sequence | SEQ ID NO: | RelB Binding Energy | (+) | (−) | HPL Vol | HPB Vol | HPB Vol/ HPL Vol | tH HPL | tH HPB | tH HPB/ tH HPL |
|---|---|---|---|---|---|---|---|---|---|---|---|
| 182 | KFRKAFKRFF | 121 | −944.8 | 6 | 1 | 696.9 | 659.8 | 0.95 | −50.8 | 16.4 | −0.32 |
| 166 | FFEHFWKEFN | 112 | −1,044.8 | 3 | 3 | 637.7 | 775.0 | 1.22 | −33.0 | 16.7 | −0.51 |
| 113 | FFFRFFFEFQ | 39 | −1,208.9 | 2 | 2 | 414.5 | 1030.4 | 2.49 | −23.5 | 25.9 | −1.10 |
| 289 | AKKKAKKKAK | 232 | −431.6 | 8 | 1 | 896.8 | 213.3 | 0.24 | −61.6 | 4.8 | −0.08 |
| 387 | AAKKAAKKAK | 173 | −338.3 | 6 | 1 | 640.5 | 355.5 | 0.55 | −44.0 | 8.0 | −0.18 |
| NF-C2 | IESKRRKKKP | 382 | −476.6 | 7 | 2 | 954.9 | 297.4 | 0.31 | −66.8 | 3.5 | −0.05 |
| NF-C3 | APGPGDGGTA | 383 | −621.1 | 1 | 1 | 115.1 | 665.7 | 5.78 | −9.2 | 8.0 | −0.87 |

*Binding energies are in kcal/mol.
Volumes are in cubic angstroms.
HPL means hydrophilic; HPB means hydrophobic.
"tH" is the total hydrophobicity (in kcal/mol), as defined by Engleman et al. (1986), "Identifying nonpolar transbilayer helices in amino acid sequences of membrane proteins," Annu. Rev. Biophys. Bioeng. 15: 321-53.

FIGS. 1 through 10 and Table 11 reveal some important aspects of the structure-function relationship for the peptides of the invention. First, all of the peptides that are predicted to bind the RelB dimerization domain binding pocket have an amphipathic secondary structure. Second, greater hydrophobic volume, a greater ratio of hydrophobic to hydrophilic volume, and a greater hydrophobic arc are all associated with increased affinity for the binding pocket of the RelB dimerization domain. Third, increased cationicity is associated with decreased binding affinity for the binding pocket of the RelB dimerization domain.

Table 4, which lists some "all hydrophilic" variants of the Class I peptides, appears to potentially refute the conclusion that increased cationicity is associated with decreased binding affinity for the binding pocket of the RelB dimerization domain. In each of the peptides in Table 4, the hydrophobic residues of a Class I, Formula II peptide have been replaced with a single type of hydrophilic residue. Significantly, RP-173 (HHHRHHHEHQ; SEQ ID NO: 99) and RP-195 (RRRRRRRERQ; SEQ ID NO: 100) both have a high affinity for the binding pocket of the RelB dimerization domain (−1,002.2 and −855.2 kcal/mol, respectively), despite have eight amino acid residues that generally have a cationic charge in solution. Because both histidine and arginine have large side chains, a potential explanation for their high RelB binding affinities is that the uncharged hydrocarbon groups in the side chains provide some hydrophobicity that would otherwise have been lost by switching from a hydrophobic residue to a hydrophilic residue. In addition, when bound to RelB, some of the histidine and arginine residues may adopt an uncharged state. Table 4 therefore sheds further light on the structure-function relationship of the peptides of the invention by indicating that histidine and arginine can function in a quasi-hydrophobic capacity, at least with regard to the binding affinities of peptides for the RelB dimerization domain binding pocket. Accordingly, in some peptides of the invention, it can be energetically advantageous to place a histidine or arginine adjacent to a hydrophobic module that is made up of one or two hydrophobic amino acid residues.

Example 3

RelB Amino Acid Residues Involved in Peptide Binding

Figure 11:
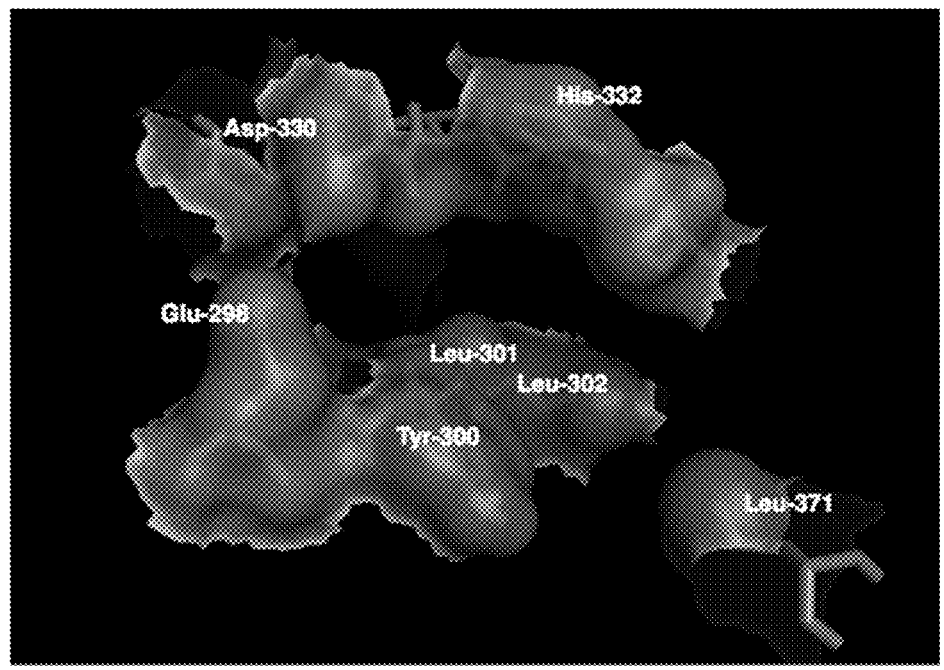
FIG. 11 depicts a structural model of the binding pocket of the RelB dimerization domain.
Figure 12:
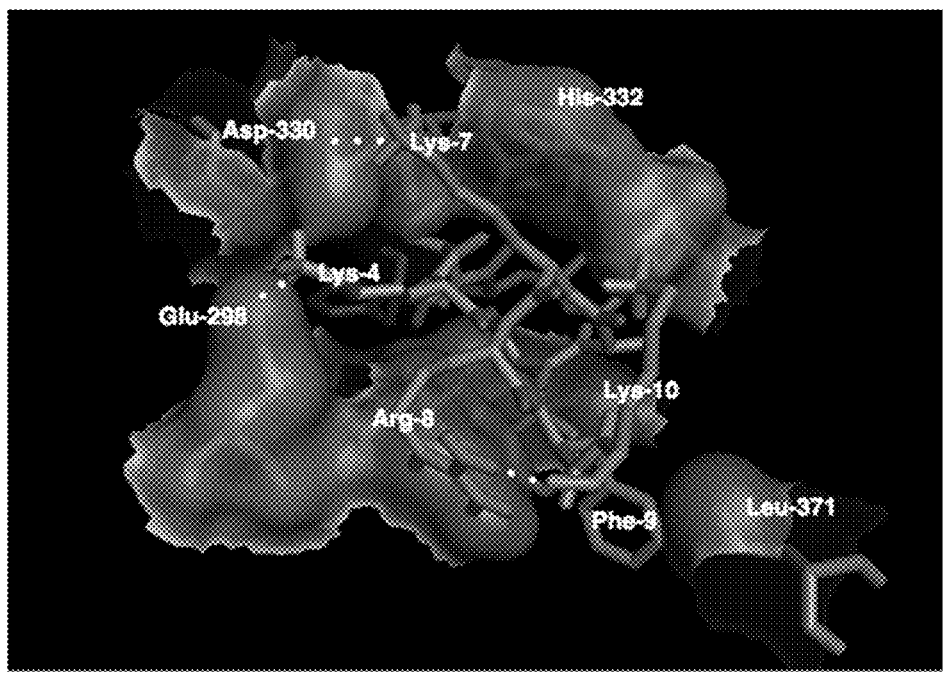
FIG. 12 depicts a structural model of the binding pocket of the RelB dimerization domain bound by RP-183.

A model of the amino acid residues that line the binding pocket of the RelB dimerization domain is shown in FIG. 11. The model shows that Glu-298, Asp-330, and His-332 are key hydrophilic amino acid residues that line the binding pocket, while Tyr-300, Leu-301, Leu-302, and Leu-371 are important hydrophobic residues. The same model, with the addition of a stick diagram of the RP-182 peptide (SEQ ID NO: 121) is shown in FIG. 12. The dotted lines in FIG. 12 show ionic bonds between (1) Lys-7 of RP-183 and Asp-330 of RelB, and (2) Lys-4 of RP-183 and Glu-298 of RelB. Further stabilizing the interaction is an intra-ionic bond formed between Arg-8 of RP-183 and the carboxy terminal Lys-10 of RP-183. In addition to the ionic binds, there are numerous Van der Waals interactions. For the sake of clarity, only that of Phe-9 of RP-182 with Leu-371 of Rel-B is shown. However, the other hydrophobic amino acid residues on the hydrophobic face of RP-183 interact with the hydrophobic "floor" of the cleft of dimerization site of Rel-B.

An analysis of the ionic and Van der Waals interactions involved with the binding of different peptides of the invention has revealed that the peptides bind to a subset of the RelB amino acid residues selected from the group consisting of Leu-281, Ile-283, Cys-284, Glu-298, Tyr-300, Leu-301, Leu-302, Cys-303, Ile-311, Ser-312, Ala-329, Asp-330, Val-331, His-332, Gln-334, and Leu-371. See Table 13, below. Tyr-300, Leu-302, and His-332 are designated in the literature as being critical for dimerization. The amino acids most critical to binding by peptides of the invention include Glu-298, Tyr-300, Leu-302, Asp-330, Gln-334, and Leu-371.

Example 4

Binding of Peptides to Protein Targets Other Than RelB

A subset of the peptides shown in Tables 3-9 were further evaluated in silico to determine whether they bind to signaling proteins involved in the inflammatory response other than RelB. In doing so, it was discovered the dimerization cleft of the RelB subunit of NF-kB has structural parallels in a number of other signaling molecules. Consistent with these structural parallels, the peptides of the invention are predicted (by the ClusPro™ algorithm) to bind with high affinity to important signaling molecules in the inflammatory cascade, including: TGFβ (NCBI Acc. No. NP_000651.3; SEQ ID NO: 368); Notch1 (GenBank Acc. No. AAG33848.1; SEQ ID NO: 369); Wnt8R (NCBI Acc. No. XP_005214377.1; SEQ ID NO: 370); TRAIL (GenBank Acc. No. EAW78466.1; SEQ ID NO: 371); IL6R (NCBI Acc. No. NP_786943.1; SEQ ID NO: 372); IL10R (NCBI Acc. No. NP_001549.2; SEQ ID NO: 373); EGFR (GenBank Acc. No. AAR85273.1; SEQ ID NO: 374); and CDK6 (NCBI Acc. No. NP_001250.1; SEQ ID NO: 375). Representative peptides of the invention and the predicted binding energies between the peptides and each of these signaling molecules is shown in Tables 12A and 12B, below.

TABLE 12A

Predicted Binding of Select Peptides to Different Inflammatory Targets

| RP# | Sequence | SEQ ID NO: | RelB | TGFβ | NOTCH1 | WNT8R | TRAIL |
|---|---|---|---|---|---|---|---|
| 185 | FFKKFFKKFK | 123 | −920.6 | −880.1 | −817.7 | −747.2 | −904.5 |
| 186 | KFKKFFKKFF | 124 | −919.6 | −846.0 | −887.7 | −739.1 | −884.3 |
| 183 | FFRKFAKRFK | 122 | −933.2 | −878.9 | −890.8 | −763.1 | −938.8 |
| 182 | KFRKAFKRFF | 121 | −944.8 | −851.8 | −1,096.3 | −733.7 | −938.8 |
| 118 | FFFRFFFNFN | 44 | −1,139.9 | −1,074.7 | −1,032.4 | −990.9 | −995.4 |

TABLE 12A -continued

Predicted Binding of Select Peptides to Different Inflammatory Targets

| RP# | Sequence | SEQ ID NO: | RelB | TGFβ | NOTCH1 | WNT8R | TRAIL |
|---|---|---|---|---|---|---|---|
| 394 | NFNFFFRFFF | 33 | −1,286.6 | −1,002.6 | −1,059.6 | −971.2 | −943.8 |
| 389 | FRFKFA | 257 | −1,009.8 | −878.4 | −846.4 | −804.5 | −916.8 |
| 390 | FRFKFKF | 256 | −1,083.3 | −933.2 | −1,005.3 | −871.0 | −1,014.4 |
| 391 | FRFKFKFR | 254 | −1,190.8 | −987.5 | −1,005.4 | −897.9 | −1,049.2 |
| 392 | RFQFKFRF | 255 | −1,170.3 | −943.2 | −923.1 | −853.8 | −1,039.6 |
| 387 | AAKKAAKKAK | 173 | −301.6 | −397.7 | −385.5 | −394.9 | −397.7 |

*All binding affinities are in kcal/mol.

TABLE 12A

Predicted Binding of Select Peptides to Different Inflammatory Targets

| RP# | Sequence | SEQ ID NO: | RelB | EGFR | IL6R | IL10R | CDK6 |
|---|---|---|---|---|---|---|---|
| 185 | FFKKFFKKFK | 123 | −920.6 | −785.4 | −747.5 | −756.3 | −753.9 |
| 186 | KFKKFFKKFF | 124 | −919.6 | −866.3 | −755.0 | −742.0 | −718.1 |
| 183 | FFRKFAKRFK | 122 | −933.2 | −795.6 | −696.7 | −738.6 | −783.0 |
| 182 | KFRKAFKRFF | 121 | −944.8 | −853.8 | −784.5 | −785.9 | −781.5 |
| 118 | FFFRFFFNFN | 44 | −1,139.9 | −1,039.4 | −1,074.8 | −881.4 | −1,020.8 |
| 394 | NFNFFFRFFF | 33 | −1,286.6 | −1,061.4 | −1,069.9 | −850.8 | −1,075.3 |
| 389 | FRFKFA | 257 | −1,009.8 | −896.0 | −812.3 | −779.2 | −900.5 |
| 390 | FRFKFKF | 256 | −1,083.3 | −1,036.3 | −952.2 | −876.2 | −861.1 |
| 391 | FRFKFKFR | 254 | −1,190.8 | −1,024.9 | −957.6 | −882.3 | −899.9 |
| 392 | RFQFKFRF | 255 | −1,170.3 | −1,010.4 | −1,052.3 | −901.7 | −870.0 |
| 387 | AAKKAAKKAK | 173 | −301.6 | −395.9 | −342.0 | −338.1 | −351.4 |

The data reveals that the strength of binding to RelB is highly correlated with the strength of binding to the various inflammatory targets. In other words, peptides that are predicted to bind with high affinity to RelB are likewise predicted to bind with high affinity to TGFβ, Notch1, Wnt8R, TRAIL, EGFR, IL6R, and IL10R.

A closer evaluation of the predicted binding interactions between the peptides of the invention and each of TGFβ, Notch1, Wnt8R, TRAIL, EGFR, IL6R, and IL10R reveals that the peptides not only bind with high affinity, but also bind to functionally critical sites on the targets. For example, peptides of the invention are predicted to bind to the receptor-binding site on TGFβ, the calcium-binding site on Notch1, the Wnt8-binding site on Wnt8R, the receptor-binding site on TRAIL, the IL6-binding site on IL6R, the IL10-binding site on IL10R, and the general ligand-binding site on EGFR. A non-exhaustive list of amino acid residues in each of these targets that are bound by the peptides of the invention is shown in Table 13.

TABLE 13

Amino Acid Residues in Target Proteins Contacted by Peptides of the Invention

| Target | SEQ ID NO: | AA Residue Contacts | Most Critical AAs |
|---|---|---|---|
| RelB | 367 | Leu-281, Ile-283, Cys-284, Glu-298, Tyr-300, Leu-301, Leu-302, Cys-303, Ile-311, Ser-312, Ala-329, Asp-330, Val-331, His-332, Gln-334, Leu-371 | Glu-298, Tyr-300, Leu-302, Asp-330, Gln-334, Leu-371 |
| TGFβ | 368 | Leu-20, Ile-22, Phe-24, Asp-27, Leu-28, Trp-30, Trp-32, Tyr-39, Phe-43, Pro-80, Leu-83, Leu-101, Ser-112 | Asp-27, Leu-28, Trp-30, Trp-32 |

TABLE 13-continued

Amino Acid Residues in Target Proteins Contacted by Peptides of the Invention

| Target | SEQ ID NO: | AA Residue Contacts | Most Critical AAs |
|---|---|---|---|
| Notch1 | 369 | Phe-1520, Gln-1523, Arg-1524, Glu-1526, Ala-1553, Glu-1556, Trp-1557, Cys-1562, His-1602, Arg-1684, Gln-1685, Cys-1686, Ser-1691, Cys-1693, Phe-1694, Phe-1703 | Phe-1520, Trp-1557, Cys-1562, Phe-1703 |
| Wnt8R | 370 | Tyr-52, Gln-56, Phe-57, Asn-58, Met-91, Tyr-100, Lys-101, Pro-103, Pro-105, Pro-106, Arg-137, Asp-145 | Tyr-52, Phe-57, Tyr-100, Asp-145 |
| TRAIL | 371 | Ala-123, His-161, Ser-162, Phe-163, Tyr-183, Tyr-185, Tyr-243, His-270, Glu-271, Phe-274, Phe-278, Leu-279, Val-280 | Phe-163, Tyr-243, Glu-271, Phe-278 |
| IL6R | 372 | Leu-108, Glu-140, Pro-162, Phe-229, Tyr-230, Phe-279 | Glu-140, Phe-229, Tyr-230, Phe-279 |
| IL10R | 373 | Leu-41, Arg-42, Tyr-43, Ile-45, Glu-46, Ser-47, Trp-48, Arg-76, Arg-78 | Tyr-43, Ile-45, Glu-46, Trp-48 |
| EGFR | 374 | Leu-10, Thr-40, Trp-41, Asp-48, Phe-51, Leu-63, His-66, Asp-68, Leu-88, Tyr-101 | Trp-41, Asp-48, Phe-51, Asp-68, Tyr-101, |
| CDK6 | 375 | Val-142, Arg-144, Asp-145, Ser-171, Val-180, Val-181, Leu-183, Arg-186, Val-190, Gln-193, Tyr-196, Val-200 | Asp-145, Val-180, Tyr-196 |
| HMT | 376 | Tyr-16, Glu-48, Tyr-50, Leu-51, Phe-52, Asn-69 | Tyr-16, Glu-48, Tyr-50, Leu-51, Phe-52, Asn-69 |
| CD47 | 377 | Tyr-37, Thr-49, Phe-50, Asp-51, Ala-53, Glu-97, Val-98, Glu-100, Leu-101, Thr-102, Glu-104, Glu-106, Gly-107 | Tyr-37, Glu-97, Glu-100, Leu-101, Glu-104, Glu-106 |
| SIRP-α | 378 | Tyr-50, Gln-52, Pro-58, Ser-66, Thr-67, Ser-77 | Tyr-50, Gln-52, Ser-66, Thr-67 |
| CD206 | 379 | Phe-708, Thr-709, Trp-710, Pro-714. Glu-719, Asn-720, Trp-721, Ala-722, Glu-725, Tyr-729, Glu-733, Asn-747, Asp-748, Ser-1691, Cys-1693, Phe-1694, Phe-1703 | Phe-708, Trp-710, Trp-721, Glu-725, Tyr-729, Glu-733 |
| TGM2 | 380 | Cys-277, His-335, Asp-358 | Cys-277, His-335, Asp-358 |

Given the large number of immunologically important signaling proteins that are targeted by the peptides of the invention, the data suggests that the peptides act in a pleiotropic manner, making many different interactions that sum together to create a broad anti-inflammatory response. This may make possible a reduction in disease conditions without the toxicity observed in the use of more highly-targeted chemotherapeutic agents.

Example 5

Binding of Peptides to Histone Modifying Enzymes and Ribonuclease Reductase

A number of the peptides of the invention were observed to share structural characteristics of the N-terminal regions of histones. Accordingly, representative peptides were evaluated in silico for their ability to bind to histone modification enzymes. In this manner, it was discovered that the peptides of the invention have high binding affinity for histone methyl transferase (HMT)(NCBI Acc. No. NP_048968.1; SEQ ID NO: 376), binding close to the active site of the enzyme. Predicted binding energies of select peptides of the invention for HMT, calculated using the ClusPro™ algorithm, are shown in Table 14. Again, the predicted binding energies correlate well with the predicted energies for binding RelB.

TABLE 14

Binding Affinities of Select Peptides to HMT, MKK7, and RNR

| RP# | Sequence | SEQ ID NO: | RelB | HMT |
|---|---|---|---|---|
| 185 | FFKKFFKKFK | 123 | −920.6 | −846.4 |
| 186 | KFKKFFKKFF | 124 | −919.6 | −795.7 |
| 183 | FFRKFAKRFK | 122 | −933.2 | −839.4 |
| 182 | KFRKAFKRFF | 121 | −944.8 | −826.6 |
| 118 | FFFRFFFNFN | 44 | −1,139.9 | −1,000.2 |
| 394 | NFNFFFRFFF | 33 | −1,286.6 | −998.4 |
| 389 | FRFKFA | 257 | −1,009.8 | −836.8 |
| 390 | FRFKFKF | 256 | −1,083.3 | −906.6 |
| 391 | FRFKFKFR | 254 | −1,190.8 | −949.2 |
| 392 | RFQFKFRF | 255 | −1,170.3 | −962.2 |
| 387 | AAKKAAKKAK | 173 | −301.6 | −334.5 |

*All binding affinities are in kcal/mol.

Figure 13:
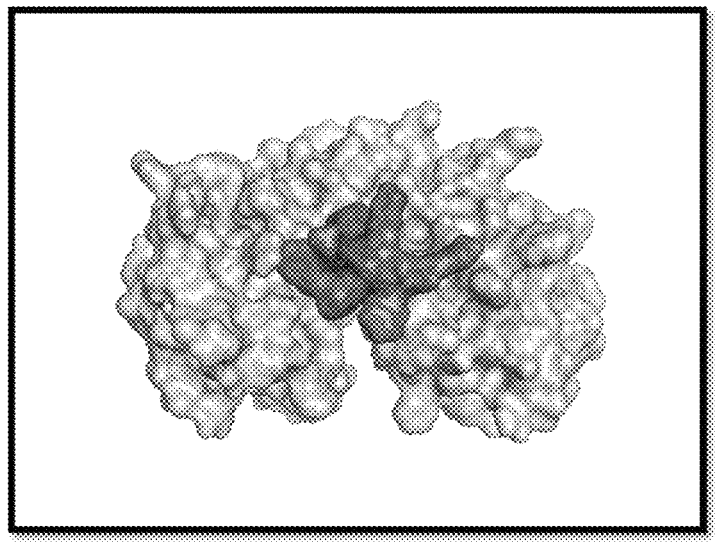
FIG. 13 depicts a structural model of histone methyl transferase enzyme bound by RP-182.

A model of Histone Methyl Transferase (HMT) bound by RP-182 is shown in FIG. 13. The orange amino acids are the active site of the histone methyl transferase enzyme. Inhibition of methyl transferase activity by RP-182 is expected since RP-182 binds to at least one residue of the active site, in a manner that appears to obstruct access to the active site.

A non-exhaustive list of amino acid residues in HMT that are bound by the peptides of the invention is shown in Table 13, above.

Peptides of the invention are also observed to display strong predicted affinities to MAP kinase kinase 7 (MKK7; SEQ ID NO: 166), a member of the mitogen-activated protein kinase kinase family involved in signal transduction mediating cell responses to proinflammatory cytokines, and therefore likely involved in peptides' anti-inflammatory activity. The predicted affinity of e.g. RP-182 for MKK7 is −738.2 kcals/mol.

In addition, peptides of the invention were observed to display substantial predicted affinities to ribonuclease reductase (RNR; SEQ ID NO: 168) also known as ribonucleoside diphosphate reductase. This is an enzyme that catalyzes the formation of deoxyribonucleotides from ribonucleotides. Deoxyribonucleotides in turn are used in the synthesis of DNA. The reaction catalyzed by RNR is strictly conserved in all living organisms. Furthermore, RNR plays a critical role in regulating the total rate of DNA synthesis, so that DNA to cell mass is maintained at a constant ratio during cell division and DNA repair. A somewhat unusual feature of the RNR enzyme is that it catalyzes a reaction that proceeds via a free radical mechanism of action. The substrates for RNR are ADP, GDP, CDP and UDP. dTDP (deoxythymidine diphosphate) is synthesized by another enzyme (thymidylate kinase) from dTMP (deoxythymidine monophosphate). The predicted affinity of e.g. RP-182 for RNR is −814.0 kcals/mol.

Example 6

Binding of Peptides to Targets Associated with Macrophage Activation

Peptides of the invention are also predicted to interact with several proteins relevant to macrophage activity and apoptosis, properties associated with inflammation and with tumor genesis and metastasis. Targets identified to date include CD47, SIRP-α, CD206, TGM2, LEGUMAIN, DC-SIGN, CSF1, CSF1R, and IL34.

CD47 (or "Cluster of Differentiation 47"), also known as integrin associated protein (IAP), is a transmembrane protein that belongs to the immunoglobulin superfamily. CD47 protein partners with membrane-bound cellular adhesion receptors known as integrins and also binds the ligands thrombospondin-1 (TSP-1) and signal-regulatory protein alpha (SIRP-α). CD47 is involved in a range of cellular processes, including apoptosis, proliferation, adhesion, and migration. Furthermore, it plays a key role in immune and angiogenic responses. CD47 is expressed in many types of human cells and has been found to be overexpressed in many different types of tumors. The overexpression of CD47 has received considerable attention as a possible protective agent for human cancers. By binding to SIRP-α on the surface of macrophages, CD47 is believed to send a "don't eat me" signal that disables the macrophages from attacking the cancer cell.

CD206 and TGM2 have likewise been identified as potentially important regulators of macrophage activity. CD206 is a C-type lectin, primarily present on the surface of macrophages and dendritic cells. It is the first member of a family of endocytic receptors that includes Endo180 (CD280), M-type PLA2R, and DEC-205 (CD205). The receptor recognizes terminal mannose, N-acetylglucosamine, and fucose residues that make up glycans, which are attached to proteins found on the surface of some microorganisms. Accordingly, the CD206 receptor appears to play a role in both the innate and adaptive immune systems. In addition, tumor-associated macrophages may use CD206 to ingest collagen, yielding degradation products capable of nourishing both themselves and tumor cells, and weakening collagen binding of tumor cells so as to encourage metastasis.

TGM2 belongs to a family of enzymes that catalyze the calcium-dependent translational modification of proteins. The family members are found both intracellularly and extracellularly. TGM2 is unique in the family because of its multi-functionality and specialized structure, which includes four distinct domains: an N-terminal β-sandwich that contains fibronectin and integrin binding sites; a catalytic core that contains the catalytic triad for acyl-transfer reactions (Cys-277, His-335, and Asp-358); and two C-terminal β-barrel domains, with the second having a phospholipase-binding sequence. TGM2 has been implicated as a regulator of extracellular matrix functions, including cell adhesion and migration, cellular growth and differentiation, apoptosis, tumor growth, and wound healing. Although TGM2 is ubiquitously expressed, it is most highly expressed in M2 macrophages. Furthermore, increased TGM2 levels are associated with scleroderma, lung and kidney fibrosis, worsening symptoms for diabetes, arthritis, and EAE, and poor outcomes in a number of different cancers, all of which can be linked to M2 macrophages.

Predicted binding energies of select peptides of the invention for CD47 (NCBI Acc. No. XP_005247966.1; SEQ ID NO: 377), SIRP-α (GenBank Acc. No. AAH26692.1; SEQ ID NO: 378), CD206 (NCBI Acc. No. NP_002429.1; SEQ ID NO: 379), and TGM2 (GenBank Acc. No. AAB95430.1; SEQ ID NO: 380) calculated using the ClusPro™ algorithm, are shown in Table 15. As with the other targets discussed above, the predicted binding energies correlate well with the predicted energies for binding RelB.

LEGUMAIN is a protein that in humans is encoded by the LGMN gene. This gene encodes a cysteine protease, legumain that has a strict specificity for hydrolysis of asparaginyl bonds. This enzyme may be involved in the processing of bacterial peptides and endogenous proteins for MHC class II presentation in the lysosomal/endosomal systems. Enzyme activation is triggered by acidic pH and appears to be autocatalytic. Protein expression occurs after monocytes differentiate into dendritic cells. A fully mature, active enzyme is produced following lipopolysaccharide expression in mature dendritic cells. Overexpression of this gene may be associated with the majority of solid tumor types. LEGUMAIN is also overexpressed in M2 macrophages, and inhibition of its activity by the disclosed peptides is expected to downregulate M2-activated macrophages.

DC-SIGN (Dendritic Cell-Specific Intercellular adhesion molecule-3-Grabbing Non-integrin) also known as CD209 (Cluster of Differentiation 209) is a protein that in humans is encoded by the CD209 gene. DC-SIGN is a C-type lectin receptor present on the surface of both macrophages and dendritic cells. DC-SIGN on macrophages recognizes and binds to mannose type carbohydrates, a class of pathogen associated molecular patterns PAMPs commonly found on viruses, bacteria and fungi. This binding interaction activates phagocytosis. On myeloid and pre-plasmacytoid dendritic cells DC-SIGN mediates dendritic cell rolling interactions with blood endothelium and activation of CD4+ T cells, as well as recognition of pathogen haptens. DC-SIGN is significantly overexpressed in M2 macrophages, and inhibition of its activity by the disclosed peptides is expected to downregulate M2-activated macrophages.

TABLE 15

Binding Affinities of Select Peptides to CD47, SIRP-α, CD206, and TGM2

| RP# | Sequence | SEQ ID NO: | RelB | SIRP-α | CD47 | CD206 | TGM2 |
|---|---|---|---|---|---|---|---|
| 185 | FFKKFFKKFK | 123 | -920.6 | -799.2 | -639.3 | -807.1 | -827.2 |
| 186 | KFKKFFKKFF | 124 | -919.6 | -711.8 | -637.4 | -881.3 | -885.3 |
| 183 | FFRKFAKRFK | 122 | -933.2 | -834.2 | -658.1 | -786.7 | -860.7 |
| 182 | KFRKAFKRFF | 121 | -944.8 | -733.1 | -723.1 | -844.5 | -869.1 |
| 118 | FFFRFFFNFN | 44 | -1,139.9 | -805.2 | -751.5 | -1,048.7 | n/a |
| 394 | NFNFFRFFF | 33 | -1,286.6 | -854.2 | -751.5 | -986.6 | n/a |
| 389 | FRFKFA | 257 | -1,009.8 | -934.6 | -688.3 | -861.9 | n/a |
| 390 | FRFKFKF | 256 | -1,083.3 | -887.2 | -783.5 | -978.1 | n/a |
| 391 | FRFKFKFR | 254 | -1,190.8 | -932.1 | -790.1 | -941.3 | n/a |
| 392 | RFQFKFRF | 255 | -1,170.3 | -982.5 | -792.1 | -981.6 | n/a |
| 387 | AAKKAAKKAK | 173 | -301.6 | -392.3 | -308.7 | -416.6 | n/a |

*All binding affinities are in kcal/mol.

Figure 14:
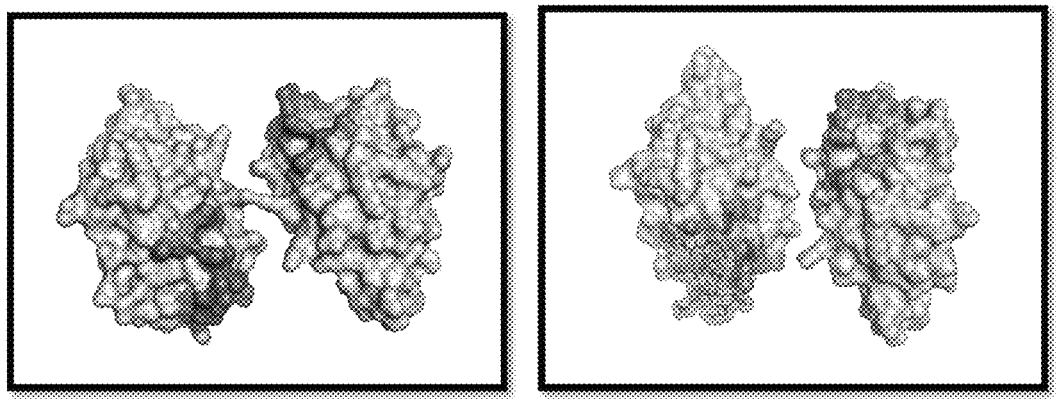
FIG. 14 depicts structural models of a CD47 dimer (left panel) and a CD47 dimer bound by RP-183.

FIG. 14 (left panel) shows a model of the ecto-domain of a CD47 dimer (top view) (SEQ ID NO: 377), with light grey- and dark grey-colored surfaces representing the polar and non-polar amino acids, respectively, that are involved in the binding of CD47 to the SIRP-α receptor. FIG. 14 (right panel) is a model of the ecto-domain of the CD47 dimer when bound by RP-183 (SEQ ID NO: 121). Based on this predicted interaction between RP-183 and CD47, peptides of the invention are expected to block the interaction between CD47 and SIRP-α.

Figure 15:
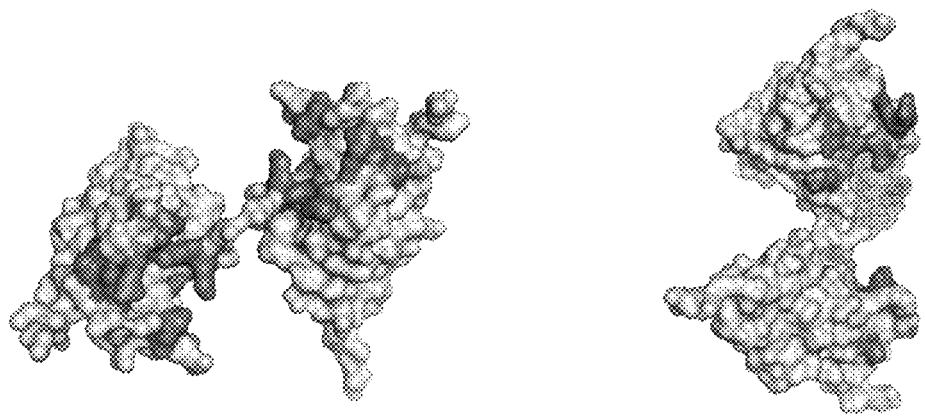
FIG. 15 depicts structural models of a SIRP-α dimer (left panel) and a SIRP-α dimer bound by RP-183.

FIG. 15 shows a model of a SIRP-α dimer (SEQ ID NO: 378), with light grey and dark grey-colored surfaces representing the polar and non-polar amino acids involved in its binding to CD47 (see left-most dimer). In a slightly-skewed view of the same SIRP-α dimer bound by RP-183 (SEQ ID NO: 122) (see right-most dimer), it can be seen that RP-183 binds tightly to the amino acids involved in binding to the CD47 receptor. It therefore appears that RP-183 (and other peptides of the invention) block the interaction between CD47 and SIRP-α by two distinct mechanisms, binding to the corresponding binding sites in both CD47 and SIRP-α. Thus, predicted activities associated with the peptides of the invention include thwarting of an important defense mechanism for cancer cells.

Figure 16:
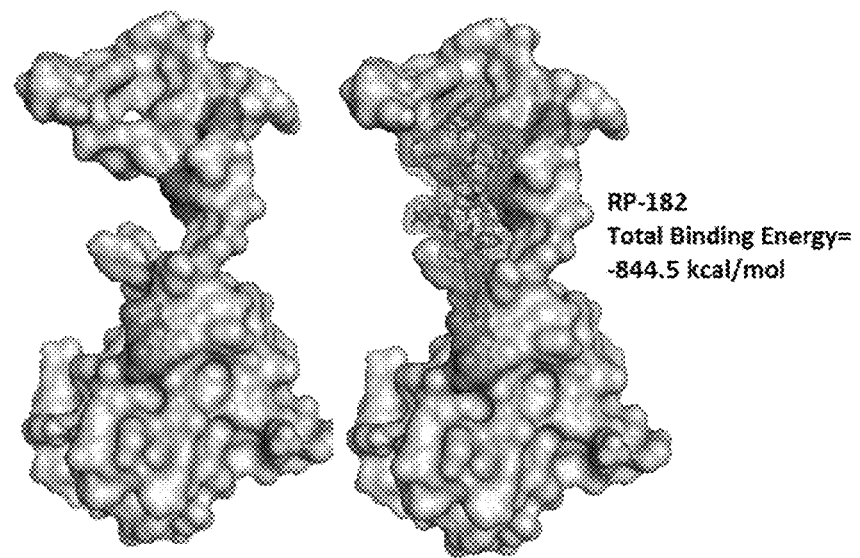
FIG. 16 depicts structural models of CD206 (left side) and CD206 bound by RP-182 (right side).

Peptides of the invention are also predicted to block key sites on the CD206 receptor subunit. FIG. 16 shows a model of CD206 (SEQ ID NO: 379) bound by RP-182 (SEQ ID NO: 121). The dark grey-colored tyrosine residue on the bend region of CD206 (left-most molecule) forms a planar, hydrophobic stacking interactions with the mannose ligands on the surface of target cells. The light grey colored amino acids are acidic residues that help chelate the required calcium ion necessary for stable interactions with the mannose receptor. The RP-182 peptide (seen in mesh on the right-most molecule) blocks activity by interacting with both of these key sites on the receptor subunit. Peptides of the invention are therefore expected to reduce the viability of M2 macrophages, which has been experimentally confirmed (as set forth below).

Figure 17:
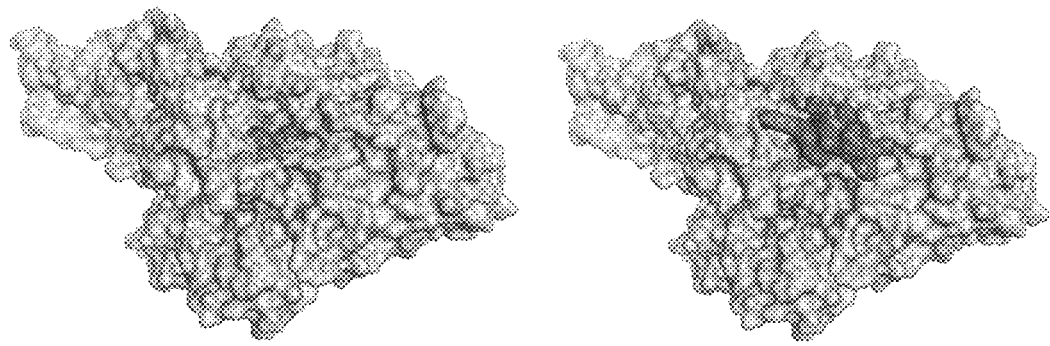
FIG. 17 depicts structural models of TGM2 (left side) and TGM2 bound by RP-182 (right side).

Furthermore, peptides of the invention are predicted to block the active site of TGM2. FIG. 17 (left panel) shows a model of TGM2 (SEQ ID NO: 380) with the active site residues highlighted in dark grey. FIG. 17 (right panel) shows the same model of TGM2 bound by RP-182 (SEQ ID NO: 121), which is colored light grey. As can be seen, RP-182 is predicted to bind to TGM2 in a manner that completely covers the active site, thereby obstructing substrate access and inhibiting TGM2 function. Significantly, decreased levels of TGM2 is associated with reduced NF-kB activation, so the interaction of the polypeptides of the invention with TGM2 would appear to reinforce and/or augment their suppression of NF-kB activity.

Non-exhaustive lists of specific amino acid residues in CD47, SIRP-α, CD206, and TGM2 that are bound by the peptides of the invention are shown in Table 13, above.

Example 7

Binding of Peptides to Checkpoint Inhibitors and Related Targets

It has also been observed that peptides of the present invention display substantial affinity to checkpoint inhibitor proteins and their ligands. Such proteins, including cytotoxic T-lymphocyte antigen 4 (CTLA-4), PD-1, and other inhibitory coreceptors, expressed on the surface of effector immune cells, when activated appear to exhaust the activity of the immune cells, serving as immune checkpoints in order to prevent uncontrolled immune reactions. Tumor cells often express ligands to the checkpoint inhibitors, e.g. PD-L1 and PD-L2, attenuating the capacity of the immune system to attack the tumor.

In particular, programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2. PD-1, functioning as an immune checkpoint plays an important role in downregulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

Programmed death-ligand 1 (PD-L1) also known as cluster of differentiation 274 (CD274) or B7 homolog 1 (B7-H1) is a protein that in humans is encoded by the CD274 gene. Programmed death-ligand 1 (PD-L1) is a 40 kDa type 1 transmembrane protein that has been speculated to play a major role in suppressing the immune system during particular events such as pregnancy, tissue allografts, autoimmune disease and other disease states such as hepatitis. Normally the immune system reacts to foreign antigens where there is some accumulation in the lymph nodes or spleen that triggers a proliferation of antigen-specific CD8+ T cell. The formation of PD-1 receptor/PD-L1 or B7.1 receptor/PD-L1 ligand complex transmits an inhibitory signal which reduces the proliferation of these CD8+ T cells at the lymph nodes and supplementary to that PD-1 is also able to control the accumulation of foreign antigen specific T cells in the lymph nodes through apoptosis which is further mediated by a lower regulation of the gene Bcl-2.

As illustrations of the binding of peptides of the present invention with checkpoint inhibitors and their ligands, the predicted affinity of RP-182 to PD-1 is −742.9, and that of RP-621 is −1,008.8. The affinity of RP-182 to PD-L1 is −677.4, and that of RP-621 to PD-L1 is −1,010.6. As with inflammatory targets, there is a striking correlation among predicted affinities to several other checkpoint inhibitors and their ligands, as well as other proteins known to play a role in modulating the immune apparatus. These include: TIM-1 (believed to play a role in T-helper cell development: predicted affinity to RP-182, -850.1); CTLA-4 (checkpoint inhibitor: predicted affinity to RP-182, −663.2); ADORA2a (modulates activity of neutrophils and mast cells: predicted affinity to RP-182, −938.7); OX40 (secondary co-stimulatory immune checkpoint: predicted affinity to RP-182, −759.9); IDO (immune checkpoint: predicted affinity to RP-182, −934.0); LAG-3 (immune checkpoint receptor: predicted affinity to RP-182, −873.1); CD73 (enzyme limiting T cell activity through adenosine receptor signaling: predicted affinity of CD73-I to RP-182, −808.7; predicted affinity of CD73-II to RP-182, −949.1); Arginase-1 (blocks activity of cytotoxic T lymphocytes: predicted affinity to RP-182, −984.2); Colony Stimulating Factor 1 (blockade shown to upregulate checkpoint molecules, as well as reprogramming macrophage responses; predicted affinity of CSF1 to RP-182, −854.7; predicted affinity of CSF1D to RP-182, −847.1; predicted affinity of CSF1R to RP-182, −774.1); and IL34 (also activates CSF1R; predicted affinity to RP-182, −828.5).

Example 8

Binding of Peptides to MKK7

Dual specificity mitogen-activated protein kinase kinase 7, also known as MAP kinase kinase 7 or MKK7, is an enzyme that in humans is encoded by the MAP2K7 gene. This protein is a member of the mitogen-activated protein kinase kinase family. The MKK7 protein exists as six different isoforms with three possible N-termini (α, β, and γ isoforms) and two possible C-termini (1 and 2 isoforms). MKK7 is involved in signal transduction mediating the cell responses to proinflammatory cytokines, and environmental stresses. This kinase specifically activates MAPK8/JNK1 and MAPK9/JNK2, and this kinase itself is phosphorylated and activated by MAP kinase kinase kinases including MAP3K1/MEKK1, MAP3K2/MEKK2, MAP3K3/MEKK5, and MAP4K2/GCK.

Example 9

Binding of Peptides to Serum Albumin

It is well-known that the most abundant protein in the circulation is serum albumin. It is also known that solid tumors will take up serum albumin into their cells (through the process of pinocytosis) and use it as an energy source. Therefore, peptides of the invention were evaluated in silico for their ability to bind to human serum albumin (HSA) (NCBI Acc. No. NP_000468.1; SEQ ID NO: 381). It was discovered that peptides of the invention have the capacity to bind to HSA with high affinity. Predicted binding energies of select peptides of the invention for binding to HSA are shown in Table 16, below.

TABLE 16

Binding Affinities of Select Peptides to Human Serum Albumin (HSA)

| RP# | Sequence | SEQ ID NO: | RelB | HSA |
|---|---|---|---|---|
| 185 | FFKKFFKKFK | 123 | −920.6 | −880.2 |
| 186 | KFKKFFKKFF | 124 | −919.6 | −850.5 |
| 183 | FFRKFAKRFK | 122 | −933.2 | −860.1 |
| 182 | KFRKAFKRFF | 121 | −944.8 | −789.0 |
| 118 | FFFRFFFNFN | 44 | −1,139.9 | −1,064.7 |
| 394 | NFNFFFRFFF | 33 | −1,286.6 | −1,016.5 |
| 389 | FRFKFA | 257 | −1,009.8 | −904.8 |
| 390 | FRFKFKF | 256 | −1,083.3 | −1,046.0 |
| 391 | FRFKFKFR | 254 | −1,190.8 | −1,021.9 |
| 392 | RFQFKFRF | 255 | −1,170.3 | −1,037.4 |
| 387 | AAKKAAKKAK | 173 | −301.6 | −410.7 |

*All binding affinities are in kcal/mol.

Figure 18:
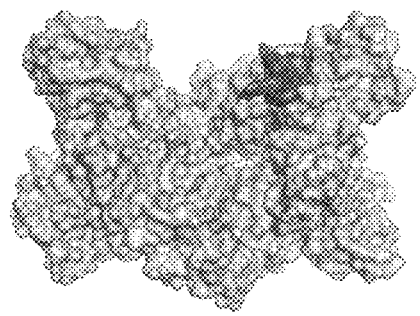
FIG. 18 depicts a structural model of human serum albumin bound by RP-183.

FIG. 18 is a model of HSA (shown in green) bound by RP-183 (blue). The computational modeling has identified a number of possible peptide binding sites on HSA. Therefore, it is believed that a single HSA molecule is able to bind to multiple peptides of the invention. The binding interaction between peptides of the invention and HSA suggest that HSA could be used as an in vivo carrier of the peptides. In this manner, HSA could protect the peptides from degradation in the blood and carry the peptides to sites of action, such as sites of inflammation and/or cancer cells, thereby increasing the efficacy of the peptides.

Example 10

In Vitro Modulation of NF-kB Activity

NF-kB activity was monitored using the a 3T3-L1 pre-adipocyte cell line stably transformed with a Nfkb-RE/GFP construct, as described in Shen et al. (2013), "Adipocyte reporter assays: Application for identification of anti-inflammatory and antioxidant properties of mangosteen xanthones," Mol. Nutr. Food Res. 00:1-9, the entire contents of which are incorporated herein by reference. NF-kB expressing adipocyte reporter cells were plated in DMEM in wells of a 24-well plate, at a seeding density of $5\times10^4$. On the second and third days post-plating, test peptides were individually added to the wells to a final concentration of 0.01 µM. The test peptides included RP-398 (SEQ ID NO: 155), and RP-185 (SEQ ID NO: 123). On day 4 post-plating, lipopolysaccharide was added to the medium to a final concentration of 20 ng/ml. Finally, on day 5 post-plating, the cells were harvested and a fluorescence assay performed to detect GFP expression levels.

In this experiment, NF-kB expression was reduced approximately 58% relative to control cells that were not exposed to RP-398 or RP-185 peptide.

Example 11

In Vivo Modulation of Macrophage Activity

A frequently observed phenotype associated with tumor genesis and metastasis is the polarization of macrophage cells into the "M2" transition state, in which they are in an inflammatory state. Such macrophages are among those designated as "tumor-associated macrophages" (TAMs). To determine whether the peptides of the invention could influence macrophage polarization, the following experiment was performed.

Primary bone marrow cells were collected from male C57BL/6J (The Jackson Laboratory, Bar Harbor, Me.). Mouse bone marrow macrophages were differentiated in vitro from the primary bone marrow cells by culturing in Dulbecco's minimal essential medium (DMEM) with 10% FBS and 30 ng/ml murine M-CSF (colony stimulating factor) for 6 days. At day 7, macrophages were plated into 12-well plates and cultured in DMEM (10% FBS) with (i) IL-4 peptide (20 ng/mL), (ii) INF-γ (10 ng/mL), or (iii) neither IL-4 nor INF-γ for 24 hours. After 24 hours, the media was replaced with pure DMEM and the cells were cultured for an additional 48 hours. The resulting macrophages were (i) M2-polarized, (ii) M1-polarized, or (iii) undifferentiated, respectively.

A macrophage sample containing approximately 70,000 undifferentiated macrophages per ml was incubated for 72 hours with 100 nM RP-182 (SEQ ID NO: 121). Following the incubation, a count of viable cells revealed that there were 68,000 cells per ml. Similarly, incubating M1-polarized macrophages for 72 hours with 100 nM RP-182 resulted in a viable cell count of 68,000 cells per ml. Thus, the RP-182 had little effect on the viability of M1 macrophages. In contrast, incubating M2-polarized macrophages for 72 hours with 100 nM RP-182 resulted in a viable cell count of only 20,000 cells per ml. The results indicate that RP-182 reduces the viability of M2 macrophages.

Example 12

Downregulation of Checkpoint Inhibitors and Ligands

Figure 19:
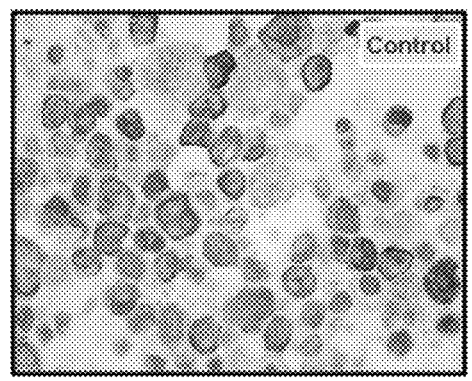
FIG. 19 shows PD-1-stained tumor cells from p53/KRAS mice treated with vehicle only (left panel) or treated with RP-182 (right panel). PD-1 expression is reduced in RP-182 treated mice.
Figure 19:
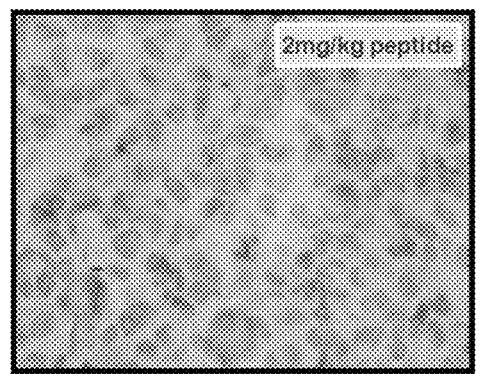
Figure 20:
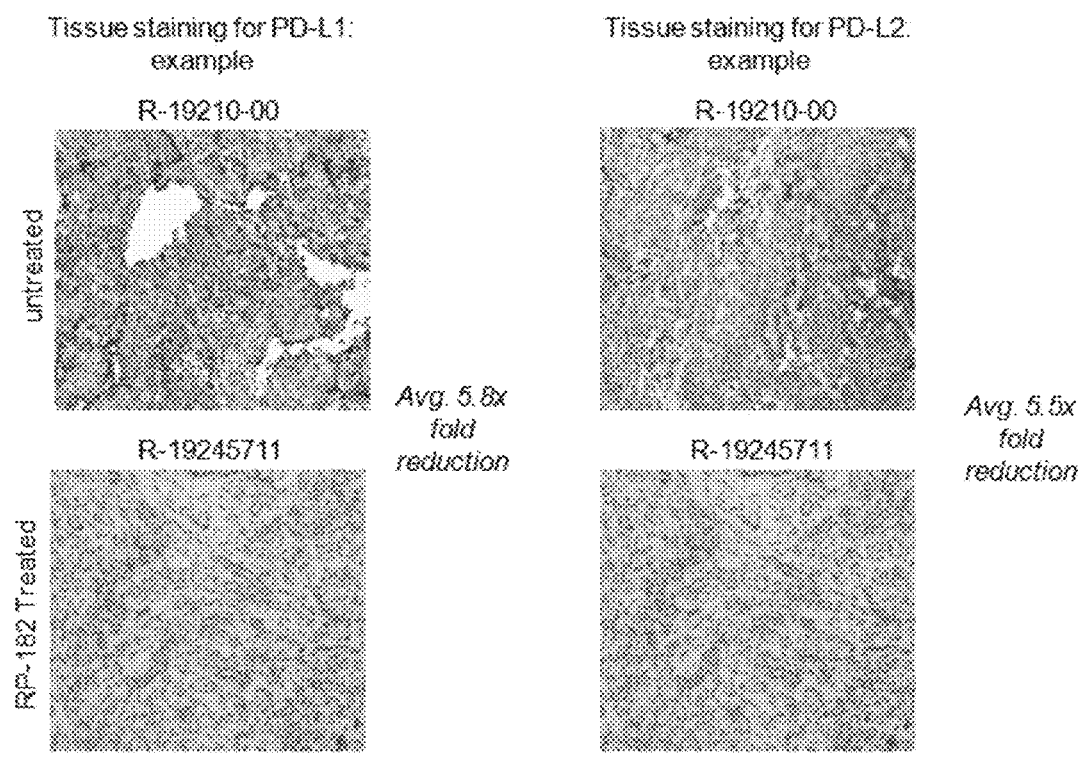
FIG. 20 shows PD-L1-stained (left panels) and PD-L2-stained (right panels) tumor cells from p53/KRAS mice treated with vehicle only (top panel in each set) or treated with RP-182 (bottom panel in each set). PD-L1 and PD-L2 expression is reduced in RP-182 treated mice.

Based on their predicted affinity to checkpoint inhibitors (e.g. PD-1) and their ligands (e.g. PD-L1 and PD-L2), the polypeptides of the invention were also evaluated to determine whether the concentration of these proteins in treated tissue would be downregulated in vivo. In one experiment, tumors in transgenic p53/KRAS mice were allowed to grow to approximately 100 m³ in volume, and the animals were then treated daily subcu for one week with either vehicle only, or 10 mg/kg RP-182, following which the animals were sacrificed and the tumors resected, formalin-fixed, and stained with antibodies to PD-1 (FIG. 19), PD-L1 and PD-L2 (FIG. 20). It is clear from the figures that both the checkpoint inhibitor PD-1 and each of its ligands PD-L1 and PD-L2 are significantly downregulated in vivo in tissue treated with peptides of the present disclosure.

Example 13

Suppression of Tumor Growth

The polypeptides of the invention were also tested for their effect on tumor growth in a mouse model of non-metastatic breast cancer. MCF-7 human non-metastatic breast cancer cells were cultured at 37° C., 5% CO2 in normal growth media. Cells were harvested at 80% to 90% confluence. Immune compromised athymic nude mice (J:NU) were divided into 2 groups (9 animals per group). All mice were injected with ~$4.5\times10^6$ MCF-7 cells which had been stained with VIVO Tracker 680 and suspended in 200 µl of PBS/Matrigel mixture. Cells were injected subcutaneously on the dorsal surface of treated animals using a 22 gauge needle fitted with a 500 µl syringe.

Animals were designated vehicle and peptide treated. The peptide treated animals were treated with the RP-397 polypeptide (SEQ ID NO: 194). Freshly prepared RP-397 peptide was dissolved in sterile saline at a concentration of 100 µM and was used to treat the animals in the peptide group. Vehicle treated animals were injected with saline buffer alone. All treatments were injected into the tumor mass two times weekly for 5 weeks using a 27½ gauge needle fitted with a 1 ml syringe. Animal weights and tumor volumes were measured 3 times weekly and the fluorescence labeling was followed by VIVO Tracker 680 and IVIS Imaging. The results are shown in Table 17, below.

TABLE 17

Suppression of Tumor Growth Using RP-397

|  | Avg. Tumor Weight | Rate of Tumor Growth | Body Weight Before | Body Weight After |
|---|---|---|---|---|
| Vehicle | 1.5 g | 63 | 25.2 | 30.2 |
| RP-397 | 0.75 g* | 20* | 25.1 | 30.1 |

The rate of tumor growth was measured in mm³/day. The "*" denotes a statistically significant difference from the vehicle control.

The data shows that polypeptides of the invention can suppress tumor growth in vivo.

Example 14

Administering Peptides in Combination with Chemotherapy

Given the significant role of inflammation in tumor genesis and metastasis, as well as the known association of M2 macrophage activity with tumor development, it was anticipated that the administration of peptides of the invention could positively influence the outcomes of cancer treatment.

Figure 21:
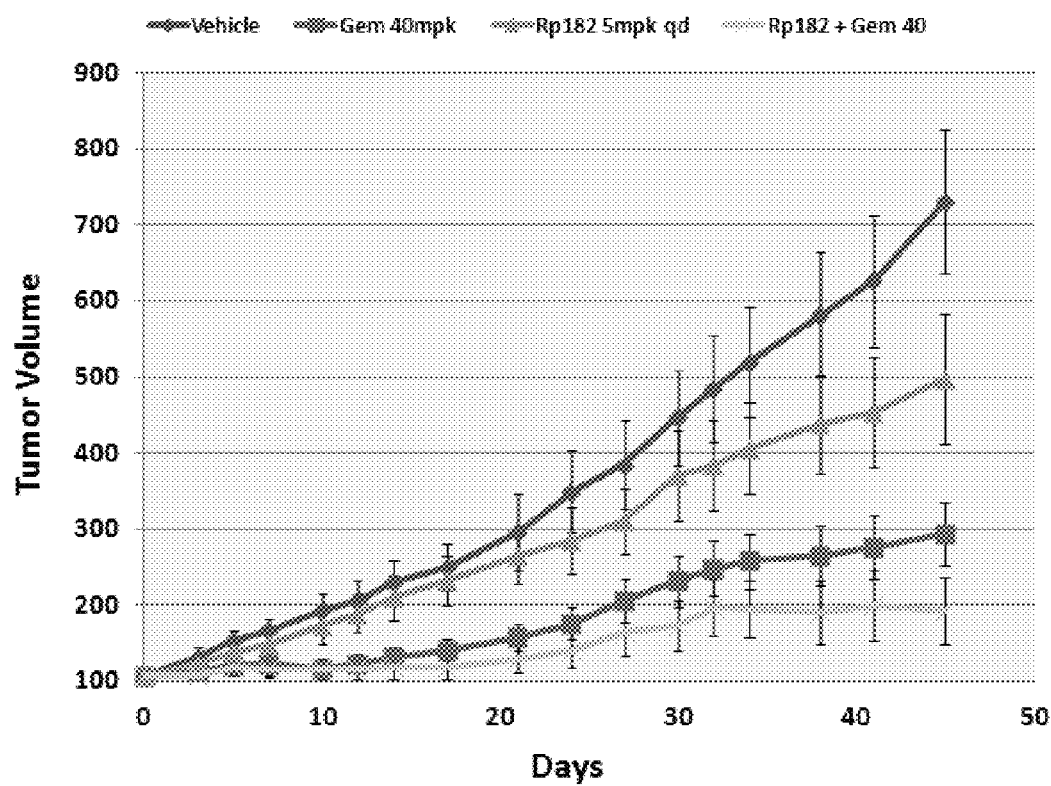
FIG. 21 shows MDA-MB-231 tumor volume in four cohorts of mice over time. Cohort 1: vehicle; Cohort 2: Gemcitabine treated; Cohort 3: RP-182 treated; Cohort 4: RP-182+Gemcitabine treated.

To test this theory, cohorts of immunocompromised ("nude") mice were injected with ~$5\times10^6$ human triple-negative breast cancer cells (MDA-MB-231) under the upper left teat. Following this administration, one cohort received only vehicle; two of the cohorts received the chemotherapeutic agent Gemcitabine, at a q4d dose of 40 mg/kg of body weight. One of these cohorts also received RP-182 (SEQ ID NO: 121) at a daily dose of 5 mg/kg body weight; and a fourth cohort received only RP-182 at a daily dose of 5 mg/kg body weight. Beginning on day 32 of the study, in the Gemcitabine+RP-182 cohort, concentrations of RP-182 were increased to 20 mg/kg body weight. Tumor volume was assessed at various time points following initial cell administration (FIG. 21). After 50 days, the mice were sacrificed.

The data demonstrates that, as compared to treatment with Gemcitabine alone, combined treatment with Gemcitabine and polypeptides of the invention resulted in reductions in mean tumor volume. When RP-182 concentration was increased to 20 mg/kg body weight, the increase in tumor volume was essentially halted.

Figure 22:
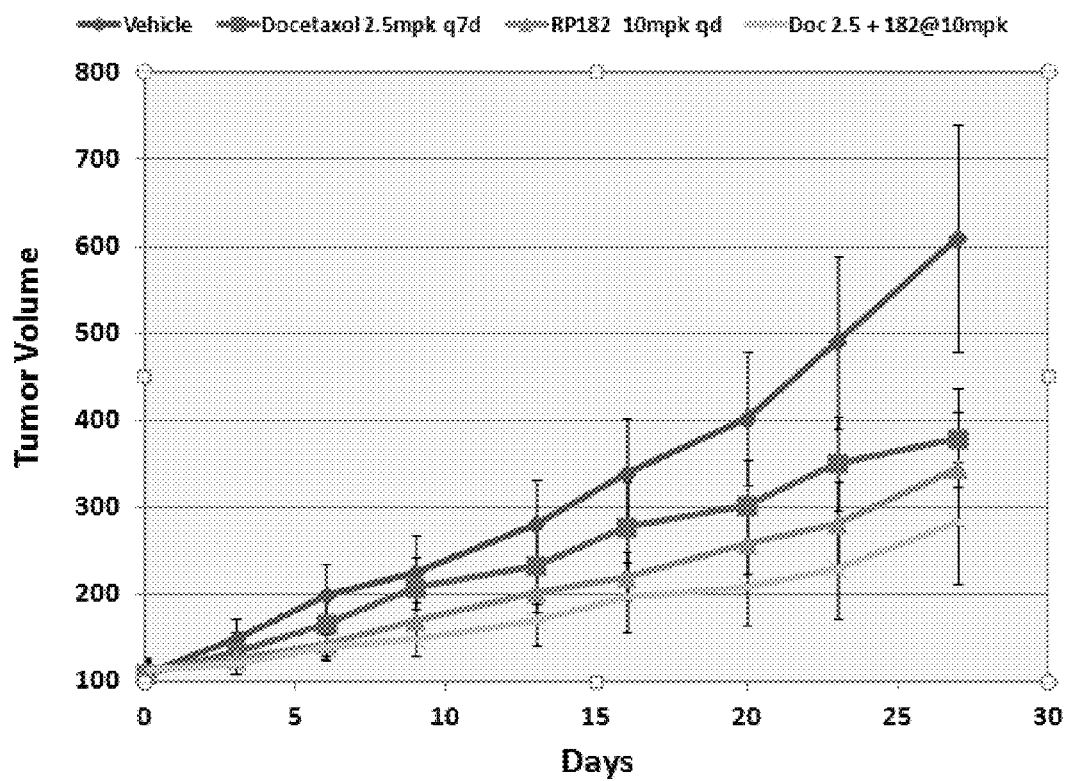
FIG. 22 shows C42B tumor volume in four cohorts of mice over time. Cohort 1: vehicle; Cohort 2: Docetaxel treated; Cohort 3: RP-182 treated; Cohort 4: RP-182+Docetaxel treated.

In a second experiment, xenografts of C42B prostate cancer cells were introduced into four cohorts of mice, and the tumors allowed to grow to approximately 100 m³ before treatment. One cohort was treated only with vehicle; a second with Docetaxel at 2.5 mg/kg body weight administered weekly; a third with RP-182 administered daily subcu at 10 mg/kg body weight; and a fourth with both Docetaxel at 2.5 mg/kg weekly and RP-182 at 10 mg/kg daily. Tumor volume was assessed at various time points following initial cell administration (FIG. 22); after 27 days, the mice were sacrificed. Similarly, the administration of RP-182 plus Docetaxel resulted in decreases in mean tumor volume compared to Docetaxel alone.

It is anticipated that the peptides of the invention will produce synergistic effects when administered with chemotherapeutic agents other than Gemcitabine and Docetaxel, as well as checkpoint inhibitor therapies and other immunotherapies. In particular, the peptides of the invention may be particularly useful when used in conjunction with recently-developed CAR-T (chimeric antigen receptor/T cell) therapies. Such therapies, while destroying tumor cells, create a very high systemic burden of dead cell material, overstimulating the immune system and creating a "cytokine storm" which can be fatal to the patient.

EMBODIMENTS

The following embodiments are provided to illustrate aspects of the present invention.

1. An anti-inflammatory composition comprising a peptide, wherein the peptide is 3 to 24 amino acid residues in length and comprises a striapathic region consisting of alternating $X_m$ and $Y_n$ modules, wherein m and n are positive integers that identify different modules, wherein each $X_m$ module consists of a sequence according to the formula $X_{ma}$-$X_{mb}$-$X_{mc}$-$X_{md}$-$X_{me}$, wherein $X_{ma}$ is selected from the group consisting of a naturally occurring hydrophilic amino acid, a non-naturally occurring hydrophilic amino acid, and a hydrophilic amino acid mimetic, and wherein $X_{mb}$, $X_{mc}$, $X_{md}$ and $X_{me}$ are each individually absent or selected from the group consisting of a naturally occurring hydrophilic amino acid, a non-naturally occurring hydrophilic amino acid, and a hydrophilic amino acid mimetic, wherein each $Y_n$ module consists of a sequence according to the formula $Y_{na}$-$Y_{nb}$-$Y_{nc}$-$Y_{nd}$-$Y_{ne}$, wherein $Y_{na}$ is selected from the group consisting of a naturally occurring hydrophobic amino acid, a non-naturally occurring hydrophobic amino acid, and a hydrophobic amino acid mimetic, and wherein $Y_{nb}$, $Y_{nc}$, $Y_{nd}$, and $Y_{ne}$ are each individually absent or selected from the group consisting of a naturally occurring hydrophobic, a non-naturally occurring hydrophobic amino acid, and a hydrophobic amino acid mimetic, and wherein the peptide binds to the dimerization site on a NFkB Class II protein.

2. The anti-inflammatory composition of embodiment 1, wherein each $X_m$ module consists of a sequence according to the formula $X_{ma}$-$X_{mb}$-$X_{mc}$-$X_{md}$, and each $Y_n$ module consists of a sequence according to the formula $Y_{na}$-$Y_{nb}$-$Y_{nc}$-$Y_{nd}$.

3. The anti-inflammatory composition of embodiment 1, wherein each $X_m$ module consists of a sequence according to the formula $X_{ma}$-$X_{mb}$-$X_{mc}$, and each $Y_n$ module consists of a sequence according to the formula $Y_{na}$-$Y_{nb}$-$Y_{nc}$.

4. The anti-inflammatory composition of any one of embodiments 1 to 3, wherein the peptide also binds to human serum albumin.

5. The anti-inflammatory composition of any one of embodiments 1 to 4, wherein the striapathic region of the peptide contains at least two $X_m$ modules ($X_1$, $X_2$, and $X_3$) and at least two $Y_n$ modules ($Y_1$, $Y_2$, and $Y_3$).

6. The anti-inflammatory composition of any one of embodiments 1 to 5, wherein the striapathic region of the peptide contains at least seven amino acid residues.

7. The anti-inflammatory composition of any one of embodiments 1 to 6, wherein the striapathic region of the peptide has a length of 7 to 12 amino acid residues.

8. The anti-inflammatory composition of any one of embodiments 1 to 7, wherein the striapathic region of the peptide constitutes at least 25% of the length of the peptide.

9. The anti-inflammatory composition of any one of embodiments 1 to 8, wherein the striapathic region of the peptide has an amphipathic conformation under physiological conditions.

10. The anti-inflammatory composition of embodiment 9, wherein the striapathic region of the peptide has an amphipathic $3_{10}$-helical conformation, an amphipathic α-helical conformation, or an amphipathic π-helical conformation when bound to the NFkB Class II protein.

11. The anti-inflammatory composition of embodiment 10, wherein the amphipathic $3_{10}$-helical, α-helical, or π-helical conformation includes a hydrophobic portion having a facial arc of at least 100°.

12. The anti-inflammatory composition of any one of embodiments 1 to 11, wherein the striapathic region contains hydrophobic amino acid residues having a total volume of at least 650 cubic angstroms.

13. The anti-inflammatory composition of any one of embodiments 1 to 12, wherein the striapathic region is characterized by a ratio of the sum of the volume of hydrophobic amino acid residues to the sum of the volume of hydrophilic amino acid residues, wherein the ratio is at least 0.75 or higher.

14. The anti-inflammatory composition of embodiment 9, wherein the striapathic region of the peptide comprises at least one proline residue and adopts an amphipathic conformation that includes a proline-rich helix.

15. The anti-inflammatory composition of embodiment 9, wherein the striapathic region of the peptide adopts an amphipathic beta-strand conformation.

16. The anti-inflammatory composition of any one of embodiments 1 to 13, wherein the striapathic region includes a sequence selected from the group of sequences defined by Formula I: $Y_{1a}$-$Y_{1b}$-$Y_{1c}$-$X_{1a}$-$Y_{2a}$-$Y_{2b}$-$Y_{2c}$ (Formula I).

17. The anti-inflammatory composition of embodiment 16, wherein the module $Y_{1a}$-$Y_{1b}$-$Y_{1c}$ has a sequence selected from the group consisting of Phe-Phe-Phe (FFF), Trp-Trp- Trp (WWW), Tyr-Tyr-Tyr (YYY), Leu-Leu-Leu (LLL), Cys-Cys-Cys (CCC), Met-Met-Met (MMM), Val-Val-Val (VVV), and Ile-Ile-Ile (III).

18. The anti-inflammatory composition of embodiment 16, wherein the module $Y_{1a}$-$Y_{1b}$-$Y_{1c}$ has a sequence selected from the group consisting of Phe-Phe-Phe (FFF), Trp-Trp-Trp (WWW), and Tyr-Tyr-Tyr (YYY).

19. The anti-inflammatory composition of any one of embodiments 16 to 18, wherein the module $Y_{2a}$-$Y_{2b}$-$Y_{2c}$ has a sequence selected from the group consisting of Phe-Phe-Phe (FFF), Trp-Trp-Trp (WWW), Tyr-Tyr-Tyr (YYY), Leu-Leu-Leu (LLL), Cys-Cys-Cys (CCC), Met-Met-Met (MMM), Val-Val-Val (VVV), and Ile-Ile-Ile (III).

20. The anti-inflammatory composition of any one of embodiments 16 to 18, wherein the module $Y_{2a}$-$Y_{2b}$-$Y_{2c}$ has a sequence selected from the group consisting of Phe-Phe-Phe (FFF), Trp-Trp-Trp (WWW), and Tyr-Tyr-Tyr (YYY).

21. The anti-inflammatory composition of embodiment 16, wherein the striapathic region includes a sequence selected from the group consisting of FFF-$X_{1a}$-FFF (SEQ ID NO: 1), WWW-$X_{1a}$-WWW (SEQ ID NO: 2), and YYY-$X_{1a}$-YYY (SEQ ID NO: 3).

22. The anti-inflammatory composition of embodiment 16, wherein the sequence of the three modules is selected from the group consisting of LLL-$X_{1a}$-LLL (SEQ ID NO: 4), CCC-$X_{1a}$-CCC (SEQ ID NO: 5), MMM-$X_{1a}$-MMM (SEQ ID NO: 6), VVV-$X_{1a}$-VVV (SEQ ID NO: 7), and III-$X_{1a}$-III (SEQ ID NO: 8).

23. The anti-inflammatory composition of any one of embodiments 16 to 22, wherein $X_{1a}$ is selected from the group consisting of Arg (R), His (H), and Lys (K).

24. The anti-inflammatory composition of any one of embodiments 16 to 22, wherein $X_{1a}$ is selected from the group consisting of Glu (E), Gln (Q), Asn (N), and Asp (D).

25. The anti-inflammatory composition of any one of embodiments 16 to 24, wherein the striapathic region includes a sequence selected from the group of sequences defined by Formula II or the group of sequences defined by Formula III: $Y_{1a}$-$Y_{1b}$-$Y_{1c}$-$X_{1a}$-$Y_{2a}$-$Y_{2b}$-$Y_{2c}$-$X_{2a}$-$Y_{3a}$-$X_{3a}$ (Formula II); $X_{2a}$-$Y_{3a}$-$X_{3a}$-$Y_{1a}$-$Y_{1b}$-$Y_{1c}$-$X_{1a}$-$Y_{2a}$-$Y_{2b}$-$Y_{2c}$ (Formula III).

26. The anti-inflammatory composition of embodiment 25, wherein $X_{2a}$ and $X_{3a}$ are each individually selected from the group consisting of Arg (R), His (H), Lys (K), Glu (E), Gln (Q), Asn (N), and Asp (D).

27. The anti-inflammatory composition of embodiment 25, wherein $X_{2a}$ and $X_{3a}$ are each individually selected from the group consisting of Glu (E), Gln (Q), Asn (N), and Asp (D).

28. The anti-inflammatory composition of any one of embodiments 25 to 27, wherein $Y_{3a}$ is selected from the group consisting of Phe (F), Trp (W), Tyr (Y), Leu (L), Cys (C), Met (M), Val (V), and Be (I).

29. The anti-inflammatory composition of any one of embodiments 25 to 27, wherein $Y_{3a}$ is selected from the group consisting of Phe (F), Trp (W), Tyr (Y), and Leu (L).

30. The anti-inflammatory composition of embodiment 25, wherein the sequence of $X_{2a}$-$Y_{3a}$-$X_{3a}$ is selected from the group consisting of EFQ, EFE, EFN, EFD, NFQ, NFE, NFN, NFD, QFQ, QFE, QFN, QFD, DFQ, DFE, DFN, DFD, EWQ, EWE, EWN, EWD, NWQ, NWE, NWN, NWD, QWQ, QWE, QWN, QWD, DWQ, DWE, DWN, DWD, EYQ, EYE, EFN, EYD, NYQ, NYE, NYN, NYD, QYQ, QYE, QYN, QYD, DYQ, DYE, DYN, DYD, ELQ, ELE, ELN, ELD, NLQ, NLE, NLN, NLD, QLQ, QLE, QLN, QLD, DLQ, DLE, DLN, DLD, RFR, RFQ, RFE, RFN, RFD, RWR, RWQ, RWE, RWN, and RWD.

31. The anti-inflammatory composition of embodiment 25, wherein the striapathic region comprises, consists essentially of, or consists of a sequence selected from the group consisting of RP394, RP108-RP123, RP125-131, RP133, RP135-RP141, RP143-RP146, RP148-RP150, RP152-RP165, RP179, RP395, RP211, RP230, RP232, RP258, RP267, RP268, RP271, and RP273.

32. The anti-inflammatory composition of embodiment 25, wherein the striapathic region comprises, consists essentially of, or consists of a sequence selected from the group consisting of RP113 (SEQ ID NO: 39), RP118 (SEQ ID NO: 44), and RP394 (SEQ ID NO: 33).

33. The anti-inflammatory composition of any one of embodiments 1 to 13, wherein the striapathic region includes a sequence selected from the group of sequences defined by Formula VII: $Y_{1a}$-$X_{1a}$-$X_{1b}$-$Y_{2a}$-$Y_{2b}$-$X_{2a}$-$X_{2b}$-$Y_{3a}$ (Formula VII).

34. The anti-inflammatory composition of embodiment 33, wherein $Y_{2a}$ is selected from the group consisting of Phe (F), Trp (W), and Tyr (Y).

35. The anti-inflammatory composition of embodiment 33, wherein $Y_{2a}$ is selected from the group consisting of Leu (L), Cys (C), Met (M), Val (V), Ile (I), and Ala (A).

36. The anti-inflammatory composition of any one of embodiments 33 to 35, wherein $Y_{2b}$ is selected from the group consisting of Phe (F), Trp (W), and Tyr (Y).

37. The anti-inflammatory composition of any one of embodiments 33 to 35, wherein $Y_{2b}$ is selected from the group consisting of Leu (L), Cys (C), Met (M), Val (V), Ile (I), and Ala (A).

38. The anti-inflammatory composition of any one of embodiments 33 to 37, wherein $X_{1b}$ is selected from the group consisting of Arg (R), Lys (K), and His (H).

39. The anti-inflammatory composition of any one of embodiments 33 to 37, wherein $X_{1b}$ is selected from the group consisting of Asn (N), Gln (Q), Asp (D), and Glu (E).

40. The anti-inflammatory composition of any one of embodiments 33 to 39, wherein $X_{2a}$ is selected from the group consisting of Arg (R), Lys (K), and His (H).

41. The anti-inflammatory composition of any one of embodiments 33 to 39, wherein $X_{2a}$ is selected from the group consisting of Asn (N), Gln (Q), Asp (D), and Glu (E).

42. The anti-inflammatory composition of embodiment 33, wherein the sequence $X_{1b}$-$Y_{2a}$-$Y_{2b}$-$X_{2a}$ is selected from the group consisting of Lys-Phe-Phe-Lys (KFFK; SEQ ID NO: 386), Lys-Trp-Trp-Lys (KWWK; SEQ ID NO: 387), Lys-Tyr-Try-Lys (KYYK; SEQ ID NO: 388), Lys-Phe-Trp-Lys (KFWK; SEQ ID NO: 389), Lys-Trp-Phe-Lys (KWFK; SEQ ID NO: 390), Lys-Phe-Tyr-Lys (KFYK; SEQ ID NO: 391), Lys-Tyr-Phe-Lys (KYFK; SEQ ID NO: 392), Lys-Trp-Tyr-Lys (KWYK; SEQ ID NO: 393), and Lys-Tyr-Trp-Lys (KYWK; SEQ ID NO: 394).

43. The anti-inflammatory composition of embodiment 33, wherein the sequence $X_{1b}$-$Y_{2a}$-$Y_{2b}$-$X_{2a}$ is selected from the group consisting of Arg-Phe-Phe-Arg (RFFR; SEQ ID NO: 395), Arg-Trp-Trp-Arg (RWWR; SEQ ID NO: 396), Arg-Tyr-Try-Arg (RYYR; SEQ ID NO: 397), Arg-Phe-Trp-Arg (RFWR; SEQ ID NO: 398), Arg-Trp-Phe-Arg (RWFR; SEQ ID NO: 399), Arg-Phe-Tyr-Arg (RFYR; SEQ ID NO: 400), Arg-Tyr-Phe-Arg (RYFR; SEQ ID NO: 401), Arg-Trp-Tyr-Arg (RWYR; SEQ ID NO: 402), and Arg-Tyr-Trp-Arg (RYWR; SEQ ID NO: 403).

44. The anti-inflammatory composition of embodiment 33, wherein the sequence $X_{1b}$-$Y_{2a}$-$Y_{2b}$l-$X_{2a}$ is selected from the group consisting of His-Phe-Phe-His (HFFH; SEQ ID NO: 404), His-Trp-Trp-His (HWWH; SEQ ID NO: 405), His-Tyr-Try-His (HYYH; SEQ ID NO: 406), His-Phe-Trp- His (HFWH; SEQ ID NO: 407), His-Trp-Phe-His (HWFH; SEQ ID NO: 408), His-Phe-Tyr-His (HFYH; SEQ ID NO: 409), His-Tyr-Phe-His (HYFH; SEQ ID NO: 410), His-Trp-Tyr-His (HWYH; SEQ ID NO: 411), and His-Tyr-Trp-His (HYWH; SEQ ID NO: 132).

45. The anti-inflammatory composition of any one of embodiments 33 to 44, wherein $X_{1a}$ is selected from the group consisting of Arg (R), Lys (K), His (H), Asn (N), Gln (Q), Asp (D), and Glu (E).

46. The anti-inflammatory composition of any one of embodiments 33 to 44, wherein $X_{1a}$ is selected from the group consisting of Arg (R) and Gln (Q).

47. The anti-inflammatory composition of any one of embodiments 33 to 46, wherein $X_{2b}$ is selected from the group consisting of Arg (R), Lys (K), His (H), Asn (N), Gln (Q), Asp (D), and Glu (E).

48. The anti-inflammatory composition of any one of embodiments 33 to 46, wherein $X_{2b}$ is selected from the group consisting of Arg (R) and Gln (Q).

49. The anti-inflammatory composition of any one of embodiments 33 to 48, wherein $Y_{1a}$ is selected from the group consisting of Phe (F), Trp (W), and Tyr (Y).

50. The anti-inflammatory composition of any one of embodiments 33 to 48, wherein $Y_{1a}$ is selected from the group consisting of Leu (L), Cys (C), Met (M), Val (V), Ile (I), and Ala (A).

51. The anti-inflammatory composition of any one of embodiments 33 to 50, wherein $Y_{3a}$ is selected from the group consisting of Phe (F), Trp (W), and Tyr (Y).

52. The anti-inflammatory composition of any one of embodiments 33 to 50, wherein $Y_{3a}$ is selected from the group consisting of Leu (L), Cys (C), Met (M), Val (V), Ile (I), and Ala (A).

53. The anti-inflammatory composition of embodiment 33, wherein the striapathic region includes a sequence selected from the group consisting of F-$X_{1a}$-$X_{1b}$-FF-$X_{2a}$-$X_{2b}$-F (SEQ ID NO: 9), F-$X_{1a}$-$X_{1b}$-FF-$X_{2a}$-$X_{2b}$-W (SEQ ID NO: 10), W-$X_{1a}$-$X_{1b}$-FF-$X_{2a}$-$X_{2b}$-F (SEQ ID NO: 11), F-$X_{1a}$-$X_{1b}$-FW-$X_{2a}$-$X_{2b}$-F (SEQ ID NO: 12), F-$X_{1a}$-$X_{1b}$-WF-$X_{2a}$-$X_{2b}$-F (SEQ ID NO: 13), F-$X_{1a}$-$X_{1b}$-WW-$X_{2a}$-$X_{2b}$-F (SEQ ID NO: 14), W-$X_{1a}$-$X_{1b}$-WW-$X_{2a}$-$X_{2b}$-F (SEQ ID NO: 15), F-$X_{1a}$-$X_{1b}$-WW-$X_{2a}$-$X_{2b}$-W (SEQ ID NO: 16), W-$X_{1a}$-$X_{1b}$-WW-$X_{2a}$-$X_{2b}$-W (SEQ ID NO: 17), F-$X_{1a}$-$X_{1b}$-FF-$X_{2a}$-$X_{2b}$-Y (SEQ ID NO: 18), Y-$X_{1a}$-$X_{1b}$-FF-$X_{2a}$-$X_{2b}$-F (SEQ ID NO: 19), F-$X_{1a}$-$X_{1b}$-FY-$X_{2a}$-$X_{2b}$-F (SEQ ID NO: 20), F-$X_{1a}$-$X_{1b}$-YF-$X_{2a}$-$X_{2b}$-F (SEQ ID NO: 21), F-$X_{1a}$-$X_{1b}$-YY-$X_{2a}$-$X_{2b}$-F (SEQ ID NO: 22), Y-$X_{1a}$-$X_{1b}$-YY-$X_{2a}$-$X_{2b}$-F (SEQ ID NO: 23), F-$X_{1a}$-$X_{1b}$-YY-$X_{2a}$-$X_{2b}$-Y (SEQ ID NO: 24), and Y-$X_{1a}$-$X_{1b}$-YY-$X_{2a}$-$X_{2b}$-Y (SEQ ID NO: 25), Y-$X_{1a}$-$X_{1b}$-YY-$X_{2a}$-$X_{2b}$-W (SEQ ID NO: 26), W-$X_{1a}$-$X_{1b}$-YY-$X_{2a}$-$X_{2b}$-Y (SEQ ID NO: 27), Y-$X_{1a}$-$X_{1b}$-YW-$X_{2a}$-$X_{2b}$-Y (SEQ ID NO: 28), Y-$X_{1a}$-$X_{1b}$-WY-$X_{2a}$-$X_{2b}$-Y (SEQ ID NO: 29), Y-$X_{1a}$-$X_{1b}$-WW-$X_{2a}$-$X_{2b}$-Y (SEQ ID NO: 30), W-$X_{1a}$-$X_{1b}$-WW-$X_{2a}$-$X_{2b}$-Y (SEQ ID NO: 31), and Y-$X_{1a}$-$X_{1b}$-WW-$X_{2a}$-$X_{2b}$-W (SEQ ID NO: 32).

54. The anti-inflammatory composition of embodiment 53, wherein $X_{1a}$, $X_{1b}$, $X_{2a}$, and $X_{2b}$ are each independently selected from the group consisting of Arg (R), Lys (K), His (H), Asn (N), Gln (Q), Asp (D), and Glu (E).

55. The anti-inflammatory composition of embodiment 53 or 54, wherein $X_{1b}$ and $X_{2a}$ are each independently selected from the group consisting of Arg (R), Lys (K), and His (H).

56. The anti-inflammatory composition of any one of embodiments 33 to 55, wherein the striapathic region includes a first additional amino acid residue directly bound to $Y_{1a}$ of Formula VII, wherein the first additional amino acid residue is a hydrophobic amino acid residue.

57. The anti-inflammatory composition of embodiment 56, wherein the first additional amino acid residue is selected from the group consisting of Phe (F), Trp (W), and Tyr (Y).

58. The anti-inflammatory composition of any one of embodiments 33 to 55, wherein the striapathic region includes a first additional amino acid residue directly bound to $Y_{3a}$ of Formula VII, wherein the first additional amino acid residue is a hydrophobic amino acid residue.

59. The anti-inflammatory composition of embodiment 58, wherein the first additional amino acid residue is selected from the group consisting of Phe (F), Trp (W), and Tyr (Y).

60. The anti-inflammatory composition of any one of embodiments 33 to 55, wherein the striapathic region includes a first additional amino acid residue directly bound to $Y_{1a}$ of Formula VII, wherein the first additional amino acid residue is a hydrophilic amino acid residue.

61. The anti-inflammatory composition of embodiment 60, wherein the first additional amino acid residue is selected from the group consisting of Arg (R), Lys (K), His (H), Asn (N), Gln (Q), Asp (D), and Glu (E).

62. The anti-inflammatory composition of any one of embodiments 33 to 55, wherein the striapathic region includes a first additional amino acid residue directly bound to $Y_{3a}$ of Formula VII, wherein the first additional amino acid residue is a hydrophilic amino acid residue.

63. The anti-inflammatory composition of embodiment 62, wherein the first additional amino acid residue is selected from the group consisting of Arg (R), Lys (K), His (H), Asn (N), Gln (Q), Asp (D), and Glu (E).

64. The anti-inflammatory composition of 56, 57, 60, or 61, wherein the striapathic region includes a second additional amino acid residue directly bound to $Y_{3a}$ of Formula VII, wherein the second additional amino acid residue is a hydrophobic amino acid residue.

65. The anti-inflammatory composition of embodiment 64, wherein the second additional amino acid residue is selected from the group consisting of Phe (F), Trp (W), and Tyr (Y).

66. The anti-inflammatory composition of 58, 59, 62, or 63, wherein the striapathic region includes a second additional amino acid residue directly bound to $Y_{1a}$ of Formula VII, wherein the second additional amino acid residue is a hydrophilic amino acid residue.

67. The anti-inflammatory composition of embodiment 66, wherein the second additional amino acid residue is selected from the group consisting of Arg (R), Lys (K), His (H), Asn (N), Gln (Q), Asp (D), and Glu (E).

68. The anti-inflammatory composition of embodiment 33, wherein the striapathic region comprises, consists essentially of, or consists of a sequence selected from the group consisting of RP124, RP132, RP134, RP142, RP147, RP151, RP166-RP172, RP175, RP177, RP182, RP183, RP185, RP186, RP 424, RP190, RP194, RP198, RP199-RP202, RP204, RP206, RP207, RP209, RP210, RP212-RP216, RP218, RP219, RP425, RP225, RP227, RP233-RP239, RP398, RP241-RP247, RP250-RP256, and RP426.

69. The anti-inflammatory composition of embodiment 33, wherein the striapathic region comprises, consists essentially of, or consists of a sequence selected from the group consisting of RP124 (SEQ ID NO: 106), RP166 (SEQ ID NO: 112), RP182 (SEQ ID NO: 121), and RP183 (SEQ ID NO: 122).

70. The anti-inflammatory composition of any one of embodiments 1 to 15, wherein the striapathic region includes a sequence selected from the group of sequences defined by any one of Formulas I-XLVIII and L: $Y_{1a}$-$Y_{1b}$-$Y_{1c}$-$X_{1a}$-$Y_{2a}$-$Y_{2b}$-$Y_{2c}$ (Formula I); $Y_{1a}$-$Y_{1b}$-$Y_{1c}$-$X_{1a}$-$Y_{2a}$-

$Y_{2b}$-$Y_{2c}$-$X_{2a}$-$Y_{3a}$-$X_{3a}$ (Formula II); $X_{2a}$-$Y_{3a}$-$X_{3a}$-$Y_{1a}$-$Y_{1b}$-$Y_{1c}$-$X_{1a}$-$Y_{2a}$-$Y_{2b}$-$Y_{2c}$ (Formula III); $X_{1a}$-$X_{1b}$-$X_{1c}$-$Y_{2a}$-$X_{2a}$-$X_{2b}$-$X_{2c}$ (Formula IV); $Y_{1a}$-$X_{1a}$-$X_{1b}$-$X_{1c}$-$Y_{2a}$-$X_{2a}$-$X_{2b}$-$X_{2c}$-$Y_{3a}$-$X_{3a}$ (Formula V); $X_{1a}$-$X_{1b}$-$Y_{2a}$-$Y_{2b}$-$X_{2a}$-$X_{2b}$ (Formula VI); $Y_{1a}$-$X_{1a}$-$X_{1b}$-$Y_{2a}$-$Y_{2b}$-$X_{2a}$-$X_{2b}$-$Y_{3a}$ (Formula VII); $Y_{1a}$-$X_{1a}$-$X_{1b}$-$Y_{2a}$-$Y_{2b}$-$X_{2a}$-$X_{2b}$-$Y_{3a}$-$Y_{3b}$-$X_{3a}$ (Formula VIII); $Y_{1a}$-$Y_{1b}$-$X_{1a}$-$X_{1b}$-$Y_{2a}$-$Y_{2b}$-$X_{2a}$-$X_{2b}$-$Y_{3a}$-$Y_{3b}$ (Formula IX); $Y_{1a}$-$Y_{1b}$-$X_{1a}$-$X_{1b}$-$Y_{2a}$-$Y_{2b}$-$X_{2a}$-$X_{2b}$-$Y_{3a}$-$X_{3a}$ (Formula X); $X_{1a}$-$Y_{1a}$-$X_{2a}$-$X_{2b}$-$Y_{2a}$-$Y_{2b}$-$X_{3a}$-$X_{3b}$-$Y_{3a}$-$Y_{3b}$ (Formula XI); $X_{1a}$-$Y_{1a}$-$Y_{1b}$-$X_{2a}$-$X_{2b}$-$Y_{2a}$-$Y_{2b}$-$X_{3a}$-$X_{3b}$-$Y_{3a}$ (Formula XII); $Y_{1a}$-$X_{1a}$-$X_{1b}$-$Y_{2a}$-$Y_{2b}$-$X_{2a}$-$X_{2b}$-$X_{2c}$-$Y_{3a}$-$Y_{3b}$ (Formula XIII); $X_{1a}$-$X_{1b}$-$X_{1c}$-$Y_{1a}$-$Y_{1b}$-$X_{2a}$-$X_{2b}$-$Y_{2a}$-$Y_{2b}$-$Y_{2c}$ (Formula XIV); $Y_{1a}$-$Y_{1b}$-$Y_{1c}$-$X_{1a}$-$X_{1b}$-$Y_{2a}$-$Y_{2b}$-$X_{2a}$-$X_{2b}$-$X_{2c}$ (Formula XV); $Y_{1a}$-$Y_{1b}$-$X_{1a}$-$X_{1b}$-$X_{1c}$-$Y_{2a}$-$Y_{2b}$-$X_{2a}$-$X_{2b}$-$Y_{3a}$ (Formula XVI); $Y_{1a}$-$Y_{1b}$-$X_{1a}$-$X_{1b}$-$Y_{2a}$-$Y_{2b}$ (Formula XVII); $X_{1a}$-$Y_{1a}$-$Y_{1b}$-$X_{2a}$-$X_{2b}$-$Y_{2a}$-$Y_{2b}$-$X_{3a}$ (Formula XVIII); $Y_{1a}$-$Y_{1b}$-$X_{1a}$-$X_{1b}$-$Y_{2a}$-$Y_{2b}$-$X_{2a}$-$Y_{3a}$-$Y_{3b}$-$X_{3a}$ (Formula XIX); $X_{1a}$-$Y_{1a}$-$Y_{1b}$-$X_{2a}$-$Y_{2a}$-$Y_{2b}$-$X_{3a}$-$X_{3b}$-$Y_{3a}$-$Y_{3b}$ (Formula XX); $Y_{1a}$-$Y_{1b}$-$X_{1a}$-$X_{1b}$-$Y_{2a}$-$X_{2a}$-$X_{2b}$-$Y_{3a}$-$Y_{3b}$ (Formula XXI); $X_{1a}$-$Y_{1a}$-$Y_{1b}$-$X_{2a}$-$X_{2b}$-$X_{2c}$-$Y_{2a}$-$X_{3a}$-$Y_{3a}$-$Y_{3b}$ (Formula XXII); $Y_{1a}$-$Y_{1b}$-$X_{1a}$-$Y_{2a}$-$X_{2a}$-$X_{2b}$-$X_{2c}$-$Y_{3a}$-$Y_{3b}$-$X_{3a}$ (Formula XXIII); $X_{1a}$-$X_{1b}$-$Y_{1a}$-$X_{2a}$-$Y_{2a}$-$X_{3a}$-$X_{3b}$ (Formula XXIV); $Y_{1a}$-$Y_{1b}$-$Y_{1c}$-$X_{1a}$-$X_{1b}$-$Y_{2a}$-$X_{2a}$-$Y_{3a}$-$X_{3a}$-$X_{3b}$ (Formula XXV); $X_{1a}$-$X_{1b}$-$Y_{1a}$-$X_{2a}$-$Y_{2a}$-$X_{3a}$-$X_{3b}$-$Y_{3a}$-$Y_{3b}$-$Y_{3c}$ (Formula XXVI); $X_{1a}$-$X_{1b}$-$X_{1c}$-$Y_{1a}$-$Y_{1b}$-$Y_{1c}$-$Y_{1d}$ (Formula XXVII); $X_{1a}$-$X_{1b}$-$X_{1c}$-$X_{1d}$-$Y_{1a}$-$Y_{1b}$-$Y_{1c}$-$Y_{1d}$ (Formula XXVIII); $Y_{1a}$-$X_{1a}$-$X_{1b}$-$X_{1c}$-$X_{1d}$-$Y_{2a}$-$Y_{2b}$-$Y_{2c}$-$Y_{2d}$-$X_{2a}$ (Formula XXIX); $X_{1a}$-$X_{1b}$-$X_{1c}$-$X_{1d}$-$X_{1e}$-$Y_{1a}$-$Y_{1b}$-$Y_{1c}$-$Y_{1d}$-$Y_{1e}$ (Formula XXX); $Y_{1a}$-$Y_{1b}$-$X_{1a}$-$X_{1b}$-$X_{1c}$-$Y_{2a}$-$Y_{2b}$-$Y_{2c}$-$X_{2a}$-$X_{2b}$ (Formula XXXI); $X_{1a}$-$Y_{1a}$-$X_{2a}$-$Y_{2a}$-$X_{3a}$-$X_{3b}$-$X_{3c}$-$Y_{3a}$-$Y_{3b}$-$Y_{3c}$ (Formula XXXII); $Y_{1a}$-$Y_{1b}$-$Y_{1c}$-$X_{1a}$-$X_{1b}$-$X_{1c}$ (Formula XXXIII); $Y_{1a}$-$Y_{1b}$-$Y_{1c}$-$Y_{1d}$-$X_{1a}$-$X_{1b}$-$X_{1c}$-$X_{1d}$ (Formula XXXIV); $X_{1a}$-$Y_{1a}$-$Y_{1b}$-$Y_{1c}$-$Y_{1d}$-$X_{2a}$-$X_{2b}$-$X_{2c}$-$X_{2d}$-$Y_{2a}$ (Formula XXXV); $Y_{1a}$-$Y_{1b}$-$Y_{1c}$-$Y_{1d}$-$Y_{1e}$-$X_{1a}$-$X_{1b}$-$X_{1c}$-$X_{1d}$-$X_{1e}$ (Formula XXXVI); $X_{1a}$-$X_{1b}$-$Y_{1a}$-$Y_{1b}$-$Y_{1c}$-$X_{2a}$-$X_{2b}$-$X_{2c}$-$Y_{2a}$-$Y_{2b}$ (Formula XXXVII); $Y_{1a}$-$Y_{1b}$-$Y_{1c}$-$X_{1a}$-$X_{1a}$-$X_{1c}$-$Y_{2a}$-$X_{2a}$-$Y_{3a}$-$X_{3a}$ (Formula XXXVIII); $Y_{1a}$-$X_{1a}$-$X_{1b}$-$X_{1c}$-$X_{1d}$-$X_{1e}$-$Y_{2a}$ (Formula XXXIX); $Y_{1a}$-$X_{1a}$-$X_{1b}$-$X_{1c}$-$X_{1d}$-$X_{1e}$-$Y_{2a}$-$Y_{2b}$-$Y_{2c}$-$Y_{2d}$ (Formula XL); $Y_{1a}$-$Y_{1b}$-$X_{1a}$-$X_{1b}$-$X_{1c}$-$X_{1d}$-$X_{1e}$-$Y_{2a}$-$Y_{2b}$-$Y_{2c}$ (Formula XLI); $Y_{1a}$-$Y_{1b}$-$Y_{1c}$-$X_{1a}$-$X_{1b}$-$X_{1c}$-$X_{1d}$-$X_{1e}$-$Y_{2a}$-$Y_{2b}$ (Formula XLII); $Y_{1a}$-$Y_{1b}$-$Y_{1c}$-$Y_{1e}$-$X_{1a}$-$X_{1b}$-$X_{1c}$-$X_{1d}$-$X_{1e}$-$Y_{2a}$ (Formula XLIII); $X_{1a}$-$Y_{1a}$-$Y_{1b}$-$Y_{1c}$-$Y_{1d}$-$Y_{1e}$-$X_{2a}$ (Formula XLIV); $X_{1a}$-$Y_{1a}$-$Y_{1b}$-$Y_{1c}$-$Y_{1d}$-$Y_{1e}$-$X_{2a}$-$X_{2b}$-$X_{2c}$-$X_{2d}$ (Formula XLV); $X_{1a}$-$X_{1b}$-$Y_{1a}$-$Y_{1b}$-$Y_{1c}$-$Y_{1d}$-$Y_{1e}$-$X_{2a}$-$X_{2b}$-$X_{2c}$ (Formula XLVI); $X_{1a}$-$X_{1b}$-$X_{1c}$-$Y_{1a}$-$Y_{1b}$-$Y_{1c}$-$Y_{1d}$-$Y_{1e}$-$X_{2a}$-$X_{2b}$ (Formula XLVII); $X_{1a}$-$X_{1b}$-$X_{1c}$-$X_{1d}$-$Y_{1a}$-$Y_{1b}$-$Y_{1c}$-$Y_{1d}$-$Y_{1e}$-$X_{2a}$ (Formula XLVIII); and $Y_{1a}$-$Y_{1b}$-$X_{1a}$-$Y_{2a}$-$Y_{2b}$-$X_{2a}$-$Y_{3a}$-$Y_{3b}$-$X_{3a}$-$Y_{4a}$ (Formula L).

71. The anti-inflammatory composition of embodiment 70, wherein $Y_{1a}$, $Y_{1b}$, $Y_{1c}$, $Y_{2a}$, $Y_{2b}$, $Y_{2c}$, $Y_{3a}$, $Y_{3b}$, and $Y_{3c}$ are each individually selected from the group consisting of Phe (F), Trp (W), Tyr (Y), Leu (L), Cys (C), Met (M), Val (V), Ile (I), and Ala (A).

72. The anti-inflammatory composition of embodiment 70, wherein $Y_{1a}$, $Y_{1b}$, $Y_{1c}$, $Y_{2a}$, $Y_{2b}$, $Y_{2c}$, $Y_{3a}$, $Y_{3b}$, and $Y_{3c}$ are each individually selected from the group consisting of Phe (F), Trp (W), and Tyr (Y).

73. The anti-inflammatory composition of any one of embodiments 70 to 72, wherein $X_{1a}$, $X_{1b}$, $X_{1c}$, $X_{2a}$, $X_{2b}$, $X_{2c}$, $X_{3a}$, and $X_{3b}$ are each individually selected from the group consisting of Arg (R), Lys (K), His (H), Asn (N), Gln (Q), Asp (D), and Glu (E).

74. The anti-inflammatory composition of any one of embodiments 70 to 73, wherein $X_{1a}$, $X_{1b}$, $X_{1c}$, $X_{2a}$, $X_{2b}$, $X_{2c}$, $X_{3a}$, and $X_{3b}$ are each individually selected from the group consisting of Arg (R), Lys (K), His (H), and Gln (Q).

75. The anti-inflammatory composition of any one of embodiments 70 to 74, wherein the striapathic region includes a first additional amino acid residue directly bound to the N-terminal end of any one of Formulas I-XLVIII and L, wherein the first additional amino acid residue is a hydrophobic amino acid residue.

76. The anti-inflammatory composition of embodiment 70, wherein the first additional amino acid residue is selected from the group consisting of Phe (F), Trp (W), and Tyr (Y).

77. The anti-inflammatory composition of any one of embodiments 70 to 74, wherein the striapathic region includes a first additional amino acid residue directly bound to the C-terminal end of any one of Formulas I-XLVIII and L, wherein the first additional amino acid residue is a hydrophobic amino acid residue.

78. The anti-inflammatory composition of embodiment 77, wherein the first additional amino acid residue is selected from the group consisting of Phe (F), Trp (W), and Tyr (Y).

79. The anti-inflammatory composition of any one of embodiments 70 to 74, wherein the striapathic region includes a first additional amino acid residue directly bound to the N-terminal end of any one of Formulas I-XLVIII and L, wherein the first additional amino acid residue is a hydrophilic amino acid residue.

80. The anti-inflammatory composition of embodiment 79, wherein the first additional amino acid residue is selected from the group consisting of Arg (R), Lys (K), His (H), Asn (N), Gln (Q), Asp (D), and Glu (E).

81. The anti-inflammatory composition of any one of embodiments 70 to 74, wherein the striapathic region includes a first additional amino acid residue directly bound to the C-terminal end of any one of Formulas I-XLVIII and L, wherein the first additional amino acid residue is a hydrophilic amino acid residue.

82. The anti-inflammatory composition of embodiment 81, wherein the first additional amino acid residue is selected from the group consisting of Arg (R), Lys (K), His (H), Asn (N), Gln (Q), Asp (D), and Glu (E).

83. The anti-inflammatory composition of any one of embodiments 75, 76, 79, or 80, wherein the striapathic region includes a second additional amino acid residue directly bound to the C-terminal end of any one of Formulas I-XLVIII and L, wherein the second additional amino acid residue is a hydrophobic amino acid residue.

84. The anti-inflammatory composition of embodiment 83, wherein the second additional amino acid residue is selected from the group consisting of Phe (F), Trp (W), and Tyr (Y).

85. The anti-inflammatory composition of any one of embodiments 77, 78, 81, or 82, wherein the striapathic region includes a second additional amino acid residue directly bound to the N-terminal end of any one of Formulas I-XLVIII and L, wherein the second additional amino acid residue is a hydrophilic amino acid residue.

86. The anti-inflammatory composition of embodiment 81, wherein the second additional amino acid residue is selected from the group consisting of Arg (R), Lys (K), His (H), Asn (N), Gln (Q), Asp (D), and Glu (E).

87. The anti-inflammatory composition of embodiment 70, wherein the striapathic region comprises, consists essentially of, or consists of a sequence selected from the group consisting of RP396, RP405, RP174, RP176, RP178, RP180-181, RP184, RP408, RP187, RP416, RP188, RP189, RP388, RP417, RP191-RP193, RP404, RP196, RP397, RP197, RP402, RP203, RP409, RP205, RP208, RP217, RP220-RP224, RP226, RP229, RP231, RP240, RP248, RP249, RP415, RP257, RP259-RP266, RP269, RP272, RP406, RP422, RP407, RP400, RP419, RP401, RP423, RP411, RP418, RP428, RP420, RP421, RP429, RP413, RP430, RP270.

88. The anti-inflammatory composition of any one of embodiments 1 to 9 or 15, wherein the striapathic region includes a sequence selected from the group of sequences defined by Formula XLIX:

$Y_{1a}$-$X_{1a}$-$Y_{2a}$-$X_{2a}$-$Y_{3a}$-$X_{3a}$ (Formula XLIX).

89. The anti-inflammatory composition of embodiment 88, wherein $Y_{1a}$, $Y_{2a}$, and $Y_{3a}$ are each independently selected from the group consisting of Phe (F), Trp (W), Tyr (Y), Leu (L), Ile (I), Cys (C), and Met (M).

90. The anti-inflammatory composition of embodiment 88, wherein $Y_{1a}$, $Y_{2a}$, and $Y_{3a}$ are each independently selected from the group consisting of Phe (F), Trp (W), and Tyr(Y).

91. The anti-inflammatory composition of any one of embodiments 88 to 90, wherein $X_{1a}$, $X_{2a}$, and $X_{3a}$ are each independently selected from the group consisting of Arg (R), Lys (K), His (H), Gln (Q), Glu (E), Asn (N), and Asp (D).

92. The anti-inflammatory composition of any one of embodiments 88 to 90, wherein $X_{1a}$, $X_{2a}$, and $X_{3a}$ are each independently selected from the group consisting of Arg (R), Lys (K), and His (H).

93. The anti-inflammatory composition of any one of embodiments 88 to 92, wherein the striapathic region includes a first additional amino acid residue directly bound to $Y_{1a}$ of Formula XLIX, wherein the first additional amino acid residue is a hydrophilic amino acid residue.

94. The anti-inflammatory composition of embodiment 93, wherein the first additional amino acid residue is selected from the group consisting of Arg (R), Lys (K), His (H), Asn (N), Gln (Q), Asp (D), and Glu (E).

95. The anti-inflammatory composition of embodiment 93, wherein the first additional amino acid residue is selected from the group consisting of Arg (R), Lys (K), and His (H).

96. The anti-inflammatory composition of any one of embodiments 88 to 92, wherein the striapathic region includes a first additional amino acid residue directly bound to $X_{3a}$ of Formula XLIX, wherein the first additional amino acid residue is a hydrophobic amino acid residue.

97. The anti-inflammatory composition of embodiment 96, wherein the first additional amino acid residue is selected from the group consisting of Phe (F), Trp (W), (Tyr), Leu (L), Ile (I), Cys (C), and Met (M).

98. The anti-inflammatory composition of embodiment 96, wherein the first additional amino acid residue is selected from the group consisting of Phe (F), Trp (W), and (Tyr).

99. The anti-inflammatory composition of any one of embodiments 93 to 95, wherein the striapathic region includes a second additional amino acid residue directly bound to $X_{3a}$ of Formula XLIX, wherein the second additional amino acid residue is a hydrophobic amino acid residue.

100. The anti-inflammatory composition of embodiment 99, wherein the second additional amino acid residue is selected from the group consisting of Phe (F), Trp (W), (Tyr), Leu (L), Ile (I), Cys (C), and Met (M).

101. The anti-inflammatory composition of embodiment 99, wherein the second additional amino acid residue is selected from the group consisting of Phe (F), Trp (W), and Tyr (Y).

102. An anti-inflammatory composition comprising a peptide, wherein the peptide is 3 to 24 amino acids residues in length and comprises a striapathic region having at least 70% identity with the sequence NFNFFFRFFF (RP394, SEQ ID NO: 33), wherein the peptide binds to the dimerization site on a NFkB Class II protein.

103. The anti-inflammatory composition of embodiment 102, wherein the peptide also binds to human serum albumin.

104. The anti-inflammatory composition of embodiment 102 or 103, wherein the differences between the striapathic region of the peptide and the sequence NFNFFFRFFF (SEQ ID NO: 33) are limited to conservative or highly conservative amino acid substitutions.

105. The anti-inflammatory composition of embodiment 102 or 103, wherein the striapathic region of the peptide differs from the sequence NFNFFFRFFF (SEQ ID NO: 33) by substitution of one or more of the phenylalanine (F) residues with an amino acid residue selected from the group consisting of Trp (W), Tyr (Y), His (H), and Leu (L).

106. The anti-inflammatory composition of embodiment 102 or 103, wherein the striapathic region of the peptide differs from the sequence NFNFFFRFFF (SEQ ID NO: 33) by the deletion of one, two, or three amino acids.

107. The anti-inflammatory composition of embodiment 106, wherein the deleted amino acids are located at the N-terminal end, the C-terminal end, or both ends of the sequence NFNFFFRFFF (SEQ ID NO: 33).

108. An anti-inflammatory composition comprising a peptide, wherein the peptide is 3 to 24 amino acids residues in length and comprises a striapathic region having at least 70% identity with the sequence FFFRFFFNFN (RP118, SEQ ID NO: 44), wherein the peptide binds to the dimerization site on a NFkB Class II protein.

109. The anti-inflammatory composition of embodiment 108, wherein the peptide also binds to human serum albumin.

110. The anti-inflammatory composition of embodiment 108 or 109, wherein the differences between the striapathic region of the peptide and the sequence FFFRFFFNFN (SEQ ID NO: 44) are limited to conservative or highly conservative amino acid substitutions.

111. The anti-inflammatory composition of embodiment 108 or 109, wherein the striapathic region of the peptide differs from the sequence FFFRFFFNFN (SEQ ID NO: 44) by substitution of one or more of the phenylalanine (F) residues with an amino acid residue selected from the group consisting of Trp (W), Tyr (Y), His (H), and Leu (L).

112. The anti-inflammatory composition of embodiment 108 or 109, wherein the striapathic region of the peptide differs from the sequence FFFRFFFNFN (SEQ ID NO: 44) by the deletion of one, two, or three amino acids.

113. The anti-inflammatory composition of embodiment 112, wherein the deleted amino acids are located at the N-terminal end, the C-terminal end, or both ends of the sequence FFFRFFFNFN (SEQ ID NO: 44).

114. An anti-inflammatory composition comprising a peptide, wherein the peptide is 3 to 24 amino acids residues in length and comprises a striapathic region having at least 70% identity with the sequence FFRKFAKRFK (RP183, SEQ ID NO: 122), wherein the peptide binds to the dimerization site on a NFkB Class II protein.

115. The anti-inflammatory composition of embodiment 114, wherein the peptide also binds to human serum albumin.

116. The anti-inflammatory composition of embodiment 114 or 115, wherein the differences between the striapathic region of the peptide and the sequence FFRKFAKRFK (SEQ ID NO: 122) are limited to conservative or highly conservative amino acid substitutions.

117. The anti-inflammatory composition of embodiment 114 or 115, wherein the striapathic region of the peptide differs from the sequence FFRKFAKRFK (SEQ ID NO: 122) by substitution of one or more of the phenylalanine (F) residues with an amino acid residue selected from the group consisting of Trp (W), Tyr (Y), and Leu (L).

118. The anti-inflammatory composition of embodiment 114 or 115, wherein the striapathic region of the peptide differs from the sequence FFRKFAKRFK (SEQ ID NO: 122) by the deletion of one, two, or three amino acids.

119. The anti-inflammatory composition of embodiment 118, wherein the deleted amino acids are located at the N-terminal end, the C-terminal end, or both ends of the sequence FFRKFAKRFK (SEQ ID NO: 122).

120. An anti-inflammatory composition comprising a peptide, wherein the peptide is 3 to 24 amino acids residues in length and comprises a striapathic region having at least 70% identity with the sequence KFRKAFKRFF (RP182, SEQ ID NO: 121), wherein the peptide binds to the dimerization site on a NFkB Class II protein.

121. The anti-inflammatory composition of embodiment 120, wherein the peptide also binds to human serum albumin.

122. The anti-inflammatory composition of embodiment 120 or 121, wherein the differences between the striapathic region of the peptide and the sequence KFRKAFKRFF (SEQ ID NO: 121) are limited to conservative or highly conservative amino acid substitutions.

123. The anti-inflammatory composition of embodiment 120 or 121, wherein the striapathic region of the peptide differs from the sequence KFRKAFKRFF (SEQ ID NO: 121) by substitution of one or more of the phenylalanine (F) residues with an amino acid residue selected from the group consisting of Trp (W), Tyr (Y), and Leu (L) .

124. The anti-inflammatory composition of embodiment 120 or 121, wherein the striapathic region of the peptide differs from the sequence KFRKAFKRFF (SEQ ID NO: 121) by the deletion of one, two, or three amino acids.

125. The anti-inflammatory composition of embodiment 124, wherein the deleted amino acids are located at the N-terminal end, the C-terminal end, or both ends of the sequence KFRKAFKRFF (SEQ ID NO: 121).

126. The anti-inflammatory composition of any one of embodiments 1 to 125, wherein the peptide binds to the dimerization site on Rel B (SEQ ID NO: 367) with a binding energy of at least −650 kcal/mol.

127. The anti-inflammatory composition of any one of embodiments 1 to 126, wherein the peptide binds to the dimerization site on Rel B (SEQ ID NO: 367) and directly contacts at least one amino acid residue of Rel B selected from the group consisting of Glu 298, Tyr-300, Leu-301, Leu-302, Asp-330, His-332, and Leu-371.

128. The anti-inflammatory composition of embodiment 127, wherein the peptide, when bound to the dimerization site on Rel B, forms an ionic bond with Asp-330, forms an ionic bond with His-332, and/or makes a hydrophobic contact with Leu-371.

129. The anti-inflammatory composition of any one of embodiments 1 to 128, wherein the peptide binds to at least one signaling molecule selected from the group consisting of TGFβ (SEQ ID NO: 368), Notch1 (SEQ ID NO: 369), Wnt8R (SEQ ID NO: 370), TRAIL (SEQ ID NO: 371), IL6R (SEQ ID NO: 372), IL10R (SEQ ID NO: 373), EGFR (SEQ ID NO: 374), CDK6 (SEQ ID NO: 375), Histone Methyl Transferase (HMT) (SEQ ID NO: 376), CD47 (SEQ ID NO: 377), SIRP-α (SEQ ID NO: 378), CD206 (SEQ ID NO: 379), TGM2 (SEQ ID NO: 380); LEGUMAIN (SEQ ID NO: 137), CD209 (SEQ ID NO: 140), FAS (SEQ ID NO: 152), PD-1 (SEQ ID NO: 159), MKK7 (SEQ ID NO: 166), and RNR (SEQ ID NO: 168).

130. The anti-inflammatory composition of embodiment 129, wherein the peptide binds to TGFβ (SEQ ID NO: 368) with a binding energy of at least −650 kcal/mol.

131. The anti-inflammatory composition of embodiment 129 or 130, wherein the peptide binds to TGFβ (SEQ ID NO: 368) and directly contacts at least one amino acid residue of TGFβ selected from the group consisting of Leu-20, Ile-22, Phe-24, Asp-27, Leu-28, Trp-30, Trp-32, Tyr-39, Phe-43, Pro-80, Leu-83, Leu-101, and Ser-112.

132. The anti-inflammatory composition of any one of embodiments 129 to 131, wherein the peptide binds to Notch1 (SEQ ID NO: 369) with a binding energy of at least −650 kcal/mol.

133. The anti-inflammatory composition of any one of embodiments 120 to 123, wherein the peptide binds to Notch (SEQ ID NO: 369) and directly contacts at least one amino acid residue of Notch selected from the group consisting of Phe-1520, Gln-1523, Arg-1524, Glu-1526, Ala-1553, Glu-1556, Trp-1557, Cys-1562, His-1602, Arg-1684, Gln-1685, Cys-1686, Ser-1691, Cys-1693, Phe-1694, and Phe-1703.

134. The anti-inflammatory composition of any one of embodiments 129 to 133, wherein the peptide binds to Wnt8R (SEQ ID NO: 370) with a binding energy of at least −600 kcal/mol.

135. The anti-inflammatory composition of any one of embodiments 129 to 134, wherein the peptide binds to Wnt8R (SEQ ID NO: 370) and directly contacts at least one amino acid residue of Wnt8R selected from the group consisting of Tyr-52, Gln-56, Phe-57, Asn-58, Met-91, Tyr-100, Lys-101, Pro-103, Pro-105, Pro-106, Arg-137, and Asp-145.

136. The anti-inflammatory composition of any one of embodiments 129 to 135, wherein the peptide binds to TRAIL (SEQ ID NO: 371) with a binding energy of at least −650 kcal/mol.

137. The anti-inflammatory composition of any one of embodiments 120 to 127, wherein the peptide binds to TRAIL (SEQ ID NO: 371) and directly contacts at least one amino acid residue of TRAIL selected from the group consisting of Arg-130, Arg-158, Ser-159, Gly-160, His-161, Phe-163, Tyr-189, Arg-189, Gln-193, Glu-195, Glu-236, Tyr-237, Leu-239, Asp-267, Asp-269, His-270, and Glu-271.

138. The anti-inflammatory composition of any one of embodiments 129 to 137, wherein the peptide binds to IL6R (SEQ ID NO: 372) with a binding energy of at least −600 kcal/mol.

139. The anti-inflammatory composition of any one of embodiments 129 to 138, wherein the peptide binds to IL6R (SEQ ID NO: 372) and directly contacts at least one amino acid residue of IL6R selected from the group consisting of Glu-163, Gly-164, Phe-168, Gln-190, Phe-229, Tyr-230, Phe-279, and Gln-281.

140. The anti-inflammatory composition of any one of embodiments 129 to 139, wherein the peptide binds to IL10R (SEQ ID NO: 373) with a binding energy of at least −600 kcal/mol.

141. The anti-inflammatory composition of any one of embodiments 129 to 140, wherein the peptide binds to IL10R (SEQ ID NO: 373) and directly contacts at least one amino acid residue of IL10R selected from the group consisting of Tyr-43, Ile-45, Glu-46, Asp-61, Asn-73, Arg-76, Asn-94, Arg-96, Phe-143, Ala-189, Ser-190, and Ser-191.

142. The anti-inflammatory composition of any one of embodiments 129 to 141, wherein the peptide binds to EGFR (SEQ ID NO: 374) with a binding energy of at least −650 kcal/mol.

143. The anti-inflammatory composition of any one of embodiments 129 to 142, wherein the peptide binds to EGFR (SEQ ID NO: 374) and directly contacts at least one amino acid residue of EGFR selected from the group consisting of Leu-10, Thr-40, Trp-41, Leu-63, His-66, Asp-68, Leu-88, Tyr-101, Asp-48, and Phe-51.

144. The anti-inflammatory composition of any one of embodiments 129 to 143, wherein the peptide binds to CDK6 (SEQ ID NO: 375) with a binding energy of at least −600 kcal/mol.

145. The anti-inflammatory composition of any one of embodiments 129 to 144, wherein the peptide binds to CDK6 (SEQ ID NO: 375) and directly contacts at least one amino acid residue of CDK6 selected from the group consisting of Val-142, Arg-144, Asp-145, Ser-171, Val-180, Val-181, Leu-183, Arg-186, Val-190, Gln-193, Tyr-196, and Val-200.

146. The anti-inflammatory composition of any one of embodiments 129 to 145, wherein the peptide binds to histone methyl transferase (HMT) (SEQ ID NO: 376) with a binding energy of at least −600 kcal/mol.

147. The anti-inflammatory composition of any one of embodiments 129 to 146, wherein the peptide binds to HMT (SEQ ID NO: 376) and directly contacts at least one amino acid residue of HMT selected from the group consisting of Asn-69, His-70, Ser-71, Lys-72, Asp-73, Pro-74, and Asn-75.

148. The anti-inflammatory composition of any one of embodiments 129 to 147, wherein the peptide binds to the SIRP-α binding site on CD47 (SEQ ID NO: 377) with a binding energy of at least −550 kcal/mol.

149. The anti-inflammatory composition of any one of embodiments 129 to 148, wherein the peptide binds to CD47 (SEQ ID NO: 377) and directly contacts at least one amino acid residue of CD47 selected from the group consisting of Glu-29, Ala-30, Glu-35, Val-36, Tyr-37, Lys-39, Thr-49, Asp-51, Glu-97, Thr-99, Leu-101, Thr-102, Arp-103, Glu-104, and Glu-106.

150. The anti-inflammatory composition of any one of embodiments 129 to 149, wherein the peptide binds to the CD47 binding site on SIRP-α (SEQ ID NO: 378) with a binding energy of at least −600 kcal/mol.

151. The anti-inflammatory composition of any one of embodiments 129 to 150, wherein the peptide binds to SIRP-α (SEQ ID NO: 378) and directly contacts at least one amino acid residue of SIRP-a selected from the group consisting of Leu-30, Gln-37, Gln-52, Lys-53, Ser-66, Thr-67, Arg-69, Met-72, Phe-74, Lys-96, and Asp-100.

152. The anti-inflammatory composition of any one of embodiments 129 to 151, wherein the peptide binds to CD206 (SEQ ID NO: 379) with a binding energy of at least −650 kcal/mol.

153. The anti-inflammatory composition of any one of embodiments 129 to 152, wherein the peptide binds to CD206 (SEQ ID NO: 379) and directly contacts at least one amino acid residue of CD206 selected from the group consisting of Glu-725, Tyr-729, Glu-733, Asn-747, and Asp-748.

154. The anti-inflammatory composition of any one of embodiments 129 to 153, wherein the peptide binds to TGM2 (SEQ ID NO: 380) with a binding energy of at least −650 kcal/mol.

155. The anti-inflammatory composition of any one of embodiments 129 to 154, wherein the peptide binds to TGM2 (SEQ ID NO: 380) and directly contacts at least one amino acid residue of TGM2 selected from the group consisting of Cys-277, His-335, and Asp-358.

156. The anti-inflammatory composition of any one of embodiments 129 to 155, wherein the peptide binds to LEGUMAIN (SEQ ID NO: 137) with a binding energy of at least −600 kcal/mol.

157. The anti-inflammatory composition of any one of embodiments 129 to 156, wherein the peptide binds to LEGUMAIN (SEQ ID NO: 137) and directly contacts at least one amino acid residue of LEGUMAIN selected from the group consisting of Asn-44, Arg-46, His-159, Glu-189, Cys-191, Ser-217, Ser-218 and Asp-233.

158. The anti-inflammatory composition of any one of embodiments 129 to 157, wherein the peptide binds to CD209 (SEQ ID NO: 140) with a binding energy of at least −600 kcal/mol.

159. The anti-inflammatory composition of any one of embodiments 129 to 158, wherein the peptide binds to CD209 (SEQ ID NO: 140) and directly contacts at least one amino acid residue of CD209 selected from the group consisting of Phe-269, Glu-280, Glu-303, Asn-305, Asn-306, Glu-310, Asp-311, Ser-316, Gly-317, Asn-321 and Lys-324.

160. The anti-inflammatory composition of any one of embodiments 129 to 159, wherein the peptide binds to FAS (SEQ ID NO: 152) with a binding energy of at least −600 kcal/mol.

161. The anti-inflammatory composition of any one of embodiments 129 to 160, wherein the peptide binds to FAS (; SEQ ID NO: 152) and directly contacts at least one amino acid residue of FAS selected from the group consisting of Lys-251, Lys-296, Lys-299, Leu-303, Leu-306, Ala-307, Glu-308, Lys-309, Gln-311, Ile-314, Leu-315, Asp-317, Ile-318 and Thr-319.

162. The anti-inflammatory composition of any one of embodiments 129 to 161, wherein the peptide binds to PD-1 (SEQ ID NO: 159) with a binding energy of at least −600 kcal/mol.

163. The anti-inflammatory composition of any one of embodiments 129 to 162, wherein the peptide binds to PD-1 (SEQ ID NO: 159) and directly contacts at least one amino acid residue of PD-1 selected from the group consisting of Val-64, Asn-66, Tyr-68, Met-70, Thr-76, Lys-78, Thr-120, Leu-122, Ala-125, and Ser-127.

164. The anti-inflammatory composition of any one of embodiments 129 to 163, wherein the peptide binds to MKK7 (SEQ ID NO: 166) with a binding energy of at least −600 kcal/mol.

165. The anti-inflammatory composition of any one of embodiments 129 to 164, wherein the peptide binds to MKK7 (SEQ ID NO: 166) and directly contacts at least one amino acid residue of MKK7 selected from the group consisting of Met-142, Val-150, Lys-152, Lys-165, Met-212, Met-215, Thr-217, Lys-221, Leu-266, Cys-276 and Asp-277.

166. The anti-inflammatory composition of any one of embodiments 129 to 165, wherein the peptide binds to RNR (SEQ ID NO: 168) with a binding energy of at least −600 kcal/mol.

167. The anti-inflammatory composition of any one of embodiments 129 to 166, wherein the peptide binds to RNR (SEQ ID NO: 168) and directly contacts at least one amino acid residue of RNR selected from the group consisting of Asn-426, Leu-427, Cys-428, Glu-430, Met-606, Pro-608 and Ala-610.

168. The anti-inflammatory composition of any one of embodiments 1 to 167, wherein the peptide binds to human serum albumin (HSA) (SEQ ID NO: 381) with a binding energy of at least −650 kcal/mol.

169. The anti-inflammatory composition of any one of embodiments 1 to 168, wherein the peptide comprises a striapathic region that is composed exclusively of D-form amino acid residues.

170. The anti-inflammatory composition of any one of embodiments 1 to 169, wherein the peptide is in solution at a concentration of about 0.1 mg/ml to about 100 mg/ml.

171. The anti-inflammatory composition of any one of embodiments 1 to 170, wherein the composition contains about 1 mg to about 500 mg of the peptide.

172. The anti-inflammatory composition of embodiment 158 or 171, wherein the composition is substantially free of protein other than the peptide.

173. An anti-inflammatory composition comprising a first peptide as defined in any one of embodiments 1 to 171 in combination with a second peptide as defined in any one of embodiments 1 to 171, wherein the first and second peptides can have the same sequence or different sequences.

174. The anti-inflammatory composition of embodiment 173, wherein the first and second peptides are linked together by a peptide bond, a peptide linker, or a non-peptide linker.

175. The anti-inflammatory composition of embodiment 173, wherein the first and second peptides are linked together by a peptide linker, wherein the peptide linker has a sequence selected from the group consisting of Gly-Gly-Gly (GGG), Gly-Gly-Gly-Arg (GGGR; SEQ ID NO: 412), Gly-Pro-Gly (GPG), and Gly-Pro-Gly-Arg (GPGR; SEQ ID NO: 413).

176. The anti-inflammatory composition of embodiment 174 or 175, wherein the linked first and second peptides bind to the dimerization site on Rel B (SEQ ID NO: 367) with a binding energy of at least −700 kcal/mol.

177. The anti-inflammatory composition of any one of embodiments 1 to 171 and embodiments 173 to 176, further comprising serum albumin.

178. The anti-inflammatory composition of embodiment 177, wherein the composition is substantially free of blood proteins other than serum albumin.

179. A pharmaceutical composition comprising the anti-inflammatory composition of any one of embodiments 1 to 178, and a pharmaceutically acceptable carrier.

180. The pharmaceutical composition of embodiment 179, wherein the composition comprises a chemotherapeutic agent.

181. A method of treating a condition associated with chronic inflammation, the method comprising administering a composition according to any one of embodiments 1 to 180 to a subject suffering from the condition.

182. The method of embodiment 181, wherein the condition is selected from the group consisting of irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, and cancer.

183. The method of embodiment 181 or 182, wherein the subject is a mammal.

184. The method of any one of embodiments 181 to 183, wherein the subject is a human.

185. The method of any one of embodiments 181 to 184, wherein the anti-inflammatory composition is administered in a dosage that includes between about 1 mg and about 500 mg of peptide.

186. The method of any one of embodiments 181 to 185, wherein the anti-inflammatory composition is administered intravenously, intraperitoneally, parenteral, orthotopically, subcutaneously, topically, nasally, by means of an implantable depot, using nanoparticle-based delivery systems, microneedle patch, microspheres, beads, osmotic or mechanical pumps, and/or other mechanical means.

187. The method of any one of embodiments 181 to 186, wherein the anti-inflammatory composition is administered in conjunction with another drug known to be effective in treating the condition.

188. The method of embodiment 187, wherein the anti-inflammatory composition is administered prior to, at the same time as, or after the administration of the other drug.

189. A method of treating fibrosis in a subject, the method comprising administering a composition according to any one of embodiments 1 to 180 to the subject.

190. The method of embodiment 189, wherein the fibrosis is selected from the group consisting of pulmonary fibrosis, dermal fibrosis, hepatic fibrosis, renal fibrosis, and fibrosis caused by ionizing radiation.

191. The method of embodiment 189 or 190, wherein the subject is a mammal.

192. The method of any one of embodiments 189 to 191, wherein the subject is a human.

193. The method of any one of embodiments 189 to 192, wherein the anti-inflammatory composition is administered in a dosage that includes between about 1 mg and about 500 mg of peptide.

194. The method of any one of embodiments 189 to 193, wherein the anti-inflammatory composition is administered intravenously, intraperitoneally, parenteral, orthotopically, subcutaneously, topically, nasally, by means of an implantable depot, using nanoparticle-based delivery systems, microneedle patch, microspheres, beads, osmotic or mechanical pumps, and/or other mechanical means.

195. The method of any one of embodiments 189 to 194, wherein the anti-inflammatory composition is administered in conjunction with another drug known to be effective in treating fibrosis.

196. The method of embodiment 195, wherein the anti-inflammatory composition is administered prior to, at the same time as, or after the administration of the other drug.

197. A method of reducing pro-inflammatory cytokine levels in a subject suffering from a chronic inflammatory condition, the method comprising administering a composition according to any one of embodiments 1 to 180 to the subject.

198. The method of embodiment 197, wherein the chronic inflammatory condition is selected from the group consisting of irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, and cancer.

199. The method of embodiment 197 or 198, wherein the method reduces the level of at least one cytokine selected from group consisting of NF-kB, TNFα, IL1, IL6, IL12, MMP-1, MMP-9, MCP-1, IL8, IL17, and IL23.

200. The method of embodiment 199, wherein the level of the at least one cytokine is reduced by at least 10%.

201. The method of any one of embodiments 197 to 200, wherein the subject is a mammal.

202. The method of any one of embodiments 197 to 201, wherein the subject is a human.

203. The method of any one of embodiments 197 to 202, wherein the anti-inflammatory composition is administered in a dosage that includes between about 1 mg and about 500 mg of peptide.

204. The method of any one of embodiments 197 to 203, wherein the anti-inflammatory composition is administered intravenously, intraperitoneally, parenteral, orthotopically, subcutaneously, topically, nasally, by means of an implantable depot, using nanoparticle-based delivery systems, microneedle patch, microspheres, beads, osmotic or mechanical pumps, and/or other mechanical means.

205. The method of any one of embodiments 197 to 204, wherein the anti-inflammatory composition is administered in conjunction with another drug known to be effective in treating the chronic inflammatory condition that the subject is suffering from.

206. The method of embodiment 205, wherein the anti-inflammatory composition is administered prior to, at the same time as, or after the administration of the other drug.

207. A method of treating cancer in a subject, the method comprising administering an anti-inflammatory composition according to any one of embodiments 1 to 180 to the subject.

208. The method of embodiment 207, wherein the cancer is selected from the group consisting of colon cancer, and breast cancer.

209. The method of embodiment 207 or 208, wherein the anti-inflammatory composition is administered in conjunction with a chemotherapeutic agent or cell therapy.

210. The method of embodiment 209, wherein the chemotherapeutic agent or cell therapy is selected from the group consisting of steroids, anthracyclines, thyroid hormone replacement drugs, thymidylate-targeted drugs, checkpoint inhibitor drugs, Chimeric Antigen Receptor/T cell therapies, and other cell therapies.

211. The method of embodiment 209, wherein the chemotherapeutic agent is selected from the group consisting of Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

212. The method of any one of embodiments 209 to 211, wherein the anti-inflammatory composition is administered prior to, at the same time as, or after the administration of the chemotherapeutic agent or cell therapy.

213. The method of embodiment 207 or 208, wherein the anti-inflammatory composition is administered in conjunction with radiation therapy.

214. The method of embodiment 213, wherein the anti-inflammatory composition is administered prior to, or after the administration of the radiation therapy.

215. The method of any one of embodiments 207 to 214, wherein the subject is a mammal.

216. The method of any one of embodiments 207 to 215, wherein the subject is a human.

217. The method of any one of embodiments 207 to 216, wherein the anti-inflammatory composition is administered in a dosage that includes between about 1 mg and about 500 mg of peptide.

218. The method of any one of embodiments 207 to 217, wherein the anti-inflammatory composition is administered intravenously, intraperitoneally, parenteral, orthotopically, subcutaneously, nasally, by means of an implantable depot, using nanoparticle-based delivery systems, microneedle patch, microspheres, beads, osmotic or mechanical pumps, and/or other mechanical means.

What is claimed:

1. An anti-inflammatory composition comprising a peptide, wherein the peptide comprises one of the amino acid sequences selected from the group consisting of: SEQ ID NO: 121, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 120.

2. The anti-inflammatory composition of claim 1, wherein the peptide binds to the dimerization site on a NFkB Class II protein.

3. The anti-inflammatory composition of claim 1, wherein the peptide binds to human serum albumin.

4. The anti-inflammatory composition of claim 1, wherein the peptide consists essentially of one of the amino acid sequences selected from the group consisting of: SEQ ID NO: 121, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 120.

5. The anti-inflammatory composition of claim 1, wherein the peptide comprises the amino acid sequence of SEQ ID NO:121.

6. The anti-inflammatory composition of claim 1, wherein the peptide consists essentially of the amino acid sequence of SEQ ID NO:121.

7. The anti-inflammatory composition of claim 2, wherein the peptide binds to the dimerization site on Rel B (SEQ ID NO: 367) and wherein:
   (i) the peptide binds with a binding energy of at least −650 kcal/mol;
   (ii) the peptide directly contacts at least one amino acid residue of Rel B selected from the group consisting of Glu 298, Tyr-300, Leu-301, Leu-302, Asp-330, His-332, and Leu-371; or
   (iii) the peptide, when bound to the dimerization site on Rel B, forms an ionic bond with Asp-330, forms an ionic bond with His-332, and/or makes a hydrophobic contact with Leu-371.

8. The anti-inflammatory composition of claim 1, wherein the peptide binds to CD206 (SEQ ID NO: 379) and wherein:
   (i) the peptide binds to the mannose-binding site on CD206 and/or interferes with or blocks the binding of SIRP-mannose to CD206;
   (ii) the peptide binds with a binding energy of at least −650 kcal/mol; or
   (iii) the peptide directly contacts at least one amino acid residue of CD206 selected from the group consisting of Phe-708, Thr-709, Trp-710, Pro-714. Glu-719, Asn-720, Trp-721, Ala-722, Glu-725, Tyr-729, Glu-733, Asn-747, Asp-748, Ser-1691, Cys-1693, Phe-1694, and Phe-1703.

9. The anti-inflammatory composition of claim 1, wherein the peptide binds to at least one signaling molecule selected from the group consisting of TGFβ (SEQ ID NO: 368), Notch1 (SEQ ID NO: 369), Wnt8R (SEQ ID NO: 370), TRAIL (SEQ ID NO: 371), IL6R (SEQ ID NO: 372), IL10R (SEQ ID NO: 373), EGFR (SEQ ID NO: 374), CDK6 (SEQ ID NO: 375), Histone Methyl Transferase (HMT) (SEQ ID NO: 376), CD47 (SEQ ID NO: 377), SIRP-α (SEQ ID NO: 378), CD206 (SEQ ID NO: 379), TGM2 (SEQ ID NO: 380); LEGUMAIN (SEQ ID NO: 413), CD209 (SEQ ID NO: 414), FAS (SEQ ID NO: 415), PD-1 (SEQ ID NO: 416), MKK7 (SEQ ID NO: 417), and RNR (SEQ ID NO: 418).

10. The anti-inflammatory composition of claim 1, wherein the composition further comprises a second peptide, wherein the second peptide comprises one of the amino acid sequences selected from the group consisting of: SEQ ID NO: 121, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 120, wherein the first and second peptides can have the same or different sequences.

11. The anti-inflammatory composition of claim 10, wherein the first and second peptides are linked together by a peptide bond, a peptide linker, or a non-peptide linker.

12. The anti-inflammatory composition of claim 1, wherein the composition is free of protein other than the peptide.

13. A pharmaceutical composition comprising the anti-inflammatory composition of claim 1 and a pharmaceutically acceptable carrier.

14. The pharmaceutical composition of claim 13, wherein the composition further comprises a chemotherapeutic agent.

15. The pharmaceutical composition of claim 13, wherein the composition further comprises a Chimeric Antigen Receptor/T Cell therapy.

16. The pharmaceutical composition of claim 14, wherein the chemotherapeutic agent is selected from the group consisting of Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, and Pemetrexed.

17. A method of treating a condition associated with chronic inflammation, the method comprising administering a pharmaceutical composition according to claim 13 to a subject suffering from the condition.

18. The method of claim 17, wherein the condition is selected from the group consisting of: irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, cancer, pulmonary fibrosis, dermal fibrosis, hepatic fibrosis, renal fibrosis, and fibrosis caused by ionized radiation.

19. The method of claim 17, wherein the subject is a mammal.

20. The method of claim 19, wherein the subject is a human.

21. The method of claim 17, wherein the method reduces the level of at least one pro-inflammatory cytokine selected from group consisting of TNFα, IL1, IL6, IL12, MMP-1, MMP-9, MCP-1, IL8, IL17, and IL23.

22. The method of claim 21, wherein the level of the at least one cytokine is reduced by at least 10%.

23. The pharmaceutical composition of claim 13, wherein the anti-inflammatory composition comprises a peptide comprising the amino acid sequence of SEQ ID NO:121.

24. The pharmaceutical composition of claim 13, wherein the anti-inflammatory composition comprises a peptide consisting essentially of the amino acid sequence of SEQ ID NO:121.

25. The method of claim 17, wherein the wherein the anti-inflammatory composition comprises a peptide comprising the amino acid sequence of SEQ ID NO:121.

26. The method of claim 17, wherein the anti-inflammatory composition comprises a peptide consisting essentially of the amino acid sequence of SEQ ID NO:121.

* * * * *